(12) United States Patent
Yang et al.

(10) Patent No.: US 11,292,849 B2
(45) Date of Patent: Apr. 5, 2022

(54) ANTI-TNFRSF9 ANTIBODIES AND USES THEREOF

(71) Applicant: Eucure (Beijing) Biopharma Co., Ltd, Beijing (CN)

(72) Inventors: Yi Yang, Beijing (CN); Jingshu Xie, Beijing (CN); Chunyan Dong, Beijing (CN); Fang Yang, Beijing (CN); Chengyuan Lu, Beijing (CN); Yuelei Shen, Beijing (CN); Jian Ni, Beijing (CN); Yanan Guo, Beijing (CN); Yunyun Chen, Beijing (CN)

(73) Assignee: Eucure (Beijing) Biopharma Co., Ltd., Beijing (CN)

(*) Notice: Subject to any disclaimer, the term of this patent is extended or adjusted under 35 U.S.C. 154(b) by 0 days.

(21) Appl. No.: 17/200,021

(22) Filed: Mar. 12, 2021

(65) Prior Publication Data
US 2021/0206867 A1 Jul. 8, 2021

Related U.S. Application Data

(63) Continuation of application No. PCT/CN2019/105315, filed on Sep. 11, 2019.

(30) Foreign Application Priority Data

Sep. 12, 2018 (WO) ................ PCT/CN2018/105162

(51) Int. Cl.
C07K 16/28 (2006.01)
A61K 47/68 (2017.01)

(52) U.S. Cl.
CPC ...... C07K 16/2878 (2013.01); A61K 47/6849 (2017.08); C07K 16/2818 (2013.01)

(58) Field of Classification Search
None
See application file for complete search history.

(56) References Cited

U.S. PATENT DOCUMENTS

| 4,522,811 A | 6/1985 | Eppstein et al. |
| 4,603,112 A | 7/1986 | Paoletti et al. |
| 4,676,980 A | 6/1987 | Segal et al. |
| 4,769,330 A | 9/1988 | Paoletti et al. |
| 4,777,127 A | 10/1988 | Suni et al. |
| 5,017,487 A | 5/1991 | Stunnenberg et al. |

(Continued)

FOREIGN PATENT DOCUMENTS

| CN | 101586460 | 3/2011 |
| EP | 0345242 | 5/1990 |
| GB | 2200651 | 6/1991 |

(Continued)

OTHER PUBLICATIONS

Carvalho et al., Regulatory and scientific advancements in gene therapy: state-of-the-aft of clinical applications and of the supporting european regulatory framework, Frontiers Med. 4:182, 18 pages, Oct. 2017.*

(Continued)

Primary Examiner — Claire Kaufman
(74) Attorney, Agent, or Firm — Fish & Richardson P.C.

(57) ABSTRACT

This disclosure relates to anti-TNFRSF9 (tumor necrosis factor receptor superfamily member 9) antibodies, antigen-binding fragments, and the uses thereof.

33 Claims, 90 Drawing Sheets
Specification includes a Sequence Listing.

(56) References Cited

U.S. PATENT DOCUMENTS

2017/0226215 A1    8/2017    Gray et al.

FOREIGN PATENT DOCUMENTS

| WO | WO 1989/01973 | 3/1989 |
|----|---------------|--------|
| WO | WO 1991/02805 | 3/1991 |
| WO | WO 1996/27011 | 9/1996 |
| WO | WO 2008/077546 | 7/2008 |
| WO | WO 2009/134389 | 11/2009 |
| WO | WO 2017/005745 | 1/2017 |

OTHER PUBLICATIONS

Chen et al., Enhancement and destruction of antibody function by somatic mutation: unequal occurrence is controlled by V gene combinatorial association, EMBO J. 14(12):2784-2794, 1995.*

MacCallum et al., Antibody-antigen interactions:contact analysis and binding site topography, J. Mol. Biol 262:732, 1996.*

Kranz et al., Restricted reassoication of heavy and light chains from hapten-specific monoclonal antiibodies, Proc. Natl. Acad. Sci, USA, 78(9):5807-5811, Sep. 1981.*

Abhinandan et al., "Analysis and improvements to Kabat and structurally correct numbering of antibody variable domains," Molecular immunology, Aug. 1, 2008, 45(14):3832-3839.

Brennan et al., "Preparation of bispecific antibodies by chemical recombination of monoclonal immunoglobulin G1 fragments," Science, Jul. 5, 1985, 229(4708):81-83.

Broll et al., "CD137 expression in tumor vessel walls: high correlation with malignant tumors," American journal of clinical pathology, Apr. 1, 2001, 115(4):543-549.

Chothia et al., "Canonical structures for the hypervariable regions of immunoglobulins," Journal of molecular biology, Aug. 20, 1987, 196(4):901-917.

Chothia et al., "Conformations of immunoglobulin hypervariable regions," Nature, Dec. 1989, 342(6252):877-883.

Cohen et al., "Naked DNA points way to vaccines," Science, Mar. 19, 1993, 259(5102):1691-1692.

Fisher-Hoch et al., "Protection of rhesus monkeys from fatal Lassa fever by vaccination with a recombinant vaccinia virus containing the Lassa virus glycoprotein gene," Proceedings of the National Academy of Sciences, Jan. 1, 1989, 86(1):317-321.

Flexner et al., "Attenuation and immunogenicity in primates of vaccinia virus recombinants expressing human interleukin-2," Vaccine, Feb. 1, 1990, 8(1):17-21.

Ghetie et al., "Homodimerization of tumor-reactive monoclonal antibodies markedly increases their ability to induce growth arrest or apoptosis of tumor cells," Proceedings of the National Academy of Sciences, Jul. 8, 1997, 94(14):7509-7514.

Guzman et al., "Efficient and selective adenovirus-mediated gene transfer into vascular neointima," Circulation, Dec. 1993, 88(6):2838-2848.

Guzman et al., "Efficient gene transfer into myocardium by direct injection of adenovirus vectors," Circulation Research, Dec. 1993, 73(6):1202-1207.

Irani et al., "Molecular properties of human IgG subclasses and their implications for designing therapeutic monoclonal antibodies against infectious diseases," Molecular immunology, Oct. 1, 2015, 67(2):171-182.

Jones et al., "Replacing the complementarity-determining regions in a human antibody with those from a mouse," Nature, May 1986, 321(6069):522-525.

Kang et al., "Anti-CD137 suppresses tumor growth by blocking reverse signaling by CD137 ligand," Cancer research, Nov. 1, 2017, 77(21):5989-6000.

Karlsson et al., "Kinetic and concentration analysis using BIA technology," Methods, Jun. 1, 1994, 6(2):99-110.

Kass-Eisler et al., "Quantitative determination of adenovirus-mediated gene delivery to rat cardiac myocytes in vitro and in vivo," Proceedings of the National Academy of Sciences, Dec. 15, 1993, 90(24):11498-11502.

Köhler et al., "Continuous cultures of fused cells secreting antibody of predefined specificity," Nature, Aug. 1975, 256(5517):495-497.

Kolls et al., "Prolonged and effective blockade of tumor necrosis factor activity through adenovirus-mediated gene transfer," Proceedings of the National Academy of Sciences, Jan. 4, 1994, 91(1):215-219.

Kozbor et al., "The production of monoclonal antibodies from human lymphocytes," Immunology Today, Mar. 1, 1983, 4(3):72-79.

Kunik et al., "Structural consensus among antibodies defines the antigen binding site," PLoS computational biology, Feb. 23, 2012, 8(2): e1002388, 12 pages.

Lefranc et al., "IMGT unique numbering for immunoglobulin and T cell receptor variable domains and Ig superfamily V-like domains," Developmental & Comparative Immunology, Jan. 1, 2003, 27(1):55-77.

Martin et al., "Molecular modeling of antibody combining sites," Methods in enzymology, Jan. 1, 1991, 203:121-153.

Martin, "Protein sequence and structure analysis of antibody variable domains," Antibody engineering, Springer Berlin Heidelberg, 2001, 422-439.

Morea et al., "Antibody structure, prediction and redesign," Biophysical chemistry, Oct. 1, 1997, 68(1-3):9-16.

Morea et al., "Conformations of the third hypervariable region in the VH domain of immunoglobulins," Journal of molecular biology, Jan. 16, 1998, 275(2):269-294.

Moss et al., "Vaccinia virus expression vectors," Ann N Y Acad Sci, 1989, 569:86-103.

Palazón et al., "Agonist anti-CD137 mAb act on tumor endothelial cells to enhance recruitment of activated T lymphocytes," Cancer research, Feb. 1, 2011, 71(3):801-811.

PCT International Search Report and Written Opinion in International Appln. PCT/CN2019/105315, dated Jan. 3, 2020, 12 pages.

Ponomarenko et al., "Antibody-protein interactions: benchmark datasets and prediction tools evaluation," BMC structural biology, Dec. 2007, 7(1):1-9.

Riechmann et al., "Reshaping human antibodies for therapy," Nature, Mar. 1988, 332(6162):323-327.

Rosenfeld et al., "Adenovirus-mediated transfer of a recombinant alpha 1-antitrypsin gene to the lung epithelium in vivo," Science, Apr. 19, 1991, 252(5004):431-434.

Silva et al., "The S228P mutation prevents in vivo and in vitro IgG4 Fab-arm exchange as demonstrated using a combination of novel quantitative immunoassays and physiological matrix preparation," Journal of Biological Chemistry, Feb. 27, 2015, 290(9):5462-5469.

Sims et al., "A humanized CD18 antibody can block function without cell destruction," The Journal of Immunology, Aug. 15, 1993, 151(4):2296-2308.

Ulmer et al., "Heterologous protection against influenza by injection of DNA encoding a viral protein," Science, Mar. 19, 1993, 259(5102):1745-1749.

Verhoeyen et al., Reshaping human antibodies: grafting an antilysozyme activity. Science. Mar. 25, 1988;239(4847):1534-1536.

Vidarsson et al., "IgG subclasses and allotypes: from structure to effector functions," Frontiers in immunology, Oct. 20, 2014, 5(520):1-17.

Wen et al., "4-1BB ligand-mediated costimulation of human T cells induces CD4 and CD8 T cell expansion, cytokine production, and the development of cytolytic effector function," The Journal of Immunology May 15, 2002, 168(10) : 4897-4906.

Wolff et al., "Monoclonal antibody homodimers: enhanced antitumor activity in nude mice," Cancer Research, Jun. 1, 1993, 53(11):2560-2565.

Wu et al., "An analysis of the sequences of the variable regions of Bence Jones proteins and myeloma light chains and their implications for antibody complementarity," Journal of Experimental Medicine, Aug. 1, 1970, 132(2):211-250.

(56) References Cited

OTHER PUBLICATIONS

Zhao et al., "Enhancing tumor targeting and apoptosis using noncovalent antibody homodimers," Journal of Immunotherapy, Sep. 1, 2002, 25(5):396-404.
PCT International Preliminary Report on Patentability in International Appln. PCT/CN2019/105315, dated Mar. 25, 2021, 8 pages.

* cited by examiner

FIG. 52

Kabat CDR

| Ab | VH CDR1 | SEQ ID: | VH CDR2 | SEQ ID: | VH CDR3 | SEQ ID: | VL CDR1 | SEQ ID: | VL CDR2 | SEQ ID: | VL CDR3 | SEQ ID: |
|---|---|---|---|---|---|---|---|---|---|---|---|---|
| 16-1C4 or humanized 16-1C4 | SSYIN | 1 | WIFAGTGGTYYN QKFTG | 2 | HSPRATLFDF | 3 | RASSSVNHMH | 4 | ATSNLAS | 5 | QQWSSNPYT | 6 |
| 29-6A5 or humanized 29-6A5 | SYWIN | 7 | NIYPSDSYTNYN QKFKD | 8 | TWEFYYDSVFDY | 9 | KASQDINSYLS | 10 | RANRLVD | 11 | LQYDELPPT | 12 |
| 30-5F9 or humanized 30-5F9 | TYDIS | 13 | VIWTGGGTNYNS SFMS | 14 | VDY | 15 | RSSQSLVHSNGNTYLH | 16 | KVSNRFS | 17 | SQNTHVPWT | 18 |
| 45-2B3 or humanized 45-2B3 | TSWMN | 19 | RIYPGDGDTDYN GRFKG | 20 | LDGYYEVFYFDY | 21 | KSSQSLLYSNGKTYLN | 22 | LVSKLDS | 23 | FQGTHFPWT | 24 |
| 45-4B9 or humanized 45-4B9 | TYVMY | 25 | YINPYNDDIRYNE KFKG | 26 | QGGDY | 27 | RASKNINKYLA | 28 | SGSTLQS | 29 | QQYNEYPLT | 30 |
| 45-7E9 or humanized 45-7E9 | TYGVH | 31 | VIWSDGNTDYN DAFIS | 32 | NSITSVSFDC | 33 | KASQNVGTTVA | 34 | SASYRYS | 35 | QQYNSYPLT | 36 |
| 45-7G9 or humanized 45-7G9 | NYWIH | 37 | NIYPASDYTNYDE KFKN | 38 | GYFGSLDY | 39 | RASQPIGTGIH | 40 | SASESIS | 41 | QQSYSWPTT | 42 |
| 45-8E11 or humanized 45-8E11 | SNWMH | 43 | VIYPGNSDTSYN QKFKG | 44 | GITTAPEY | 45 | KASENVGIYVS | 46 | GASNRYT | 47 | GHTYNYPFT | 48 |

FIG. 52 (CONTINUED)

| | | | | | | | | | | |
|---|---|---|---|---|---|---|---|---|---|---|
| 45-8E2 or humanized 45-8E2 | RYWMS | 49 | EIHPDSSAINYTPSLKD | 50 | SYYGRVFDY | 51 | RASQSISDYLH | 52 | YASQSIS | 53 | QDGHSFPPT | 54 |
| 45-8F1 or humanized 45-8F1 | SYWMH | 55 | VIYPGNSDTSYNQKFKG | 56 | GITTAPDY | 57 | KASENVGIHVS | 58 | GASSGYN | 59 | GQTYSYPFT | 60 |
| 54-8B11 or humanized 54-8B11 | NYGMN | 61 | WINTYTGEPTYADDFKG | 62 | REYYPWVFVY | 63 | SASSSVSYMH | 64 | DTSKLAS | 65 | FQGSGYPLT | 66 |
| 55-8F6 or humanized 55-8F6 | SYWIN | 67 | NIYPSDSYTNYNQKFKD | 68 | FHYGSSPFDN | 69 | RASQDISHYLN | 70 | YTSRLHS | 71 | QQGHTLPRT | 72 |
| 56-2A6 or humanized 56-2A6 | NYGMN | 73 | WINTYTGEPTYADDFKG | 74 | RDYLGAMDY | 75 | RASSSVSSSYLH | 76 | STSNLAS | 77 | QQYSAYLYT | 78 |
| 59-5E4 or humanized 59-5E4 | TYWIN | 79 | NIYPSDSYTNYNQKFKD | 80 | EAGDGTHYYAIDY | 81 | KASENVGTYVS | 82 | GASNRYP | 83 | GQGYSYLRT | 84 |
| 61-6A7 or humanized 61-6A7 | DYYMH | 85 | WIDPENGNTIYDPKFQD | 86 | GLPWYFDY | 87 | SASSSVSDMN | 88 | LTSNLSS | 89 | QQWSGNPLT | 90 |
| 69-3C2 or humanized 69-3C2 | SFGMH | 91 | YISSGSSAIYYADTVKG | 92 | DWVDY | 93 | RASENIYSNLV | 94 | TATKLTN | 95 | QHFWDTPYT | 96 |
| 70-3F9 or humanized 70-3F9 | SYWIN | 97 | NIFPSDSYTNYNQKFKD | 98 | FGSSGYPDYYTMEY | 99 | RASGNIDNYLA | 100 | NAKTLAE | 101 | QQYWTIPYT | 102 |
| 70-6F10 or humanized 70-6F10 | NSWMN | 103 | RIVPGDGDTDYNGKFKG | 104 | LDGNYYYWYFDV | 105 | KSSQSLLDSDGKTYLN | 106 | LVSKLDS | 107 | WQGTHFPQT | 108 |

FIG. 53
Chothia CDR

| Ab | VH CDR1 | SEQ ID: | VH CDR2 | SEQ ID: | VH CDR3 | SEQ ID: | VL CDR1 | SEQ ID: | VL CDR2 | SEQ ID: | VL CDR3 | SEQ ID: |
|---|---|---|---|---|---|---|---|---|---|---|---|---|
| 16-1C4 or humanized 16-1C4 | GFTFS SSYIN | 109 | FAGTGG | 110 | HSPRATLFDF | 111 | RASSSVNHMH | 112 | ATSNLAS | 113 | QQWSSNPYT | 114 |
| 29-6A5 or humanized 29-6A5 | GYTFS SYWIN | 115 | YPSDSY | 116 | TWEFYDSVFDY | 117 | KASQDINSYLS | 118 | RANRLVD | 119 | LQYDELPPT | 120 |
| 30-5F9 or humanized 30-5F9 | GFSLT TYDIS | 121 | WTGGG | 122 | VDY | 123 | RSSQSLVHSNGNTYLH | 124 | KVSNRFS | 125 | SQNTHVPWT | 126 |
| 45-2B3 or humanized 45-2B3 | GYAFS TSWMN | 127 | YPGDGD | 128 | LDGYYEVFYFDY | 129 | KSSQSLLYSNGKTYLN | 130 | LVSKLDS | 131 | FQGTHFPWT | 132 |
| 45-4B9 or humanized 45-4B9 | GYTFT TVMY | 133 | NPYNDD | 134 | QGGDY | 135 | RASKNINKYLA | 136 | SGSTLQS | 137 | QQYNEYPLT | 138 |
| 45-7E9 or humanized 45-7E9 | GFSLT TYGVH | 139 | WSDGN | 140 | NSITSVSFDC | 141 | KASQNVGTTVA | 142 | SASYRYS | 143 | QQYNSYPLT | 144 |
| 45-7G9 or humanized 45-7G9 | GYTFS NYWIH | 145 | YPASDY | 146 | GYFGSLDY | 147 | RASQPIGTGIH | 148 | SASESIS | 149 | QQSYSWPTT | 150 |
| 45-8E11 or humanized 45-8E11 | GYSFT SNWMH | 151 | YPGNSD | 152 | GITTAPEY | 153 | KASENVGIYVS | 154 | GASNRYT | 155 | GHTYNYPFT | 156 |
| 45-8E2 or humanized 45-8E2 | GFDFS RYWMS | 157 | HPDSSA | 158 | SYYGRVFDY | 159 | RASQSISDYLH | 160 | YASQSIS | 161 | QDGHSFPPT | 162 |

FIG. 53 (CONTINUED)

| | | 163 | | 164 | | 165 | | 166 | | 167 | | 168 |
|---|---|---|---|---|---|---|---|---|---|---|---|---|
| 45-8F1 or humanized 45-8F1 | GYSFT SYWM H | | YPGNSD | | GITTAPDY | | KASENVGIHVS | | GASSGYN | | GQTYSYP FT | |
| 54-8B11 or humanized 54-8B11 | KFTFT NYGM N | 169 | NTYTGE | 170 | REYYPWVFV Y | 171 | SASSSVSYMH | 172 | DTSKLAS | 173 | FQGSGYP LT | 174 |
| 55-8F6 or humanized 55-8F6 | GYIFTS YWIN | 175 | YPSDSY | 176 | FHYGSSPFD N | 177 | RASQDISHYLN | 178 | YTSRLHS | 179 | QQGHTL PRT | 180 |
| 56-2A6 or humanized 56-2A6 | GYTFT NYGM N | 181 | NTYTGE | 182 | RDYLGAMD Y | 183 | RASSSVSSSYL H | 184 | STSNLAS | 185 | QQYSAYL YT | 186 |
| 59-5E4 or humanized 59-5E4 | GYTFT TYWIN | 187 | YPSDSY | 188 | EAGDGTHYY AIDY | 189 | KASENVGTYVS | 190 | GASNRYP | 191 | GQGYSYL RT | 192 |
| 61-6A7 or humanized 61-6A7 | GFNIK DYYM H | 193 | DPENGN | 194 | GLPWYFDY | 195 | SASSSVSDMN | 196 | LTSNLSS | 197 | QQWSGN PLT | 198 |
| 69-3C2 or humanized 69-3C2 | GFSFS SFGM H | 199 | SSGSSA | 200 | DWVDY | 201 | RASENIYSNLV | 202 | TATKLTN | 203 | QHFWDT PYT | 204 |
| 70-3F9 or humanized 70-3F9 | GYTFT SYWIN | 205 | FPSDSY | 206 | FGSSGYPDY YTMEY | 207 | RASGNIDNYLA | 208 | NAKTLAE | 209 | QQYWTIP YT | 210 |
| 70-6F10 or humanized 70-6F10 | GYAFN NSW MN | 211 | YPGDGD | 212 | LDGNYYYW YFDV | 213 | KSSQSLLDSDG KTYLN | 214 | LVSKLDS | 215 | WQGTHF PQT | 216 |

| Protein | Amino acid sequence | SEQ ID NO: |
|---|---|---|
| Human 4-1BB (h4-1BB) NP_001552.2 | MGNSCYNIVA TLLLVLNFER TRSLQDPCSN CPAGTFCDNN RNQICSPCPP NSFSSAGGQR TCDICRQCKG VFRTRKECSS TSNAECDCTP GFHCLGAGCS MCEQDCKQGQ ELTKKGCKDC CFGTFNDQKR GICRPWTNCS LDGKSVLVNG TKERDVVCGP SPADLSPGAS SVTPPAPARE PGHSPQIISF FLALTSTALL FLLFFLTLRF SVVKRGRKKL LYIFKQPFMR PVQTTQEEDG CSCRFPEEEE GGCEL | 217 |
| Mouse 4-1BB (m4-1BB) NP_035742.1 | MGNNCYNVVV IVLLLVGCEK VGAVQNSCDN CQPGTFCRKY NPVCKSCPPS TFSSIGGQPN CNICRVCAGY FRFKKFCSST HNAECECIEG FHCLGPQCTR CEKDCRPGQE LTKQGCKTCS LGTFNDQNGT GVCRPWTNCS LDGRSVLKTG TTEKDVVCGP PVVSFSPSTT ISVTPEGGPG GHSLQVLTLF LALTSALLLA LIFITLLFSV LKWIRKKFPH IFKQPFKKTT GAAQEEDACS CRCPQEEEGG GGGYEL | 218 |
| Monkey 4-1BB (rm4-1BB) NP_001253057.1 | MGNSCYNIVA TLLLVLNFER TRSLQDLCSN CPAGTFCDNN RSQICSPCPP NSFSSAGGQR TCDICRQCKG VFRTRKECSS TSNAECDCIS GYHCLGAECS MCEQDCKQGQ ELTKKGCKDC CFGTFNDQKR GICRPWTNCS LDGKSVLVNG TKERDVVCGP SPADLSPGAS SATPPAPARE PGHSPQIIFF LALTSTVVLF LLFFLVLRFS VVKRSRKKLL YIFKQPFMRP VQTTQEEDGC SCRFPEEEEG GCEL | 219 |
| Chimeric 4-1BB (chi4-1BB) (Humanized 4-1BB) | MGNSCYNIVATLLLVLNFERTRSLQDPCSNCPAGTFCDNNRNQICSPCPPNSFSSAGGQRTCDICRQCKGVF RTRKECSSTSNAECDCTPGFHCLGAGCSMCEQDCKQGQELTKKGCKDCCFGTFNDQKRGICRPWTNCSLD GKSVLVNGTKERDVVCGPSPADLSPGASSVTPPAPAREPGHSLQVTLFLALTSALLLALIFITLLFSVLKWIRK KFPHIFKQPFKKTTGAAQEEDACSCRCPQEEEGGGGGYEL | 220 |

| Humanized antibody variable domains | Description | AMINO ACID SEQUENCE | SEQ ID NO: |
|---|---|---|---|
| 1C4 Humanized heavy chain variable domain (H1) | HuVhv1: humanization percentage 83.7%; top hit to human and Macaca fascicularis | QVQMVQSGAEVKKPGASVKLSCKASGFTFSSSYINWLRQAPGQRLE WMGWIFAGTGGTTYNQKFTGRVTITRDTSASTAYMELSSLRSEDTA IYYCARHSPRATLFDFWGQGTTLTVSS | 221 |
| 1C4 Humanized heavy chain variable domain (H2) | HuVhv2: humanization percentage 80.6%; top hit to human and Macaca fascicularis | QVQMVQSGAEVKKPGASVKLSCKASGFTFSSSYINWLRQAPGQSLE WIGWIFAGTGGTTYNQKFTGRVQITRDTSASTAYMELSLRSEDTAI YYCARHSPRATLFDFWGQGTTLTVSS | 222 |
| 1C4 Humanized heavy chain variable domain (H3) | HuVhv3: humanization percentage 79.6%; top hit to human and Macaca fascicularis | QVQMVQSGAEVKKPGASVKLSCKASGFTFSSSYINWLRQAPGQSLE WIGWIFAGTGGTTYNQKFTGRAQITRDTSASTAYMELSSLRSEDTAI YYCARHSPRATLFDFWGQGTTLTVSS | 223 |
| 1C4 Humanized heavy chain variable domain (H4) | HuVhv4: humanization percentage 74.5%; top hit to human and Macaca fascicularis | QGQMVQSGAEVKKPGASVKLSCKTSGFTFSSSYINWLRQAPGQSLE WIAWIFAGTGGTTYNQKFTGRAQLTVDTSASTAYMELSSLRSEDTAI YYCARHSPRATLFDFWGQGTTLTVSS | 224 |
| 1C4 Humanized light chain variable domain (K1) | HuVlv1: humanization percentage 84.2%; top hit to human and Macaca fascicularis | EIVLTQSPATLSLSPGERATLSCRASSSVNHMHWYQQKPGQAPRALI YATSNLASGIPARFSGSGSGTSFTLTISSLEPEDFAVYYCQQWSSNPY TFGGGTKLEIK | 225 |
| 1C4 Humanized light chain variable domain (K2) | HuVlv2: humanization percentage 83.2%; top hit to human and Macaca fascicularis | EIVLTQSPATLSLSPGERATLSCRASSSVNHMHWYQQKPGQAPRALI YATSNLASGIPARFSGSGSGTSFTLTISSLEPEDFATYYCQQWSSNPYT FGGGTKLEIK | 226 |
| 1C4 Humanized light chain variable domain (K3) | HuVlv3: humanization percentage 78.9%; Non top hit to human and Macaca fascicularis | EIVLTQSPATLSLSPGERATMSCRASSSVNHMHWYQQKPGFSPRA WIYATSNLASGIPARFSGSGSGTSFTLTISSLEPEDFATYYCQQWSSN PYTFGGGTKLEIK | 227 |
| 1C4 Humanized light chain variable domain (K4) | HuVlv3: humanization percentage 73.7%; Non top hit to human and Macaca fascicularis | EIVLTQSPATLSASPGERVTMSCRASSSVNHMHWYQQRPGFSPRA WIYATSNLASGIPARFSGSGSGTSYSLTISSLEPEDFATYYCQQWSSN PYTFGGGTKLEIK | 228 |

FIG. 56

| Humanized antibody variable domains | Description | AMINO ACID SEQUENCE | SEQ ID NO: |
|---|---|---|---|
| 6A5 Humanized heavy chain variable domain (H1) | HuVHv1: humanization percentage 82.7%; top hit to human and *Macaca fascicularis* | QVQLVQSGAEVKKPGSSVKLSCKASGYTFSSYWINWVRQAPGQGL EWMMGNIYPSDSYTNYNQKFKDRVTLTVDKSTSTAYMELSSLRSEDT AVYYCTRTWEFYYDSVFDYWGQGTLVTVSS | 229 |
| 6A5 Humanized heavy chain variable domain (H2) | HuVHv2: humanization percentage 80.6%; Non top hit to human and *Macaca fascicularis* | QVQLVQSGAEVKKPGSSVKLSCKASGYTFSSYWINWVRQAPGQGL EWIGNIYPSDSYTNYNQKFKDRATLTVDKSTSTAYMELSSLRSEDTA VYYCTRTWEFYYDSVFDYWGQGTLVTVSS | 230 |
| 6A5 Humanized heavy chain variable domain (H3) | HuVHv3: humanization percentage 78.6%; Non top hit to human and *Macaca fascicularis* | QVQLVQSGAEVKKPGSSVKLSCKASGYTFSSYWINWVKQAPGQGL EWIGNIYPSDSYTNYNQKFKDKATLTVDKSTSTAYMELSSLRSEDTA VYYCTRTWEFYYDSVFDYWGQGTTLTVSS | 231 |
| 6A5 Humanized light chain variable domain (K1) | HuVLv1: humanization percentage 84.2%; Non top hit to human and *Macaca fascicularis* | DIqMTQSPSSlsASLGERVTITCKASQDINSYLSWyQQKPGKaPKlLIY RANRLVDGVPSRFSGSGSGQDFTLTISSLqpEDiatYYCLQYDELPPTF GGGTKvEIK | 232 |
| 6A5 Humanized light chain variable domain (K2) | HuVLv2: humanization percentage 83.2%; Non top hit to human and *Macaca fascicularis* | DIQMTQSPSSLSASLGERVTITCKASQDINSYLSWYQQKPGKAPKTLI YRANRLVDGVPSRFSGSGSGQDFTLTISSLQPEDIATYYCLQYDELPP TFGGGTKVEIK | 233 |
| 6A5 Humanized light chain variable domain (K3) | HuVLv3: humanization percentage 82.1%; Non top hit to human and *Macaca fascicularis* | DIQMTQSPSSLSASLGERVTITCKASQDINSYLSWFQQKPGKAPKTLI YRANRLVDGVPSRFSGSGSGQDFTLTISSLQPEDIATYYCLQYDELPP TFGGGTKVEIK | 234 |
| 6A5 Humanized light chain variable domain (K4) | HuVLv3: humanization percentage 81.1%; Non top hit to human and *Macaca fascicularis* | DIQMTQSPSSLSASLGERVTITCKASQDINSYLSWFQQKPGKAPKTLI YRANRLVDGVPSRFSGSGSGQDYTLTISSLQPEDIATYYCLQYDELPP TFGGGTKLEIK | 235 |

FIG. 57

| Humanized antibody variable domains | Description | AMINO ACID SEQUENCE | SEQ ID NO: |
|---|---|---|---|
| 5F9 Humanized heavy chain variable domain (H1) | HuVHv1: humanization percentage 82.5%; top hit to human and *Macaca fascicularis* | QVQLQESGPGLVKPSETLSLTCTVSGFSLTTYDISWVRQPPGKGLEW IGVIWTGGGTNYNSSFMSRVTISKDTSKNQVSLKLSSVTAADTAVYY CERVDYWGQGTTVTVSS | 236 |
| 5F9 Humanized heavy chain variable domain (H2) | HuVHv2: humanization percentage 79.4%; Non top hit to human and *Macaca fascicularis* | QVQLKESGPGLVKPSETLSLTCTVSGFSLTTYDISWVRQPPGKGLEW LGVIWTGGGTNYNSSFMSRVTISKDTSKNQVSLKLSSVTAADTAIYY CERVDYWGQGTTVTVSS | 237 |
| 5F9 Humanized heavy chain variable domain (H3) | HuVHv3: humanization percentage 77.3%; top hit to human and *Macaca fascicularis* | QVQLKESGPGLVKPSETLSITCTVSGFSLTTYDISWVRQPPGKGLEWL GVIWTGGGTNYNSSFMSRVTISKDNSKNQVSLKLSSVTAADTAIYC ERVDYWGQGTTLTVSS | 238 |
| 5F9 Humanized light chain variable domain (K1) | HuVLv1: humanization percentage 91%; top hit to human and *Macaca fascicularis* | DVVMTQSPLSLPVTLGQPASISCRSSQSLVHSNGNTYLHWFQQRPG QSPRLLIYKVSNRFSGVPDRFSGSGSGTAFTFKISRVEAEDVGVYYCS QNTHVPWTFGGGTKVEIK | 239 |
| 5F9 Humanized light chain variable domain (K2) | HuVLv2: humanization percentage 90%; top hit to human and *Macaca fascicularis* | DVVMTQSPLSLPVTLGQPASISCRSSQSLVHSNGNTYLHWFQQRPG QSPKLLIYKVSNRFSGVPDRFSGSGSGTAFTFKISRVEAEDVGVYYCS QNTHVPWTFGGGTKVEIK | 240 |
| 5F9 Humanized light chain variable domain (K3) | HuVLv3: humanization percentage 89%; Non top hit to human and *Macaca fascicularis* | DVVMTQSPLSLPVTLGQPASISCRSSQSLVHSNGNTYLHWYQQRPG QSPKLLIYKVSNRFSGVPDRFSGSGSGTAFTFKISRVEAEDVGVYYCS QNTHVPWTFGGGTKLEIK | 241 |
| 5F9 Humanized light chain variable domain (K4) | HuVLv3: humanization percentage 87%; Non top hit to human and *Macaca fascicularis* | DVVMTQSPLSLPVTLGDPASISCRSSQSLVHSNGNTYLHWYLQRPG QSPKLLIYKVSNRFSGVPDRFSGSGSGTAFTFKISRVEAEDVGVYYCS QNTHVPWTFGGGTKLEIK | 242 |

FIG. 58

16-1C4 ("1C4") Heavy chain variable region (SEQ ID NO:243)
QGQMQQSGAELVKPGASVKLSCKTSGFTFSSSYINWLKQKPGQSLEWIAMIFAGTGGTYYNQKFTGKAQLTVDTSSGTAYMQFSSLTTEDSAIYYCAR
HSPRATLFDFWGQGTTLTVSS

16-1C4 ("1C4") Light chain variable region (SEQ ID NO: 244)
QIVLSQSPAILSASPGEKVTMTCRASSSVNHMHWYQQRTGFSPKAWIYATSNLASGVPARFSGSGSGTSYSLTISRVEAEDAATYYCQQWSSNPYTFG
GGTKLEIK

29-6A5 ("6A5") Heavy chain variable region (SEQ ID NO: 245)
QVQLQQPGAELVRPGASVKLSCKASGYTFSSYWINWVKQRPGQGLEWIGNIYPSDSYTNYNQKFKDKATLTVDKSSSTAYMQLSSPTSDDSAVYYCTR
TWEFYYDSVFDYWGQGTTLTVSS

29-6A5 ("6A5") Light chain variable region (SEQ ID NO: 246)
DIKMTQSPSSMYASLGERVTITCKASQDINSYLSWFQQKPGKSPKTLIYRANRLVDGVPSRFSGSGSGQDYSLTISSLEYEDMGIYYCLQYDELPPTF
GGGTKLEIK

30-5F9 ("5F9") Heavy chain variable region (SEQ ID NO: 247)
QVQLKESGPGLVAPSQSLSITCTVSGFSLTTYDISWVRQPPGKGLEWLGVIWTGGGTNYNSSFMSRLSISKDNSKNQVFLKMNSLQVDDTAIYCERV
DYWGQGTTLTVSS

30-5F9 ("5F9") Light chain variable region (SEQ ID NO: 248)
DVVMTQTPLSLPVSLGDQASISCRSSQSLVHSNGNTYLHWYLQKPGQSPKLLIYKVSNRFSGVPDRFSGSGSGTAFTFKISRVEAEDLGVYFCSQNTH
VPWTFGGGTKLEIK

45-2B3 ("2B3") Heavy chain variable region (SEQ ID NO: 249)
QVQLQQSGPELVKPGASVKISCKTSGYAFSTSWMNWVKQRPGQGLEWIGRIYPGDGDTDYNGRFKGKATLTADKSSSTAYLQLSSLTSVDSAVYFCAR
LDGYYEVEYFDYWGQGTTLTVSS

FIG. 58 (CONTINUED)

45-2B3 ("2B3") Light chain variable region (SEQ ID NO: 250)
DVVMTQTPLTLSVTIGQPASISCKSSQSLLYSNGKTYLNWLLQRPGQSPKRLIYLVSKLDSGVPDRFTGSGSGTDFTLKISRVEAEDLGIYYCFQGTH
FPWTFGGGTKLEIK 45-4B9 ("4B9") Heavy chain variable region (SEQ ID NO: 251)
EVQLQQSGPELVKPGASVKMSCKASGYTFTTYVMYWVKQRPGQGLEWIGYINPYNDDIRYNEKFKGKATLTSDRSSSTAYMELSSLTSEDSAVYLCAR
QGGDYWGQGTILTVSS 45-4B9 ("4B9") Light chain variable region (SEQ ID NO: 252)
DVQITQSPSYLAASPGETITVNCRASKNINKYLAWYQEKPGKTNKLLIYSGSTLQSGIPSRFSGSGSGTDFTLTISSLEPEDFAVYHCQQYNEYPLTF
GAGTKLEMK 45-7E9 ("7E9") Heavy chain variable region (SEQ ID NO: 253)
QVQLKQSGPGLVQPSQSLSITCTVSGFSLTTYGVHWVRQPPGKGLEWLGVIWSDGNTDYNDAFISRLSITKDNSTSQVFFKMNGLQADDTAIYYCARN
SITSVSFDCWGQGTTLTVSS 45-7E9 ("7E9") Light chain variable region (SEQ ID NO: 254)
DIVMTQSQKFMSTSVGDRVSVTCKASQNVGTTVAWYQQRPGQSPKALICSASYRYSGVPDRFTGSGSGTDFTLTISNVQSEDLAEYFCQQYNSYPLTF
GSGTKLEIK 45-7G9 ("7G9") Heavy chain variable region (SEQ ID NO: 255)
QVQLQQPGSALVRPGASVKLSCKASGYTFSNYWIHWVKQRHGQGLEWIGNIYPASDYTNYDEKFKNKGTLTVDTSSSTAYMHLSSLTSEDSAVYYCSR
GYFGSLDYWGQGTSVTVSA 45-7G9 ("7G9") Light chain variable region (SEQ ID NO: 256)
DILLTQSPAILSVNPGERVSFSCRASQPIGTGIHWYQQRTNGSPRLLIKSASESISGIPSRFSGSGSGTDFTLTINNVESDDVGDYYCQQSYSWPTTF
GGGTKLKIN

FIG. 58 (CONTINUED)

45-8E11 ("8E11") Heavy chain variable region (SEQ ID NO: 257)
EVQLQQSGTVLARPGASVKMSCKASGYSFTSNWMHWVKQRPGQGLEWIGVIYPGNSDTSYNQKFKGKAKLTAVTSASTAYMELSSLTNEDSAVYYCTR
GITTAPEYWGQGTTLTVSS 45-8E11 ("8E11") Light chain variable region (SEQ ID NO: 258)
NIVMTQSPKSMSMSVGERVTLSCKASENVGIYVSWYQQKPEQSPKLLIYGASNRYTGVPDRFTGSGSATDFTLTISSVQPEDLADYHCGHTYNYPFTF
GSGTKLEIK 45-8E2 ("8E2") Heavy chain variable region (SEQ ID NO: 259)
EVKLLESGGGLVQPGGSLKLSCAASGFDFSRYWMSWVRQAPGKGLEWIGEIHPDSSAINYTPSLKDKFIISRDNAKNTLYLQMSKVRSEDTALYYCAR
SYYGRVFDYWGQGTTLTVSS 45-8E2 ("8E2") Light chain variable region (SEQ ID NO: 260)
DIVMTQSPATLSVTPGDRVSLSCRASQSISDYLHWYQQKSHESPRLLIKYASQSISGIPPRFSGSGSGSDFTLSINSVEPEDVGMYYCQDGHSFPPTF
GAGTKLELK 45-8F1 ("8F1") Heavy chain variable region (SEQ ID NO: 261)
EVQLQQSGTVLARPGASVKMSCKASGYSFTSYWMHWVKQRPGQGLEWIGVIYPGNSDTSYNQKFKGKAKLTAVTSASTAYMDLSSLTNEDSAVYYCTR
GITTAPDYWGQGTTLTVSS 45-8F1 ("8F1") Light chain variable region (SEQ ID NO: 262)
NIVMTQSPKSMSMSVGERVTLSCKASENVGIHVSWYQQKPEQSPKLLIYGASSGYNGVPDRFTGSGSATDFTLTISSVQPEDLADYHCGQTYSYPFTF
GSGTKLEIK 54-8B11 ("8B11") Heavy chain variable region (SEQ ID NO: 263)
QIQLVQSGPELKKPGETVKISCKASKFTFTNYGMNWVKQAPGKALKWMGWINTYTGEPTYADDFKGRFDFSLETSATTAYLQINNLKNEDTATYFCAR
REYYPWVFVYWGQGTLVTVSA 54-8B11 ("8B11") Light chain variable region (SEQ ID NO: 264)

FIG. 58 (CONTINUED)

ENVLTQSPAIMSASPGEKVTMTCSASSSVSYMHWYQQKSSTSPKLMIYDTSKLASGVPGRFSGSGSGNSYSLTISMEAEDVATYYCFQGSGYPLTFGGGTKLEIK

55-8F6 ("8F6") Heavy chain variable region (SEQ ID NO: 265)
QVQLQQPGAELVRPGASVKLSCKASGYIFTSYWINWVKQRPGQGLEWIGNIYPSDSYTNYNQKFKDKATLTVDKSSSTAYMQLSSPTSEDSAVYYCTRFHYGSSPFDNWGQGTTLTVSS

55-8F6 ("8F6") Light chain variable region (SEQ ID NO: 266)
DIQMTQSTSSLSASLGDRVTISCRASQDISHYLNWYQQKPDGTVKLLIYYTSRLHSGVPSRFSGSGSGTDYSLTISNLEQEDFATYFCQQGHTLPRTFGGGTKLEIK

56-2A6 ("2A6") Heavy chain variable region (SEQ ID NO: 267)
QIQLVQSGPELKKPGETVKISCKASGYTFTNYGMNWVKQAPGKGFKWMGWINTYTGEPTYADDFKGRFAFSLEISASTAYLQINNLKNEDTATYFCARRDYLGAMDYWGQGTSVTVSS

56-2A6 ("2A6") Light chain variable region (SEQ ID NO: 268)
ENVLTQSPAIMSASPGEKVTMTCRASSSVSSSYLHWYQQKSGASPKLWIYSTSNLASGVPARFSGSGSGTSYSLTISSVEAEDAATYYCQQYSAYLYTFGGGTKLEIK

59-5E4 ("5E4") Heavy chain variable region (SEQ ID NO: 269)
QVQLQQPGAELVRPGASVKLSCKASGYTFTTYWINWVRQRPGQGLEWIGNIYPSDSYTNYNQKFKDKASLTVDKSSNTAYMQLSSPTSEDSAVYYCAREAGDGTHYYAIDYWGQGTSVTVSS

59-5E4 ("5E4") Light chain variable region (SEQ ID NO: 270)
NIVMTQSPKSMSMSVGERVTLSCKASENVGTYVSWYQQKPEQSPKLLIYGASNRYPGVPDRFTGSGSATDFTLTISSLQAEDLADYHCGQGYSYLRTFGGGTNLEIK

61-6A7 ("6A7") Heavy chain variable region (SEQ ID NO: 271)

FIG. 58 (CONTINUED)

EVQLQQSGAELVRPGALVKLSCKASGFNIKDYYMHWVKRRPEQGLEWIGWIDPENGNTIYDPKFQDKASITADTSSNTAYLQLSSLTSEDTAVYYCAE
GLPWYFDYWGQGTTLTVSS 61-6A7 ("6A7") Light chain variable region (SEQ ID NO: 272)
QIILTQSPALMSASPGEKVTMTCSASSSVSDMNWYQQKPRSSPTPWIYLTSNLSSGVPDRFSGSGSGTSYSLTISSMEAEDAATYYCQQWSGNPLTFG
AGTRLELK 69-3C2 ("3C2") Heavy chain variable region (SEQ ID NO: 273)
DVQLVESGGGLVQPGGSRKLSCAASGFSSFGMHWMRQAPEKGLEWVAYISSGSSAIYYADTVKGRFTISRDNPKNTLFLQMTSLRSEDTAMYYCAR
DMVDYWGQGTTLTVSS 69-3C2 ("3C2") Light chain variable region (SEQ ID NO: 274)
DIQMTQSPASLSVSVGETVTITCRASENIYSNLVWYQQKQGKSPQLLVYTATKLTNGVPSRFSGSGSGTQYSLKINSLQSEDFGTYYCQHFWDTPYTF
GGGTKLEMK 70-3F9 ("3F9") Heavy chain variable region (SEQ ID NO: 275)
QVQLQQPGAELVRPGASVKLSCKASGYTFTSYWINWVKQRPGQGLEWIGNIFPSDSYTNYNQKFKDRAKLTVDKSSSTAYMQLSSPTSEDSAVYYCTR
FGSSGYPDYYTMEYWGQGTSVTVSS 70-3F9 ("3F9") Light chain variable region (SEQ ID NO: 276)
DIQMTQSPASLSASVGETVTITCRASGNIDNYLAWYQQKQGKSPQLLVYNAKTLAEGVPSRFSGSGSGTEYSLKINSLQPEDFGSYHCQQYWTIPYTF
GGGTKLEIK 70-6F10 ("6F10") Heavy chain variable region (SEQ ID NO: 277)
QVQLQQSGPELVKPGASVKISCKASGYAFNNSWMNWVKQRPGQGLEWIGRIYPGDGDTDYNGKFKGKATLTADKSSSTAYMQLSSLTSVDSAVYFCAR
LDGNYYYWYFDVWGAGTTVTVSS 70-6F10 ("6F10") Light chain variable region (SEQ ID NO: 278)
DVVMTQTPLTLSVTIGQPASISCKRSSQSLLDSDGKTYLNWLLQRPGQSPKRLIYLVSKLDSGVPDRFTGSGSGTDFTLKISRVEAEDLGVYYCWQGTH
FPQTFGGGTKLEIK

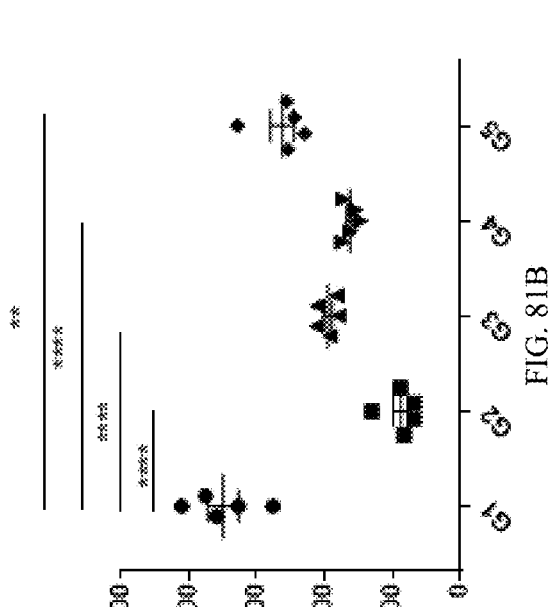
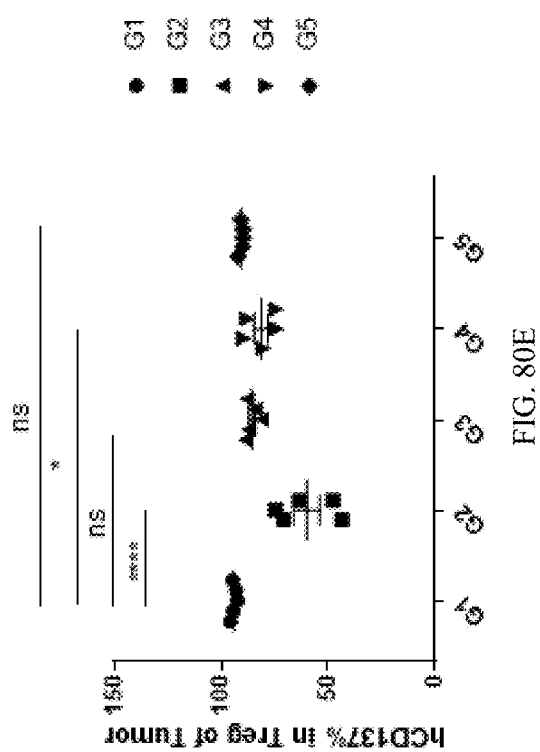
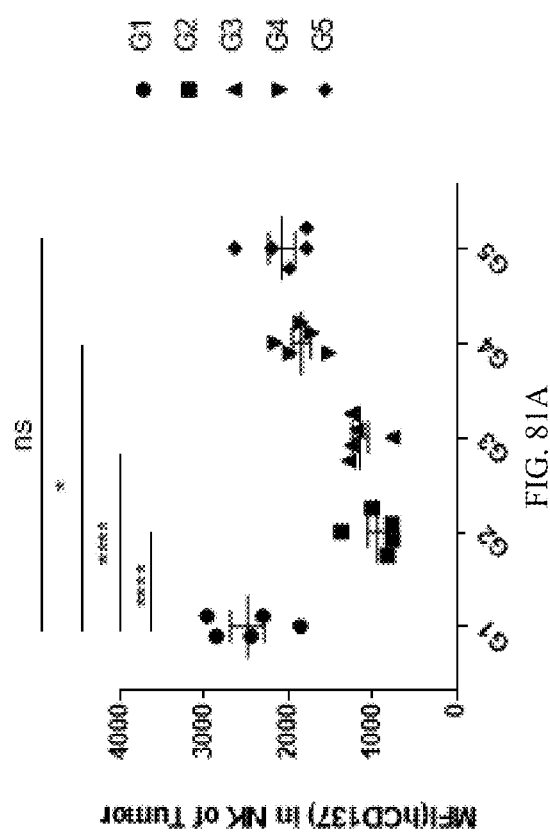
FIG. 80E
FIG. 81A
FIG. 81B

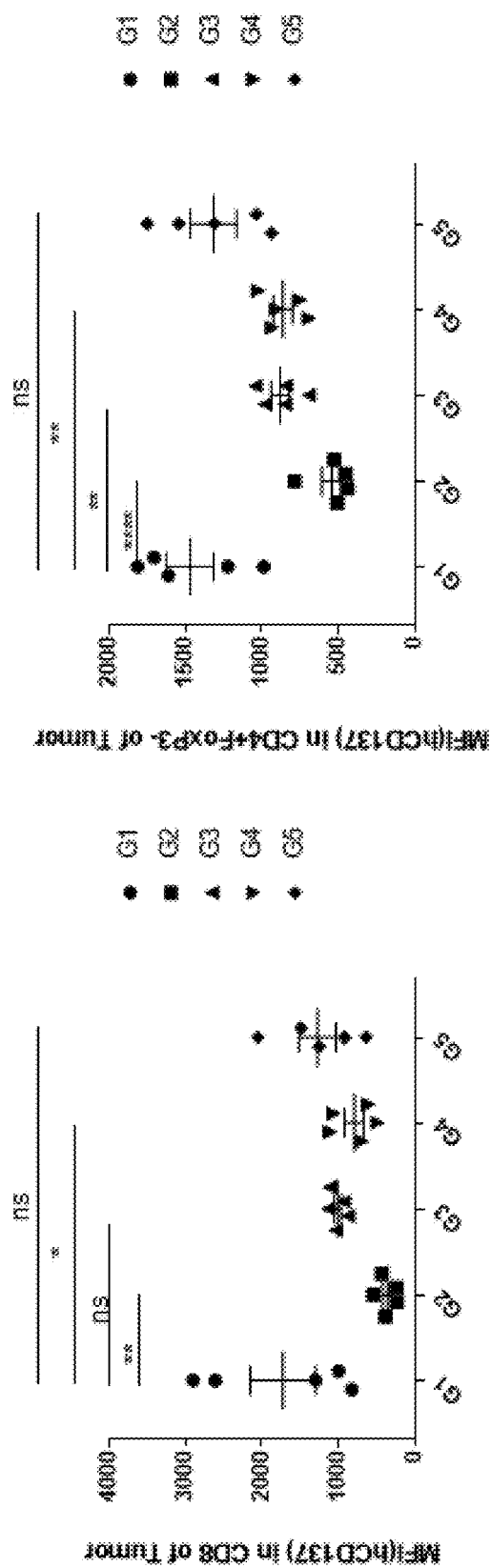
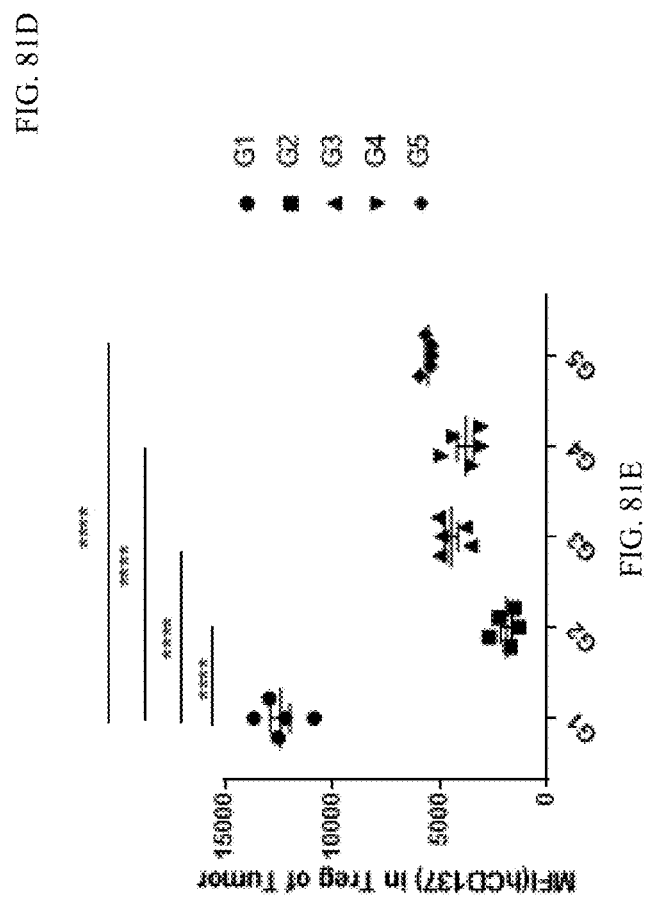
FIG. 81C
FIG. 81D
FIG. 81E

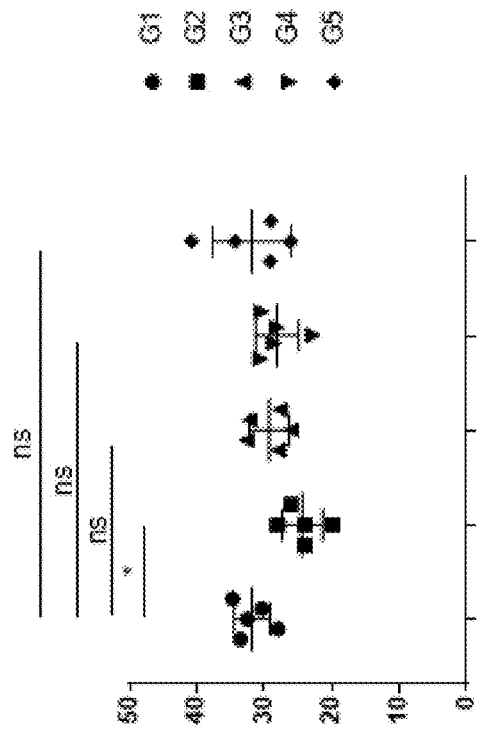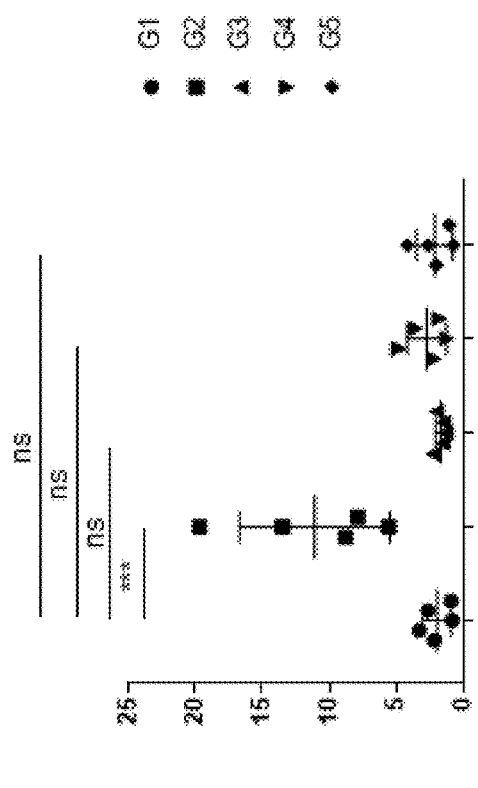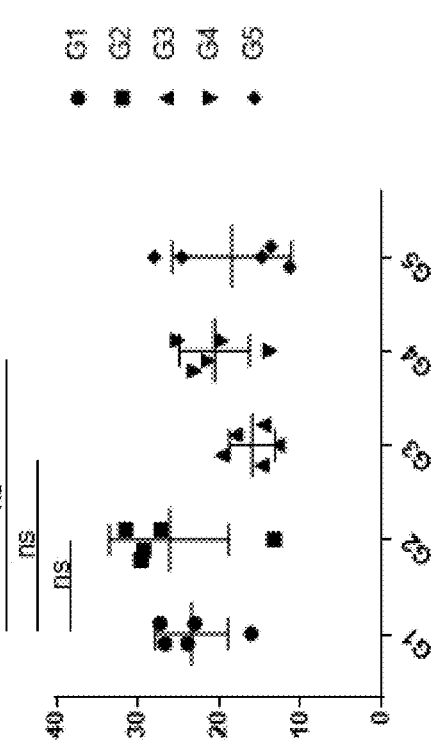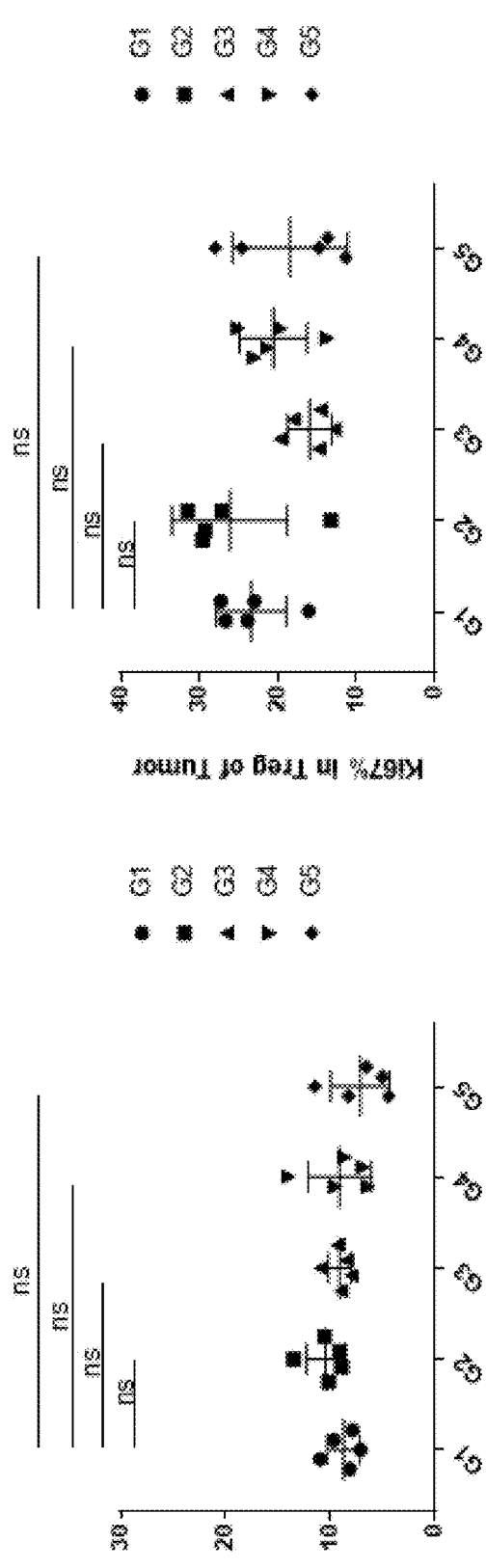
FIG. 82A
FIG. 82B
FIG. 82C
FIG. 82D

ANTI-TNFRSF9 ANTIBODIES AND USES THEREOF

CLAIM OF PRIORITY

This application is a continuation of International Application No. PCT/CN2019/105315, filed on Sep. 11, 2019, which claims the benefit of International Application No. PCT/CN2018/105162, filed on Sep. 12, 2018 under 35 U.S.C. § 365(b). The entire contents of the foregoing applications are incorporated herein by reference.

TECHNICAL FIELD

This disclosure relates to anti-TNFRSF9 (tumor necrosis factor receptor superfamily member 9) antibodies, antigen-binding fragments, and the uses thereof.

BACKGROUND

Cancer is currently one of the diseases that have the highest human mortality. According to the World Health Organization statistical data, in 2012, the number of global cancer incidence and death cases reached 14 million and 8.2 million, respectively. In China, the newly diagnosed cancer cases are 3.07 million, and the death toll is 2.2 million.

Recent clinical and commercial success of anticancer antibodies has created great interest in antibody-based therapeutics. There is a need to develop anti-cancer antibodies for use in various antibody-based therapeutics to treat cancers.

SUMMARY

This disclosure relates to anti-TNFRSF9 (tumor necrosis factor receptor superfamily member 9; also known as "4-1BB" or "CD137") antibodies, antigen-binding fragment thereof, and the uses thereof.

In one aspect, the disclosure relates to an antibody or antigen-binding fragment thereof that binds to 4-1BB (TNF Receptor Superfamily Member 9) comprising: a heavy chain variable region (VH) comprising complementarity determining regions (CDRs) 1, 2, and 3, wherein the VH CDR1 region comprises an amino acid sequence that is at least 80%, 85%, 90%, 95%, or 100% identical to a selected VH CDR1 amino acid sequence, the VH CDR2 region comprises an amino acid sequence that is at least 80%, 85%, 90%, 95%, or 100% identical to a selected VH CDR2 amino acid sequence, and the VH CDR3 region comprises an amino acid sequence that is at least 80%, 85%, 90%, 95%, or 100% identical to a selected VH CDR3 amino acid sequence; and a light chain variable region (VL) comprising CDRs 1, 2, and 3, wherein the VL CDR1 region comprises an amino acid sequence that is at least 80%, 85%, 90%, 95%, or 100% identical to a selected VL CDR1 amino acid sequence, the VL CDR2 region comprises an amino acid sequence that is at least 80%, 85%, 90%, 95%, or 100% identical to a selected VL CDR2 amino acid sequence, and the VL CDR3 region comprises an amino acid sequence that is at least 80%, 85%, 90%, 95%, or 100% identical to a selected VL CDR3 amino acid sequence, wherein the selected VH CDRs 1, 2, and 3 amino acid sequences and the selected VL CDRs, 1, 2, and 3 amino acid sequences are one of the following:

(1) the selected VH CDRs 1, 2, 3 amino acid sequences are set forth in SEQ ID NOs: 1, 2, 3, respectively, and the selected VL CDRs 1, 2, 3 amino acid sequences are set forth in SEQ ID NOs: 4, 5, 6, respectively;

(2) the selected VH CDRs 1, 2, 3 amino acid sequences are set forth in SEQ ID NOs: 7, 8, 9, respectively, and the selected VL CDRs 1, 2, 3 amino acid sequences are set forth in SEQ ID NOs: 10, 11, 12, respectively;

(3) the selected VH CDRs 1, 2, 3 amino acid sequences are set forth in SEQ ID NOs: 13, 14, 15, respectively, and the selected VL CDRs 1, 2, 3 amino acid sequences are set forth in SEQ ID NOs: 16, 17, 18, respectively;

(4) the selected VH CDRs 1, 2, 3 amino acid sequences are set forth in SEQ ID NOs: 19, 20, 21, respectively, and the selected VL CDRs 1, 2, 3 amino acid sequences are set forth in SEQ ID NOs: 22, 23, 24, respectively;

(5) the selected VH CDRs 1, 2, 3 amino acid sequences are set forth in SEQ ID NOs: 25, 26, 27, respectively, and the selected VL CDRs 1, 2, 3 amino acid sequences are set forth in SEQ ID NOs: 28, 29, 30, respectively;

(6) the selected VH CDRs 1, 2, 3 amino acid sequences are set forth in SEQ ID NOs: 31, 32, 33, respectively, and the selected VL CDRs 1, 2, 3 amino acid sequences are set forth in SEQ ID NOs: 34, 35, 36, respectively;

(7) the selected VH CDRs 1, 2, 3 amino acid sequences are set forth in SEQ ID NOs: 37, 38, 39, respectively, and the selected VL CDRs 1, 2, 3 amino acid sequences are set forth in SEQ ID NOs: 40, 41, 42, respectively;

(8) the selected VH CDRs 1, 2, 3 amino acid sequences are set forth in SEQ ID NOs: 43, 44, 45, respectively, and the selected VL CDRs 1, 2, 3 amino acid sequences are set forth in SEQ ID NOs: 46, 47, 48, respectively;

(9) the selected VH CDRs 1, 2, 3 amino acid sequences are set forth in SEQ ID NOs: 49, 50, 51, respectively, and the selected VL CDRs 1, 2, 3 amino acid sequences are set forth in SEQ ID NOs: 52, 53, 54, respectively;

(10) the selected VH CDRs 1, 2, 3 amino acid sequences are set forth in SEQ ID NOs: 55, 56, 57, respectively, and the selected VL CDRs 1, 2, 3 amino acid sequences are set forth in SEQ ID NOs: 58, 59, 60, respectively;

(11) the selected VH CDRs 1, 2, 3 amino acid sequences are set forth in SEQ ID NOs: 61, 62, 63, respectively, and the selected VL CDRs 1, 2, 3 amino acid sequences are set forth in SEQ ID NOs: 64, 65, 66, respectively;

(12) the selected VH CDRs 1, 2, 3 amino acid sequences are set forth in SEQ ID NOs: 67, 68, 69, respectively, and the selected VL CDRs 1, 2, 3 amino acid sequences are set forth in SEQ ID NOs: 70, 71, 72, respectively;

(13) the selected VH CDRs 1, 2, 3 amino acid sequences are set forth in SEQ ID NOs: 73, 74, 75, respectively, and the selected VL CDRs 1, 2, 3 amino acid sequences are set forth in SEQ ID NOs: 76, 77, 78, respectively;

(14) the selected VH CDRs 1, 2, 3 amino acid sequences are set forth in SEQ ID NOs: 79, 80, 81, respectively, and the selected VL CDRs 1, 2, 3 amino acid sequences are set forth in SEQ ID NOs: 82, 83, 84, respectively;

(15) the selected VH CDRs 1, 2, 3 amino acid sequences are set forth in SEQ ID NOs: 85, 86, 87, respectively, and the selected VL CDRs 1, 2, 3 amino acid sequences are set forth in SEQ ID NOs: 88, 89, 90, respectively;

(16) the selected VH CDRs 1, 2, 3 amino acid sequences are set forth in SEQ ID NOs: 91, 92, 93, respectively, and the selected VL CDRs 1, 2, 3 amino acid sequences are set forth in SEQ ID NOs: 94, 95, 96, respectively;

(17) the selected VH CDRs 1, 2, 3 amino acid sequences are set forth in SEQ ID NOs: 97, 98, 99, respectively, and the selected VL CDRs 1, 2, 3 amino acid sequences are set forth in SEQ ID NOs: 100, 101, 102, respectively;

(18) the selected VH CDRs 1, 2, 3 amino acid sequences are set forth in SEQ ID NOs: 103, 104, 105, respectively, and the selected VL CDRs 1, 2, 3 amino acid sequences are set forth in SEQ ID NOs: 106, 107, 108, respectively.

In some embodiments, the VH comprises CDRs 1, 2, 3 with the amino acid sequences set forth in SEQ ID NOs: 1, 2, and 3 respectively, and the VL comprises CDRs 1, 2, 3 with the amino acid sequences set forth in SEQ ID NOs: 4, 5, and 6, respectively.

In some embodiments, the VH comprises CDRs 1, 2, 3 with the amino acid sequences set forth in SEQ ID NOs: 7, 8, and 9, respectively, and the VL comprises CDRs 1, 2, 3 with the amino acid sequences set forth in SEQ ID NOs: 10, 11, and 12, respectively.

In some embodiments, the VH comprises CDRs 1, 2, 3 with the amino acid sequences set forth in SEQ ID NOs: 13, 14, and 15, respectively, and the VL comprises CDRs 1, 2, 3 with the amino acid sequences set forth in SEQ ID NOs: 16, 17, and 18, respectively.

In some embodiments, the antibody or antigen-binding fragment specifically binds to human 4-1BB. In some embodiments, the antibody or antigen-binding fragment is a humanized antibody or antigen-binding fragment thereof. In some embodiments, the antibody or antigen-binding fragment is a single-chain variable fragment (scFv).

In one aspect, the disclosure also relates to a nucleic acid comprising a polynucleotide encoding a polypeptide comprising:

(1) an immunoglobulin heavy chain or a fragment thereof comprising a heavy chain variable region (VH) comprising complementarity determining regions (CDRs) 1, 2, and 3 comprising the amino acid sequences set forth in SEQ ID NOs: 1, 2, and 3, respectively, and wherein the VH, when paired with a light chain variable region (VL) comprising the amino acid sequence set forth in SEQ ID NO: 225, 226, 227, 228, or 244 binds to 4-1BB;

(2) an immunoglobulin light chain or a fragment thereof comprising a VL comprising CDRs 1, 2, and 3 comprising the amino acid sequences set forth in SEQ ID NOs: 4, 5, and 6, respectively, and wherein the VL, when paired with a VH comprising the amino acid sequence set forth in SEQ ID NO: 221, 222, 223, 224, or 243 binds to 4-1BB;

(3) an immunoglobulin heavy chain or a fragment thereof comprising a heavy chain variable region (VH) comprising CDRs 1, 2, and 3 comprising the amino acid sequences set forth in SEQ ID NOs: 7, 8, and 9, respectively, and wherein the VH, when paired with a light chain variable region (VL) comprising the amino acid sequence set forth in SEQ ID NO: 232, 233, 234, 235, or 246 binds to 4-1BB;

(4) an immunoglobulin light chain or a fragment thereof comprising a VL comprising CDRs 1, 2, and 3 comprising the amino acid sequences set forth in SEQ ID NOs: 10, 11, and 12, respectively, and wherein the VL, when paired with a VH comprising the amino acid sequence set forth in SEQ ID NO: 229, 230, 231, or 245 binds to 4-1BB;

(5) an immunoglobulin heavy chain or a fragment thereof comprising a heavy chain variable region (VH) comprising CDRs 1, 2, and 3 comprising the amino acid sequences set forth in SEQ ID NOs: 13, 14, and 15, respectively, and wherein the VH, when paired with a light chain variable region (VL) comprising the amino acid sequence set forth in SEQ ID NO: 239, 240, 241, 242, or 248 binds to 4-1BB;

(6) an immunoglobulin light chain or a fragment thereof comprising a VL comprising CDRs 1, 2, and 3 comprising the amino acid sequences set forth in SEQ ID NOs: 16, 17, and 18, respectively, and wherein the VL, when paired with a VH comprising the amino acid sequence set forth in SEQ ID NO: 236, 237, 238, or 247 binds to 4-1BB;

(7) an immunoglobulin heavy chain or a fragment thereof comprising a VH comprising CDRs 1, 2, and 3 comprising the amino acid sequences set forth in SEQ ID NOs: 19, 20, 21, respectively, and wherein the VH, when paired with a VL comprising the amino acid sequence set forth in SEQ ID NO: 250 binds to 4-1BB;

(8) an immunoglobulin light chain or a fragment thereof comprising a VL comprising CDRs 1, 2, and 3 comprising the amino acid sequences set forth in SEQ ID NOs: 22, 23, 24, respectively, and wherein the VL, when paired with a VH comprising the amino acid sequence set forth in SEQ ID NO: 249 binds to 4-1BB;

(9) an immunoglobulin heavy chain or a fragment thereof comprising a VH comprising CDRs 1, 2, and 3 comprising the amino acid sequences set forth in SEQ ID NOs: 25, 26, 27, respectively, and wherein the VH, when paired with a VL comprising the amino acid sequence set forth in SEQ ID NO: 252 binds to 4-1BB;

(10) an immunoglobulin light chain or a fragment thereof comprising a VL comprising CDRs 1, 2, and 3 comprising the amino acid sequences set forth in SEQ ID NOs: 28, 29, 30, respectively, and wherein the VL, when paired with a VH comprising the amino acid sequence set forth in SEQ ID NO: 251 binds to 4-1BB;

(11) an immunoglobulin heavy chain or a fragment thereof comprising a VH comprising CDRs 1, 2, and 3 comprising the amino acid sequences set forth in SEQ ID NOs: 31, 32, 33, respectively, and wherein the VH, when paired with a VL comprising the amino acid sequence set forth in SEQ ID NO: 254 binds to 4-1BB;

(12) an immunoglobulin light chain or a fragment thereof comprising a VL comprising CDRs 1, 2, and 3 comprising the amino acid sequences set forth in SEQ ID NOs: 34, 35, 36, respectively, and wherein the VL, when paired with a VH comprising the amino acid sequence set forth in SEQ ID NO: 253 binds to 4-1BB;

(13) an immunoglobulin heavy chain or a fragment thereof comprising a VH comprising CDRs 1, 2, and 3 comprising the amino acid sequences set forth in SEQ ID NOs: 37, 38, 39, respectively, and wherein the VH, when paired with a VL comprising the amino acid sequence set forth in SEQ ID NO: 256 binds to 4-1BB;

(14) an immunoglobulin light chain or a fragment thereof comprising a VL comprising CDRs 1, 2, and 3 comprising the amino acid sequences set forth in SEQ ID NOs: 40, 41, 42, respectively, and wherein the VL, when paired with a VH comprising the amino acid sequence set forth in SEQ ID NO: 255 binds to 4-1BB;

(15) an immunoglobulin heavy chain or a fragment thereof comprising a VH comprising CDRs 1, 2, and 3 comprising the amino acid sequences set forth in SEQ ID NOs: 43, 44, 45, respectively, and wherein the VH, when paired with a VL comprising the amino acid sequence set forth in SEQ ID NO: 258 binds to 4-1BB;

(16) an immunoglobulin light chain or a fragment thereof comprising a VL comprising CDRs 1, 2, and 3 comprising the amino acid sequences set forth in SEQ ID NOs: 46, 47, 48, respectively, and wherein the VL, when paired with a VH comprising the amino acid sequence set forth in SEQ ID NO: 257 binds to 4-1BB;

(17) an immunoglobulin heavy chain or a fragment thereof comprising a VH comprising CDRs 1, 2, and 3 comprising the amino acid sequences set forth in SEQ ID NOs: 49, 50, 51, respectively, and wherein the VH, when paired with a VL comprising the amino acid sequence set forth in SEQ ID NO: 260 binds to 4-1BB;

(18) an immunoglobulin light chain or a fragment thereof comprising a VL comprising CDRs 1, 2, and 3 comprising the amino acid sequences set forth in SEQ ID NOs: 52, 53, 54, respectively, and wherein the VL, when paired with a VH comprising the amino acid sequence set forth in SEQ ID NO: 259 binds to 4-1BB;

(19) an immunoglobulin heavy chain or a fragment thereof comprising a VH comprising CDRs 1, 2, and 3 comprising the amino acid sequences set forth in SEQ ID NOs: 55, 56, 57, respectively, and wherein the VH, when paired with a VL comprising the amino acid sequence set forth in SEQ ID NO: 262 binds to 4-1BB;

(20) an immunoglobulin light chain or a fragment thereof comprising a VL comprising CDRs 1, 2, and 3 comprising the amino acid sequences set forth in SEQ ID NOs: 58, 59, 60, respectively, and wherein the VL, when paired with a VH comprising the amino acid sequence set forth in SEQ ID NO: 261 binds to 4-1BB;

(21) an immunoglobulin heavy chain or a fragment thereof comprising a VH comprising CDRs 1, 2, and 3 comprising the amino acid sequences set forth in SEQ ID NOs: 61, 62, 63, respectively, and wherein the VH, when paired with a VL comprising the amino acid sequence set forth in SEQ ID NO: 264 binds to 4-1BB;

(22) an immunoglobulin light chain or a fragment thereof comprising a VL comprising CDRs 1, 2, and 3 comprising the amino acid sequences set forth in SEQ ID NOs: 64, 65, 66, respectively, and wherein the VL, when paired with a VH comprising the amino acid sequence set forth in SEQ ID NO: 263 binds to 4-1BB;

(23) an immunoglobulin heavy chain or a fragment thereof comprising a VH comprising CDRs 1, 2, and 3 comprising the amino acid sequences set forth in SEQ ID NOs: 67, 68, 69, respectively, and wherein the VH, when paired with a VL comprising the amino acid sequence set forth in SEQ ID NO: 266 binds to 4-1BB;

(24) an immunoglobulin light chain or a fragment thereof comprising a VL comprising CDRs 1, 2, and 3 comprising the amino acid sequences set forth in SEQ ID NOs: 70, 71, 72, respectively, and wherein the VL, when paired with a VH comprising the amino acid sequence set forth in SEQ ID NO: 265 binds to 4-1BB;

(25) an immunoglobulin heavy chain or a fragment thereof comprising a VH comprising CDRs 1, 2, and 3 comprising the amino acid sequences set forth in SEQ ID NOs: 73, 74, 75, respectively, and wherein the VH, when paired with a VL comprising the amino acid sequence set forth in SEQ ID NO: 268 binds to 4-1BB;

(26) an immunoglobulin light chain or a fragment thereof comprising a VL comprising CDRs 1, 2, and 3 comprising the amino acid sequences set forth in SEQ ID NOs: 76, 77, 78, respectively, and wherein the VL, when paired with a VH comprising the amino acid sequence set forth in SEQ ID NO: 267 binds to 4-1BB;

(27) an immunoglobulin heavy chain or a fragment thereof comprising a VH comprising CDRs 1, 2, and 3 comprising the amino acid sequences set forth in SEQ ID NOs: 79, 80, 81, respectively, and wherein the VH, when paired with a VL comprising the amino acid sequence set forth in SEQ ID NO: 270 binds to 4-1BB;

(28) an immunoglobulin light chain or a fragment thereof comprising a VL comprising CDRs 1, 2, and 3 comprising the amino acid sequences set forth in SEQ ID NOs: 82, 83, 84, respectively, and wherein the VL, when paired with a VH comprising the amino acid sequence set forth in SEQ ID NO: 269 binds to 4-1BB;

(29) an immunoglobulin heavy chain or a fragment thereof comprising a VH comprising CDRs 1, 2, and 3 comprising the amino acid sequences set forth in SEQ ID NOs: 85, 86, 87, respectively, and wherein the VH, when paired with a VL comprising the amino acid sequence set forth in SEQ ID NO: 272 binds to 4-1BB;

(30) an immunoglobulin light chain or a fragment thereof comprising a VL comprising CDRs 1, 2, and 3 comprising the amino acid sequences set forth in SEQ ID NOs: 88, 89, 90, respectively, and wherein the VL, when paired with a VH comprising the amino acid sequence set forth in SEQ ID NO: 271 binds to 4-1BB;

(31) an immunoglobulin heavy chain or a fragment thereof comprising a VH comprising CDRs 1, 2, and 3 comprising the amino acid sequences set forth in SEQ ID NOs: 91, 92, 93, respectively, and wherein the VH, when paired with a VL comprising the amino acid sequence set forth in SEQ ID NO: 274 binds to 4-1BB;

(32) an immunoglobulin light chain or a fragment thereof comprising a VL comprising CDRs 1, 2, and 3 comprising the amino acid sequences set forth in SEQ ID NOs: 94, 95, 96, respectively, and wherein the VL, when paired with a VH comprising the amino acid sequence set forth in SEQ ID NO: 273 binds to 4-1BB;

(33) an immunoglobulin heavy chain or a fragment thereof comprising a VH comprising CDRs 1, 2, and 3 comprising the amino acid sequences set forth in SEQ ID NOs: 97, 98, 99, respectively, and wherein the VH, when paired with a VL comprising the amino acid sequence set forth in SEQ ID NO: 276 binds to 4-1BB;

(34) an immunoglobulin light chain or a fragment thereof comprising a VL comprising CDRs 1, 2, and 3 comprising the amino acid sequences set forth in SEQ ID NOs: 100, 101, 102, respectively, and wherein the VL, when paired with a VH comprising the amino acid sequence set forth in SEQ ID NO: 275 binds to 4-1BB;

(35) an immunoglobulin heavy chain or a fragment thereof comprising a VH comprising CDRs 1, 2, and 3 comprising the amino acid sequences set forth in SEQ ID NOs: 103, 104, 105, respectively, and wherein the VH, when paired with a VL comprising the amino acid sequence set forth in SEQ ID NO: 278 binds to 4-1BB;

(36) an immunoglobulin light chain or a fragment thereof comprising a VL comprising CDRs 1, 2, and 3 comprising the amino acid sequences set forth in SEQ ID NOs: 106, 107, 108, respectively, and wherein the VL, when paired with a VH comprising the amino acid sequence set forth in SEQ ID NO: 277 binds to 4-1BB.

In some embodiments, the nucleic acid comprises a polynucleotide encoding a polypeptide comprising an immunoglobulin heavy chain or a fragment thereof comprising a VH comprising CDRs 1, 2, and 3 comprising the amino acid sequences set forth in SEQ ID NOs: 1, 2, and 3, respectively.

In some embodiments, the nucleic acid comprises a polynucleotide encoding a polypeptide comprising an immunoglobulin light chain or a fragment thereof comprising a VL comprising CDRs 1, 2, and 3 comprising the amino acid sequences set forth in SEQ ID NOs: 4, 5, and 6, respectively.

In some embodiments, the nucleic acid comprises a polynucleotide encoding a polypeptide comprising an immunoglobulin heavy chain or a fragment thereof comprising a VH comprising CDRs 1, 2, and 3 comprising the amino acid sequences set forth in SEQ ID NOs: 7, 8, and 9, respectively.

In some embodiments, the nucleic acid comprises a polynucleotide encoding a polypeptide comprising an immunoglobulin light chain or a fragment thereof comprising a VL comprising CDRs 1, 2, and 3 comprising the amino acid sequences set forth in SEQ ID NOs: 10, 11, and 12, respectively.

In some embodiments, the nucleic acid comprises a polynucleotide encoding a polypeptide comprising an immunoglobulin heavy chain or a fragment thereof comprising a VH comprising CDRs 1, 2, and 3 comprising the amino acid sequences set forth in SEQ ID NOs: 13, 14, and 15, respectively.

In some embodiments, the nucleic acid comprises a polynucleotide encoding a polypeptide comprising an immunoglobulin light chain or a fragment thereof comprising a VL comprising CDRs 1, 2, and 3 comprising the amino acid sequences set forth in SEQ ID NOs: 16, 17, and 18, respectively.

In some embodiments, the VH when paired with a VL specifically binds to human 4-1BB, or the VL when paired with a VH specifically binds to human 4-1BB.

In some embodiments, the immunoglobulin heavy chain or the fragment thereof is a humanized immunoglobulin heavy chain or a fragment thereof, and the immunoglobulin light chain or the fragment thereof is a humanized immunoglobulin light chain or a fragment thereof.

In some embodiments, the nucleic acid encodes a single-chain variable fragment (scFv). In some embodiments, the nucleic acid is cDNA.

In one aspect, the disclosure relates to a vector comprising one or more of the nucleic acids as described herein. In one aspect, the disclosure also relates to a vector comprising two of the nucleic acids as described herein. In some embodiments, the vector encodes the VL region and the VH region that together bind to 4-1BB.

In one aspect, the disclosure relates to a pair of vectors, wherein each vector comprises one of the nucleic acids as described herein, wherein together the pair of vectors encodes the VL region and the VH region that together bind to 4-1BB.

In one aspect, the disclosure relates to a cell comprising the vector or the pair of vectors as described herein. In some embodiments, the cell is a CHO cell.

In one aspect, the disclosure relates to a cell comprising one or more of the nucleic acids as described herein. In one aspect, the disclosure relates to a cell comprising two of the nucleic acids as described herein. In some embodiments, the two nucleic acids together encode the VL region and the VH region that together bind to 4-1BB.

In one aspect, the disclosure relates to a method of producing an antibody or an antigen-binding fragment thereof, the method comprising
(a) culturing the cell as described herein under conditions sufficient for the cell to produce the antibody or the antigen-binding fragment; and
(b) collecting the antibody or the antigen-binding fragment produced by the cell.

In one aspect, the disclosure relates to an antibody or antigen-binding fragment thereof that binds to 4-1BB comprising a heavy chain variable region (VH) comprising an amino acid sequence that is at least 80%, 85%, 90%, 95%, or 100% identical to a selected VH sequence, and a light chain variable region (VL) comprising an amino acid sequence that is at least 80%, 85%, 90%, 95%, or 100% identical to a selected VL sequence, wherein the selected VH sequence and the selected VL sequence are one of the following:

(1) the selected VH sequence is SEQ ID NOs: 221, 222, 223, 224, or 243, and the selected VL sequence is SEQ ID NOs: 225, 226, 227, 228, or 244;
(2) the selected VH sequence is SEQ ID NOs: 229, 230, 231, or 245, and the selected VL sequence is SEQ ID NOs: 232, 233, 234, 235, or 246;
(3) the selected VH sequence is SEQ ID NO: 236, 237, 238, or 247, and the selected VL sequence is SEQ ID NO: 239, 240, 241, 242, or 248;
(4) the selected VH sequence is SEQ ID NO: 249, and the selected VL sequence is SEQ ID NO: 250;
(5) the selected VH sequence is SEQ ID NO: 251, and the selected VL sequence is SEQ ID NO: 252;
(6) the selected VH sequence is SEQ ID NO: 253, and the selected VL sequence is SEQ ID NO: 254;
(7) the selected VH sequence is SEQ ID NO: 255, and the selected VL sequence is SEQ ID NO: 256;
(8) the selected VH sequence is SEQ ID NO: 257, and the selected VL sequence is SEQ ID NO: 258;
(9) the selected VH sequence is SEQ ID NO: 259, and the selected VL sequence is SEQ ID NO: 260;
(10) the selected VH sequence is SEQ ID NO: 261, and the selected VL sequence is SEQ ID NO: 262;
(11) the selected VH sequence is SEQ ID NO: 263, and the selected VL sequence is SEQ ID NO: 264;
(12) the selected VH sequence is SEQ ID NO: 265, and the selected VL sequence is SEQ ID NO: 266;
(13) the selected VH sequence is SEQ ID NO: 267, and the selected VL sequence is SEQ ID NO: 268;
(14) the selected VH sequence is SEQ ID NO: 269, and the selected VL sequence is SEQ ID NO: 270;
(15) the selected VH sequence is SEQ ID NO: 271, and the selected VL sequence is SEQ ID NO: 272;
(16) the selected VH sequence is SEQ ID NO: 273, and the selected VL sequence is SEQ ID NO: 274;
(17) the selected VH sequence is SEQ ID NO: 275, and the selected VL sequence is SEQ ID NO: 276;
(18) the selected VH sequence is SEQ ID NO: 277, and the selected VL sequence is SEQ ID NO: 278.

In some embodiments, the antibody or antigen-binding fragment specifically binds to human 4-1BB.

In some embodiments, the antibody or antigen-binding fragment is a humanized antibody or antigen-binding fragment thereof.

In some embodiments, the antibody or antigen-binding fragment is a single-chain variable fragment (scFv).

In one aspect, the disclosure relates to an antibody-drug conjugate comprising the antibody or antigen-binding fragment thereof as described herein, covalently bound to a therapeutic agent. In some embodiments, the therapeutic agent is a cytotoxic or cytostatic agent.

In one aspect, the disclosure relates to a method of treating a subject having cancer, the method comprising administering a therapeutically effective amount of a composition comprising the antibody or antigen-binding fragment thereof as described herein, or the antibody-drug conjugate as described herein, to the subject.

In some embodiments, the subject has a solid tumor. In some embodiments, the cancer is breast cancer, oropharyngeal cancer, ovarian cancer, B cell lymphoma, or Non-Hodgkin's lymphoma. In some embodiments, the cancer is non-small cell lung cancer (NSCLC), melanoma, B-cell non-Hodgkin lymphoma, colorectal cancer, or multiple myeloma.

In one aspect, the disclosure relates to a method of decreasing the rate of tumor growth, the method comprising administering to a subject in need thereof an effective amount of a composition comprising an antibody or antigen-binding fragment thereof as described herein, or the antibody-drug conjugate as described herein.

In one aspect, the disclosure relates to a method of killing a tumor cell, the method comprising administering to a subject in need thereof an effective amount of a composition comprising the antibody or antigen-binding fragment thereof as described herein, or the antibody-drug conjugate as described herein.

In one aspect, the disclosure relates to a pharmaceutical composition comprising the antibody or antigen-binding fragment thereof as described herein, and a pharmaceutically acceptable carrier.

In one aspect, the disclosure relates to a pharmaceutical composition comprising the antibody drug conjugate as described herein, and a pharmaceutically acceptable carrier.

In some embodiments, the antibody is an IgG1 antibody. In some embodiments, the antibody is a human IgG1 antibody.

In one aspect, the disclosure relates to an IgG1 antibody or antigen-binding fragment thereof that binds to 4-1BB comprising: a heavy chain variable region (VH) comprising complementarity determining regions (CDRs) 1, 2, and 3, wherein the VH CDR1 region comprises an amino acid sequence that is at least 80%, 85%, 90%, 95%, or 100% identical to a selected VH CDR1 amino acid sequence, the VH CDR2 region comprises an amino acid sequence that is at least 80%, 85%, 90%, 95%, or 100% identical to a selected VH CDR2 amino acid sequence, and the VH CDR3 region comprises an amino acid sequence that is at least 80%, 85%, 90%, 95%, or 100% identical to a selected VH CDR3 amino acid sequence; and a light chain variable region (VL) comprising CDRs 1, 2, and 3, wherein the VL CDR1 region comprises an amino acid sequence that is at least 80%, 85%, 90%, 95%, or 100% identical to a selected VL CDR1 amino acid sequence, the VL CDR2 region comprises an amino acid sequence that is at least 80%, 85%, 90%, 95%, or 100% identical to a selected VL CDR2 amino acid sequence, and the VL CDR3 region comprises an amino acid sequence that is at least 80%, 85%, 90%, 95%, or 100% identical to a selected VL CDR3 amino acid sequence, wherein the selected VH CDRs 1, 2, and 3 amino acid sequences and the selected VL CDRs, 1, 2, and 3 amino acid sequences are selected from one of the antibodies as set forth in Table 3. In some embodiments, the antibody is a human IgG1 antibody.

In one aspect, the disclosure relates to an IgG1 antibody or antigen-binding fragment thereof that binds to 4-1BB comprising: a heavy chain variable region (VH) comprising an amino acid sequence that is at least 80%, 85%, 90%, 95%, or 100% identical to a selected VH sequence, and a light chain variable region (VL) comprising an amino acid sequence that is at least 80%, 85%, 90%, 95%, or 100% identical to a selected VL sequence, wherein the selected VH sequence and the selected VL sequence are selected from one of the antibodies as set forth in Table 3. In some embodiments, the antibody is a human IgG1 antibody.

In one aspect, the disclosure relates to a method of treating a subject having cancer, the method comprising administering to the subject a therapeutically effective amount of an anti-4-1BB IgG1 antibody or antigen-binding fragment thereof and a therapeutically effective amount of an anti-PD-1 antibody or antigen-binding fragment thereof.

In some embodiments, the anti-PD-1 antibody is an anti-PD-1 IgG4 antibody. In some embodiments, the anti-PD-1 antibody is pembrolizumab.

In one aspect, the disclosure relates to a method of treating a subject having cancer, the method comprising administering to the subject a therapeutically effective amount of an anti-4-1BB IgG1 antibody or antigen-binding fragment thereof and a therapeutically effective amount of an anti-CTLA4 antibody or antigen-binding fragment thereof.

In some embodiments, the anti-CTLA4 antibody is an anti-CTLA IgG1 antibody or an anti-CTLA IgG2 antibody. In some embodiments, the anti-CTLA4 antibody is ipilimumab or tremelimumab.

As used herein, the term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, and cancer of the small intestine. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knock-out of a tumor suppressor gene, and cancer caused by infections, e.g., viral infections. The term "carcinoma" is art recognized and refers to malignancies of epithelial or endocrine tissues. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. The term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof.

As used herein, the term "antibody" refers to any antigen-binding molecule that contains at least one (e.g., one, two, three, four, five, or six) complementary determining region (CDR) (e.g., any of the three CDRs from an immunoglobulin light chain or any of the three CDRs from an immunoglobulin heavy chain) and is capable of specifically binding to an epitope. Non-limiting examples of antibodies include: monoclonal antibodies, polyclonal antibodies, multi-specific antibodies (e.g., bi-specific antibodies), single-chain antibodies, chimeric antibodies, human antibodies, and humanized antibodies. In some embodiments, an antibody can contain an Fc region of a human antibody. The term antibody also includes derivatives, e.g., bi-specific antibodies, single-chain antibodies, diabodies, linear antibodies, and multi-specific antibodies formed from antibody fragments.

As used herein, the term "antigen-binding fragment" refers to a portion of a full-length antibody, wherein the portion of the antibody is capable of specifically binding to an antigen. In some embodiments, the antigen-binding fragment contains at least one variable domain (e.g., a variable domain of a heavy chain or a variable domain of light chain).

Non-limiting examples of antibody fragments include, e.g., Fab, Fab', F(ab')2, and Fv fragments.

As used herein, the term "human antibody" refers to an antibody that is encoded by an endogenous nucleic acid (e.g., rearranged human immunoglobulin heavy or light chain locus) present in a human. In some embodiments, a human antibody is collected from a human or produced in a human cell culture (e.g., human hybridoma cells). In some embodiments, a human antibody is produced in a non-human cell (e.g., a mouse or hamster cell line). In some embodiments, a human antibody is produced in a bacterial or yeast cell. In some embodiments, a human antibody is produced in a transgenic non-human animal (e.g., a bovine) containing an unrearranged or rearranged human immunoglobulin locus (e.g., heavy or light chain human immunoglobulin locus).

As used herein, the term "chimeric antibody" refers to an antibody that contains a sequence present in at least two different antibodies (e.g., antibodies from two different mammalian species such as a human and a mouse antibody). A non-limiting example of a chimeric antibody is an antibody containing the variable domain sequences (e.g., all or part of a light chain and/or heavy chain variable domain sequence) of a non-human (e.g., mouse) antibody and the constant domains of a human antibody. Additional examples of chimeric antibodies are described herein and are known in the art.

As used herein, the term "humanized antibody" refers to a non-human antibody which contains minimal sequence derived from a non-human (e.g., mouse) immunoglobulin and contains sequences derived from a human immunoglobulin. In non-limiting examples, humanized antibodies are human antibodies (recipient antibody) in which hypervariable (e.g., CDR) region residues of the recipient antibody are replaced by hypervariable (e.g., CDR) region residues from a non-human antibody (e.g., a donor antibody), e.g., a mouse, rat, or rabbit antibody, having the desired specificity, affinity, and capacity. In some embodiments, the Fv framework residues of the human immunoglobulin are replaced by corresponding non-human (e.g., mouse) immunoglobulin residues. In some embodiments, humanized antibodies may contain residues which are not found in the recipient antibody or in the donor antibody. These modifications can be made to further refine antibody performance. In some embodiments, the humanized antibody contains substantially all of at least one, and typically two, variable domains, in which all or substantially all of the hypervariable loops (CDRs) correspond to those of a non-human (e.g., mouse) immunoglobulin and all or substantially all of the framework regions are those of a human immunoglobulin. The humanized antibody can also contain at least a portion of an immunoglobulin constant region (Fc), typically, that of a human immunoglobulin. Humanized antibodies can be produced using molecular biology methods known in the art. Non-limiting examples of methods for generating humanized antibodies are described herein.

As used herein, the term "single-chain antibody" refers to a single polypeptide that contains at least two immunoglobulin variable domains (e.g., a variable domain of a mammalian immunoglobulin heavy chain or light chain) that is capable of specifically binding to an antigen. Non-limiting examples of single-chain antibodies are described herein.

As used herein, the term "multimeric antibody" refers to an antibody that contains four or more (e.g., six, eight, or ten) immunoglobulin variable domains. In some embodiments, the multimeric antibody is able to crosslink one target molecule (e.g., 4-1BB) to at least one second target molecule (e.g., HER2) on the surface of a mammalian cell (e.g., a human T-cell, a human tumor cell).

As used herein, the terms "subject" and "patient" are used interchangeably throughout the specification and describe an animal, human or non-human, to whom treatment according to the methods of the present invention is provided. Veterinary and non-veterinary applications are contemplated by the present invention. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

As used herein, when referring to an antibody, the phrases "specifically binding" and "specifically binds" mean that the antibody interacts with its target molecule (e.g., 4-1BB) preferably to other molecules, because the interaction is dependent upon the presence of a particular structure (i.e., the antigenic determinant or epitope) on the target molecule; in other words, the reagent is recognizing and binding to molecules that include a specific structure rather than to all molecules in general. An antibody that specifically binds to the target molecule may be referred to as a target-specific antibody. For example, an antibody that specifically binds to a 4-1BB molecule may be referred to as a 4-1BB-specific antibody or an anti-4-1BB antibody.

As used herein, the terms "polypeptide," "peptide," and "protein" are used interchangeably to refer to polymers of amino acids of any length of at least two amino acids.

As used herein, the terms "polynucleotide," "nucleic acid molecule," and "nucleic acid sequence" are used interchangeably herein to refer to polymers of nucleotides of any length of at least two nucleotides, and include, without limitation, DNA, RNA, DNA/RNA hybrids, and modifications thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 52 lists CDR sequences of several anti-h4-1BB antibodies and CDR sequences of the humanized anti-h4-1BB antibodies thereof as defined by Kabat numbering.

FIG. 53 lists CDR sequences of several anti-h4-1BB antibodies and CDR sequences of humanized anti-h4-1BB antibodies thereof as defined by Chothia numbering.

FIG. 54 lists amino acid sequences of human 4-1BB ("h4-1BB"), mouse 4-1BB ("m4-1BB"), monkey 4-1BB ("rm4-1BB" or "r4-1BB"), and chimeric 4-1BB ("chi4-1BB" or "c4-1BB").

FIG. 55 lists amino acid sequences of heavy chain variable regions and light chain variable regions of humanized antibodies based on 1C4.

FIG. 56 lists amino acid sequences of heavy chain variable regions and light chain variable regions of humanized antibodies based on 6A5.

FIG. 57 lists amino acid sequences of heavy chain variable regions and light chain variable regions of humanized antibodies based on 5F9.

FIG. 58 lists the amino acid sequence of the heavy chain variable regions and light chain variable regions of several mouse anti-h4-1BB antibodies.

FIG. 80E is a graph showing percentage of hCD137+ cells in Treg cells in tumor sample.

FIG. 81A is a graph showing counts of hCD137+ cells in NK cells in tumor sample.

FIG. 81B is a graph showing counts of hCD137+ cells in CD3+ cells in tumor sample.

FIG. 81C is a graph showing counts of hCD137+ cells in CD8+ cells in tumor sample.

FIG. 81D is a graph showing counts of hCD137+ cells in CD4+FoxP3− cells in tumor sample.

FIG. 81E is a graph showing counts of hCD137+ cells in Treg cells in tumor sample.

FIG. 82A is a graph showing percentage of CD8+/Treg cells in CD3+ cells in tumor sample.

FIG. 82B is a graph showing percentage of Ki67+ cells in CD8+ cells in tumor sample.

FIG. 82C is a graph showing percentage of Ki67+ cells in CD4+FoxP3− cells in tumor sample.

FIG. 82D is a graph showing percentage of Ki67+ cells in Treg cells in tumor sample.

STATEMENT REGARDING SEQUENCE LISTING

Figure 1:
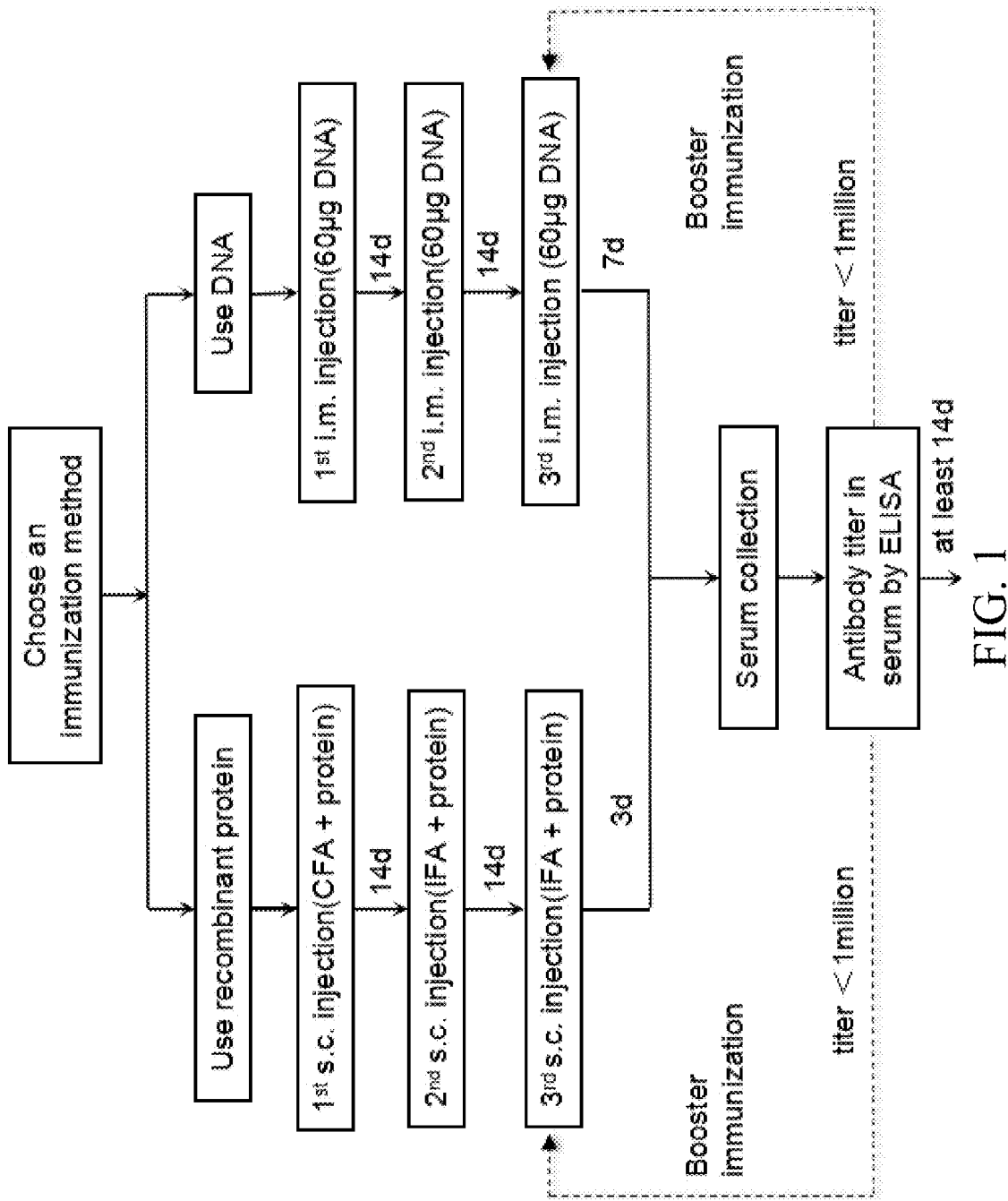
FIG. 1 is a flow chart showing the first part of an exemplary protocol of making anti-h4-1BB antibodies.

The Sequence Listing associated with this application is provided in text form in lieu of a paper copy, and is hereby incorporated by reference into the specification. The name of the text file containing the Sequence Listing is 45124-0021001 SL-updated.txt. The text file is 211,962 bytes, and was created and submitted electronically via EFS-Web on Mar. 25, 2021.

DETAILED DESCRIPTION

The present disclosure provides examples of antibodies, antigen-binding fragments thereof, that bind to TNFRSF9 (tumor necrosis factor receptor superfamily member 9; also known as "4-1BB" or "CD137").

4-1BB and Cancer

The immune system can differentiate between normal cells in the body and those it sees as "foreign," which allows the immune system to attack the foreign cells while leaving the normal cells alone. This mechanism sometimes involves proteins called immune checkpoints. Immune checkpoints are molecules in the immune system that either turn up a signal (co-stimulatory molecules) or turn down a signal.

Checkpoint inhibitors can prevent the immune system from attacking normal tissue and thereby preventing autoimmune diseases. Many tumor cells also express checkpoint inhibitors. These tumor cells escape immune surveillance by co-opting certain immune-checkpoint pathways, particularly in T cells that are specific for tumor antigens (Creelan, Benjamin C. "Update on immune checkpoint inhibitors in lung cancer." Cancer Control 21.1 (2014): 80-89). Because many immune checkpoints are initiated by ligand-receptor interactions, they can be readily blocked by antibodies against the ligands and/or their receptors.

4-1BB ("TNFRSF9" or "CD137") is a member of the tumor necrosis factor (TNF) receptor family. It has three N-glycosylation sites and one potential O-glycosylation site. It is a type I transmembrane protein, and is mainly expressed on the surface of T cells, natural killer (NK) cells, neutrophils, and dendritic cells (DC) cells. The human CD137 gene is located on 1P36 region (chromosome 1) with NCBI gene ID 3604, and encodes 255 amino acids. The human CD137 protein molecule has two forms: membrane-bound and soluble, encoded by the 2.8 kb and 1.4 kb mRNAs, respectively. The soluble form does not have the transmembrane domain. The ligand for CD137 is CD137L (4-1BBL). CD137L belongs to the TNF superfamily and is expressed on the surface of antigen presenting cells, including e.g., dendritic cells, B cells, and macrophages. The synergistic stimulatory signal produced by the interaction of CD137 and its receptor CD137L induces activation and proliferation of T cells and NK cells, and the production of cytokines.

The mouse CD137 gene is located on 4E2 region (chromosome 4) with the NCBI gene ID 21942. Human CD137 protein is about 58% identical to mouse CD137 protein. Human CD137 contains notable differences in its cytoplasmic tail from mouse CD137. In particular, the single tyrosine residue in the cytoplasmic domain of CD137 is found at position 220 of human CD137 and at position 254 of mouse CD137. Human CD137 also diverges from mouse CD137 at the putative Lck binding site, with mouse CD137 expressing the CXCP Lck binding motif, whereas in human CD137 this sequence is altered to CXFP. Both human and mouse CD137 have in common two sites for binding TNFR-associated factor 2, an adaptor protein that is essential for mediating downstream signaling events leading to cytokine (e.g., IL-2) production in response to CD137L signaling.

The abnormal expression of CD137 and its ligand in tumor tissue indicates that CD137 and its ligand may have co-stimulatory signal disruption or inactivation during tumorigenesis. Particularly, CD137 expression in tumor vessel walls is correlated with tumor malignancy, and evidence shows that agonist anti-CD137 antibody can act on tumor endothelial cells to enhance recruitment of activated T lymphocytes, which suggests an additional mechanism of action that can explain the immunotherapeutic effects of agonist CD137 antibodies.

A large number of studies have shown that CD137 is one of the potential targets for antitumor biological therapy. Anti-CD137 antibody can kill tumor cells or inhibit tumor growth probably by inducing activation and proliferation of T cells and NK cells, increasing the production of cytokines, upregulating the immune response, and/or recruiting activated T lymphocytes to the tumor. To date, two antibodies to the CD137 pathway (Urelumab (BMS-663513) from Bristol-Myers Squibb and Utomilumab (PF-05082566) from Pfizer) have been tested in clinical trials for treating melanoma, lymphoma, non-Hodgkin lymphoma and some advanced solid tumor. Some clinical trials already have promising preliminary clinical results. For example, PF-05082566 can reduce 40% of follicular lymphomas (FL) with minimal side effects similar to PD-1 inhibitors; it has been used in combination with other drugs, including e.g., anti-PD-1 antibody, or anti-OX40 antibody. Preliminary experimental evidence also shows that cancer-targeting drugs can increase the expression of CD137 on the surface of NK cells. Thus, if anti-CD137 antibody is administered in combination with cancer-targeting drugs, it can enhance the killing effect of NK cells and improve the therapeutic effect.

A detailed description of CD137 and its function can be found, e.g., in Wen et al., "4-1BB ligand-mediated costimulation of human T cells induces CD4 and CD8 T cell expansion, cytokine production, and the development of cytolytic effector function," The Journal of Immunology 168.10 (2002): 4897-4906; Broll et al., "CD137 expression in tumor vessel walls: high correlation with malignant tumors," American journal of clinical pathology 115.4 (2001): 543-549; and Palazón et al., "Agonist anti-CD137 mAb act on tumor endothelial cells to enhance recruitment of activated T lymphocytes," Cancer research 71.3 (2011): 801-811; Kang, et al., "Anti-CD137 suppresses tumor growth by blocking reverse signaling by CD137 ligand." Cancer research (2017): canres-0610; each of which is incorporated by reference in its entirety.

The present disclosure provides anti-4-1BB antibodies, antigen-binding fragments thereof, and methods of using these anti-4-1BB antibodies and antigen-binding fragments to inhibit tumor growth and to treat cancers.

Antibodies and Antigen Binding Fragments

The present disclosure provides anti-4-1BB antibodies and antigen-binding fragments thereof that comprise complementary determining regions (CDRs), heavy chain variable regions, light chain variable regions, heavy chains, or light chains described herein.

In general, antibodies (also called immunoglobulins) are made up of two classes of polypeptide chains, light chains and heavy chains. A non-limiting antibody of the present disclosure can be an intact, four immunoglobulin chain antibody comprising two heavy chains and two light chains. The heavy chain of the antibody can be of any isotype including IgM, IgG, IgE, IgA, or IgD or subclasses including IgG1, IgG2, IgG2a, IgG2b, IgG3, IgG4, IgE1, IgE2, etc. The light chain can be a kappa light chain or a lambda light chain. An antibody can comprise two identical copies of a light chain and two identical copies of a heavy chain. The heavy chains, which each contain one variable domain (or variable region, VH) and multiple constant domains (or constant regions), bind to one another via disulfide bonding within their constant domains to form the "stem" of the antibody. The light chains, which each contain one variable domain (or variable region, VL) and one constant domain (or constant region), each bind to one heavy chain via disulfide binding. The variable region of each light chain is aligned with the variable region of the heavy chain to which it is bound. The variable regions of both the light chains and heavy chains contain three hypervariable regions sandwiched between more conserved framework regions (FR).

These hypervariable regions, known as the complementary determining regions (CDRs), form loops that comprise the principle antigen binding surface of the antibody. The four framework regions largely adopt a beta-sheet conformation and the CDRs form loops connecting, and in some cases forming part of, the beta-sheet structure. The CDRs in each chain are held in close proximity by the framework regions and, with the CDRs from the other chain, contribute to the formation of the antigen-binding region.

Methods for identifying the CDR regions of an antibody by analyzing the amino acid sequence of the antibody are well known, and a number of definitions of the CDRs are commonly used. The Kabat definition is based on sequence variability, and the Chothia definition is based on the location of the structural loop regions. A more recent definition for CDRs is the IMGT definition. The IMGT definition is based on the IMGT database which curates nucleotide sequence information for immunoglobulins (IG), T-cell receptors (TcR) and Major Histocompatibility Complex (MHC) molecules. It proposes a uniform numbering system for IG and TcR sequences, based on aligning more than 5000 IG and TcR variable region sequences, taking into account and combining the Kabat definition of FRs and CDRs, structural data and Chothia's characterization of the hypervariable loops. The IMGT numbering scheme does not differentiate between various immunoglobulins (i.e., IG or TcR), the chain type (i.e., heavy or light) or the species. These methods for identifying the CDR regions and various definitions are described in, e.g., Martin, "Protein sequence and structure analysis of antibody variable domains," Antibody engineering, Springer Berlin Heidelberg, 2001. 422-439; Abhinandan, et al. "Analysis and improvements to Kabat and structurally correct numbering of antibody variable domains," Molecular immunology 45.14 (2008): 3832-3839; Wu, T. T. and Kabat, E. A. (1970) J. Exp. Med. 132: 211-250; Martin et al., Methods Enzymol. 203:121-53 (1991); Morea et al., Biophys Chem. 68(1-3):9-16 (October 1997); Morea et al., J Mol Biol. 275(2):269-94 (January 1998); Chothia et al., Nature 342(6252):877-83 (December 1989); Ponomarenko and Bourne, BMC Structural Biology 7:64 (2007); Lefranc, et al., "IMGT unique numbering for immunoglobulin and T cell receptor variable domains and Ig superfamily V-like domains." Developmental & Comparative Immunology 27.1 (2003): 55-77; Kunik, et al., "Structural consensus among antibodies defines the antigen binding site." PLoS computational biology 8.2 (2012): e1002388; each of which is incorporated herein by reference in its entirety.

The CDRs are important for recognizing an epitope of an antigen. As used herein, an "epitope" is the smallest portion of a target molecule capable of being specifically bound by the antigen binding domain of an antibody. The minimal size of an epitope may be about three, four, five, six, or seven amino acids, but these amino acids need not be in a consecutive linear sequence of the antigen's primary structure, as the epitope may depend on an antigen's three-dimensional configuration based on the antigen's secondary and tertiary structure.

In some embodiments, the antibody is an intact immunoglobulin molecule (e.g., IgG1, IgG2a, IgG2b, IgG3, IgG4, IgM, IgD, IgE, IgA). The IgG subclasses (IgG1, IgG2, IgG3, and IgG4) are highly conserved, differ in their constant region, particularly in their hinges and upper CH2 domains. The sequences and differences of the IgG subclasses are known in the art, and are described, e.g., in Vidarsson, et al, "IgG subclasses and allotypes: from structure to effector functions." Frontiers in immunology 5 (2014); Irani, et al. "Molecular properties of human IgG subclasses and their implications for designing therapeutic monoclonal antibodies against infectious diseases." Molecular immunology 67.2 (2015): 171-182; Shakib, Farouk, ed. The human IgG subclasses: molecular analysis of structure, function and regulation. Elsevier, 2016; each of which is incorporated herein by reference in its entirety.

The antibody can also be an immunoglobulin molecule that is derived from any species (e.g., human, rodent, mouse, rat, camelid). Antibodies disclosed herein also include, but are not limited to, polyclonal, monoclonal, monospecific, polyspecific antibodies, and chimeric antibodies that include an immunoglobulin binding domain fused to another polypeptide. The term "antigen binding domain" or "antigen binding fragment" is a portion of an antibody that retains specific binding activity of the intact antibody, i.e., any portion of an antibody that is capable of specific binding to an epitope on the intact antibody's target molecule. It includes, e.g., Fab, Fab', F(ab')2, and variants of these fragments. Thus, in some embodiments, an antibody or an antigen binding fragment thereof can be, e.g., a scFv, a Fv, a Fd, a dAb, a bispecific antibody, a bispecific scFv, a diabody, a linear antibody, a single-chain antibody molecule, a multi-specific antibody formed from antibody fragments, and any polypeptide that includes a binding domain which is, or is homologous to, an antibody binding domain. Non-limiting examples of antigen binding domains include, e.g., the heavy chain and/or light chain CDRs of an intact antibody, the heavy and/or light chain variable regions of an intact antibody, full length heavy or light chains of an intact antibody, or an individual CDR from either the heavy chain or the light chain of an intact antibody.

In some embodiments, the antigen binding fragment can form a part of a chimeric antigen receptor (CAR). In some embodiments, the chimeric antigen receptor are fusions of single-chain variable fragments (scFv) as described herein, fused to CD3-zeta transmembrane- and endodomain. In some embodiments, the chimeric antigen receptor also comprises intracellular signaling domains from various costimulatory protein receptors (e.g., CD28, 41BB, ICOS). In some embodiments, the chimeric antigen receptor comprises multiple signaling domains, e.g., CD3z-CD28-41BB or CD3z-

CD28-OX40, to increase potency. Thus, in one aspect, the disclosure further provides cells (e.g., T cells) that express the chimeric antigen receptors as described herein.

In some embodiments, the scFV has one heavy chain variable domain, and one light chain variable domain. In some embodiments, the scFV has two heavy chain variable domains, and two light chain variable domains. In some embodiments, the scFV has two antigen binding regions, and the two antigen binding regions can bind to the respective target antigens.

Anti-4-1BB Antibodies and Antigen-Binding Fragments

The disclosure provides antibodies and antigen-binding fragments thereof that specifically bind to 4-1BB. The antibodies and antigen-binding fragments described herein are capable of binding to 4-1BB and can promote 4-1BB signaling pathway thus increase immune response.

The disclosure provides several anti-4-1BB antibodies, e.g., 16-1C4 ("1C4"), 29-6A5 ("6A5"), 30-5F9 ("5F9"), 45-2B3 ("2B3"), 45-4B9 ("4B9"), 45-7E9 ("7E9"), 45-7G9 ("7G9"), 45-8E11 ("8E11"), 45-8E2 ("8E2"), 45-8F1 ("8F1"), 54-8B11 ("8B11"), 55-8F6 ("8F6"), 56-2A6 ("2A6"), 59-5E4 ("5E4"), 61-6A7 ("6A7"), 69-3C2 ("3C2"), 70-3F9 ("3F9"), and 70-6F10 ("6F10"), including e.g., mouse antibodies, chimeric antibodies thereof, and the humanized antibodies thereof. The CDR sequences (Kabat definition) and the sequences of the heavy chain variable region and light chain variable region of some of the disclosed antibodies are shown in the table below. The CDR sequences (Chothia definition) are provided in FIG. 53.

TABLE 1

| Ab | VH CDR1 | VH CDR2 | VH CDR3 | VL CDR1 | VL CDR2 | VL CDR3 | VH | VL |
|---|---|---|---|---|---|---|---|---|
| 16-1C4 | 1 | 2 | 3 | 4 | 5 | 6 | 243 | 244 |
| 29-6A5 | 7 | 8 | 9 | 10 | 11 | 12 | 245 | 246 |
| 30-5F9 | 13 | 14 | 15 | 16 | 17 | 18 | 247 | 248 |
| 45-2B3 | 19 | 20 | 21 | 22 | 23 | 24 | 249 | 250 |
| 45-4B9 | 25 | 26 | 27 | 28 | 29 | 30 | 251 | 252 |
| 45-7E9 | 31 | 32 | 33 | 34 | 35 | 36 | 253 | 254 |
| 45-7G9 | 37 | 38 | 39 | 40 | 41 | 42 | 255 | 256 |
| 45-8E11 | 43 | 44 | 45 | 46 | 47 | 48 | 257 | 258 |
| 45-8E2 | 49 | 50 | 51 | 52 | 53 | 54 | 259 | 260 |
| 45-8F1 | 55 | 56 | 57 | 58 | 59 | 60 | 261 | 262 |
| 54-8B11 | 61 | 62 | 63 | 64 | 65 | 66 | 263 | 264 |
| 55-8F6 | 67 | 68 | 69 | 70 | 71 | 72 | 265 | 266 |
| 56-2A6 | 73 | 74 | 75 | 76 | 77 | 78 | 267 | 268 |
| 59-5E4 | 79 | 80 | 81 | 82 | 83 | 84 | 269 | 270 |
| 61-6A7 | 85 | 86 | 87 | 88 | 89 | 90 | 271 | 272 |
| 69-3C2 | 91 | 92 | 93 | 94 | 95 | 96 | 273 | 274 |
| 70-3F9 | 97 | 98 | 99 | 100 | 101 | 102 | 275 | 276 |
| 70-6F10 | 103 | 104 | 105 | 106 | 107 | 108 | 277 | 278 |

For example, as shown in the table above, FIG. 52, and FIG. 53, the CDR sequences for 1C4, and 1C4 derived antibodies (e.g., chimeric antibodies or humanized antibodies) include CDRs of the heavy chain variable domain, SEQ ID NOs: 1-3, and CDRs of the light chain variable domain, SEQ ID NOs: 4-6 as defined by Kabat numbering. The CDRs can also be defined by Chothia system. Under the Chothia numbering, the CDR sequences of the heavy chain variable domain are set forth in SEQ ID NOs: 109-111 and CDR sequences of the light chain variable domain are set forth in SEQ ID NOs: 112-114.

Similarly, the CDR sequences for 6A5, and 6A5 derived antibodies include CDRs of the heavy chain variable domain, SEQ ID NOs: 7-9, and CDRs of the light chain variable domain, SEQ ID NOs: 10-12, as defined by Kabat numbering. Under Chothia numbering, the CDR sequences of the heavy chain variable domain are set forth in SEQ ID NOs: 115-117, and CDRs of the light chain variable domain are set forth in SEQ ID NOs: 118-120.

The CDR sequences for 5F9, and 5F9 derived antibodies include CDRs of the heavy chain variable domain, SEQ ID NOs: 13-15, and CDRs of the light chain variable domain, SEQ ID NOs: 16-18, as defined by Kabat numbering. Under Chothia numbering, the CDR sequences of the heavy chain variable domain are set forth in SEQ ID NOs: 121-123, and CDRs of the light chain variable domain are set forth in SEQ ID NOs: 124-126.

Similarly, the CDR sequences (Kabat) and the VH and VL sequences for 2B3, 4B9, 7E9, 7G9, 8E11, 8E2, 8F1, 8B11, 8F6, 2A6, 5E4, 6A7, 3C2, 3F9, 6F10, and the antibodies derived from these antibodies are provided in Table 1. The CDR sequence (Chothia) for 2B3, 4B9, 7E9, 7G9, 8E11, 8E2, 8F1, 8B11, 8F6, 2A6, 5E4, 6A7, 3C2, 3F9, 6F10, and the antibodies derived from these antibodies can be found in FIG. 53.

The amino acid sequences for heavy chain variable regions and light variable regions of the humanized antibodies are also provided. As there are different ways to humanize a mouse antibody (e.g., a sequence can be modified with different amino acid substitutions), the heavy chain and the light chain of an antibody can have more than one version of humanized sequences. The amino acid sequences for the heavy chain variable regions of humanized 1C4 antibody are set forth in SEQ ID NOs: 221-224. The amino acid sequences for the light chain variable regions of humanized 1C4 antibody are set forth in SEQ ID NOs: 225-228. Any of these heavy chain variable region sequences (SEQ ID NO: 221-224) can be paired with any of these light chain variable region sequences (SEQ ID NO: 225-228).

Similarly, the amino acid sequences for the heavy chain variable region of humanized 6A5 antibody are set forth in SEQ ID NOs: 229-231. The amino acid sequences for the light chain variable region of humanized 6A5 antibody are set forth in SEQ ID NOs: 232-235. Any of these heavy chain variable region sequences (SEQ ID NO: 229-231) can be paired with any of these light chain variable region sequences (SEQ ID NO: 232-235).

The amino acid sequences for the heavy chain variable region of humanized 5F9 antibody are set forth in SEQ ID NOs: 236-238. The amino acid sequences for the light chain variable region of humanized 6A5 antibody are set forth in SEQ ID NOs: 239-242. Any of these heavy chain variable region sequences (SEQ ID NO: 236-238) can be paired with any of these light chain variable region sequences (SEQ ID NO: 239-242).

As shown in FIGS. 55-57, humanization percentage means the percentage identity of the heavy chain or light chain variable region sequence as compared to human antibody sequences in International Immunogenetics Information System (IMGT) database. The top hit means that the heavy chain or light chain variable region sequence is closer to a particular species than to other species. For example, top hit to human means that the sequence is closer to human than to other species. Top hit to human and *Macaca fascicularis* means that the sequence has the same percentage identity to the human sequence and the *Macaca fascicularis* sequence, and these percentages identities are highest as compared to the sequences of other species. In some embodiments, humanization percentage is greater than 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95%. A detailed description regarding how to determine humanization percentage and how to determine top hits is known in the art, and is described, e.g., in Jones, Tim D., et al. "The INNs and outs of antibody nonproprietary names." MAbs. Vol. 8. No. 1. Taylor & Francis, 2016, which is incorporated herein by reference in its entirety. A high humanization percentage often has various advantages, e.g., more safe and more effective in humans, more likely to be tolerated by a human subject, and/or less likely to have side effects.

The present disclosure also provides chimeric antibodies. These chimeric antibodies have VH and VL from mouse antibodies. However, the constant domains of these chimeric antibodies are from human antibodies (e.g., human IgG1, human IgG2, human IgG3, or human IgG4). These chimeric antibodies are labeled as mHvKv-IgG Some of the chimeric antibodies and humanized antibodies that are described in the present disclosure are shown in the table below.

TABLE 2

| Type | Antibody name | VH SEQ ID NO: | VL SEQ ID NO: | Constant regions |
|---|---|---|---|---|
| Chimeric antibody based on 1C4 | 1C4-mHvKv-IgG | 243 | 244 | Human IgG (e.g., IgG1, IgG2, IgG3, or IgG4) |
| Humanized antibodies based on 1C4 | 1C4-H1K1-IgG | 221 | 225 | Human IgG (e.g., IgG1, IgG2, IgG3, or IgG4) |
| | 1C4-H1K2-IgG | 221 | 226 | Human IgG (e.g., IgG1, IgG2, IgG3, or IgG4) |
| | 1C4-H1K3-IgG | 221 | 227 | Human IgG (e.g., IgG1, IgG2, IgG3, or IgG4) |
| | 1C4-H1K4-IgG | 221 | 228 | Human IgG (e.g., IgG1, IgG2, IgG3, or IgG4) |
| | 1C4-H2K1-IgG | 222 | 225 | Human IgG (e.g., IgG1, IgG2, IgG3, or IgG4) |
| | 1C4-H2K2-IgG | 222 | 226 | Human IgG (e.g., IgG1, IgG2, IgG3, or IgG4) |
| | 1C4-H2K3-IgG | 222 | 227 | Human IgG (e.g., IgG1, IgG2, IgG3, or IgG4) |
| | 1C4-H2K4-IgG | 222 | 228 | Human IgG (e.g., IgG1, IgG2, IgG3, or IgG4) |
| | 1C4-H3K1-IgG | 223 | 225 | Human IgG (e.g., IgG1, IgG2, IgG3, or IgG4) |
| | 1C4-H3K2-IgG | 223 | 226 | Human IgG (e.g., IgG1, IgG2, IgG3, or IgG4) |
| | 1C4-H3K3-IgG | 223 | 227 | Human IgG (e.g., IgG1, IgG2, IgG3, or IgG4) |
| | 1C4-H3K4-IgG | 223 | 228 | Human IgG (e.g., IgG1, IgG2, IgG3, or IgG4) |
| | 1C4-H4K1-IgG | 224 | 225 | Human IgG (e.g., IgG1, IgG2, IgG3, or IgG4) |
| | 1C4-H4K2-IgG | 224 | 226 | Human IgG (e.g., IgG1, IgG2, IgG3, or IgG4) |
| | 1C4-H4K3-IgG | 224 | 227 | Human IgG (e.g., IgG1, IgG2, IgG3, or IgG4) |
| | 1C4-H4K4-IgG | 224 | 228 | Human IgG (e.g., IgG1, IgG2, IgG3, or IgG4) |
| Chimeric antibody based on 6A5 | 6A5-mHvKv-IgG | 245 | 246 | Human IgG (e.g., IgG1, IgG2, IgG3, or IgG4) |
| Humanized antibodies based on 6A5 | 6A5-H1K1-IgG | 229 | 232 | Human IgG (e.g., IgG1, IgG2, IgG3, or IgG4) |
| | 6A5-H1K2-IgG | 229 | 233 | Human IgG (e.g., IgG1, IgG2, IgG3, or IgG4) |
| | 6A5-H1K3-IgG | 229 | 234 | Human IgG (e.g., IgG1, IgG2, IgG3, or IgG4) |
| | 6A5-H1K4-IgG | 229 | 235 | Human IgG (e.g., IgG1, IgG2, IgG3, or IgG4) |
| | 6A5-H2K1-IgG | 230 | 232 | Human IgG (e.g., IgG1, IgG2, IgG3, or IgG4) |
| | 6A5-H2K2-IgG | 230 | 233 | Human IgG (e.g., IgG1, IgG2, IgG3, or IgG4) |
| | 6A5-H2K3-IgG | 230 | 234 | Human IgG (e.g., IgG1, IgG2, IgG3, or IgG4) |
| | 6A5-H2K4-IgG | 230 | 235 | Human IgG (e.g., IgG1, IgG2, IgG3, or IgG4) |
| | 6A5-H3K1-IgG | 231 | 232 | Human IgG (e.g., IgG1, IgG2, IgG3, or IgG4) |
| | 6A5-H3K2-IgG | 231 | 233 | Human IgG (e.g., IgG1, IgG2, IgG3, or IgG4) |
| | 6A5-H3K3-IgG | 231 | 234 | Human IgG (e.g., IgG1, IgG2, IgG3, or IgG4) |
| | 6A5-H3K4-IgG | 231 | 235 | Human IgG (e.g., IgG1, IgG2, IgG3, or IgG4) |
| Chimeric antibody based on 5F9 | 5F9-mHvKv-IgG | 247 | 248 | Human IgG (e.g., IgG1, IgG2, IgG3, or IgG4) |
| Humanized antibodies based on 5F9 | 5F9-H1K1-IgG | 236 | 239 | Human IgG (e.g., IgG1, IgG2, IgG3, or IgG4) |
| | 5F9-H1K2-IgG | 236 | 240 | Human IgG (e.g., IgG1, IgG2, IgG3, or IgG4) |
| | 5F9-H1K3-IgG | 236 | 241 | Human IgG (e.g., IgG1, IgG2, IgG3, or IgG4) |
| | 5F9-H1K4-IgG | 236 | 242 | Human IgG (e.g., IgG1, IgG2, IgG3, or IgG4) |
| | 5F9-H2K1-IgG | 237 | 239 | Human IgG (e.g., IgG1, IgG2, IgG3, or IgG4) |
| | 5F9-H2K2-IgG | 237 | 240 | Human IgG (e.g., IgG1, IgG2, IgG3, or IgG4) |
| | 5F9-H2K3-IgG | 237 | 241 | Human IgG (e.g., IgG1, IgG2, IgG3, or IgG4) |
| | 5F9-H2K4-IgG | 237 | 242 | Human IgG (e.g., IgG1, IgG2, IgG3, or IgG4) |
| | 5F9-H3K1-IgG | 238 | 239 | Human IgG (e.g., IgG1, IgG2, IgG3, or IgG4) |
| | 5F9-H3K2-IgG | 238 | 240 | Human IgG (e.g., IgG1, IgG2, IgG3, or IgG4) |
| | 5F9-H3K3-IgG | 238 | 241 | Human IgG (e.g., IgG1, IgG2, IgG3, or IgG4) |
| | 5F9-H3K4-IgG | 238 | 242 | Human IgG (e.g., IgG1, IgG2, IgG3, or IgG4) |

Furthermore, in some embodiments, the antibodies or antigen-binding fragments thereof described herein can also contain one, two, or three heavy chain variable region CDRs selected from the group of SEQ ID NOs: 1-3, SEQ ID NOs: 7-9, SEQ ID NOs: 13-15, SEQ ID NOs: 19-21, SEQ ID NOs: 25-27, SEQ ID NOs: 31-33, SEQ ID NOs: 37-39, SEQ ID NOs: 43-45, SEQ ID NOs: 49-51, SEQ ID NOs: 55-57, SEQ ID NOs: 61-63, SEQ ID NOs: 67-69, SEQ ID NOs: 73-75, SEQ ID NOs: 79-81, SEQ ID NOs: 85-87, SEQ ID NOs: 91-93, SEQ ID NOs: 97-99, or SEQ ID NOs: 103-105; and/or one, two, or three light chain variable region CDRs selected from the group of SEQ ID NOs: 4-6, SEQ ID NOs: 10-12, SEQ ID NOs: 16-18, SEQ ID NOs: 22-24, SEQ ID NOs: 28-30, SEQ ID NOs: 34-36, SEQ ID NOs: 40-42, SEQ ID NOs: 46-48, SEQ ID NOs: 52-54, SEQ ID NOs: 58-60, SEQ ID NOs: 64-66, SEQ ID NOs: 70-72, SEQ ID NOs: 76-78, SEQ ID NOs: 82-84, SEQ ID NOs: 88-90, SEQ ID NOs: 94-96, SEQ ID NOs: 100-102, or SEQ ID NOs: 106-108.

In some embodiments, the antibodies can have a heavy chain variable region (VH) comprising complementarity determining regions (CDRs) 1, 2, 3, wherein the CDR1 region comprises or consists of an amino acid sequence that is at least 80%, 85%, 90%, or 95% identical to a selected VH CDR1 amino acid sequence, the CDR2 region comprises or consists of an amino acid sequence that is at least 80%, 85%, 90%, or 95% identical to a selected VH CDR2 amino acid sequence, and the CDR3 region comprises or consists of an amino acid sequence that is at least 80%, 85%, 90%, or 95% identical to a selected VH CDR3 amino acid sequence, and a light chain variable region (VL) comprising CDRs 1, 2, 3, wherein the CDR1 region comprises or consists of an amino acid sequence that is at least 80%, 85%, 90%, or 95% identical to a selected VL CDR1 amino acid sequence, the CDR2 region comprises or consists of an amino acid sequence that is at least 80%, 85%, 90%, or 95% identical to a selected VL CDR2 amino acid sequence, and the CDR3 region comprises or consists of an amino acid sequence that is at least 80%, 85%, 90%, or 95% identical to a selected VL CDR3 amino acid sequence. The selected VH CDRs 1, 2, 3 amino acid sequences and the selected VL CDRs, 1, 2, 3 amino acid sequences are shown in FIG. 52 (Kabat CDR) and FIG. 53 (Chothia CDR).

In some embodiments, the antibody or an antigen-binding fragment described herein can contain a heavy chain variable domain containing one, two, or three of the CDRs selected from SEQ ID NOs: 1-3, SEQ ID NOs: 7-9, SEQ ID NOs: 13-15, SEQ ID NOs: 19-21, SEQ ID NOs: 25-27, SEQ ID NOs: 31-33, SEQ ID NOs: 37-39, SEQ ID NOs: 43-45, SEQ ID NOs: 49-51, SEQ ID NOs: 55-57, SEQ ID NOs: 61-63, SEQ ID NOs: 67-69, SEQ ID NOs: 73-75, SEQ ID NOs: 79-81, SEQ ID NOs: 85-87, SEQ ID NOs: 91-93, SEQ ID NOs: 97-99, or SEQ ID NOs: 103-105 with zero, one or two amino acid insertions, deletions, or substitutions on one, two, or three of the selected CDRs. For example, the antibody or an antigen-binding fragment described herein can contain a heavy chain variable domain containing one, two, or three of the CDRs of SEQ ID NO: 1 with zero, one or two amino acid insertions, deletions, or substitutions; SEQ ID NO: 2 with zero, one or two amino acid insertions, deletions, or substitutions; SEQ ID NO: 3 with zero, one or two amino acid insertions, deletions, or substitutions.

In some embodiments, the antibody or an antigen-binding fragment described herein can contain a light chain variable domain containing one, two, or three of the CDRs selected from SEQ ID NOs: 4-6, SEQ ID NOs: 10-12, SEQ ID NOs: 16-18, SEQ ID NOs: 22-24, SEQ ID NOs: 28-30, SEQ ID NOs: 34-36, SEQ ID NOs: 40-42, SEQ ID NOs: 46-48, SEQ ID NOs: 52-54, SEQ ID NOs: 58-60, SEQ ID NOs: 64-66, SEQ ID NOs: 70-72, SEQ ID NOs: 76-78, SEQ ID NOs: 82-84, SEQ ID NOs: 88-90, SEQ ID NOs: 94-96, SEQ ID NOs: 100-102, or SEQ ID NOs: 106-108 with zero, one or two amino acid insertions, deletions, or substitutions on one, two, or three of the selected CDRs. For example, the antibody or an antigen-binding fragment described herein can contain a light chain variable domain containing one, two, or three of the CDRs of SEQ ID NO: 4 with zero, one or two amino acid insertions, deletions, or substitutions; SEQ ID NO: 5 with zero, one or two amino acid insertions, deletions, or substitutions; SEQ ID NO: 6 with zero, one or two amino acid insertions, deletions, or substitutions.

In some embodiments, the CDRs with zero, one or two amino acid insertions, deletions, or substitutions are shown in Table 1, Table 3, FIG. 52, and FIG. 53.

The insertions, deletions, and substitutions can be within the CDR sequence, or at one or both terminal ends of the CDR sequence.

The disclosure also provides antibodies or antigen-binding fragments thereof that bind to 4-1BB, wherein the antibodies or antigen-binding fragments have VH CDR1, VH CDR2, VH CDR3, VL CDR1, VL CDR2, and VL CDR3. In some embodiments, the sequences for VH CDR1, VH CDR2, VH CDR3, VL CDR1, VL CDR2, and VL CDR3 are determined based on various CDR definitions known in the art, e.g., the Kabat definition, the Chothia definition, or the IMGT definition. The sequences for VH CDR1, VH CDR2, VH CDR3, VL CDR1, VL CDR2, and VL CDR3 are set forth in Table 1, Table 3, FIG. 52, and FIG. 53.

The disclosure also provides antibodies or antigen-binding fragments thereof that bind to 4-1BB. The antibodies or antigen-binding fragments thereof contain a heavy chain variable region (VH) comprising or consisting of an amino acid sequence that is at least 80%, 85%, 90%, or 95% identical to a selected VH sequence, and a light chain variable region (VL) comprising or consisting of an amino acid sequence that is at least 80%, 85%, 90%, or 95% identical to a selected VL sequence. In some embodiments, the selected VH sequence and the selected VL sequence is in Table 1 and Table 3. In some embodiments, the selected VH sequence is SEQ ID NO: 221, 222, 223, 224, or 243, and the selected VL sequence is SEQ ID NO: 225, 226, 227, 228, or 244. In some embodiments, the selected VH sequence is SEQ ID NO: 229, 230, 231, or 245 and the selected VL sequence is SEQ ID NO: 232, 233, 234, 235, or 246. In some embodiments, the selected VH sequence is SEQ ID NO: 236, 237, 238, or 247, and the selected VL sequence is SEQ ID NO: 239, 240, 241, 242, or 248.

The disclosure also provides nucleic acid comprising a polynucleotide encoding a polypeptide comprising an immunoglobulin heavy chain or an immunoglobulin light chain. The immunoglobulin heavy chain or immunoglobulin light chain comprises CDRs as shown in Table 1, Table 3, FIG. 52 or FIG. 53, or have sequences as shown in Table 1, Table 3, and FIGS. 55-58. When the polypeptides are paired with corresponding polypeptide (e.g., a corresponding heavy chain variable region or a corresponding light chain variable region), the paired polypeptides bind to 4-1BB (e.g., human 4-1BB).

In some aspects, the disclosure also provides an antibody or an antigen-binding fragment thereof, which cross-competes for binding to 4-1BB (e.g., human 4-1BB) with a reference antibody or antigen-binding fragment thereof (e.g., any anti-4-1BB antibody or antigen-binding fragment as described herein).

The anti-4-1BB antibodies and antigen-binding fragments can also be antibody variants (including derivatives and conjugates) of antibodies or antibody fragments and multi-specific (e.g., bi-specific) antibodies or antibody fragments. Additional antibodies provided herein are polyclonal, monoclonal, multi-specific (multimeric, e.g., bi-specific), human antibodies, chimeric antibodies (e.g., human-mouse chimera), single-chain antibodies, intracellularly-made antibodies (i.e., intrabodies), and antigen-binding fragments thereof. The antibodies or antigen-binding fragments thereof can be of any type (e.g., IgG, IgE, IgM, IgD, IgA, and IgY), or of any subclass (e.g., IgG1, IgG2, IgG3, IgG4, IgA1, and IgA2). In some embodiments, the antibody or antigen-binding fragment thereof is an IgG antibody or antigen-binding fragment thereof. In some embodiments, the antibody or antigen-binding fragment thereof is an IgG1 antibody or antigen-binding fragment thereof.

Fragments of antibodies are suitable for use in the methods provided so long as they retain the desired affinity and specificity of the full-length antibody. Thus, a fragment of an antibody that binds to 4-1BB will retain an ability to bind to 4-1BB. An Fv fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the VH-VL dimer. Collectively, the six CDRs or a subset thereof confer antigen binding specificity to the antibody. However, even a single variable domain (or half of an Fv comprising only three CDRs specific for an antigen) can have the ability to recognize and bind antigen, although usually at a lower affinity than the entire binding site.

Single-chain Fv or (scFv) antibody fragments comprise the VH and VL domains (or regions) of antibody, wherein these domains are present in a single polypeptide chain. Generally, the scFv polypeptide further comprises a polypeptide linker between the VH and VL domains, which enables the scFv to form the desired structure for antigen binding.

The Fab fragment contains a variable and constant domain of the light chain and a variable domain and the first constant domain (CH1) of the heavy chain. F(ab')2 antibody fragments comprise a pair of Fab fragments which are generally covalently linked near their carboxy termini by hinge cysteines between them. Other chemical couplings of antibody fragments are also known in the art.

Diabodies are small antibody fragments with two antigen-binding sites, which fragments comprise a VH connected to a VL in the same polypeptide chain (VH and VL). By using a linker that is too short to allow pairing between the two domains on the same chain, the domains are forced to pair with the complementary domains of another chain and create two antigen-binding sites.

Linear antibodies comprise a pair of tandem Fd segments (VH-CH1-VH-CH1) which, together with complementary light chain polypeptides, form a pair of antigen binding regions. Linear antibodies can be bispecific or monospecific.

Antibodies and antibody fragments of the present disclosure can be modified in the Fc region to provide desired effector functions or serum half-life.

Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers and other higher-order antibody multimers.

Alternatively, antibody homodimers can be formed through chemical linkage techniques known in the art. For example, heterobifunctional crosslinking agents including, but not limited to SMCC (succinimidyl 4-(maleimidomethyl)cyclohexane-1-carboxylate) and SATA (N-succinimidyl S-acethylthio-acetate) can be used to form antibody multimers. An exemplary protocol for the formation of antibody homodimers is described in Ghetie et al. (*Proc. Natl. Acad. Sci. U.S.A.* 94: 7509-7514, 1997). Antibody homodimers can be converted to Fab'2 homodimers through digestion with pepsin. Another way to form antibody homodimers is through the use of the autophilic T15 peptide described in Zhao et al. (*J. Immunol.* 25:396-404, 2002).

In some embodiments, the multi-specific antibody is a bi-specific antibody. Bi-specific antibodies can be made by engineering the interface between a pair of antibody molecules to maximize the percentage of heterodimers that are recovered from recombinant cell culture. For example, the interface can contain at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. This method is described, e.g., in WO 96/27011, which is incorporated by reference in its entirety.

Bi-specific antibodies include cross-linked or "heteroconjugate" antibodies. For example, one of the antibodies in the heteroconjugate can be coupled to avidin and the other to biotin. Heteroconjugate antibodies can also be made using any convenient cross-linking methods. Suitable cross-linking agents and cross-linking techniques are well known in the art and are disclosed in U.S. Pat. No. 4,676,980, which is incorporated herein by reference in its entirety.

Methods for generating bi-specific antibodies from antibody fragments are also known in the art. For example, bi-specific antibodies can be prepared using chemical linkage. Brennan et al. (Science 229:81, 1985) describes a procedure where intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab' TNB derivatives is then reconverted to the Fab' thiol by reduction with mercaptoethylamine, and is mixed with an equimolar amount of another Fab' TNB derivative to form the bi-specific antibody.

Any of the antibodies or antigen-binding fragments described herein may be conjugated to a stabilizing molecule (e.g., a molecule that increases the half-life of the antibody or antigen-binding fragment thereof in a subject or in solution). Non-limiting examples of stabilizing molecules include: a polymer (e.g., a polyethylene glycol) or a protein (e.g., serum albumin, such as human serum albumin). The conjugation of a stabilizing molecule can increase the half-life or extend the biological activity of an antibody or an antigen-binding fragment in vitro (e.g., in tissue culture or when stored as a pharmaceutical composition) or in vivo (e.g., in a human).

In some embodiments, the antibodies or antigen-binding fragments described herein can be conjugated to a therapeutic agent. The antibody-drug conjugate comprising the antibody or antigen-binding fragment thereof can covalently or non-covalently bind to a therapeutic agent. In some embodiments, the therapeutic agent is a cytotoxic or cytostatic agent (e.g., cytochalasin B, gramicidin D, ethidium bromide, emetine, mitomycin, etoposide, tenoposide, vincristine, vinblastine, colchicin, doxorubicin, daunorubicin, dihydroxy anthracin, maytansinoids such as DM-1 and DM-4, dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs).

Antibody Characteristics

In some embodiments, the antibodies or antigen-binding fragments thereof described herein can block the binding between 4-1BB and the 4-1BB ligand (4-1BBL).

In some embodiments, by binding to 4-1BB, the antibody can upregulates the immune response. Thus, in some embodiments, the antibodies or antigen-binding fragments thereof as described herein are 4-1BB agonist. In some embodiments, the antibodies or antigen-binding fragments thereof are 4-1BB antagonist.

In some embodiments, the antibodies or antigen-binding fragments thereof as described herein can increase immune response, activity or number of immune cells (e.g., T cells, natural killer (NK) cells, neutrophils, dendritic cells (DC) cells, macrophages, antigen-presenting cells, CD8+ and/or CD4+ T cells) by at least 10%, 20%, 30%, 40%, 50%, 60%, 70%, 80%, 90%, 100%, 2 folds, 3 folds, 5 folds, 10 folds, or 20 folds. In some embodiments, the antibodies or antigen-binding fragments thereof as described herein can decrease the activity or number of immune cells by at least 10%, 20%, 30%, 40%, 50%, 60%, 70%, 80%, 90%, 100%, 2 folds, 3 folds, 5 folds, 10 folds, or 20 folds.

In some implementations, the antibody (or antigen-binding fragments thereof) specifically binds to 4-1BB (e.g., human 4-1BB, monkey 4-1BB, mouse 4-1BB, and/or chimeric 4-1BB) with a dissociation rate (koff) of less than 0.1 s$^{-1}$, less than 0.01 s$^{-1}$, less than 0.001 s$^{-1}$, less than 0.0001 s$^{-1}$, or less than 0.00001 s$^{-1}$. In some embodiments, the dissociation rate (koff) is greater than 0.01 s$^{-1}$, greater than 0.001 s$^{-1}$, greater than 0.0001 s$^{-1}$, greater than 0.00001 s$^{-1}$, or greater than 0.000001 s$^{-1}$.

In some embodiments, kinetic association rates (kon) is greater than $1\times10^2$/Ms, greater than $1\times10^3$/Ms, greater than $1\times10^4$/Ms, greater than $1\times10^5$/Ms, or greater than $1\times10^6$/Ms. In some embodiments, kinetic association rates (kon) is less than $1\times10^5$/Ms, less than $1\times10^6$/Ms, or less than $1\times10^7$/Ms.

Affinities can be deduced from the quotient of the kinetic rate constants (KD=koff/kon). In some embodiments, KD is less than $1\times10^{-6}$ M, less than $1\times10^{-7}$ M, less than $1\times10^{-8}$ M, less than $1\times10^{-9}$ M, or less than $1\times10^{-10}$ M. In some embodiments, the KD is less than 50 nM, 40 nM, 30 nM, 20 nM, 15 nM, 10 nM, 9 nM, 8 nM, 7 nM, 6 nM, 5 nM, 4 nM, 3 nM, 2 nM, or 1 nM. In some embodiments, KD is greater than $1\times10^{-7}$ M, greater than $1\times10^{-8}$ M, greater than $1\times10^{-9}$ M, greater than $1\times10^{-10}$ M, greater than $1\times10^{-11}$ M, or greater than $1\times10^{-11}$ M. In some embodiments, the antibody binds to human 4-1BB with KD less than or equal to about 0.9 nM, 0.8 nM, 0.7 nM, 0.6 nM, 0.5 nM, 0.4 nM, 0.3 nM, 0.2 nM, or 0.1 nM. In some embodiments, the antibody binds to human 4-1BB with KD less than or equal to about 0.5 nM or 0.4 nM.

General techniques for measuring the affinity of an antibody for an antigen include, e.g., ELISA, RIA, and surface plasmon resonance (SPR). In some embodiments, the antibody binds to human 4-1BB (SEQ ID NO: 217), monkey 4-1BB (e.g., rhesus macaque 4-1BB, SEQ ID NO: 219), chimeric 4-1BB (SEQ ID NO: 220), and/or mouse 4-1BB (SEQ ID NO: 218). In some embodiments, the antibody does not bind to human 4-1BB (SEQ ID NO: 217), monkey 4-1BB (e.g., rhesus macaque 4-1BB, SEQ ID NO: 219; or cynomolgus 4-1BB), chimeric 4-1BB (SEQ ID NO: 220), and/or mouse 4-1BB (SEQ ID NO: 218).

In some embodiments, thermal stabilities are determined. The antibodies or antigen binding fragments as described herein can have a Tm greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

As IgG can be described as a multi-domain protein, the melting curve sometimes shows two transitions, or three transitions, with a first denaturation temperature, Tm D1, and a second denaturation temperature Tm D2, and optionally a third denaturation temperature Tm D3. When there are two peaks, one peak indicates the denaturation of the Fc domains (Tm D1), and the other peak indicates the denaturation of the Fab domains (Tm D2).

In some embodiments, the antibodies or antigen binding fragments as described herein has a Tm D1 greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some embodiments, the antibodies or antigen binding fragments as described herein has a Tm D2 greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some embodiments, the antibodies or antigen binding fragments as described herein has a Tm D3 greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

In some embodiments, Tm, Tm D1, Tm D2, Tm D3 are less than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

In some embodiments, the antibodies or antigen binding fragments as described herein do not form aggregation when the temperate is less than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

In some embodiments, the antibody has a tumor growth inhibition percentage (TGI %) that is greater than 10%, 20%, 30%, 40%, 50%, 60%, 70%, 80%, 90%, 100%, 110%, 120%, 130%, 140%, 150%, 160%, 170%, 180%, 190%, or 200%. In some embodiments, the antibody has a tumor growth inhibition percentage that is less than 60%, 70%, 80%, 90%, 100%, 110%, 120%, 130%, 140%, 150%, 160%, 170%, 180%, 190%, or 200%. The TGI % can be determined, e.g., at 3, 4, 5, 6, 7, 8, 9, 10, 11, 12, 13, 14, 15, 16, 17, 18, 19, 20, 21, 22, 23, 24, 25, 26, 27, 28, 29, or 30 days after the treatment starts, or 1, 2, 3, 4, 5, 6, 7, 8, 9, 10, 11, or 12 months after the treatment starts. As used herein, the tumor growth inhibition percentage (TGI %) is calculated using the following formula:

$$TGI\ (\%)=[1-(Ti-T0)/(Vi-V0)]\times 100$$

Ti is the average tumor volume in the treatment group on day i. T0 is the average tumor volume in the treatment group on day zero. Vi is the average tumor volume in the control group on day i. V0 is the average tumor volume in the control group on day zero.

In some embodiments, the antibodies or antigen-binding fragments thereof as described herein are 4-1BB agonist. In some embodiments, the antibodies or antigen-binding fragments thereof as described herein are 4-1BB antagonist. In some embodiments, the antibodies or antigen binding fragments can increase or decrease 4-1BB signal transduction in a target cell that expresses 4-1BB.

In some embodiments, the antibodies or antigen binding fragments can enhance immune cell function (e.g., CD8+ T cells, CD4+ T cells, B cells, natural killer cells, neutrophils, monocytes, macrophages, and/or dendritic cells), for example, by increasing immune cell proliferation and/or increasing cytokine production by the immune cell (e.g., as compared to proliferation and/or cytokine production prior to treatment with the antibodies or antigen binding fragments). In some embodiments, the cytokine is gamma interferon.

In some embodiments, the antibodies or antigen binding fragments increase number of intratumoral (infiltrating) CD8+ effector T cells (e.g., total number of CD8+ effector T cells, or e.g., percentage of CD8+ in CD45+ cells), e.g., as compared to number of intratumoral (infiltrating) CD8+ T effector cells prior to treatment. In some embodiments, the antibodies or antigen binding fragments increase number of intratumoral (infiltrating) CD8+ effector T cells that express gamma interferon (e.g., percentage of CD8+ cells that express gamma interferon in total CD8+ cells), e.g., compared to number of intratumoral (infiltrating) CD8+ T cells that express gamma interferon prior to treatment with anti-human 4-1BB antibody.

In some embodiments, the antibodies or antigen binding fragments increase number of intratumoral (infiltrating)

CD4+ effector T cells (e.g., total number of CD4+ effector T cells, or e.g., percentage of CD4+ cells in CD45+ cells), e.g., as compared to number of intratumoral (infiltrating) CD4+ T cells prior to treatment with antibodies or antigen binding fragments. In some embodiments, the antibodies or antigen binding fragments increase number of intratumoral (infiltrating) CD4+ effector T cells that express gamma interferon (e.g., total gamma interferon expressing CD4+ cells, or e.g., percentage of gamma interferon expressing CD4+ cells in total CD4+ cells), e.g., as compared to number of intratumoral (infiltrating) CD4+ T cells that express gamma interferon prior to treatment.

In some embodiments, the antibodies or antigen binding fragments enhance memory T cell function, for example by increasing memory T cell proliferation and/or increasing cytokine (e.g., gamma interferon) production by the memory T cell.

In some embodiments, the antibodies or antigen binding fragments have a functional Fc region. In some embodiments, effector function of a functional Fc region is antibody-dependent cell-mediated cytotoxicity (ADCC). In some embodiments, effector function of a functional Fc region is phagocytosis. In some embodiments, effector function of a functional Fc region is ADCC and phagocytosis. In some embodiments, the Fc region is human IgG1, human IgG2, human IgG3, or human IgG4.

In some embodiments, the antibodies or antigen binding fragments do not have a functional Fc region. For example, the antibodies or antigen binding fragments are Fab, Fab', F(ab')2, and Fv fragments.

Anti-h4-1BB IgG1 Antibody

The present disclosure also shows that IgG1 subclass antibodies unexpectedly have much better tumor inhibitory effects than other subclasses. Based on the results and without wishing to be bound by theory, it has been hypothesized that the anti-h1BB antibody inhibits tumor growth primarily through antibody-dependent cell-mediated cytotoxicity (ADCC). FcγRIIIa is the major receptor involved in the activation of ADCC. IgG subclasses vary in their ability to bind to FcγRIIIa and this differential binding determines their ability to elicit a range of functional responses (e.g., ADCC). Thus, it may be due to the fact that IgG1 subclass may have a stronger binding affinity with FcγRIIIa, IgG1 antibodies have better tumor inhibitory effects than other subclasses. Therefore, in some embodiments, the present disclosure provides an IgG1 antibody (e.g., human IgG1 antibody) that has CDRs, VH, and VL as described herein.

In some embodiments, the IgG1 antibody or the antigen binding fragment thereof has CDRs (e.g., in Kabat definition, Chothia definition, or IMGT definition), VH and VL as shown in the table below. Thus, the present disclosure provides an IgG1 antibody (e.g., human IgG1 antibody or humanized IgG1 antibody) comprising a heavy chain variable region (VH) comprising complementarity determining regions (CDRs) 1, 2, and 3, wherein the VH CDR1 region comprises an amino acid sequence that is at least 80%, 85%, 90%, 95%, or 100% identical to a selected VH CDR1 amino acid sequence, the VH CDR2 region comprises an amino acid sequence that is at least 80%, 85%, 90%, 95%, or 100% identical to a selected VH CDR2 amino acid sequence, and the VH CDR3 region comprises an amino acid sequence that is at least 80%, 85%, 90%, 95%, or 100% identical to a selected VH CDR3 amino acid sequence; and a light chain variable region (VL) comprising CDRs 1, 2, and 3, wherein the VL CDR1 region comprises an amino acid sequence that is at least 80%, 85%, 90%, 95%, or 100% identical to a selected VL CDR1 amino acid sequence, the VL CDR2 region comprises an amino acid sequence that is at least 80%, 85%, 90%, 95%, or 100% identical to a selected VL CDR2 amino acid sequence, and the VL CDR3 region comprises an amino acid sequence that is at least 80%, 85%, 90%, 95%, or 100% identical to a selected VL CDR3 amino acid sequence, wherein the VH CDR1, VH CDR2, VH CDR3, VL CDR1, VL CDR2, VL CDR3 are set forth in Table 3. In some embodiments, the CDRs of the IgG1 antibody or the antigen binding fragment thereof are defined by Kabat definition, Chothia definition, or IMGT definition. In some embodiments, the VH CDR1, VH CDR2, VH CDR3, VL CDR1, VL CDR2, VL CDR3 (CDRs as defined by Kabat definition) of the IgG1 antibody or the antigen binding fragment thereof have sequences that are set forth in Table 3. In some embodiments, the VH CDR1, VH CDR2, VH CDR3, VL CDR1, VL CDR2, VL CDR3 (CDRs as defined by IMGT definition) of the IgG1 antibody or the antigen binding fragment thereof have sequences that are set forth in Table 3.

In some embodiments, the present disclosure provides an antibody or antigen-binding fragment thereof that binds to 4-1BB comprising a heavy chain variable region (VH) comprising an amino acid sequence that is at least 80%, 85%, 90%, 95%, or 100% identical to a selected VH sequence, and a light chain variable region (VL) comprising an amino acid sequence that is at least 80%, 85%, 90%, 95%, or 100% identical to a selected VL sequence, wherein the selected VH sequence and the selected VL sequence are set forth in the table below.

TABLE 3

| Ab | VH CDR1 SEQ ID: | VH CDR2 SEQ ID: | VH CDR3 SEQ ID: | VL CDR1 SEQ ID: | VL CDR2 SEQ ID: | VL CDR3 SEQ ID: | VH SEQ ID: | VL SEQ ID: |
|---|---|---|---|---|---|---|---|---|
| AB1 | 279 | 280 | 281 | 282 | 283 | 284 | 459 | 460 |
| AB2 | 285 | 286 | 287 | 288 | 289 | 290 | 461 | 462 |
| AB3 | 291 | 292 | 293 | 294 | 295 | 296 | 463 | 464 |
| AB4 | 297 | 298 | 299 | 300 | 301 | 302 | 465 | 466 |
| AB5 | 303 | 304 | 305 | 306 | 307 | 308 | 467 | 468 |
| AB6 | 309 | 310 | 311 | 312 | 313 | 314 | 469 | 470 |
| AB7 | 315 | 316 | 317 | 318 | 319 | 320 | 471 | 472 |
| AB8 | 321 | 322 | 323 | 324 | 325 | 326 | 473 | 474 |
| AB9 | 327 | 328 | 329 | 330 | 331 | 332 | 475 | 476 |
| AB10 | 333 | 334 | 335 | 336 | 337 | 338 | 477 | 478 |
| AB11 | 339 | 340 | 341 | 342 | 343 | 344 | 479 | 480 |
| AB12 | 345 | 346 | 347 | 348 | 349 | 350 | 481 | 482 |
| AB13 | 351 | 352 | 353 | 354 | 355 | 356 | 483 | 484 |
| AB14 | 357 | 358 | 359 | 360 | 361 | 362 | 485 | 486 |
| AB15 | 363 | 364 | 365 | 366 | 367 | 368 | 487 | 488 |
| AB16 | 369 | 370 | 371 | 372 | 373 | 374 | 489 | 490 |
| AB17 | 375 | 376 | 377 | 378 | 379 | 380 | 491 | 492 |
| AB18 | 381 | 382 | 383 | 384 | 385 | 386 | 493 | 494 |
| AB19 | 387 | 388 | 389 | 390 | 391 | 392 | 495 | 496 |
| AB20 | 393 | 394 | 395 | 396 | 397 | 398 | 497 | 498 |
| AB21 | 399 | 400 | 401 | 402 | 403 | 404 | 499 | 500 |
| AB22 | 405 | 406 | 407 | 408 | 409 | 410 | 501 | 502 |
| AB23 | 411 | 412 | 413 | 414 | 415 | 416 | 503 | 504 |
| AB24 | 417 | 418 | 419 | 420 | 421 | 422 | 505 | 506 |
| AB25 | 423 | 424 | 425 | 426 | 427 | 428 | 507 | 508 |
| AB26 | 429 | 430 | 431 | 432 | 433 | 434 | 509 | 510 |
| AB27 | 435 | 436 | 437 | 438 | 439 | 440 | 511 | 512 |
| AB28 | 441 | 442 | 443 | 444 | 445 | 446 | 513 | 514 |
| AB29 | 447 | 448 | 449 | 450 | 451 | 452 | 515 | 516 |
| AB30 | 453 | 454 | 455 | 456 | 457 | 458 | 517 | 518 |

Furthermore, the antibodies as described herein can have various mutations. In some embodiments, the antibodies (e.g., IgG1 antibodies) can have N297A (EU numbering) mutation, FC-SI mutations (EU Numbering: F243L/R292P/Y300L/V305I/P396L), or the FC-V11 mutations (EU numbering: (G237D/P238D/H268D/P271G/A330R). In some embodiments, the Fc region of the antibodies as described herein can have one or more of the following mutations: N297A, F243L, R292P, Y300L, V305I, P396L, G237D, P238D, H268D, P271G, and A330R.

Methods of Making Anti-4-1BB Antibodies

An isolated fragment of human 4-1BB can be used as an immunogen to generate antibodies using standard techniques for polyclonal and monoclonal antibody preparation. Polyclonal antibodies can be raised in animals by multiple injections (e.g., subcutaneous or intraperitoneal injections) of an antigenic peptide or protein. In some embodiments, the antigenic peptide or protein is injected with at least one adjuvant. In some embodiments, the antigenic peptide or protein can be conjugated to an agent that is immunogenic in the species to be immunized. Animals can be injected with the antigenic peptide or protein more than one time (e.g., twice, three times, or four times).

The full-length polypeptide or protein can be used or, alternatively, antigenic peptide fragments thereof can be used as immunogens. The antigenic peptide of a protein comprises at least 8 (e.g., at least 10, 15, 20, or 30) amino acid residues of the amino acid sequence of 4-1BB and encompasses an epitope of the protein such that an antibody raised against the peptide forms a specific immune complex with the protein. As described above, the full length sequence of human 4-1BB is known in the art (SEQ ID NO: 217).

An immunogen typically is used to prepare antibodies by immunizing a suitable subject (e.g., human or transgenic animal expressing at least one human immunoglobulin locus). An appropriate immunogenic preparation can contain, for example, a recombinantly-expressed or a chemically-synthesized polypeptide (e.g., a fragment of human 4-1BB). The preparation can further include an adjuvant, such as Freund's complete or incomplete adjuvant, or a similar immunostimulatory agent.

Polyclonal antibodies can be prepared as described above by immunizing a suitable subject with a 4-1BB polypeptide, or an antigenic peptide thereof (e.g., part of 4-1BB) as an immunogen. The antibody titer in the immunized subject can be monitored over time by standard techniques, such as with an enzyme-linked immunosorbent assay (ELISA) using the immobilized 4-1BB polypeptide or peptide. If desired, the antibody molecules can be isolated from the mammal (e.g., from the blood) and further purified by well-known techniques, such as protein A of protein G chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler et al. (*Nature* 256:495-497, 1975), the human B cell hybridoma technique (Kozbor et al., *Immunol. Today* 4:72, 1983), the EBV-hybridoma technique (Cole et al., Monoclonal Antibodies and Cancer Therapy, Alan R. Liss, Inc., pp. 77-96, 1985), or trioma techniques. The technology for producing hybridomas is well known (see, generally, Current Protocols in Immunology, 1994, Coligan et al. (Eds.), John Wiley & Sons, Inc., New York, N.Y.). Hybridoma cells producing a monoclonal antibody are detected by screening the hybridoma culture supernatants for antibodies that bind the polypeptide or epitope of interest, e.g., using a standard ELISA assay.

Variants of the antibodies or antigen-binding fragments described herein can be prepared by introducing appropriate nucleotide changes into the DNA encoding a human, humanized, or chimeric antibody, or antigen-binding fragment thereof described herein, or by peptide synthesis. Such variants include, for example, deletions, insertions, or substitutions of residues within the amino acids sequences that make-up the antigen-binding site of the antibody or an antigen-binding domain. In a population of such variants, some antibodies or antigen-binding fragments will have increased affinity for the target protein, e.g., 4-1BB. Any combination of deletions, insertions, and/or combinations can be made to arrive at an antibody or antigen-binding fragment thereof that has increased binding affinity for the target. The amino acid changes introduced into the antibody or antigen-binding fragment can also alter or introduce new post-translational modifications into the antibody or antigen-binding fragment, such as changing (e.g., increasing or decreasing) the number of glycosylation sites, changing the type of glycosylation site (e.g., changing the amino acid sequence such that a different sugar is attached by enzymes present in a cell), or introducing new glycosylation sites.

Antibodies disclosed herein can be derived from any species of animal, including mammals. Non-limiting examples of native antibodies include antibodies derived from humans, primates, e.g., monkeys and apes, cows, pigs, horses, sheep, camelids (e.g., camels and llamas), chicken, goats, and rodents (e.g., rats, mice, hamsters and rabbits), including transgenic rodents genetically engineered to produce human antibodies.

Human and humanized antibodies include antibodies having variable and constant regions derived from (or having the same amino acid sequence as those derived from) human germline immunoglobulin sequences. Human antibodies may include amino acid residues not encoded by human germline immunoglobulin sequences (e.g., mutations introduced by random or site-specific mutagenesis in vitro or by somatic mutation in vivo), for example in the CDRs.

A humanized antibody, typically has a human framework (FR) grafted with non-human CDRs. Thus, a humanized antibody has one or more amino acid sequence introduced into it from a source which is non-human. These non-human amino acid residues are often referred to as "import" residues, which are typically taken from an "import" variable domain. Humanization can be essentially performed by e.g., substituting rodent CDRs or CDR sequences for the corresponding sequences of a human antibody. These methods are described in e.g., Jones et al., Nature, 321:522-525 (1986); Riechmann et al., Nature, 332:323-327 (1988); Verhoeyen et al., Science, 239:1534-1536 (1988); each of which is incorporated by reference herein in its entirety. Accordingly, "humanized" antibodies are chimeric antibodies wherein substantially less than an intact human V domain has been substituted by the corresponding sequence from a non-human species. In practice, humanized antibodies are typically mouse antibodies in which some CDR residues and some FR residues are substituted by residues from analogous sites in human antibodies.

The choice of human VH and VL domains to be used in making the humanized antibodies is very important for reducing immunogenicity. According to the so-called "best-fit" method, the sequence of the V domain of a mouse antibody is screened against the entire library of known human-domain sequences. The human sequence which is closest to that of the mouse is then accepted as the human FR for the humanized antibody (Sims et al., J. Immunol., 151:2296 (1993); Chothia et al., J. Mol. Biol., 196:901 (1987)).

It is further important that antibodies be humanized with retention of high specificity and affinity for the antigen and other favorable biological properties. To achieve this goal, humanized antibodies can be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved.

Ordinarily, amino acid sequence variants of the human, humanized, or chimeric anti-4-1BB antibody will contain an amino acid sequence having at least 75%, 80%, 85%, 90%, 95%, 96%, 97%, 98%, or 99% percent identity with a sequence present in the light or heavy chain of the original antibody.

Identity with respect to an original sequence is usually the percentage of amino acid residues present within the candidate sequence that are identical with a sequence present within the human, humanized, or chimeric anti-4-1BB antibody or fragment, after aligning the sequences and introducing gaps, if necessary, to achieve the maximum percent sequence identity, and not considering any conservative substitutions as part of the sequence identity.

Additional modifications to the anti-4-1BB antibodies or antigen-binding fragments can be made. For example, a cysteine residue(s) can be introduced into the Fc region, thereby allowing interchain disulfide bond formation in this region. The homodimeric antibody thus generated may have any increased half-life in vitro and/or in vivo. Homodimeric antibodies with increased half-life in vitro and/or in vivo can also be prepared using heterobifunctional cross-linkers as described, for example, in Wolff et al. (*Cancer Res.* 53:2560-2565, 1993). Alternatively, an antibody can be engineered which has dual Fc regions (see, for example, Stevenson et al., *Anti-Cancer Drug Design* 3:219-230, 1989).

In some embodiments, a covalent modification can be made to the anti-4-1BB antibody or antigen-binding fragment thereof. These covalent modifications can be made by chemical or enzymatic synthesis, or by enzymatic or chemical cleavage. Other types of covalent modifications of the antibody or antibody fragment are introduced into the molecule by reacting targeted amino acid residues of the antibody or fragment with an organic derivatization agent that is capable of reacting with selected side chains or the N- or C-terminal residues.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues; or position 314 in Kabat numbering); however, Asn297 may also be located about ±3 amino acids upstream or downstream of position 297, i.e., between positions 294 and 300, due to minor sequence variations in antibodies. Such fucosylation variants may have improved ADCC function. In some embodiments, to reduce glycan heterogeneity, the Fc region of the antibody can be further engineered to replace the Asparagine at position 297 with Alanine (N297A).

In some embodiments, to facilitate production efficiency by avoiding Fab-arm exchange, the Fc region of the antibodies was further engineered to replace the serine at position 228 (EU numbering) of IgG4 with proline (S228P). A detailed description regarding S228 mutation is described, e.g., in Silva et al. "The S228P mutation prevents in vivo and in vitro IgG4 Fab-arm exchange as demonstrated using a combination of novel quantitative immunoassays and physiological matrix preparation." Journal of Biological Chemistry 290.9 (2015): 5462-5469, which is incorporated by reference in its entirety.

In some aspects, the disclosure also provides the use of the antibodies or antigen fragments thereof described herein for manufacture of a medicament for cancer treatment.

Recombinant Vectors

The present disclosure also provides recombinant vectors (e.g., an expression vectors) that include an isolated polynucleotide disclosed herein (e.g., a polynucleotide that encodes a polypeptide disclosed herein), host cells into which are introduced the recombinant vectors (i.e., such that the host cells contain the polynucleotide and/or a vector comprising the polynucleotide), and the production of recombinant antibody polypeptides or fragments thereof by recombinant techniques.

As used herein, a "vector" is any construct capable of delivering one or more polynucleotide(s) of interest to a host cell when the vector is introduced to the host cell. An "expression vector" is capable of delivering and expressing the one or more polynucleotide(s) of interest as an encoded polypeptide in a host cell into which the expression vector has been introduced. Thus, in an expression vector, the polynucleotide of interest is positioned for expression in the vector by being operably linked with regulatory elements such as a promoter, enhancer, and/or a poly-A tail, either within the vector or in the genome of the host cell at or near or flanking the integration site of the polynucleotide of interest such that the polynucleotide of interest will be translated in the host cell introduced with the expression vector.

A vector can be introduced into the host cell by methods known in the art, e.g., electroporation, chemical transfection (e.g., DEAE-dextran), transformation, transfection, and infection and/or transduction (e.g., with recombinant virus). Thus, non-limiting examples of vectors include viral vectors (which can be used to generate recombinant virus), naked DNA or RNA, plasmids, cosmids, phage vectors, and DNA or RNA expression vectors associated with cationic condensing agents.

In some implementations, a polynucleotide disclosed herein (e.g., a polynucleotide that encodes a polypeptide disclosed herein) is introduced using a viral expression system (e.g., vaccinia or other pox virus, retrovirus, or adenovirus), which may involve the use of a non-pathogenic (defective), replication competent virus, or may use a replication defective virus. In the latter case, viral propagation generally will occur only in complementing virus packaging cells. Suitable systems are disclosed, for example, in Fisher-Hoch et al., 1989, Proc. Natl. Acad. Sci. USA 86:317-321; Flexner et al., 1989, Ann. N.Y. Acad Sci. 569:86-103;

Flexner et al., 1990, Vaccine, 8:17-21; U.S. Pat. Nos. 4,603, 112, 4,769,330, and 5,017,487; WO 89/01973; U.S. Pat. No. 4,777,127; GB 2,200,651; EP 0,345,242; WO 91/02805; Berkner-Biotechniques, 6:616-627, 1988; Rosenfeld et al., 1991, Science, 252:431-434; Kolls et al., 1994, Proc. Natl. Acad. Sci. USA, 91:215-219; Kass-Eisler et al., 1993, Proc. Natl. Acad. Sci. USA, 90:11498-11502; Guzman et al., 1993, Circulation, 88:2838-2848; and Guzman et al., 1993, Cir. Res., 73:1202-1207. Techniques for incorporating DNA into such expression systems are well known to those of ordinary skill in the art. The DNA may also be "naked," as described, for example, in Ulmer et al., 1993, Science, 259:1745-1749, and Cohen, 1993, Science, 259:1691-1692. The uptake of naked DNA may be increased by coating the DNA onto biodegradable beads that are efficiently transported into the cells.

For expression, the DNA insert comprising an antibody-encoding or polypeptide-encoding polynucleotide disclosed herein can be operatively linked to an appropriate promoter (e.g., a heterologous promoter), such as the phage lambda PL promoter, the *E. coli* lac, trp and tac promoters, the SV40 early and late promoters and promoters of retroviral LTRs, to name a few. Other suitable promoters are known to the skilled artisan. The expression constructs can further contain sites for transcription initiation, termination and, in the transcribed region, a ribosome binding site for translation. The coding portion of the mature transcripts expressed by the constructs may include a translation initiating at the beginning and a termination codon (UAA, UGA, or UAG) appropriately positioned at the end of the polypeptide to be translated.

As indicated, the expression vectors can include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces*, and *Salmonella typhimurium* cells; fungal cells, such as yeast cells; insect cells such as *Drosophila* S2 and *Spodoptera* Sf9 cells; animal cells such as CHO, COS, Bowes melanoma, and HK 293 cells; and plant cells. Appropriate culture mediums and conditions for the host cells described herein are known in the art.

Non-limiting vectors for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Non-limiting eukaryotic vectors include pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Non-limiting bacterial promoters suitable for use include the *E. coli* lad and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

In the yeast *Saccharomyces cerevisiae*, a number of vectors containing constitutive or inducible promoters such as alpha factor, alcohol oxidase, and PGH may be used. For reviews, see Ausubel et al. (1989) Current Protocols in Molecular Biology, John Wiley & Sons, New York, N.Y., and Grant et al., *Methods Enzymol.*, 153: 516-544 (1997).

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986), which is incorporated herein by reference in its entirety.

Transcription of DNA encoding an antibody of the present disclosure by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at base pairs 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide (e.g., antibody) can be expressed in a modified form, such as a fusion protein (e.g., a GST-fusion) or with a histidine-tag, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties can be added to the polypeptide to facilitate purification. Such regions can be removed prior to final preparation of the polypeptide. The addition of peptide moieties to polypeptides to engender secretion or excretion, to improve stability and to facilitate purification, among others, are familiar and routine techniques in the art.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein.

The disclosure also provides a nucleic acid sequence that has a homology of at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% to any nucleotide sequence as described herein, and an amino acid sequence that has a homology of at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% to any amino acid sequence as described herein.

In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, 200, 250, 300, 350, or 400 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

The percentage of residues conserved with similar physicochemical properties (percent homology), e.g. leucine and isoleucine, can also be used to measure sequence similarity. Families of amino acid residues having similar physicochemical properties have been defined in the art. These families include e.g., amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The homology percentage, in many cases, is higher than the identity percentage.

Methods of Treatment

The antibodies or antibody or antigen-binding fragments thereof of the present disclosure can be used for various therapeutic purposes. In one aspect, the disclosure provides methods for treating a cancer in a subject, methods of reducing the rate of the increase of volume of a tumor in a subject over time, methods of reducing the risk of developing a metastasis, or methods of reducing the risk of developing an additional metastasis in a subject. In some embodiments, the treatment can halt, slow, retard, or inhibit progression of a cancer. In some embodiments, the treatment can result in the reduction of in the number, severity, and/or duration of one or more symptoms of the cancer in a subject.

In one aspect, the disclosure features methods that include administering a therapeutically effective amount of an antibody or antigen-binding fragment thereof disclosed herein to a subject in need thereof (e.g., a subject having, or identified or diagnosed as having, a cancer), e.g., breast cancer (e.g., triple-negative breast cancer), carcinoid cancer, cervical cancer, endometrial cancer, glioma, head and neck cancer, liver cancer, lung cancer, small cell lung cancer, lymphoma, melanoma, ovarian cancer, pancreatic cancer, prostate cancer, renal cancer, colorectal cancer, gastric cancer, testicular cancer, thyroid cancer, bladder cancer, urethral cancer, or hematologic malignancy. In some embodiments, the cancer is unresectable melanoma or metastatic melanoma, non-small cell lung carcinoma (NSCLC), small cell lung cancer (SCLC), bladder cancer, or metastatic hormone-refractory prostate cancer. In some embodiments, the subject has a solid tumor. In some embodiments, the cancer is squamous cell carcinoma of the head and neck (SCCHN), renal cell carcinoma (RCC), triple-negative breast cancer (TNBC), or colorectal carcinoma. In some embodiments, the subject has Hodgkin's lymphoma. In some embodiments, the subject has triple-negative breast cancer (TNBC), gastric cancer, urothelial cancer, Merkel-cell carcinoma, or head and neck cancer. In some embodiments, the antibody or antigen-binding fragment thereof is an anti-4-1BB antibody or antigen-binding fragment thereof. In some embodiments, the antibody is an IgG1 anti-4-1BB antibody (e.g., human IgG1 anti-4-1BB antibody).

In some embodiments, the compositions and methods disclosed herein can be used for treatment of patients at risk for a cancer. Patients with cancer can be identified with various methods known in the art.

Furthermore, as the anti-4-1BB antibodies can promote immune response, the disclosure provides methods for treating infection in a subject. Types of infection include e.g., bacterial, fungal, viral, protozoan, and parasitic diseases. In some embodiments, the treatment can halt, slow, retard, or inhibit progression of the disease. In addition, 4-1BB antibody treatment (e.g., agonistic antibody or antagonistic antibody) can also be used to treat autoimmune disease, asthma, and additionally as a means to improve vaccination. These methods generally involve administering a therapeutically effective amount of an antibody or antigen-binding fragment thereof disclosed herein to a subject in need thereof.

As used herein, by an "effective amount" is meant an amount or dosage sufficient to effect beneficial or desired results including halting, slowing, retarding, or inhibiting progression of a disease, e.g., a cancer, or an autoimmune disease. An effective amount will vary depending upon, e.g., an age and a body weight of a subject to which the antibody, antigen binding fragment, antibody-encoding polynucleotide, vector comprising the polynucleotide, and/or compositions thereof is to be administered, a severity of symptoms and a route of administration, and thus administration can be determined on an individual basis.

An effective amount can be administered in one or more administrations. By way of example, an effective amount of an antibody or an antigen binding fragment is an amount sufficient to ameliorate, stop, stabilize, reverse, inhibit, slow and/or delay progression of a cancer in a patient or is an amount sufficient to ameliorate, stop, stabilize, reverse, slow and/or delay proliferation of a cell (e.g., a biopsied cell, any of the cancer cells described herein, or cell line (e.g., a cancer cell line)) in vitro. As is understood in the art, an effective amount of an antibody or antigen binding fragment may vary, depending on, inter alia, patient history as well as other factors such as the type (and/or dosage) of antibody used.

Effective amounts and schedules for administering the antibodies, antibody-encoding polynucleotides, and/or compositions disclosed herein may be determined empirically, and making such determinations is within the skill in the art. Those skilled in the art will understand that the dosage that must be administered will vary depending on, for example, the mammal that will receive the antibodies, antibody-encoding polynucleotides, and/or compositions disclosed herein, the route of administration, the particular type of antibodies, antibody-encoding polynucleotides, antigen binding fragments, and/or compositions disclosed herein used and other drugs being administered to the mammal. Guidance in selecting appropriate doses for antibody or antigen binding fragment can be found in the literature on therapeutic uses of antibodies and antigen binding fragments, e.g., Handbook of Monoclonal Antibodies, Ferrone et al., eds., Noges Publications, Park Ridge, N.J., 1985, ch. 22 and pp. 303-357; Smith et al., Antibodies in Human Diagnosis and Therapy, Haber et al., eds., Raven Press, New York, 1977, pp. 365-389.

A typical daily dosage of an effective amount of an antibody is 0.01 mg/kg to 100 mg/kg. In some embodiments, the dosage can be less than 100 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, or 0.1 mg/kg. In some embodiments, the dosage can be greater than 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, 0.1 mg/kg, 0.05 mg/kg, or 0.01 mg/kg. In some embodiments, the dosage is about 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.9 mg/kg, 0.8 mg/kg, 0.7 mg/kg, 0.6 mg/kg, 0.5 mg/kg, 0.4 mg/kg, 0.3 mg/kg, 0.2 mg/kg, or 0.1 mg/kg.

In any of the methods described herein, the at least one antibody, antigen-binding fragment thereof, or pharmaceutical composition (e.g., any of the antibodies, antigen-binding fragments, or pharmaceutical compositions described herein) and, optionally, at least one additional therapeutic agent can be administered to the subject at least once a week (e.g., once a week, twice a week, three times a week, four times a week, once a day, twice a day, or three times a day). In some embodiments, at least two different antibodies and/or antigen-binding fragments are administered in the same composition (e.g., a liquid composition). In some embodiments, at least one antibody or antigen-binding fragment and at least one additional therapeutic agent are administered in the same composition (e.g., a liquid composition). In some embodiments, the at least one antibody or antigen-binding fragment and the at least one additional therapeutic agent are administered in two different compositions (e.g., a liquid composition containing at least one antibody or antigen-binding fragment and a solid oral composition containing at least one additional therapeutic agent). In some embodiments, the at least one additional therapeutic agent is administered as a pill, tablet, or capsule. In some embodiments, the at least one additional therapeutic agent is administered in a sustained-release oral formulation.

In some embodiments, the one or more additional therapeutic agents can be administered to the subject prior to, or after administering the at least one antibody, antigen-binding antibody fragment, or pharmaceutical composition (e.g., any of the antibodies, antigen-binding antibody fragments, or pharmaceutical compositions described herein). In some embodiments, the one or more additional therapeutic agents and the at least one antibody, antigen-binding antibody fragment, or pharmaceutical composition (e.g., any of the antibodies, antigen-binding antibody fragments, or pharmaceutical compositions described herein) are administered to the subject such that there is an overlap in the bioactive period of the one or more additional therapeutic agents and the at least one antibody or antigen-binding fragment (e.g., any of the antibodies or antigen-binding fragments described herein) in the subject.

In some embodiments, the subject can be administered the at least one antibody, antigen-binding antibody fragment, or pharmaceutical composition (e.g., any of the antibodies, antigen-binding antibody fragments, or pharmaceutical compositions described herein) over an extended period of time (e.g., over a period of at least 1 week, 2 weeks, 3 weeks, 1 month, 2 months, 3 months, 4 months, 5 months, 6 months, 7 months, 8 months, 9 months, 10 months, 11 months, 12 months, 1 year, 2 years, 3 years, 4 years, or 5 years). A skilled medical professional may determine the length of the treatment period using any of the methods described herein for diagnosing or following the effectiveness of treatment (e.g., the observation of at least one symptom of cancer). As described herein, a skilled medical professional can also change the identity and number (e.g., increase or decrease) of antibodies or antigen-binding antibody fragments (and/or one or more additional therapeutic agents) administered to the subject and can also adjust (e.g., increase or decrease) the dosage or frequency of administration of at least one antibody or antigen-binding antibody fragment (and/or one or more additional therapeutic agents) to the subject based on an assessment of the effectiveness of the treatment (e.g., using any of the methods described herein and known in the art).

In some embodiments, one or more additional therapeutic agents can be administered to the subject. The additional therapeutic agent can comprise one or more inhibitors selected from the group consisting of an inhibitor of B-Raf, an EGFR inhibitor, an inhibitor of a MEK, an inhibitor of ERK, an inhibitor of K-Ras, an inhibitor of c-Met, an inhibitor of anaplastic lymphoma kinase (ALK), an inhibitor of a phosphatidylinositol 3-kinase (PI3K), an inhibitor of an Akt, an inhibitor of mTOR, a dual PI3K/mTOR inhibitor, an inhibitor of Bruton's tyrosine kinase (BTK), and an inhibitor of Isocitrate dehydrogenase 1 (IDH1) and/or Isocitrate dehydrogenase 2 (IDH2). In some embodiments, the additional therapeutic agent is an inhibitor of indoleamine 2,3-dioxygenase-1) (IDO1) (e.g., epacadostat).

In some embodiments, the additional therapeutic agent can comprise one or more inhibitors selected from the group consisting of an inhibitor of HER3, an inhibitor of LSD1, an inhibitor of MDM2, an inhibitor of BCL2, an inhibitor of CHK1, an inhibitor of activated hedgehog signaling pathway, and an agent that selectively degrades the estrogen receptor.

In some embodiments, the additional therapeutic agent can comprise one or more therapeutic agents selected from the group consisting of Trabectedin, nab-paclitaxel, Trebananib, Pazopanib, Cediranib, Palbociclib, everolimus, fluoropyrimidine, IFL, regorafenib, Reolysin, Alimta, Zykadia, Sutent, temsirolimus, axitinib, everolimus, sorafenib, Votrient, Pazopanib, IMA-901, AGS-003, cabozantinib, Vinflunine, an Hsp90 inhibitor, Ad-GM-CSF, Temazolomide, IL-2, IFNa, vinblastine, Thalomid, dacarbazine, cyclophosphamide, lenalidomide, azacytidine, lenalidomide, bortezomid, amrubicine, carfilzomib, pralatrexate, and enzastaurin.

In some embodiments, the additional therapeutic agent can comprise one or more therapeutic agents selected from the group consisting of an adjuvant, a TLR agonist, tumor necrosis factor (TNF) alpha, IL-1, HMGB1, an IL-10 antagonist, an IL-4 antagonist, an IL-13 antagonist, an IL-17 antagonist, an HVEM antagonist, an ICOS agonist, a treatment targeting CX3CL1, a treatment targeting CXCL9, a treatment targeting CXCL10, a treatment targeting CCL5, an LFA-1 agonist, an ICAM1 agonist, and a Selectin agonist.

In some embodiments, carboplatin, nab-paclitaxel, paclitaxel, cisplatin, pemetrexed, gemcitabine, FOLFOX, or FOLFIRI are administered to the subject.

In some embodiments, the additional therapeutic agent is an anti-OX40 antibody, an anti-PD-L1 antibody, an anti-PD-L2 antibody, an anti-LAG-3 antibody, an anti-TIGIT antibody, an anti-BTLA antibody, an anti-CTLA-4 antibody, or an anti-GITR antibody.

In some embodiments, the additional therapy is chemotherapy or chemoradiation. In some embodiments, the additional therapeutic agent is an anti-CTLA4 antibody (e.g., ipilimumab), an anti-CD20 antibody (e.g., rituximab), an anti-EGFR antibody (e.g., cetuximab), an anti-CD319 antibody (e.g., elotuzumab), or an anti-PD1 antibody (e.g., nivolumab).

In some embodiments, the additional therapeutic agent is an antibody that specifically binds to PD-1, CTLA-4, BTLA, PD-L1, CD27, CD28, CD40, CD47, CD137, CD154, TIGIT, TIM-3, GITR, or OX40.

The present disclosure also shows that the combination of anti-4-1BB IgG1 subclass antibodies with additional therapeutic agents have better tumor inhibitory effects than the combination of anti-4-1BB IgG4 subclass antibodies with some additional therapeutic agents. Thus, in one aspect, the present disclosure provides methods of treating a subject or killing tumors by administering to the subject a therapeutically effective amount of an anti-4-1BB IgG1 antibody or antigen-binding fragment thereof and an additional therapeutic agent. In some embodiments, the additional therapeutic agent is an anti-PD-1 antibody, an anti-CTLA4 antibody, or an-anti-OX40 antibody.

Pharmaceutical Compositions and Routes of Administration

Also provided herein are pharmaceutical compositions that contain at least one (e.g., one, two, three, or four) of the antibodies or antigen-binding fragments described herein. Two or more (e.g., two, three, or four) of any of the antibodies or antigen-binding fragments described herein can be present in a pharmaceutical composition in any combination. The pharmaceutical compositions may be formulated in any manner known in the art.

Pharmaceutical compositions are formulated to be compatible with their intended route of administration (e.g., intravenous, intraarterial, intramuscular, intradermal, subcutaneous, or intraperitoneal). The compositions can include a sterile diluent (e.g., sterile water or saline), a fixed oil, polyethylene glycol, glycerine, propylene glycol or other synthetic solvents, antibacterial or antifungal agents, such as benzyl alcohol or methyl parabens, chlorobutanol, phenol, ascorbic acid, thimerosal, and the like, antioxidants, such as ascorbic acid or sodium bisulfate, chelating agents, such as ethylenediaminetetraacetic acid, buffers, such as acetates, citrates, or phosphates, and isotonic agents, such as sugars (e.g., dextrose), polyalcohols (e.g., mannitol or sorbitol), or salts (e.g., sodium chloride), or any combination thereof. Liposomal suspensions can also be used as pharmaceutically acceptable carriers (see, e.g., U.S. Pat. No. 4,522,811). Preparations of the compositions can be formulated and enclosed in ampules, disposable syringes, or multiple dose vials. Where required (as in, for example, injectable formulations), proper fluidity can be maintained by, for example, the use of a coating, such as lecithin, or a surfactant. Absorption of the antibody or antigen-binding fragment thereof can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Compositions containing one or more of any of the antibodies or antigen-binding fragments described herein can be formulated for parenteral (e.g., intravenous, intraarterial, intramuscular, intradermal, subcutaneous, or intraperitoneal) administration in dosage unit form (i.e., physically discrete units containing a predetermined quantity of active compound for ease of administration and uniformity of dosage).

Toxicity and therapeutic efficacy of compositions can be determined by standard pharmaceutical procedures in cell cultures or experimental animals (e.g., monkeys). One can, for example, determine the LD50 (the dose lethal to 50% of the population) and the ED50 (the dose therapeutically effective in 50% of the population): the therapeutic index being the ratio of LD50:ED50. Agents that exhibit high therapeutic indices are preferred. Where an agent exhibits an undesirable side effect, care should be taken to minimize potential damage (i.e., reduce unwanted side effects). Toxicity and therapeutic efficacy can be determined by other standard pharmaceutical procedures.

Data obtained from cell culture assays and animal studies can be used in formulating an appropriate dosage of any given agent for use in a subject (e.g., a human). A therapeutically effective amount of the one or more (e.g., one, two, three, or four) antibodies or antigen-binding fragments thereof (e.g., any of the antibodies or antibody fragments described herein) will be an amount that treats the disease in a subject (e.g., kills cancer cells) in a subject (e.g., a human subject identified as having cancer), or a subject identified as being at risk of developing the disease (e.g., a subject who has previously developed cancer but now has been cured), decreases the severity, frequency, and/or duration of one or more symptoms of a disease in a subject (e.g., a human). The effectiveness and dosing of any of the antibodies or antigen-binding fragments described herein can be determined by a health care professional or veterinary professional using methods known in the art, as well as by the observation of one or more symptoms of disease in a subject (e.g., a human). Certain factors may influence the dosage and timing required to effectively treat a subject (e.g., the severity of the disease or disorder, previous treatments, the general health and/or age of the subject, and the presence of other diseases).

Exemplary doses include milligram or microgram amounts of any of the antibodies or antigen-binding fragments described herein per kilogram of the subject's weight (e.g., about 1 µg/kg to about 500 mg/kg; about 100 µg/kg to about 500 mg/kg; about 100 µg/kg to about 50 mg/kg; about 10 µg/kg to about 5 mg/kg; about 10 µg/kg to about 0.5 mg/kg; about 1 µg/kg to about 50 µg/kg; about 500 µg/kg to about 5 mg/kg; or about 500 µg/kg to about 2 mg/kg). While these doses cover a broad range, one of ordinary skill in the art will understand that therapeutic agents, including antibodies and antigen-binding fragments thereof, vary in their potency, and effective amounts can be determined by methods known in the art. Typically, relatively low doses are administered at first, and the attending health care professional or veterinary professional (in the case of therapeutic application) or a researcher (when still working at the development stage) can subsequently and gradually increase the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, and the half-life of the antibody or antibody fragment in vivo.

The pharmaceutical compositions can be included in a container, pack, or dispenser together with instructions for administration. The disclosure also provides methods of manufacturing the antibodies or antigen binding fragments thereof for various uses as described herein.

EXAMPLES

The invention is further described in the following examples, which do not limit the scope of the invention described in the claims.

Example 1. Generating Mouse Anti-H4-1Bb Antibodies

Figure 2:
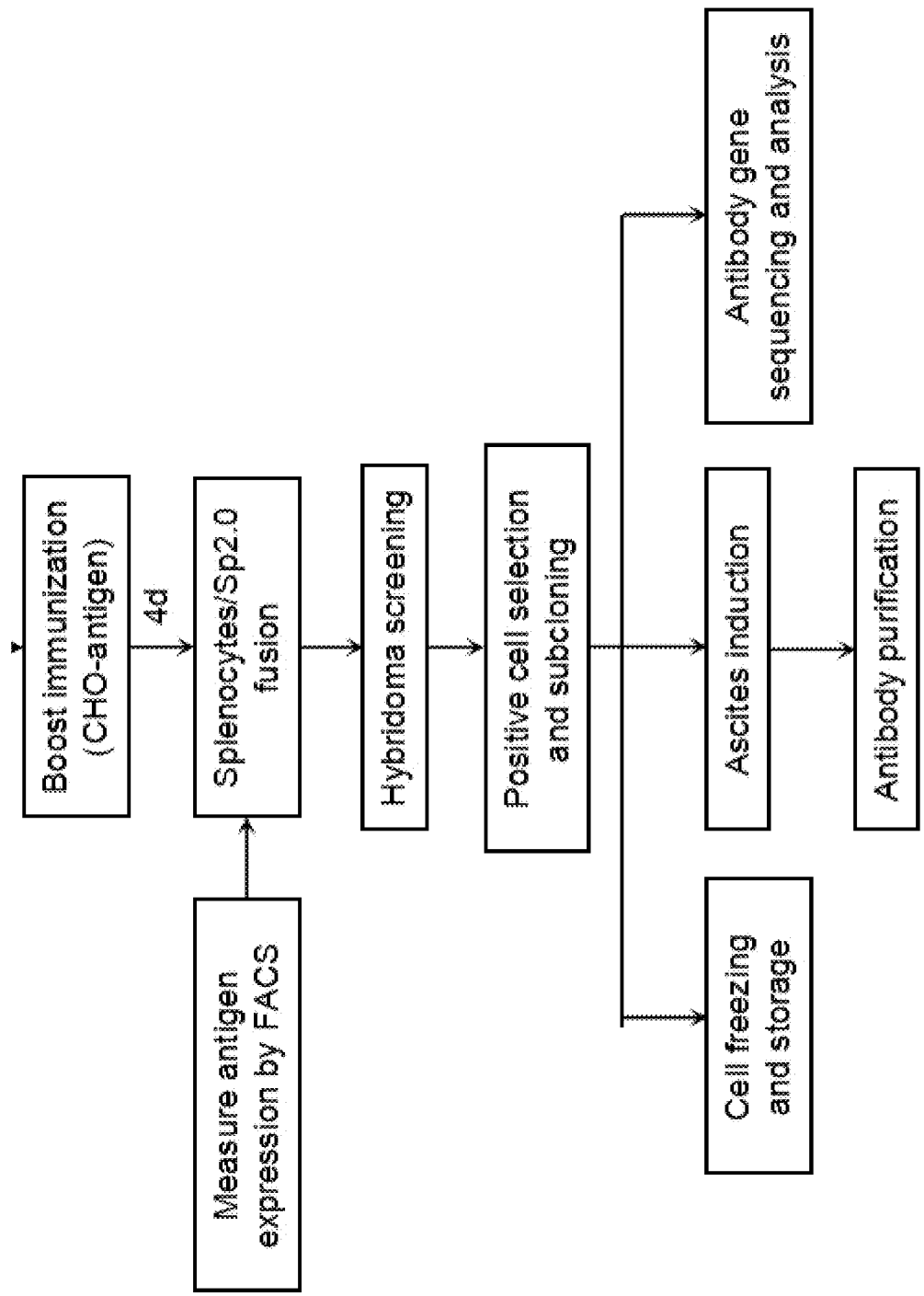
FIG. 2 is a flow chart showing the second part of an exemplary protocol of making anti-h4-1BB antibodies.

To generate mouse antibodies against human 4-1BB (h4-1BB; SEQ ID NO: 217), 6-8 weeks old female BALB/c mice were immunized with human 4-1BB. Anti-h4-1BB antibodies were collected by the methods as described below and shown in FIG. 1 and FIG. 2.

Immunization of Mice 6-8 weeks old female BALB/c mice were immunized with His-tagged human 4-1BB proteins at 20 µg/mouse at a concentration of 100 µg/ml. The His-tagged human 4-1BB proteins were emulsified with adjuvant and injected at four positions on the back of the mice. For the first subcutaneous (s.c.) injection, the diluted antigen was emulsified with Complete Freund's Adjuvant (CFA) in equal volume. In the following subcutaneous injections, the protein was emulsified with Incomplete Freund's Adjuvant (IFA) in equal volume. Three days after the third injection or the booster immunization, blood (serum) was collected and analyzed for antibody titer using ELISA.

In another experiment, 6-8 weeks old female BALB/c mice were immunized by injecting the expression plasmid encoding human 4-1BB into the mice. The plasmids encoding the antigen were injected into the tibialis anterior muscle (intramuscular injection; i.m. injection) of the mice by using gene guns at the concentration of 1000 µg/ul at 60 µg per mouse. At least four injections were performed with at least 14 days between two injections. Blood (serum) was collected seven days after the last immunization and the serum was tested for antibody titer by ELISA.

Procedures to enhance immunization were also performed at least fourteen days after the previous immunization (either by injecting the plasmid or by injecting the proteins). CHO cells that express 4-1BB antigen on the surface were intravenously injected into the mice through tail veins. Spleen was then collected four days after the injection.

Fusion of SP2/0 Cells and Spleen Cells

Spleen tissues were grinded. Spleen cells were first selected by CD3c Microbeads and anti-Mouse IgM Microbeads, and then fused with SP2/0 cells. The cells were then plated in 96-well plates with hypoxanthine-aminopterin-thymidine (HAT) medium.

Primary Screening of Hybridoma

Primary screening of the hybridoma supernatant in the 96-well plates was performed using Fluorescence-Activated Cell Sorting (FACS) pursuant to standard procedures. Chinese hamster ovary (CHO) cells were added to 96-well plates ($2\times10^4$ cells per well) before the screening. 50 µl of supernatant was used. The antibodies that were used in experiments were (1) Fluorescein (FITC)-conjugated AffiniPure F(ab)$_2$ Fragment Goat Anti-Mouse IgG, Fcγ Fragment Specific, and (2) Alexa Fluor® 647-conjugated AffiniPure F(ab)$_2$ Fragment Goat Anti-Human IgG, Fcγ Fragment Specific.

Sub-Cloning

Sub-cloning was performed using ClonePix2. In short, the positive wells identified during the primary screening were transferred to semisolid medium, and IgG positive clones were identified and tested. FITC anti-mouse IgG Fc antibody was used.

Ascites Fluid Antibodies $1\times10^6$ positive hybridoma cells were injected intraperitoneally to B-NDG™ mice (Beijing Biocytogen, Beijing, China). Monoclonal antibodies were produced by growing hybridoma cells within the peritoneal cavity of the mouse. The hybridoma cells multiplied and produced ascites fluid in the abdomens of the mice. The fluid contained a high concentration of antibody which can be harvested for later use.

Purification of Antibodies

Antibodies in ascites fluid were purified using GE AKTA protein chromatography (GE Healthcare, Chicago, Ill., United States). At least 27 mouse antibodies were produced. A few antibodies were selected because of the desired properties. These selected mouse antibodies produced by the methods described above include e.g., 16-1C4 ("1C4"), 29-6A5 ("6A5"), 30-5F9 ("5F9"), 45-2B3 ("2B3"), 45-4B9 ("4B9"), 45-7E9 ("7E9"), 45-7G9 ("7G9"), 45-8E11 ("8E11"), 45-8E2 ("8E2"), 45-8F1 ("8F1"), 54-8B11 ("8B11"), 55-8F6 ("8F6"), 56-2A6 ("2A6"), 59-5E4 ("5E4"), 61-6A7 ("6A7"), 69-3C2 ("3C2"), 70-3F9 ("3F9"), and 70-6F10 ("6F10"), etc.

The VH, VL and CDR regions of the antibodies were determined. The heavy chain CDR1, CDR2, CDR3, and light chain CDR1, CDR2, and CDR3 amino acid sequences of these antibodies are shown in Table 1, FIG. 52 and FIG. 53.

Example 2. Humanization of the Mouse Antibodies

The starting point for humanization was the mouse antibodies (e.g., 1C4, 6A5, and 5F9). The amino acid sequences for the heavy chain variable region and the light chain variable region of these mouse antibodies were determined.

Four humanized heavy chain variable region variants (SEQ ID NOs: 221-224) and four humanized light chain variable region variants (SEQ ID NOs: 225-228) for 1C4 were constructed, containing different modifications or substitutions.

Three humanized heavy chain variable region variants (SEQ ID NOs: 229-231) and four humanized light chain variable region variants (SEQ ID NOs: 232-235) for 6A5 were constructed, containing different modifications or substitutions.

Three humanized heavy chain variable region variants (SEQ ID NOs: 236-238) and four humanized light chain variable region variants (SEQ ID NOs: 239-242) for 5F9 were constructed, containing different modifications or substitutions.

These humanized heavy chain variable region variants can be combined with any of the light chain variable region variants derived from the same mouse antibody. For example, 1C4-H1 (SEQ ID NO: 221) can be combined with any humanized light chain variable region variant based on the same mouse antibody 1C4 (e.g., SEQ ID NO: 225-228), and the antibody will be labeled accordingly. For example, if 1C4-H1 is combined with 1C4-K3 (SEQ ID NO: 227), the antibody is labeled as 1C4-H1K3.

Example 3. Binding Activity of Anti-h4-1BB Antibodies Against Human 4-1BB

The anti-h4-1BB antibodies were collected from mouse ascites fluid and purified by chromatography. 25 μl CHO cells transiently transfected with human 4-1BB were added to each well in a plate. The purified antibodies were titrated to final concentrations of 10, 1, 0.1, 0.01, 0.001 μg/ml. The titrated antibodies were added to each well at 4° C. and incubated for 30 minutes.

After being washed with phosphate-buffered saline (PBS) (1200 rpm, 5 minutes) twice, 50 μl of FITC labeled anti-mouse IgG Fc antibody (anti-mIgG Fc-FITC) at 1:100 dilution was added into each well, and incubated for 30 minutes at 4° C., followed by PBS wash (1200 rpm, 5 minutes). The signal for FITC was detected by flow cytometry.

Figure 3:
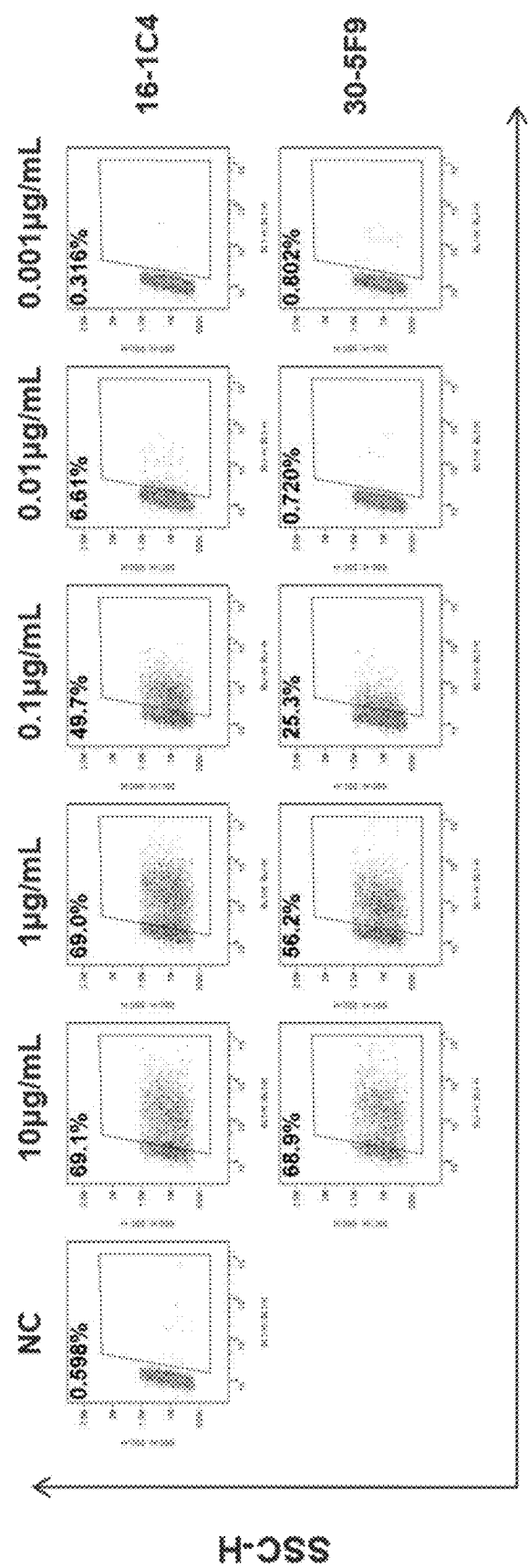
FIG. 3 is a set of flow cytometry results showing that the binding activity of anti-h4-1BB antibodies with human 4-1BB.

As shown in FIG. 3, 1C4 and 5F9 had strong binding activity with h4-1BB. In FIG. 3, NC stands for negative control.

The table below summarizes the percentage of tested cells that had FITC signals in the flow cytometry analysis. A higher percentage at a lower antibody concertation indicates a higher binding affinity.

TABLE 4

| Antibody | 10 μg/ml | 1 μg/ml | 0.1 μg/ml | 0.01 μg/ml | 0.001 μg/ml |
| --- | --- | --- | --- | --- | --- |
| 16-1C4 | 69.1% | 69.0% | 49.7% | 6.61% | 0.316% |
| 29-6A5 | 80.5% | 73.4% | 70.8% | 47.4% | NA |
| 30-5F9 | 68.9% | 56.2% | 25.3% | 0.720% | 0.802% |
| 45-2B3 | 62.2% | 51.8% | 12.0% | 0.622% | 0.504% |
| 45-4B9 | 56.2% | 49.3% | 10.4% | 1.20% | 1.86% |
| 45-7G9 | 57.6% | 58.4% | 50.0% | 12.7% | 0.703% |
| 45-7G9 | 57.9% | 55.1% | 25.9% | 0.960% | 1.00% |
| 45-8E2 | 58.9% | 60.1% | 49.8% | 9.06% | 1.52% |
| 45-8F1 | 58.6% | 56.1% | 43.9% | 6.21% | 1.38% |
| 54-8B11 | 49.8% | 45.0% | 16.5% | 0.445% | 0.111% |
| 55-8F6 | 53.6% | 52.3% | 36.1% | 0.571% | 0.375% |
| 56-2A6 | 46.6% | 40.9% | 17.1% | 0.890% | 0.250% |
| 61-6A7 | 63.0% | 60.1% | 51.1% | 17.0% | 3.43% |
| 69-3C2 | 58.5% | 62.9% | 52.3% | 26.2% | 0.183% |
| 70-3F9 | 56.7% | 56.4% | 9.06% | 3.37% | 1.25% |
| 70-6F10 | 52.9% | 23.7% | 1.14% | 0.913% | 0.962% |

Example 4. Cross-Reactivity of Anti-h4-1BB Antibodies Against Monkey, Mouse, and Human-Mouse Chimeric 4-1BB In each experiment, the CHO cells were transfected with mouse 4-1BB (m4-1BB, SEQ ID NO: 218), monkey (rhesus macaque) 4-1BB (r4-1BB, SEQ ID NO: 219), or chimeric (mouse and human) 4-1BB (c4-1BB, SEQ ID NO: 220).

25 μl CHO cells were added to each well. 25 μl purified anti-h4-1BB antibodies (1 μg/ml) were added to each well and were incubated at 4° C. for 30 minutes.

After being washed with PBS (1200 rmp, 5 min) twice, 50 μl of FITC labeled anti-mouse IgG Fc antibody (anti-mIgG Fc-FITC) was added into each well at 1:100 dilution, followed by incubating at 4° C. for 30 minutes, and then PBS wash (1200 rmp, 5 min). In some cases, PE labeled anti-mouse IgG Fc antibody (anti-mIgG Fc-PE) was used to label the antibody instead, and was added into each tested well at 1:500 dilution. The signals for FITC and PE were determined by flow cytometry.

Figure 4:
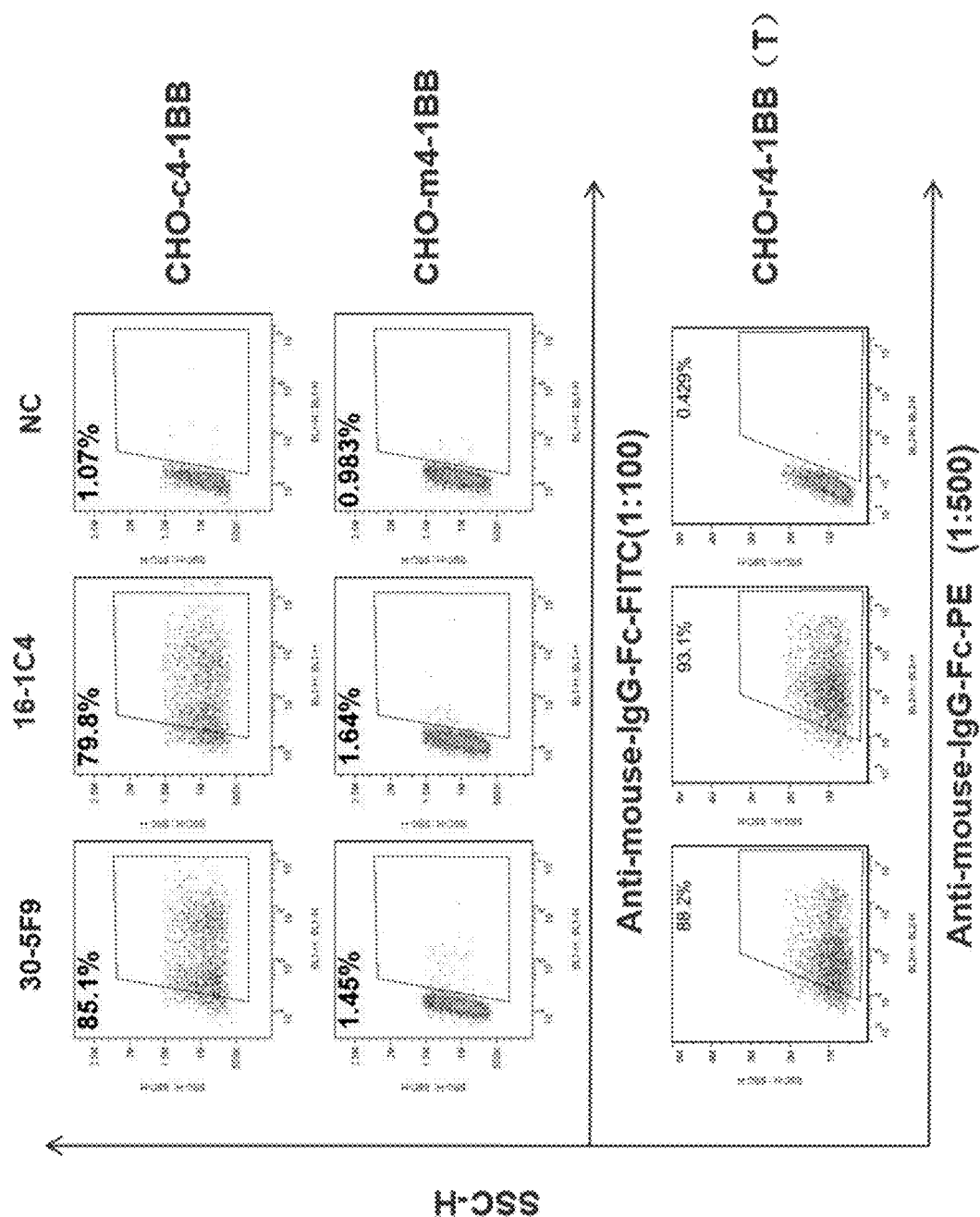
FIG. 4 is a set of graphs showing flow cytometry results of analyzing the anti-h4-1BB antibodies' cross-reactivity with monkey 4-1BB (CHO-r4-1BB), mouse 4-1BB (CHOm4-1BB), and human-mouse chimeric 4-1BB (CHO-c4-1BB). NC stands for negative control.

As shown in FIG. 4, 1C4 and 5F9 did not cross react with mouse 4-1BB, but had strong cross reactivity with monkey 4-1BB (r4-1BB) and strong cross reactivity with chimeric 4-1BB (c4-1BB). In FIG. 4, NC stands for negative control.

The cross reactivity for the tested antibodies with monkey (r4-1BB), mouse (m4-1BB), and human-mouse chimeric 4-1BB (c4-1BB) is summarized in the table below.

TABLE 5

| | h4-1BB (human) | r4-1BB (Monkey) | m4-1BB (Mouse) | c4-1BB (Chimeric) |
| --- | --- | --- | --- | --- |
| 16-1C4 | Yes | Yes | No | Yes |
| 30-5F9 | Yes | Yes | No | Yes |
| 29-4A10 | Yes | Yes | No | Yes |
| 29-5F10 | Yes | Yes | No | Yes |
| 29-6A5 | Yes | Yes | No | Yes |
| 45-4B9 | Yes | Yes | No | Yes |
| 45-8F1 | Yes | Yes | No | Yes |
| 45-2B3 | Yes | Yes | No | Yes |
| 45-2C11 | Yes | Yes | No | Yes |
| 45-7E9 | Yes | Yes | No | Yes |
| 45-7G9 | Yes | Yes | No | Yes |
| 45-8E2 | Yes | Yes | No | Yes |
| 54-8B11 | Yes | Yes | No | Yes |
| 54-1A11 | Yes | Yes | No | Yes |
| 55-1E3 | Yes | Yes | No | Yes |
| 55-8H5 | Yes | Yes | No | Yes |
| 55-8F6 | Yes | Yes | No | Yes |
| 56-1G6 | Yes | No | No | Yes |
| 61-6A7 | Yes | Yes | No | Yes |
| 58-4B8 | Yes | Yes | No | Yes |
| 56-2A6 | Yes | Very weak | No | Yes |
| 69-3C2 | Yes | Yes | No | Yes |
| 70-3F9 | Yes | Yes | No | Yes |
| 70-6F10 | Yes | Yes | No | Yes |
| 69-4B11 | Yes | Yes | No | Yes |

Example 5. Binding Affinity of Anti-h4-1BB Antibodies

The binding affinity of the anti-h4-1BB antibodies were measured using surface plasmon resonance (SPR) using Biacore (Biacore, INC, Piscataway N.J.) T200 biosensor equipped with pre-immobilized Protein A sensor chips.

Figure 5:
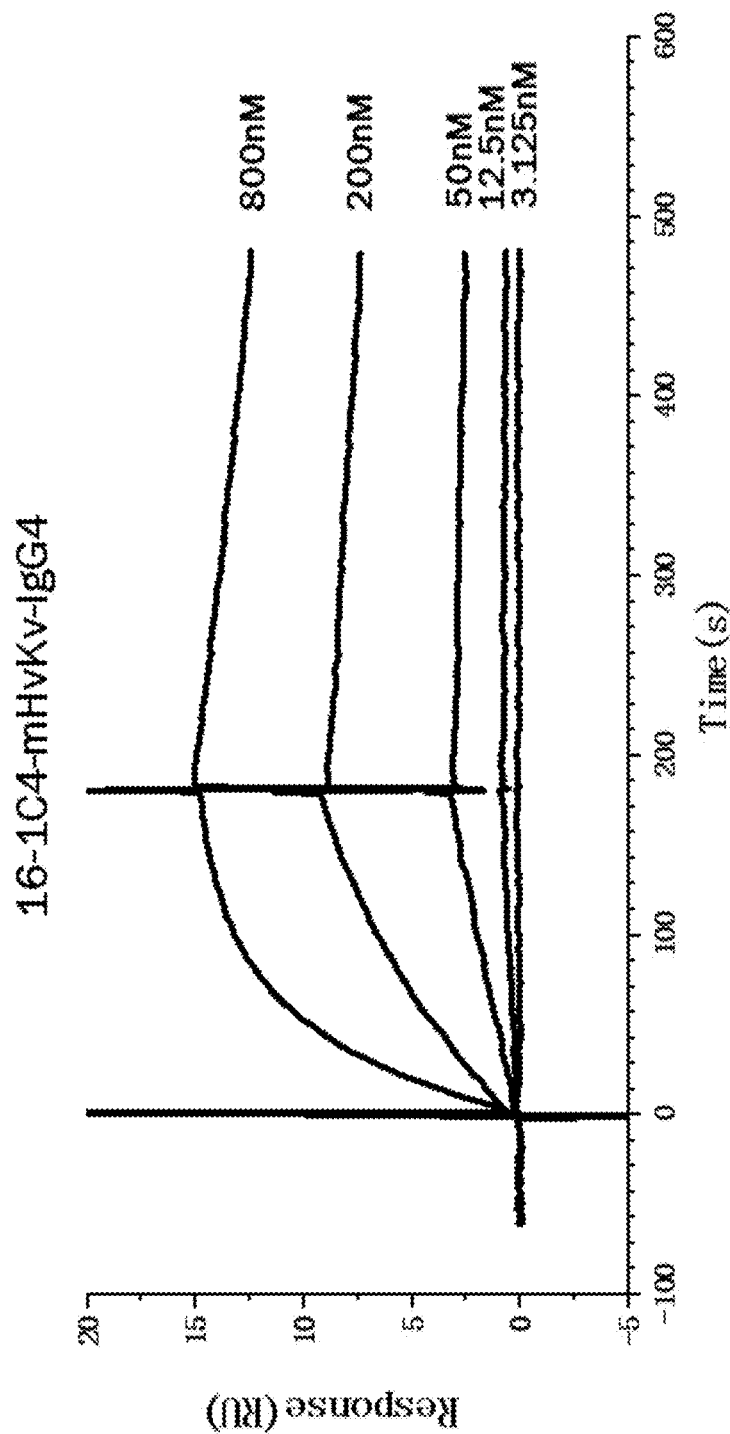
FIG. 5 is a graph showing the results of surface plasma resonance (SPR) using the chimeric anti-h4-1BB antibody 16-1C4-mHvKv-IgG4 and human 4-1BB.

Chimeric anti-h4-1BB antibody 16-1C4-mHvKv-IgG4 (1 μg/mL) were injected into Biacore T200 biosensor at 10 μL/min for 20 seconds to achieve to a desired protein density (about 51.6 response units (RU)). Histidine-tagged human 4-1BB proteins (h4-1BB-His) at the concentration of 800, 200, 50, 12.5, 3.125 nM were then injected at 30 μL/min for 180 seconds. Dissociation was monitored for 300 seconds. The chip was regenerated after the last injection of each titration with Glycine (pH 2.0, 30 μL/min for 5 seconds). The result for 16-1C4-mHvKv-IgG4 is shown in FIG. 5.

Kinetic association rates (kon) and dissociation rates (koff) were obtained simultaneously by fitting the data globally to a 1:1 Langmuir binding model (Karlsson, R. Roos, H. Fagerstam, L. Petersson, B., 1994. Methods Enzymology 6. 99-110) using Biacore T200 Evaluation Software 3.0. Affinities were calculated from the quotient of the kinetic rate constants (KD=koff/kon).

Figure 6:
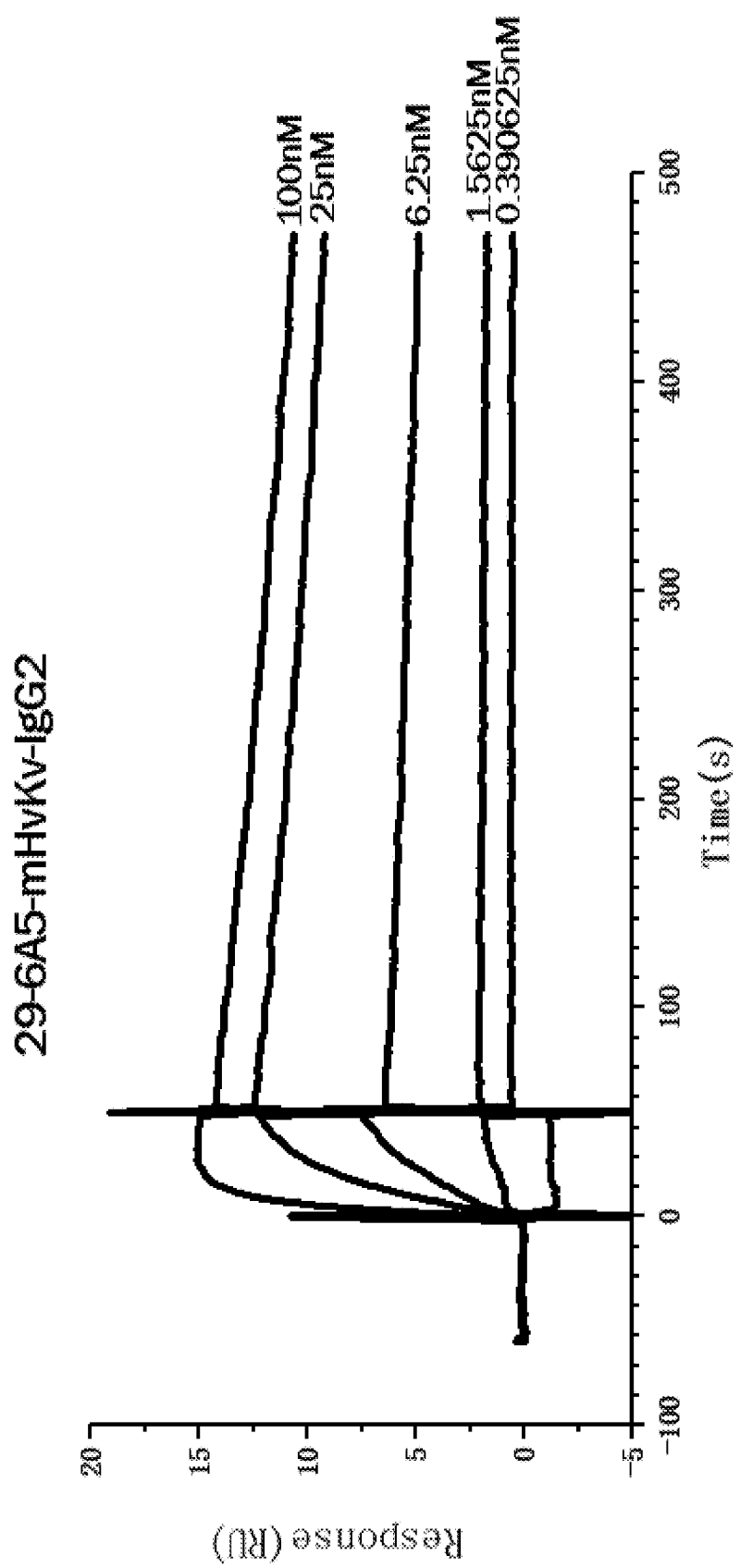
FIG. 6 is a graph showing the results of surface plasma resonance (SPR) using the chimeric anti-h4-1BB antibody 29-6A5-mHvKv-IgG2 and human 4-1BB.

As a person of ordinary skill in the art would understand, the same method with appropriate adjustments for parameters (e.g., antibody concentration) was performed for each tested antibody. For example, the results of 29-6A5-mHvKv-IgG2 are shown in FIG. 6. The results for the tested antibodies are summarized in the table below.

TABLE 6

| Anti-h4-1BB antibodies | Association rate kon (1/Ms) | Dissociation rate koff (1/s) | Affinity KD (M) |
| --- | --- | --- | --- |
| 16-1C4-mHvKv-IgG4 | 2.44E+04 | 5.02E-04 | 2.05E-08 |
| 29-6A5-mHvKv-IgG2 | 1.93E+06 | 7.15E-04 | 3.71E-10 |
| 30-5F9-mHvKv-IgG4 | 2.49E+05 | 2.47E-03 | 9.91E-09 |
| 45-2B3-mHvKv-IgG2 | 2.77E+04 | 1.38E-04 | 4.96E-09 |
| 45-4B9-mHvKv-IgG2 | 2.72E+04 | 2.98E-03 | 1.10E-07 |
| 45-7E9-mHvKv-IgG2 | 6.00E+05 | 9.16E-03 | 1.53E-08 |
| 45-7G9-mHvKv-IgG2 | 1.77E+05 | 4.10E-03 | 2.31E-08 |
| 45-8E11-mHvKv-IgG2 | 2.14E+05 | 1.27E-04 | 5.97E-10 |
| 45-8E2-mHvKv-IgG2 | 3.23E+05 | 4.13E-04 | 1.28E-09 |
| 45-8F1-mHvKv-IgG2 | 4.70E+04 | 2.93E-03 | 6.23E-08 |
| 54-8B11-mHvKv-IgG2 | 4.17E+05 | 5.02E-03 | 1.20E-08 |
| 55-8F6-mHvKv-IgG2 | 1.57E+06 | 3.41E-03 | 2.18E-09 |
| 56-2A6-mHvKv-IgG2 | 1.01E+05 | 1.41E-03 | 1.40E-08 |
| 59-5E4-m HvKv -IgG2 | 1.06E+06 | 3.31E-04 | 3.13E-10 |
| 61-6A7-mHvKv-IgG2 | 1.43E+06 | 5.13E-04 | 3.59E-10 |
| 69-3C2-mHvKv-IgG2 | 1.16E+06 | 5.21E-04 | 4.50E-10 |
| 70-3F9-mHvKv-IgG2 | 9.99E+05 | 1.59E-04 | 1.60E-10 |
| 70-6F10-mHvKv-IgG2 | 2.41E+04 | 2.63E-04 | 1.09E-08 |
| urelumab | 6.81E+04 | 3.02E-03 | 4.43E-08 |
| utomllumab | 1.55E+06 | 1.07E-02 | 6.93E-09 |
| 1C4-H1K1-IgG4 | 2.67E+04 | 6.16E-04 | 2.31E-08 |
| 1C4-H1K2-IgG4 | 2.75E+04 | 6.05E-04 | 2.20E-08 |
| 1C4-H1K3-IgG4 | 2.85E+04 | 6.23E-04 | 2.18E-08 |
| 1C4-H1K4-IgG4 | 2.57E+04 | 6.14E-04 | 2.39E-08 |
| 1C4-H2K1-IgG4 | 2.59E+04 | 5.02E-04 | 1.94E-08 |
| 1C4-H2K2-IgG4 | 2.58E+04 | 6.46E-04 | 2.51E-08 |
| 1C4-H2K3-IgG4 | 2.85E+04 | 5.02E-04 | 1.76E-08 |
| 1C4-H2K4-IgG4 | 2.52E+04 | 5.21E-04 | 2.07E-08 |
| 1C4-H3K2-IgG4 | 2.77E+04 | 4.53E-04 | 1.63E-08 |
| 1C4-H3K3-IgG4 | 3.12E+04 | 5.33E-04 | 1.71E-08 |
| 1C4-H3K4-IgG4 | 3.00E+04 | 4.76E-04 | 1.59E-08 |
| 1C4-H4K1-IgG4 | 2.84E+04 | 5.16E-04 | 1.82E-08 |
| 1C4-H4K2-IgG4 | 2.96E+04 | 4.90E-04 | 1.66E-08 |
| 1C4-H4K3-IgG4 | 3.29E+04 | 5.56E-04 | 1.69E-08 |
| 1C4-H4K4-IgG4 | 2.90E+04 | 5.60E-04 | 1.93E-08 |
| 5F9-H1K1-IgG4 | 2.22E+05 | 2.53E-03 | 1.14E-08 |
| 5F9-H1K2-IgG4 | 2.05E+05 | 2.47E-03 | 1.20E-08 |
| 5F9-H1K3-IgG4 | 2.06E+05 | 2.08E-03 | 1.01E-08 |
| 5F9-H1K4-IgG4 | 2.46E+05 | 2.44E-03 | 9.95E-09 |
| 5F9-H2K1-IgG4 | 2.02E+05 | 2.25E-03 | 1.12E-08 |
| 5F9-H2K2-IgG4 | 1.94E+05 | 2.61E-03 | 1.34E-08 |
| 5F9-H2K3-IgG4 | 2.12E+05 | 2.07E-03 | 9.81E-09 |
| 5F9-H2K4-IgG4 | 2.16E+05 | 2.69E-03 | 1.24E-08 |
| 5F9-H3K1-IgG4 | 1.98E+05 | 2.42E-03 | 1.22E-08 |
| 5F9-H3K2-IgG4 | 1.88E+05 | 2.58E-03 | 1.37E-08 |
| 5F9-H3K3-IgG4 | 2.10E+05 | 2.20E-03 | 1.05E-08 |
| 5F9-H3K4-IgG4 | 2.36E+05 | 2.70E-03 | 1.14E-08 |
| 6A5-H1K1-IgG2 | 2.85E+13 | 3.33E+04 | 1.17E-09 |
| 6A5-H1K2-IgG2 | 2.38E+06 | 6.62E-04 | 2.78E-10 |
| 6A5-H1K3-IgG2 | 2.22E+06 | 4.75E-04 | 2.14E-10 |
| 6A5-H1K4-IgG2 | 2.16E+06 | 6.93E-04 | 3.21E-10 |
| 6A5-H2K1-IgG2 | 6.68E+05 | 1.55E-03 | 2.32E-09 |
| 6A5-H2K2-IgG2 | 2.33E+06 | 6.52E-04 | 2.80E-10 |
| 6A5-H2K3-IgG2 | 2.28E+06 | 5.04E-04 | 2.21E-10 |
| 6A5-H2K4-IgG2 | 2.24E+06 | 5.81E-04 | 2.60E-10 |
| 6A5-H3K1-IgG2 | 6.50E+05 | 1.81E-03 | 2.78E-09 |
| 6A5-H3K2-IgG2 | 2.05E+06 | 8.25E-04 | 4.02E-10 |
| 6A5-H3K3-IgG2 | 2.14E+06 | 5.38E-04 | 2.52E-10 |
| 6A5-H3K4-IgG2 | 1.87E+06 | 7.47E-04 | 4.00E-10 |

As described in Example 1, 16-1C4, 29-6A5, 30-5F9, 45-2B3, 45-4B9, 45-7E9, 45-7G9, 45-8E11, 45-8E2, 45-8F1, 54-8B11, 55-8F6, 56-2A6, 59-5E4, 61-6A7, 69-3C2, 70-3F9, and 70-6F10 are mouse anti-h4-1BB antibodies. Based on these mouse anti-h4-1BB antibodies, the chimeric anti-h4-1BB antibodies including e.g., 16-1C4-mHvKv-IgG4, 29-6A5-mHvKv-IgG2, 30-5F9-mHvKv-IgG4, 45-2B3-mHvKv-IgG2, 45-4B9-mHvKv-IgG2, 45-7E9-mHvKv-IgG2, 45-7G9-mHvKv-IgG2, 45-8E11-mHvKv-IgG2, 45-8E2-mHvKv-IgG2, 45-8F1-mHvKv-IgG2, 54-8B11-mHvKv-IgG2, 55-8F6-mHvKv-IgG2, 56-2A6-mHvKv-IgG2, 59-5E4-mHvKv-IgG2, 61-6A7-mHvKv-IgG2, 69-3C2-mHvKv-IgG2, 70-3F9-mHvKv-IgG2, and 70-6F10-mHvKv-IgG2 were generated. The chimeric antibodies have the heavy chain variable domain and the light chain variable domain from the corresponding mouse anti-h4-1BB antibodies, and the constant domains from human IgG antibodies (including, e.g., the CL, CH1, CH2, and CH3 domains).

The tested antibodies also include humanized antibodies, e.g., 1C4-H1K1-IgG4, 1C4-H1K2-IgG4, 1C4-H1K3-IgG4, 1C4-H1K4-IgG4, 1C4-H2K1-IgG4, 1C4-H2K2-IgG4, 1C4-H2K3-IgG4, 1C4-H2K4-IgG4, 1C4-H3K1-IgG4, 1C4-H3K2-IgG4, 1C4-H3K3-IgG4, 1C4-H3K4-IgG4, 1C4-H4K1-IgG4, 1C4-H4K2-IgG4, 1C4-H4K3-IgG4, 1C4-H4K4-IgG4, 5F9-H1K1-IgG4, 5F9-H1K2-IgG4, 5F9-H1K3-IgG4, 5F9-H1K4-IgG4, 5F9-H2K1-IgG4, 5F9-H2K2-IgG4, 5F9-H2K3-IgG4, 5F9-H2K4-IgG4, 5F9-H3K1-IgG4, 5F9-H3K2-IgG4, 5F9-H3K3-IgG4, 5F9-H3K4-IgG4, 6A5-H1K1-IgG2, 6A5-H1K2-IgG2, 6A5-H1K3-IgG2, 6A5-H1K4-IgG2, 6A5-H2K1-IgG2, 6A5-H2K2-IgG2, 6A5-H2K3-IgG2, 6A5-H2K4-IgG2, 6A5-H3K1-IgG2, 6A5-H3K2-IgG2, 6A5-H3K3-IgG2, and 6A5-H3K4-IgG2, etc. The humanized antibodies have human antibody constant domains (including, e.g., the CL, CH1, CH2, and CH3 domains). The humanized variable domains of the heavy chain are numbered H1, H2, H3 etc.; and the humanized variable domains of the light chain are numbered K1, K2, K3 etc. The sequences of the humanized variable domains are summarized in FIG. 55, FIG. 56, and FIG. 57. For example, 1C4-H1K1-IgG4 is based on the mouse antibody 1C4 and has the humanized heavy chain variable domain H1 (SEQ ID NO: 221) and humanized light chain variable domain K1 (SEQ ID NO: 225). Similarly, 5F9-H1K2-IgG4 is based on mouse antibody 5F9 and has humanized heavy chain variable domain H1 (SEQ ID NO: 236) and humanized light chain variable domain K2 (SEQ ID NO: 240).

Example 6. Thermal Stability of Anti-h4-1BB Antibodies

Thermofluor assay was performed using the Protein Thermal Shift™ Dye Kit (Thermo Fisher Scientific) and QuantStudio™ 5 Real Time PCR Systems (Thermo Fisher Scientific). This assay measured thermostability using a fluorescent dye that binds to hydrophobic patches exposed as the protein unfolds.

The experiments were performed according to the manufacturer's protocol. 2 µL of antibody, 10.5 µL of water, 5 µL of Protein Thermal Shift buffer, and 2.5 µL of diluted Protein Thermal Shift Dye were mixed. Samples were heated to 25° C. at 1.6° C./second, and then heated to 99° C. at 0.05° C./second.

The table below summarizes the Tm for several humanized or chimeric anti-h4-1BB antibodies.

TABLE 7

| Antibody | Variable Domains | Type (constant domains) | Thermal stability (Tm D2 (Fab) ° C.) |
|---|---|---|---|
| 1C4-H1K1-IgG4 | 1C4 H1K1 | Human IgG4 | 80.60 |
| 1C4-H1K2-IgG4 | 1C4 H1K2 | Human IgG4 | 80.38 |
| 16-1C4-mHvKv-IgG1 | 1C4 mHvKv | Human IgG1 | 78.09 |
| 16-1C4-mHvKv-IgG2 | 1C4 mHvKv | Human IgG2 | 78.16 |
| 16-1C4-mHvKv-IgG4 | 1C4 mHvKv | Human IgG4 | 77.79 |
| 5F9-H1K1-IgG4 | 5F9 H1K1 | Human IgG4 | 80.23 |
| 5F9-H1K2-IgG4 | 5F9 H1K2 | Human IgG4 | 80.08 |
| 30-5F9-mHvKv-IgG2 | 5F9 mHvKv | Human IgG2 | 80.60 |
| 30-5F9-mHvKv-IgG4 | 5F9 mHvKv | Human IgG4 | 80.01 |
| 6A5-H2K2-IgG2 | 6A5 H2K2 | Human IgG2 | 88.66 |
| 6A5-H2K3-IgG2 | 6A5 H2K3 | Human IgG2 | 88.29 |
| 6A5-H1K3-IgG2 | 6A5 H1K3 | Human IgG2 | 88.43 |
| 6A5-H1K2-IgG2 | 6A5 H1K2 | Human IgG2 | 88.36 |
| Utomilumab | Human | Human IgG2 | 72.61 |
| Urelumab | Human | Human IgG4 | 59.90 |

The results show that the anti-h4-1BB antibodies described herein have a higher Tm than utomilumab and urelumab.

Example 7. In Vivo Testing of Mouse Anti-h4-1BB Antibodies

In order to test the anti-h4-1BB antibodies in vivo and to predict the effects of these antibodies in human, a humanized 4-1BB mouse model was generated. The humanized 4-1BB mouse model was engineered to express a chimeric 4-1BB protein (SEQ ID NO: 220) wherein a part of the extracellular region of the mouse 4-1BB protein was replaced with the corresponding human 4-1BB extracellular region. The amino acid residues 1-183 of mouse 4-1BB (SEQ ID NO: 218) were replaced by amino acid residues 1-184 of human 4-1BB (SEQ ID NO: 217). The humanized mouse model (B-h4-1BB) provides a new tool for testing new therapeutic treatments in a clinical setting by significantly decreasing the difference between clinical outcome in human and in ordinary mice expressing mouse 4-1BB. A detailed description regarding humanized 4-1BB mouse model can be found in PCT/CN2017/120388, which is incorporated herein by reference in its entirety.

The anti-h4-1BB antibodies were tested for their effect on tumor growth in vivo in a model of colon carcinoma. About $5 \times 10^5$ MC-38 cancer tumor cells (colon adenocarcinoma cell) were injected subcutaneously in B-h4-1BB mice. When the tumors in the mice reached a volume of $150 \pm 50$ mm$^3$, the mice were randomly placed into different groups based on the volume of the tumor.

The mice were then injected with physiological saline (PS) and anti-h4-1BB antibodies by intraperitoneal (i.p.) administration.

The injected volume was calculated based on the weight of the mouse at 1 mg/kg or 3 mg/kg. The length of the long axis and the short axis of the tumor were measured and the volume of the tumor was calculated as $0.5 \times (\text{long axis}) \times (\text{short axis})^2$. The weight of the mice was also measured before the injection, when the mice were placed into different groups (before the first antibody injection), twice a week during the antibody injection period, and before euthanization.

The tumor growth inhibition percentage (TGI %) was calculated using the following formula: TGI (%)=[1−(Ti−T0)/(Vi−V0)]×100. Ti is the average tumor volume in the treatment group on day i. TO is the average tumor volume in the treatment group on day zero. Vi is the average tumor volume in the control group on day i. VO is the average tumor volume in the control group on day zero.

T-test was performed for statistical analysis. A TGI % higher than 60% indicates clear suppression of tumor growth. $P<0.05$ is a threshold to indicate significant difference.

In Vivo Results for Mouse Anti-h4-1BB Antibodies 16-1C4 ("1C4") and 30-5F9 ("5F9")

In each group, B-h4-1BB mice were injected with physiological saline (PS) (G1), 1 mg/kg Urelumab (G2), 3 mg/kg Urelumab (G3), 1 mg/kg of the mouse anti-h4-1BB antibody 16-1C4 (G4), 3 mg/kg of 16-1C4 (G5), 1 mg/kg of the mouse anti-h4-1BB antibody 30-5F9 (G6) or 3 mg/kg of 30-5F9 (G7).

TABLE 8

| Group | No. of mice | Antibodies | Dosage (mg/kg) | Route | Frequency | Total No. of administration |
|---|---|---|---|---|---|---|
| G1 | 5 | PS (control) | — | i.p. | Day 1, 4/wk | 6 |
| G2 | 5 | Urelumab | 1 mg/kg | i.p. | Day 1, 4/wk | 6 |
| G3 | 5 | Urelumab | 3 mg/kg | i.p. | Day 1, 4/wk | 6 |
| G4 | 5 | 16-1C4 | 1 mg/kg | i.p. | Day 1, 4/wk | 6 |
| G5 | 5 | 16-1C4 | 3 mg/kg | i.p. | Day 1, 4/wk | 6 |
| G6 | 5 | 30-5F9 | 1 mg/kg | i.p. | Day 1, 4/wk | 6 |
| G7 | 5 | 30-5F9 | 3 mg/kg | i.p. | Day 1, 4/wk | 6 |

Figure 7:
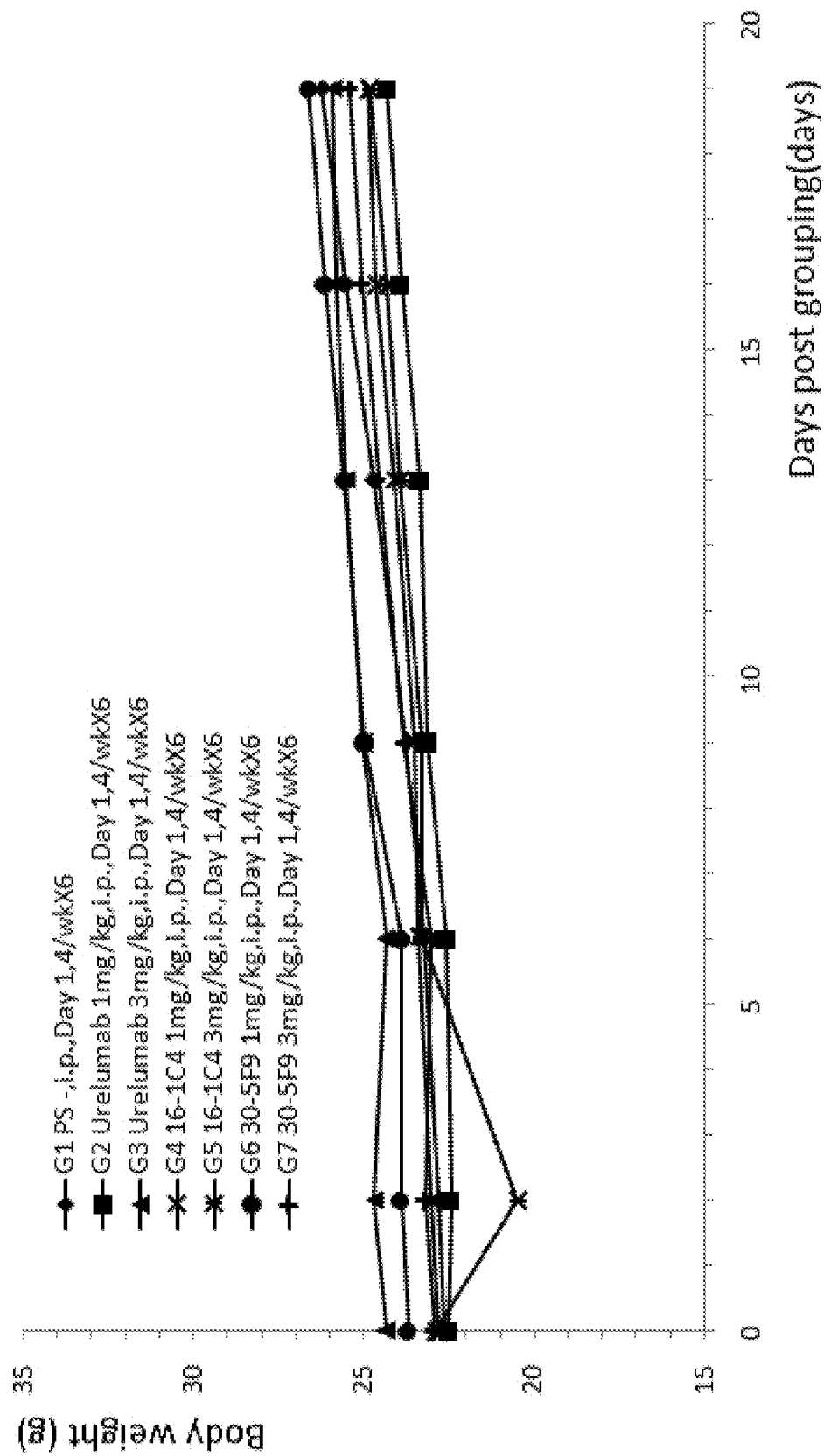
FIG. 7 is a graph showing body weight over time of humanized 4-1BB mice (B-h4-1BB) with MC-38 tumor cells treated with mouse anti-h4-1BB antibodies 1C4 and 5F9, and urelumab.
Figure 8:
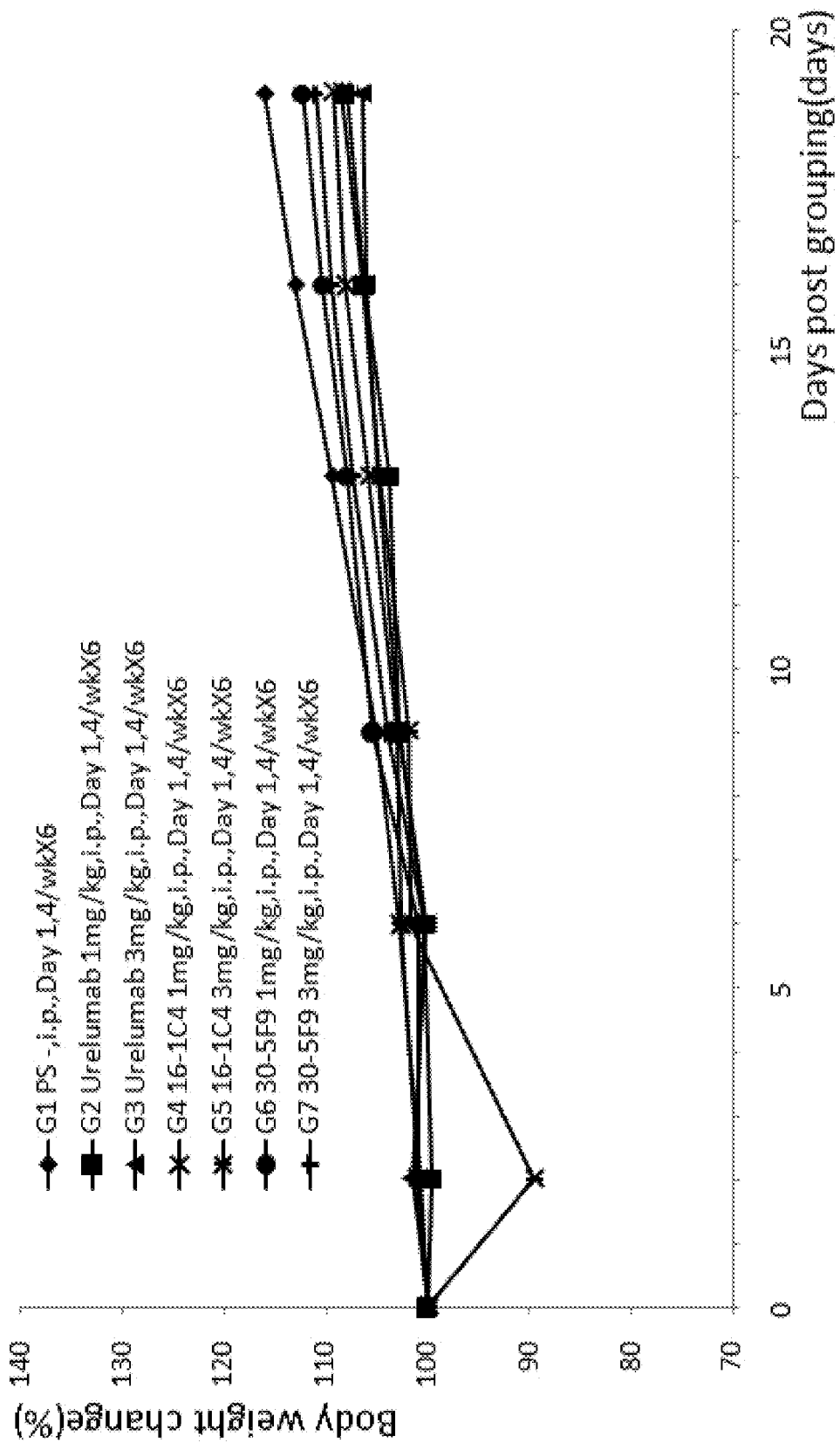
FIG. 8 is a graph showing percentage change of body weight over time of humanized 4-1BB mice (B-h4-1BB) with MC-38 tumor cells treated with mouse anti-h4-1BB antibodies 1C4 and 5F9, and urelumab.

The weight of the mice was monitored during the entire treatment period. The average weight of mice in different groups all increased to different extents (FIG. 7, and FIG. 8). No obvious difference in weight was observed among different groups at the end of the treatment periods. The results showed that 1C4 and 6A5 were well tolerated and were not obviously toxic to the mice.

Figure 9:
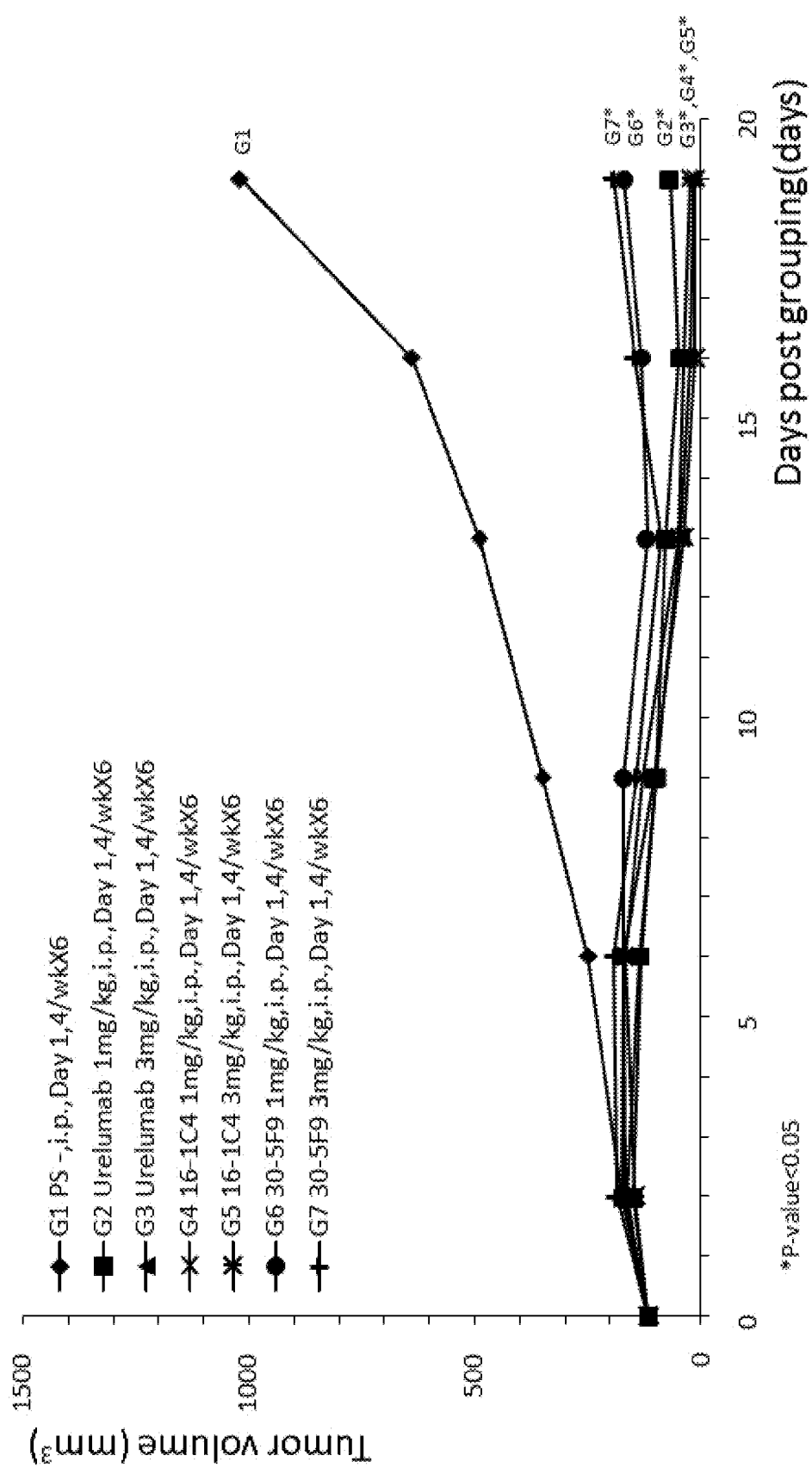
FIG. 9 is a graph showing tumor size over time in humanized 4-1BB mice (B-h4-1BB) with MC-38 tumor cells treated with mouse anti-h4-1BB antibodies 1C4 and 5F9, and urelumab.

The tumor size in groups treated with urelumab, 1C4, or 6A5 all decreased (FIG. 9).

The TGI % at day 19 (19 days after grouping) was also calculated as shown in the table below.

TABLE 9

| | | Tumor volume (mm$^3$) | | | | Survival | TGI % | P value | |
|---|---|---|---|---|---|---|---|---|---|
| | | Day 0 | Day 6 | Day 13 | Day 19 | | | Body weight | Tumor Volume |
| Control | G1 | 117 ± 17 | 250 ± 40 | 491 ± 75 | 1020 ± 244 | 5/5 | n.a. | n.a. | n.a. |
| Treat | G2 | 117 ± 17 | 133 ± 51 | 77 ± 42 | 69 ± 47 | 5/5 | 105.4% | 0.101 | 0.005 |
| | G3 | 117 ± 19 | 137 ± 58 | 46 ± 30 | 19 ± 15 | 5/5 | 110.9% | 0.793 | 0.003 |
| | G4 | 118 ± 18 | 170 ± 44 | 39 ± 27 | 12 ± 9 | 5/5 | 111.7% | 0.241 | 0.003 |
| | G5 | 117 ± 22 | 169 ± 34 | 49 ± 20 | 26 ± 13 | 5/5 | 110.1% | 0.145 | 0.004 |
| | G6 | 117 ± 19 | 174 ± 61 | 119 ± 42 | 170 ± 77 | 5/5 | 94.1% | 0.759 | 0.010 |
| | G7 | 118 ± 18 | 192 ± 71 | 90 ± 55 | 194 ± 137 | 5/5 | 91.5% | 0.479 | 0.018 |

The results showed that anti-h4-1BB antibodies 1C4 and 5F9 significantly inhibited tumor growth. Furthermore, 1C4 and 5F9 had similar TGI % at 1 mg/kg and 3 mg/kg. This result suggests that a higher dosage of 1C4 and 5F9 does not clearly improve tumor inhibitory effects.

In Vivo Results for Mouse Anti-h4-1BB Antibodies 29-6A5 ("6A5"), 29-4A10 ("4A10"), 29-5F10 ("5F10"), 45-8F1 ("8F1"), and 45-4B9 ("4B9")

B-h4-1BB mice were injected with physiological saline (PS) as a control (G1), 3 mg/kg 29-6A5 (G2), 3 mg/kg 29-4A10 (G3), 3 mg/kg 29-5F10 (G4), 3 mg/kg 45-8F1 (G5), and 3 mg/kg 45-4B9 (G6). 3 mg/kg urelumab was also administered to the mice for comparison purpose (G7).

TABLE 10

| Group | No. of mice | Antibodies | Dosage (mg/kg) | Route | Frequency | Total No. of administration |
|---|---|---|---|---|---|---|
| G1 | 5 | PS (control) | — | i.p. | Day 1, 4/wk | 6 |
| G2 | 5 | 29-6A5 | 3 mg/kg | i.p. | Day 1, 4/wk | 6 |
| G3 | 5 | 29-4A10 | 3 mg/kg | i.p. | Day 1, 4/wk | 6 |
| G4 | 5 | 29-5F10 | 3 mg/kg | i.p. | Day 1, 4/wk | 6 |
| G5 | 5 | 45-8F1 | 3 mg/kg | i.p. | Day 1, 4/wk | 6 |
| G6 | 5 | 45-489 | 3 mg/kg | i.p. | Day 1, 4/wk | 6 |
| G7 | 5 | Urelumab | 3 mg/kg | i.p. | Day 1, 4/wk | 6 |

Figure 10:
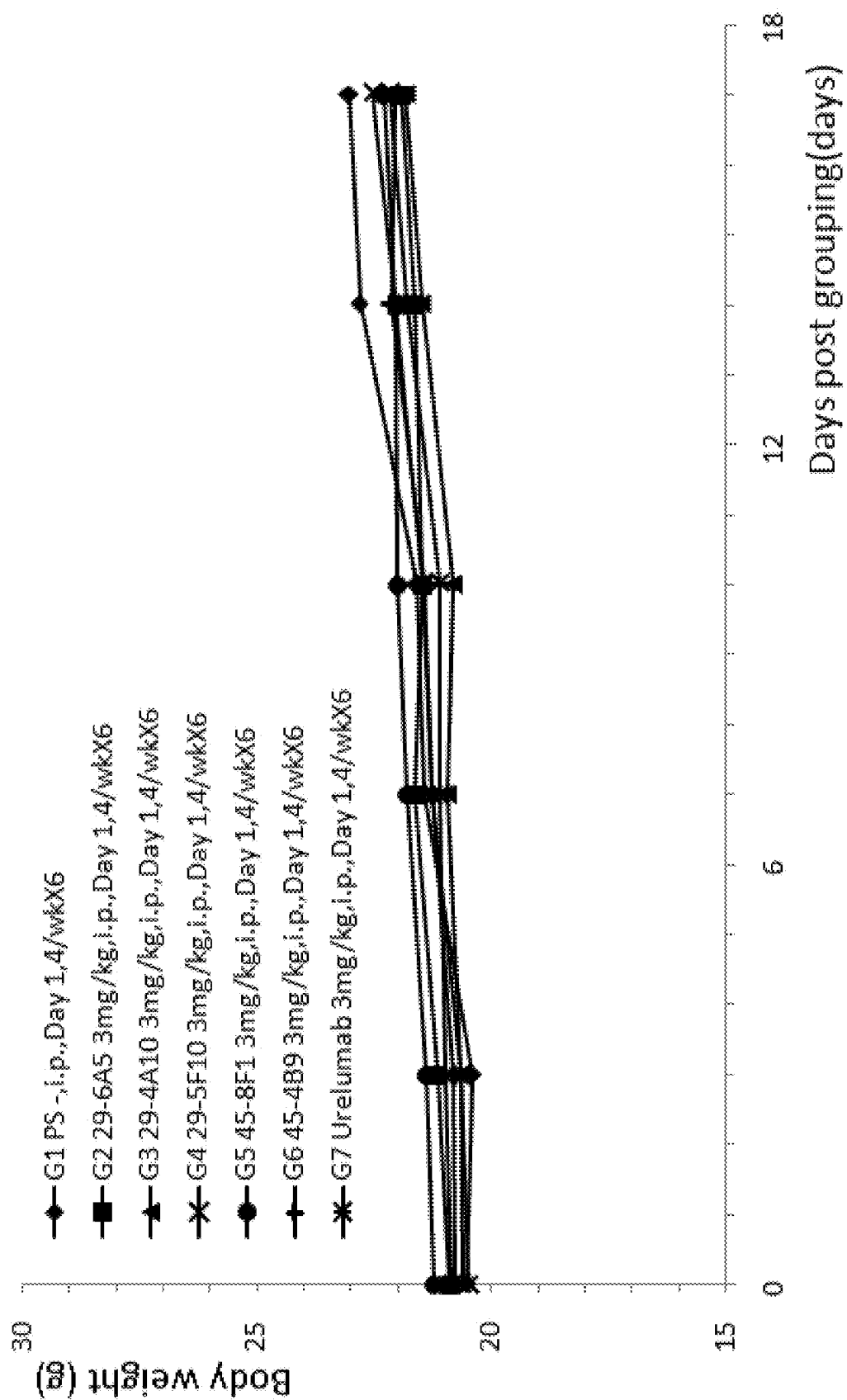
FIG. 10 is a graph showing body weight over time of humanized 4-1BB mice (B-h4-1BB) with MC-38 tumor cells treated with mouse anti-h4-1BB antibodies 29-6A5, 29-4A10, 29-5F10, 45-8F1, 45-4B9, and urelumab.
Figure 11:
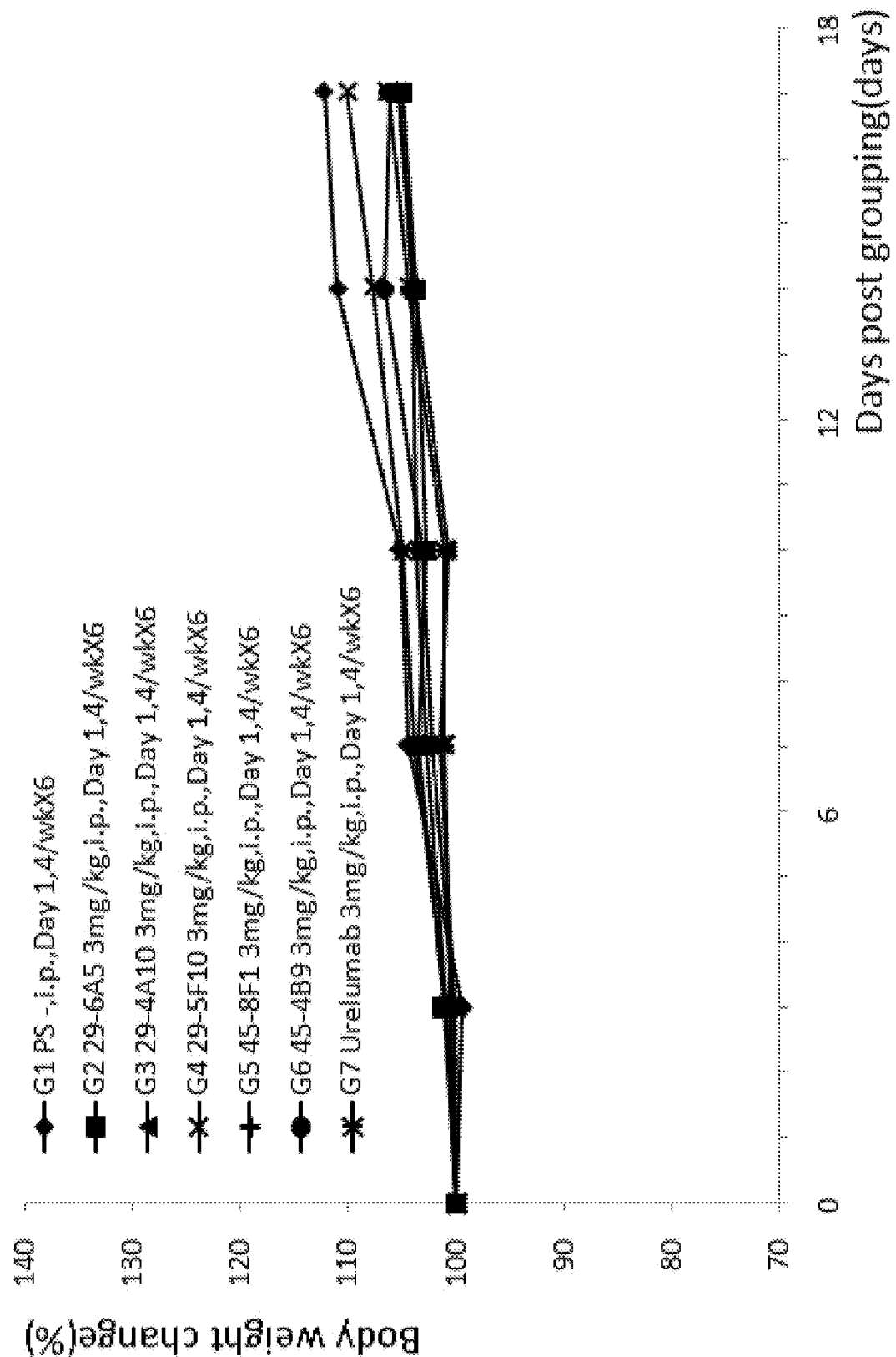
FIG. 11 is a graph showing percentage change of body weight over time of humanized 4-1BB mice (B-h4-1BB) with MC-38 tumor cells treated with mouse anti-h4-1BB antibodies 29-6A5, 29-4A10, 29-5F10, 45-8F1, 45-4B9, and urelumab.
Figure 12:
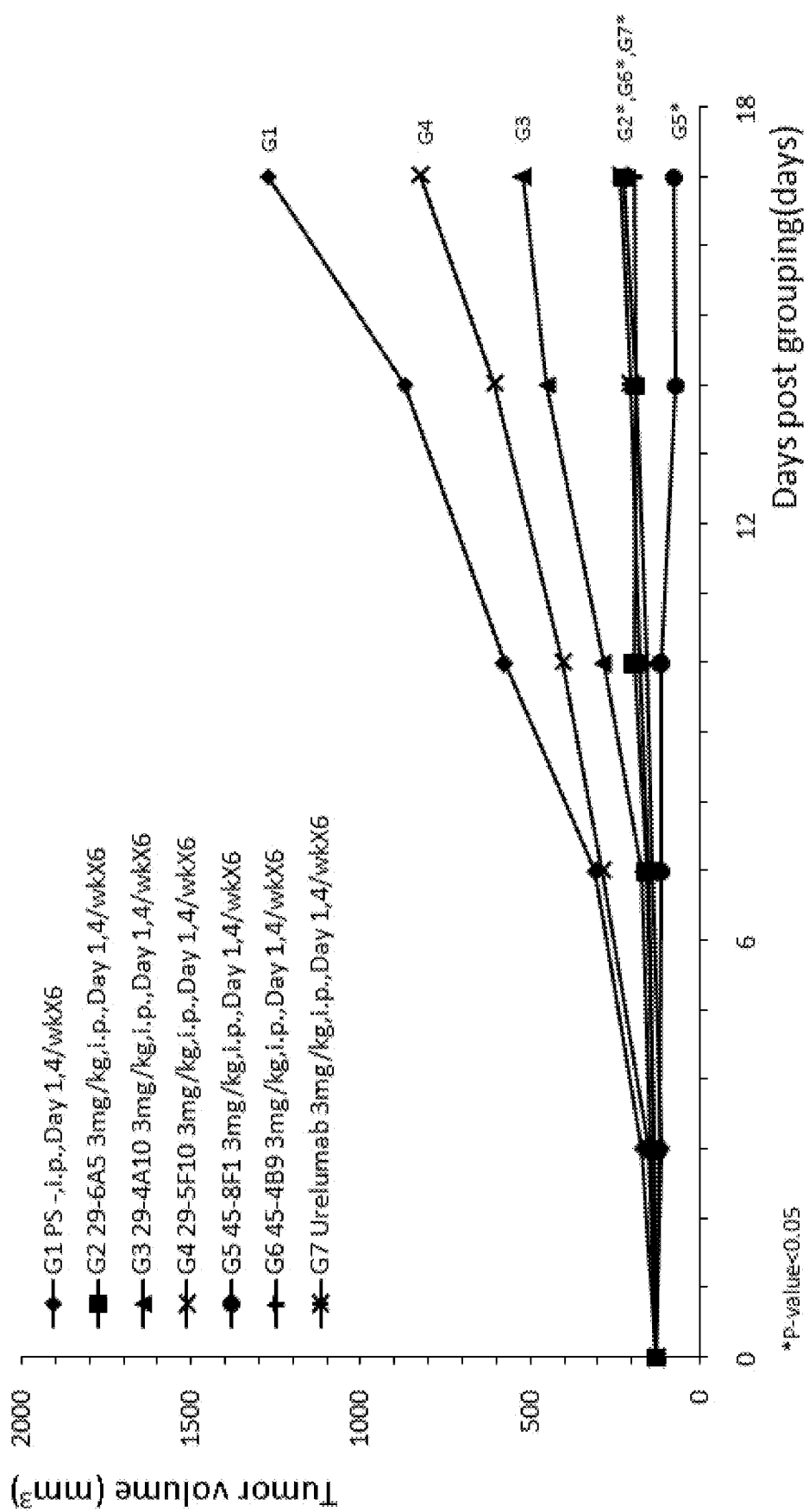
FIG. 12 is a graph showing tumor size over time in humanized 4-1BB mice (B-h4-1BB) with MC-38 tumor cells treated with mouse anti-h4-1BB antibodies 29-6A5, 29-4A10, 29-5F10, 45-8F1, 45-4B9, and urelumab.

The weight of the mice was monitored during the entire treatment period. The weight of mice in different groups all increased at the end of the treatment period (FIG. 10, and FIG. 11). No obvious difference in weight was observed among different groups. The results showed that these anti-h4-1BB antibodies were well tolerated and were not obviously toxic to the mice. The tumor size in groups treated with 29-6A5, 29-4A10, 29-5F10, 45-8F1, and 45-4B9 is shown in FIG. 12.

The TGI % at day 17 (17 days after grouping) was also calculated as shown in the table below.

TABLE 11

| | | Tumor volume (mm$^3$) | | | | | P value | |
|---|---|---|---|---|---|---|---|---|
| | | Day 0 | Day 7 | Day 14 | Day 17 | Survival | TGI % | Body weight | Tumor Volume |
| Control | G1 | 131 ± 7 | 310 ± 56 | 873 ± 190 | 1274 ± 282 | 5/5 | n.a. | n.a. | n.a. |
| Treat | G2 | 131 ± 7 | 161 ± 34 | 191 ± 67 | 228 ± 87 | 5/5 | 91.5% | 0.267 | 0.008 |
| | G3 | 131 ± 6 | 173 ± 40 | 452 ± 222 | 524 ± 242 | 5/5 | 65.6% | 0.455 | 0.078 |
| | G4 | 132 ± 10 | 293 ± 64 | 608 ± 115 | 824 ± 132 | 5/5 | 39.4% | 0.597 | 0.186 |
| | G5 | 131 ± 7 | 116 ± 24 | 72 ± 25 | 78 ± 35 | 5/5 | 104.7% | 0.481 | 0.003 |
| | G6 | 131 ± 8 | 140 ± 29 | 190 ± 63 | 197 ± 67 | 5/5 | 94.3% | 0.226 | 0.006 |
| | G7 | 131 ± 10 | 151 ± 40 | 204 ± 99 | 239 ± 131 | 5/5 | 90.6% | 0.287 | 0.010 |

The results showed that anti-h4-1BB antibodies 6A5, 4A10, 8F1, 4B9 all inhibited tumor growth. Furthermore, 6A5 and 8F1 had higher TGI % than the other tested antibodies (e.g., Urelumab).

In Vivo Results for Mouse Anti-h4-1BB Antibodies 45-8E2 ("8E2"), 45-7E9 ("7E9"), 45-7G9 ("7G9"), 45-2B3 ("2B3"), and 45-2C11 ("2C11")

B-h4-1BB mice were injected with physiological saline (PS) as a control (G1), 1 mg/kg 45-8E2 (G2), 1 mg/kg 45-7E9 (G3), 1 mg/kg 45-7G9 (G4), 1 mg/kg 45-2B3 (G5), and 1 mg/kg 45-2C11 (G6). 1 mg/kg Urelumab was also administered to the mice for comparison purpose (G7).

TABLE 12

| Group | No. of mice | Antibodies | Dosage (mg/kg) | Route | Frequency | Total No. of administration |
|---|---|---|---|---|---|---|
| G1 | 5 | PS (control) | — | i.p. | Day 2, 5/wk | 6 |
| G2 | 5 | 45-8E2 | 1 mg/kg | i.p. | Day 2, 5/wk | 6 |
| G3 | 5 | 45-7E9 | 1 mg/kg | i.p. | Day 2, 5/wk | 6 |
| G4 | 5 | 45-7G9 | 1 mg/kg | i.p. | Day 2, 5/wk | 6 |
| G5 | 5 | 45-2B3 | 1 mg/kg | i.p. | Day 2, 5/wk | 6 |
| G6 | 5 | 45-2C11 | 1 mg/kg | i.p. | Day 2, 5/wk | 6 |
| G7 | 5 | Urelumab | 1 mg/kg | i.p. | Day 2, 5/wk | 6 |

Figure 13:
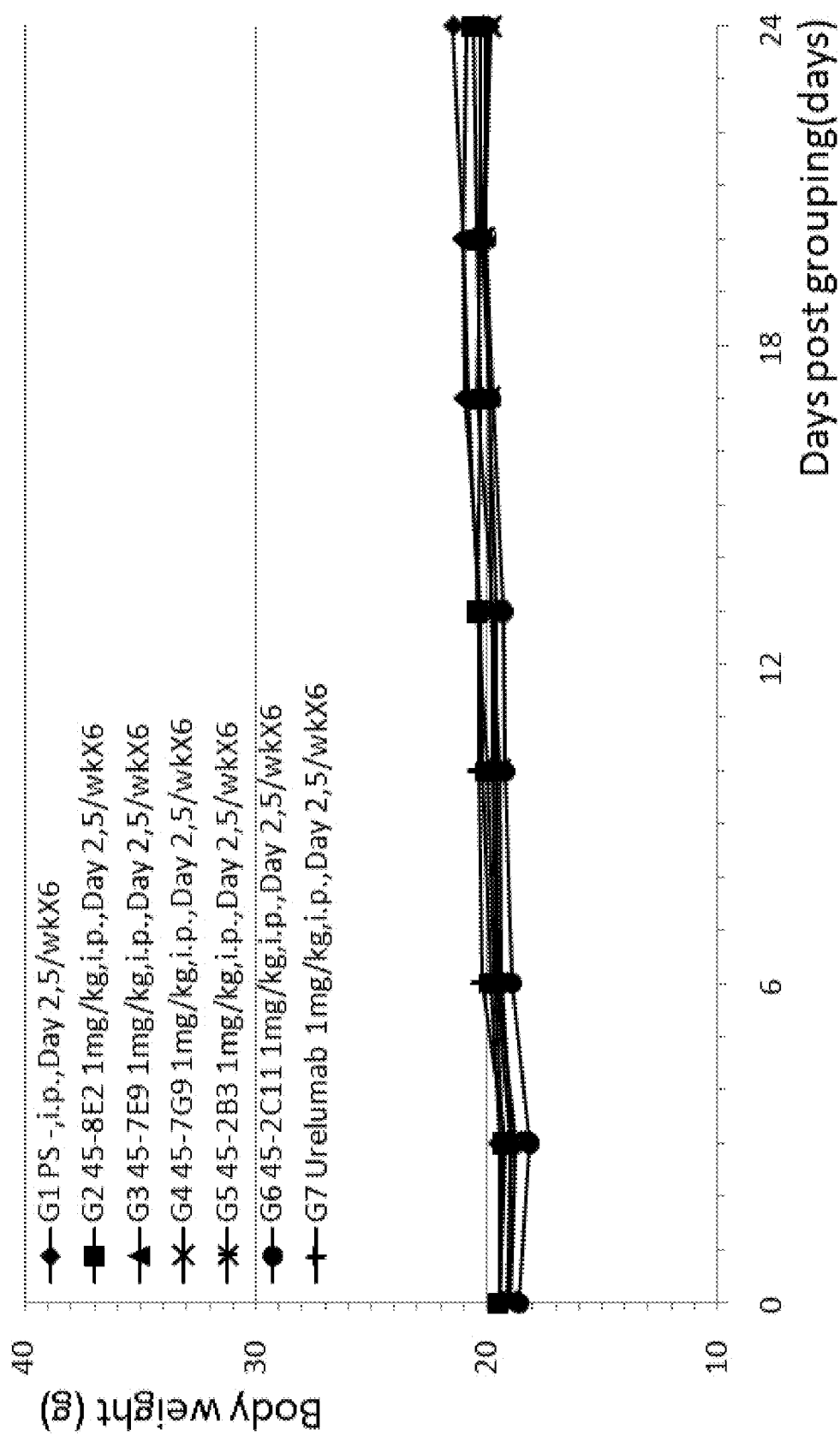
FIG. 13 is a graph showing body weight over time of humanized 4-1BB mice (B-h4-1BB) with MC-38 tumor cells treated with urelumab and mouse anti-h4-1BB antibodies 45-8E2, 45-7E9, 45-7G9, 45-2B3, and 45-2C11.
Figure 14:
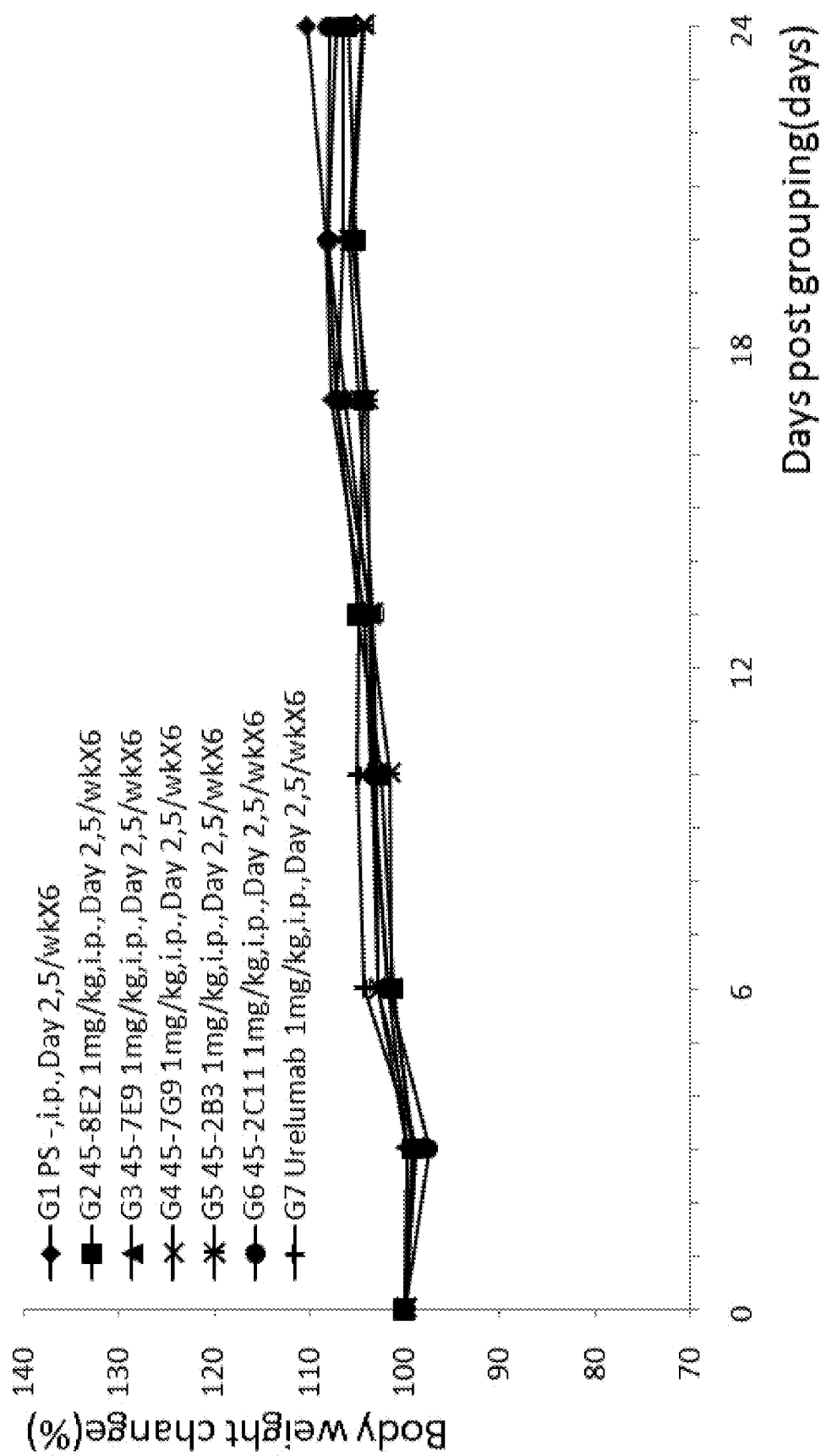
FIG. 14 is a graph showing percentage change of body weight over time of humanized 4-1BB mice (B-h4-1BB) with MC-38 tumor cells treated with urelumab and mouse anti-h4-1BB antibodies 45-8E2, 45-7E9, 45-7G9, 45-2B3, and 45-2C11.

The weight of the mice was monitored during the entire treatment period. The average weight of mice in different groups all increased at the end of the treatment period (FIG. 13, and FIG. 14). No significant difference in weight was observed among different groups. The results showed that these anti-h4-1BB antibodies were well tolerated and were not obviously toxic to the mice.

Figure 15:
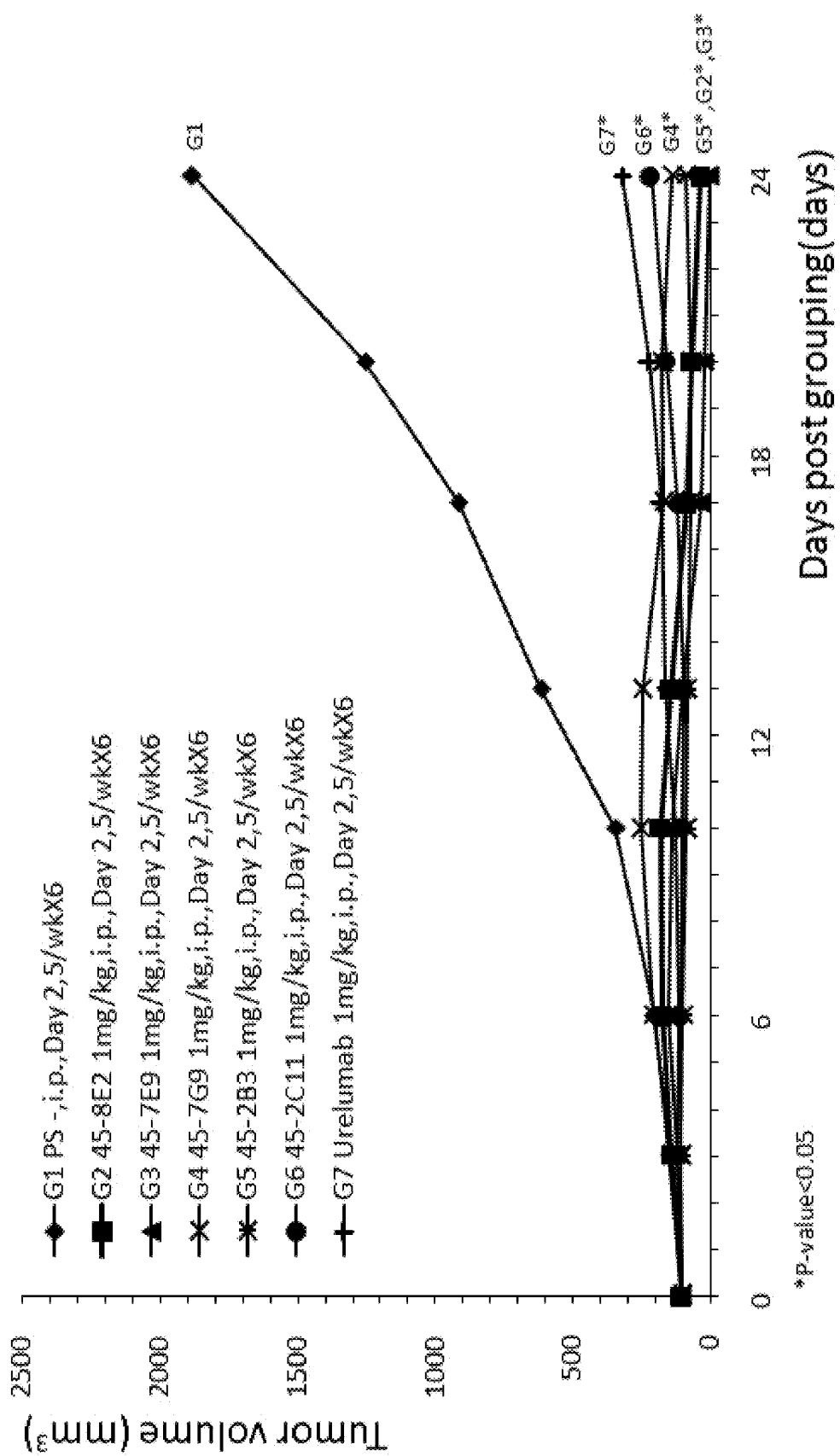
FIG. 15 is a graph showing tumor size over time in humanized 4-1BB mice (B-h4-1BB) with MC-38 tumor cells treated with urelumab and mouse anti-h4-1BB antibodies 45-8E2, 45-7E9, 45-7G9, 45-2B3, and 45-2C11.

As compared to the control group, 45-8E2, 45-7E9, 45-7G9, 45-2B3, and 45-2C11 all inhibited tumor growth (FIG. 15). The TGI % at day 24 (24 days after grouping) was also calculated as shown in the table below.

TABLE 13

| | | Tumor volume (mm³) | | | | Survival | TGI % | P value | |
|---|---|---|---|---|---|---|---|---|---|
| | | Day 0 | Day 10 | Day 17 | Day 24 | | | Body weight | Tumor Volume |
| Control | G1 | 106 ± 16 | 346 ± 20 | 916 ± 102 | 1882 ± 180 | 5/5 | n.a. | n.a. | n.a. |
| Treat | G2 | 106 ± 11 | 182 ± 67 | 91 ± 53 | 41 ± 37 | 5/5 | 103.7% | 0.573 | 8.5E-06 |
| | G3 | 106 ± 10 | 142 ± 13 | 36 ± 12 | 5 ± 3 | 5/5 | 105.7% | 0.405 | 6.3E-06 |
| | G4 | 106 ± 9 | 256 ± 42 | 170 ± 34 | 141 ± 39 | 5/5 | 98.0% | 0.304 | 1.3E-05 |
| | G5 | 106 ± 11 | 90 ± 21 | 73 ± 38 | 90 ± 54 | 5/5 | 100.9% | 0.251 | 1.2E-05 |
| | G6 | 106 ± 12 | 101 ± 28 | 122 ± 53 | 218 ± 100 | 5/5 | 93.7% | 0.384 | 4.1E-05 |
| | G7 | 106 ± 15 | 129 ± 60 | 181 ± 144 | 323 ± 265 | 5/5 | 87.8% | 0.735 | 0.001 |

The results showed that anti-h4-1BB antibodies 45-8E2, 45-7E9, 45-7G9, 45-2B3, and 45-2C11 all significantly inhibited tumor growth. Furthermore, 45-8E2, 45-7E9, 45-7G9, 45-2B3, and 45-2C11 all had higher TGI % than Urelumab.

In Vivo Results for Mouse Anti-h4-1BB Antibodies 16-1C4 ("1C4"), 55-8F6 ("8F6"), and 54-8B11 ("8B11")

B-h4-1BB mice were injected with physiological saline (PS) as a control (G1), 1 mg/kg 16-1C4 (G2), 1 mg/kg 55-8F6 (G3), and 1 mg/kg 54-8B11 (G4). 1 mg/kg Urelumab was also administered to the mice for comparison purpose (G5).

TABLE 14

| Group | No. of mice | Antibodies | Dosage (mg/kg) | Route | Frequency | Total No. of administration |
|---|---|---|---|---|---|---|
| G1 | 5 | PS (control) | — | i.p. | Day 2, 5/wk | 6 |
| G2 | 5 | 16-1C4 | 1 mg/kg | i.p. | Day 2, 5/wk | 6 |
| G3 | 5 | 55-8F6 | 1 mg/kg | i.p. | Day 2, 5/wk | 6 |
| G4 | 5 | 54-8B11 | 1 mg/kg | i.p. | Day 2, 5/wk | 6 |
| G5 | 5 | Urelumab | 1 mg/kg | i.p. | Day 2, 5/wk | 6 |

Figure 16:
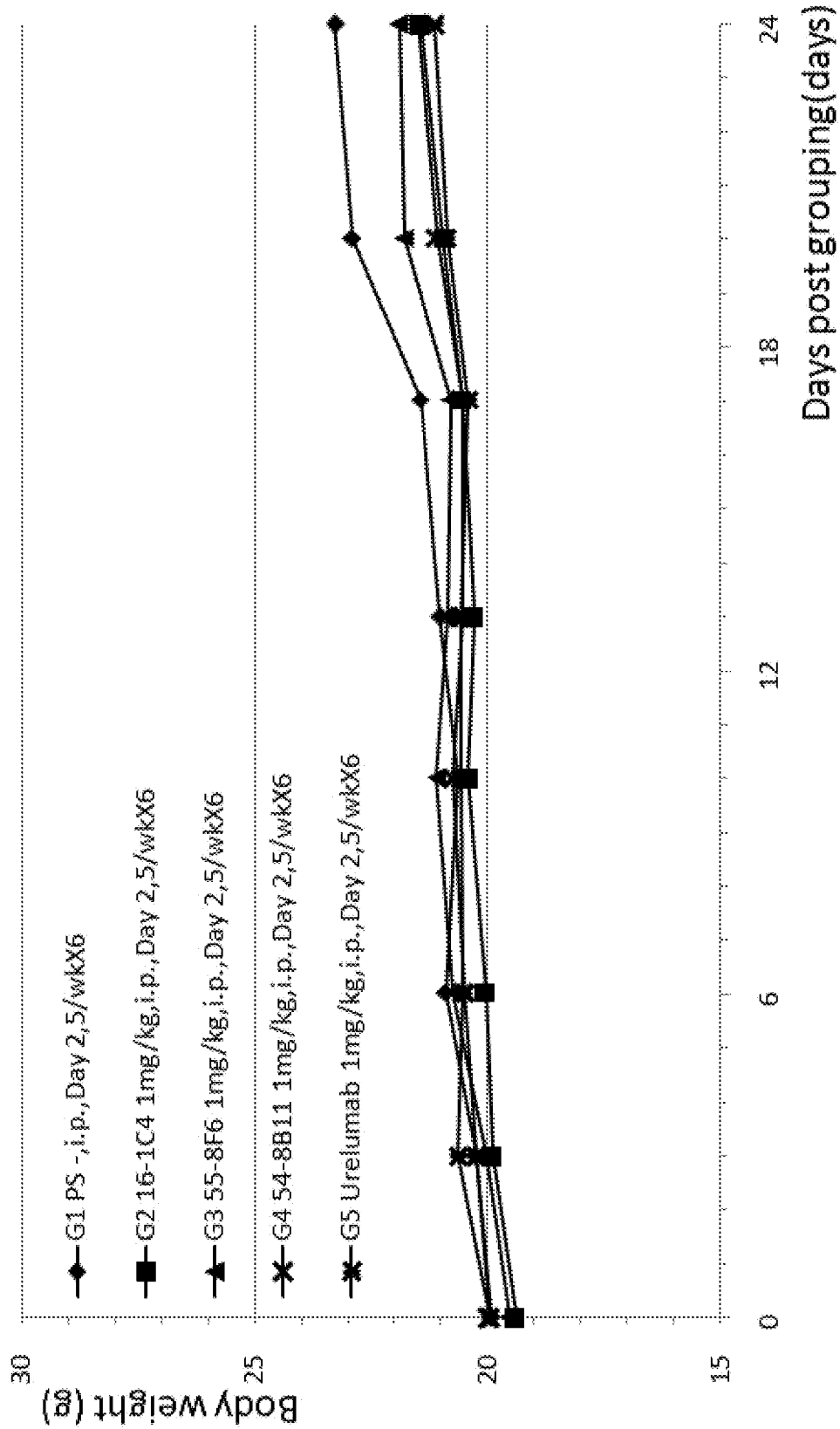
FIG. 16 is a graph showing body weight over time of humanized 4-1BB mice (B-h4-1BB) with MC-38 tumor cells treated with urelumab and mouse anti-h4-1BB antibodies 16-1C4, 55-8F6, and 54-8B11.
Figure 17:
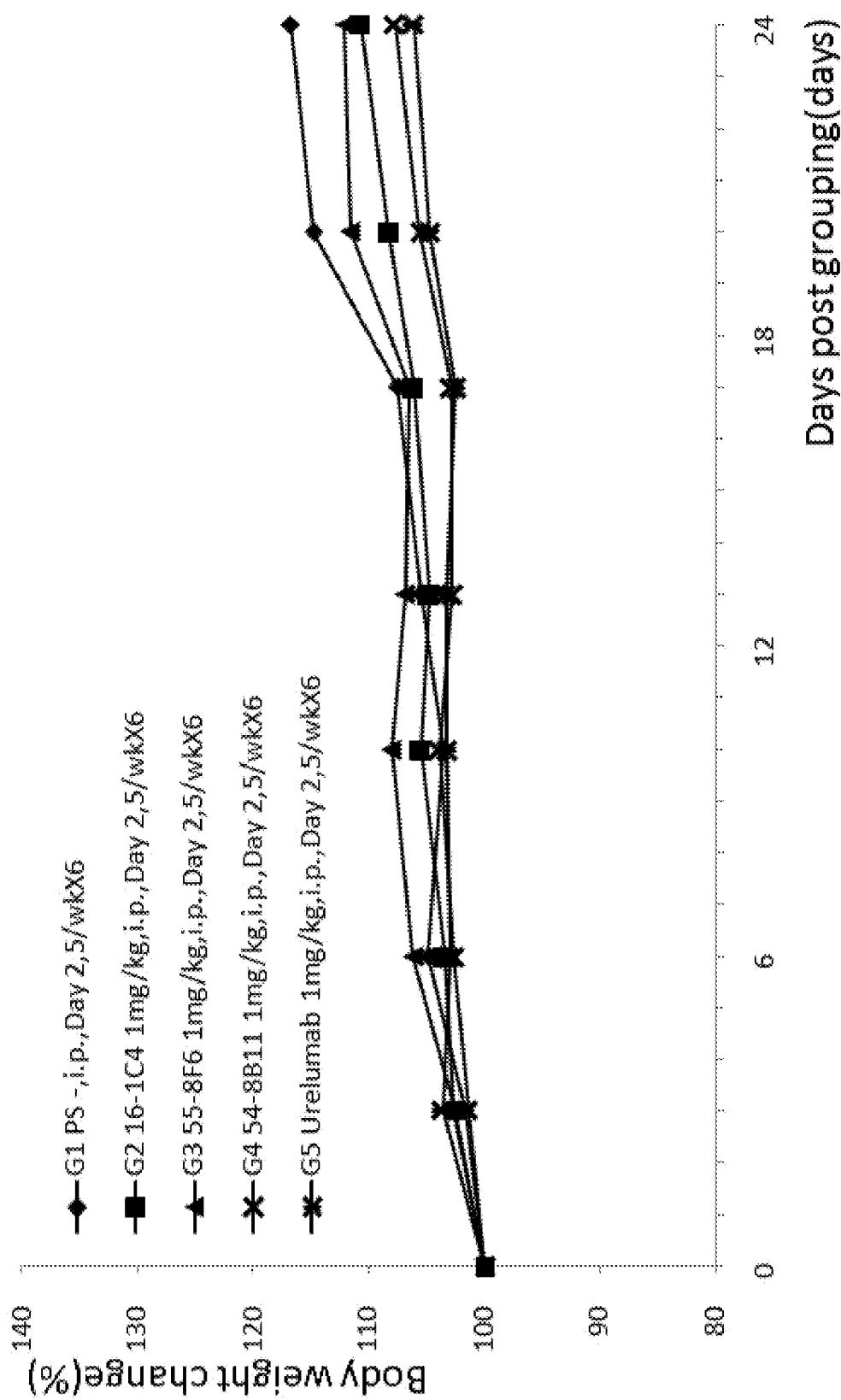
FIG. 17 is a graph showing percentage change of body weight over time of humanized 4-1BB mice (B-h4-1BB) with MC-38 tumor cells treated with urelumab and mouse anti-h4-1BB antibodies 16-1C4, 55-8F6, and 54-8B11.
Figure 18:
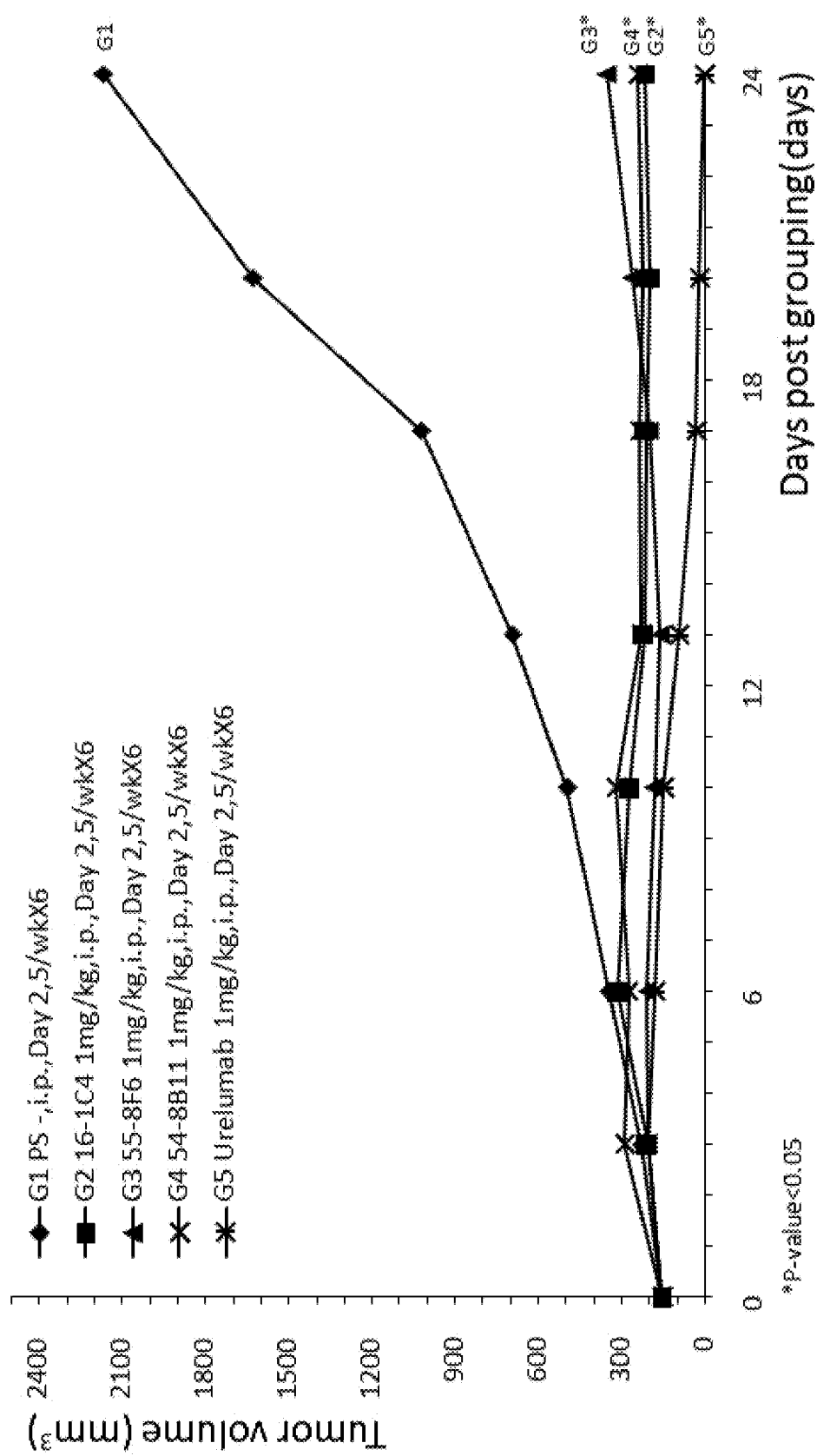
FIG. 18 is a graph showing tumor size over time in humanized 4-1BB mice (B-h4-1BB) with MC-38 tumor cells treated with urelumab and mouse anti-h4-1BB antibodies 16-1C4, 55-8F6, and 54-8B11.

The weight of the mice was monitored during the entire treatment period. The average weight of mice in different groups all increased at the end of the treatment period (FIG. 16, and FIG. 17). No obvious difference in weight was observed among different groups. The results showed that these anti-h4-1BB antibodies were well tolerated and were not obviously toxic to the mice. As compared to the control group, 16-1C4, 55-8F6, and 54-8B11 all inhibited tumor growth (FIG. 18).

The TGI % at day 24 (24 days after grouping) was also calculated as shown in the table below.

TABLE 15

| | | Tumor volume (mm³) | | | | Survival | TGI % | P value | |
|---|---|---|---|---|---|---|---|---|---|
| | | Day 0 | Day 10 | Day 17 | Day 24 | | | Body weight | Tumor Volume |
| Control | G1 | 153 ± 22 | 495 ± 72 | 1019 ± 127 | 2166 ± 268 | 5/5 | n.a. | n.a. | n.a. |
| Treat | G2 | 153 ± 20 | 268 ± 55 | 210 ± 130 | 214 ± 181 | 5/5 | 96.9% | 0.104 | 3.1E-04 |
| | G3 | 153 ± 21 | 180 ± 59 | 200 ± 111 | 352 ± 220 | 5/5 | 90.1% | 0.149 | 7.9E-04 |
| | G4 | 153 ± 24 | 317 ± 82 | 237 ± 111 | 240 ± 164 | 5/5 | 95.7% | 0.051 | 2.8E-04 |
| | G5 | 152 ± 21 | 147 ± 19 | 30 ± 10 | 0 ± 0 | 5/5 | 107.6% | 0.024 | 4.0E-05 |

The results showed that anti-h4-1BB antibodies 16-1C4, 55-8F6, and 54-8B11 all significantly inhibited tumor growth.

In Vivo Results for Mouse Anti-h4-1BB Antibodies 54-1A11 ("1A11"), 55-1E3 ("1E3"), 55-8H5 ("8H5"), and 56-2A6 ("2A6")

B-h4-1BB mice were injected with physiological saline (PS) (G1), 1 mg/kg 54-1A11 (G2), 1 mg/kg 55-1E3 (G3), 1 mg/kg 55-8H5 (G4), and 1 mg/kg 56-2A6 (G5). 1 mg/kg Urelumab was also administered to the mice for comparison purpose (G6).

TABLE 16

| Group | No. of mice | Antibodies | Dosage (mg/kg) | Route | Frequency | Total No. of administration |
|---|---|---|---|---|---|---|
| G1 | 5 | PS (control) | — | i.p. | Day 1, 4/wk | 6 |
| G2 | 5 | 54-1A11 | 1 mg/kg | i.p. | Day 1, 4/wk | 6 |
| G3 | 5 | 55-1E3 | 1 mg/kg | i.p. | Day 1, 4/wk | 6 |
| G4 | 5 | 55-8H5 | 1 mg/kg | i.p. | Day 1, 4/wk | 6 |
| G5 | 5 | 56-2A6 | 1 mg/kg | i.p. | Day 1, 4/wk | 6 |
| G6 | 5 | Urelumab | 1 mg/kg | i.p. | Day 1, 4/wk | 6 |

Figure 19:
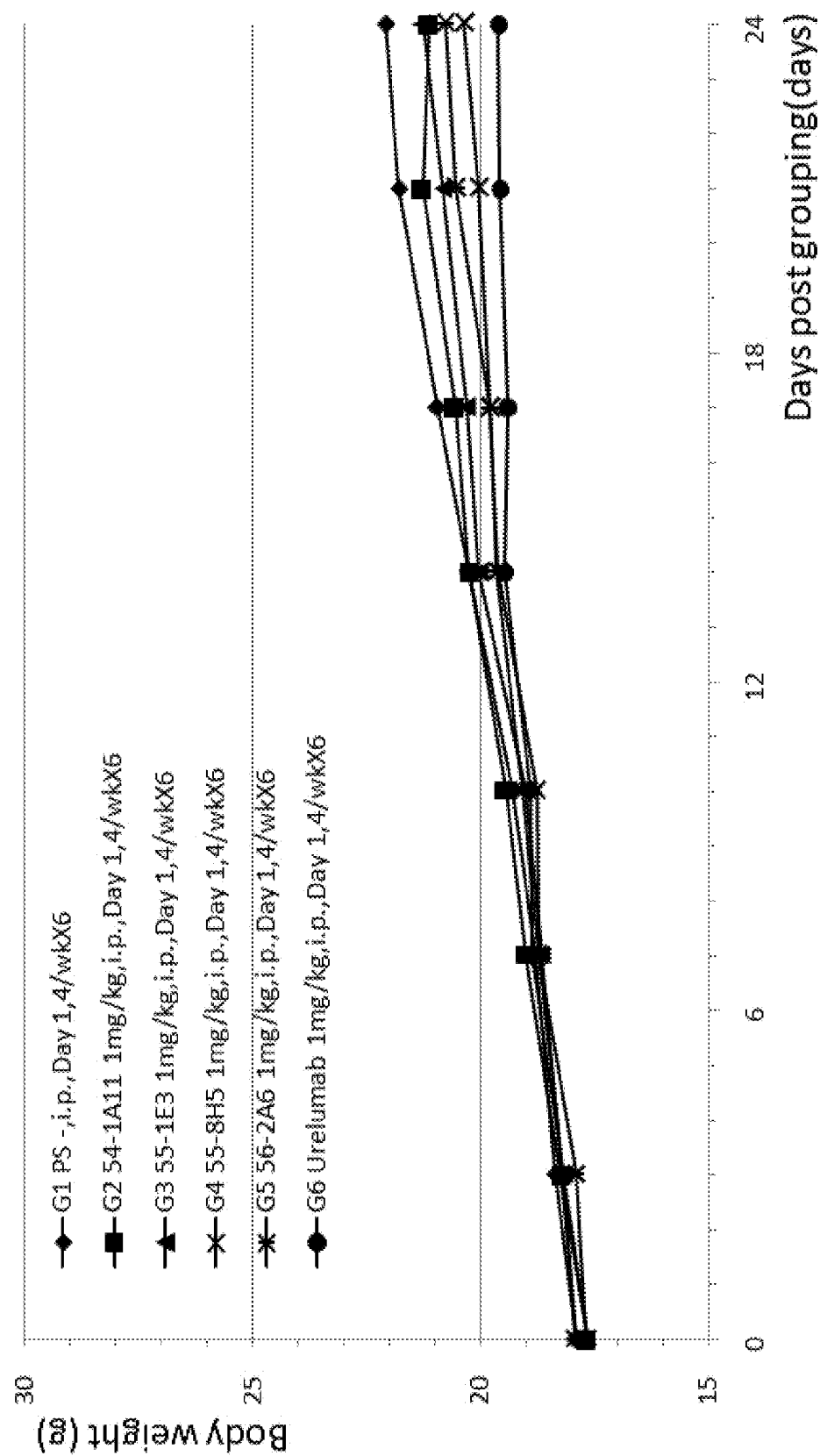
FIG. 19 is a graph showing body weight over time of humanized 4-1BB mice (B-h4-1BB) with MC-38 tumor cells treated with urelumab and mouse anti-h4-1BB antibodies 54-1A11, 55-1E3, 55-8H5, and 56-2A6.
Figure 20:
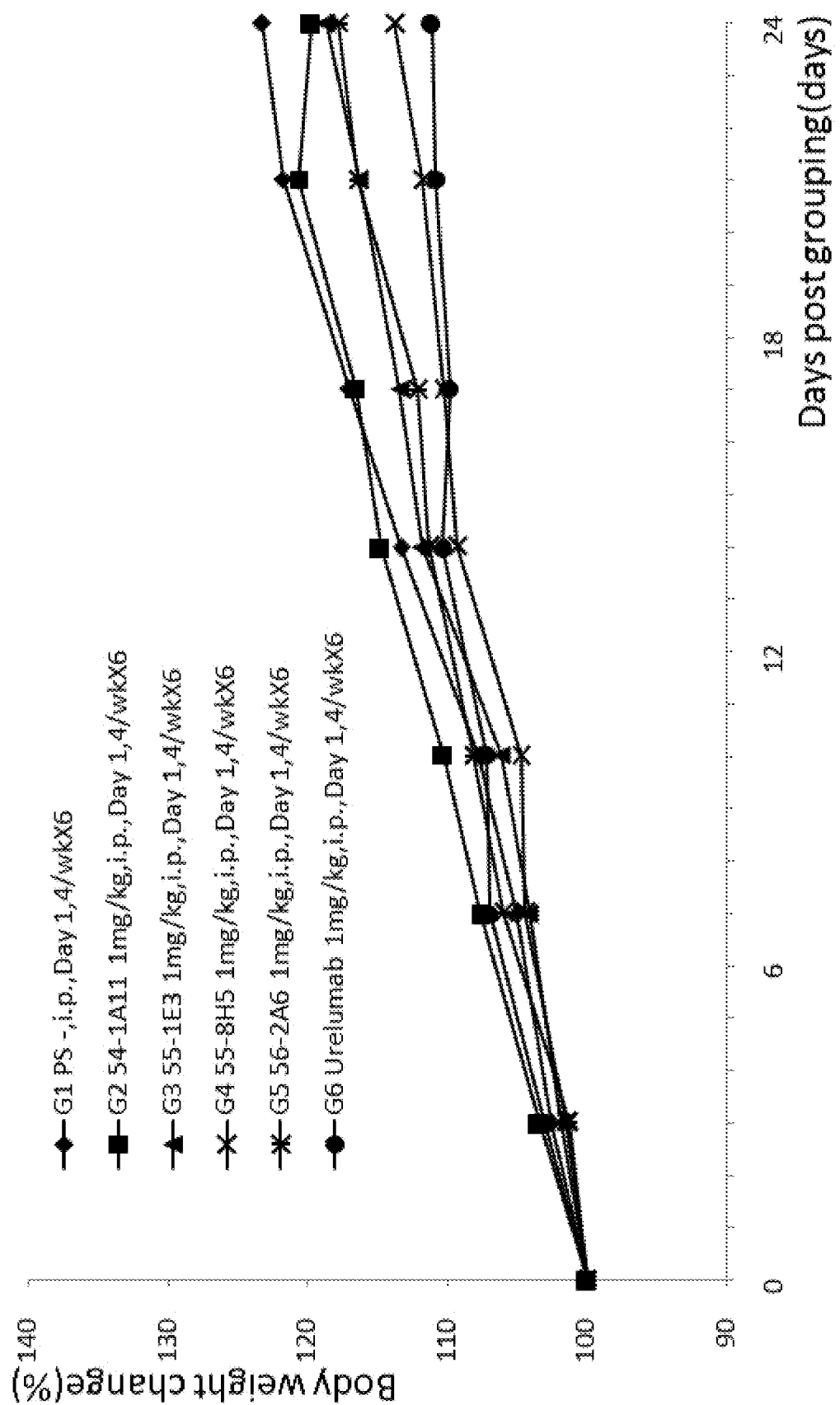
FIG. 20 is a graph showing percentage change of body weight over time of humanized 4-1BB mice (B-h4-1BB) with MC-38 tumor cells treated with urelumab and mouse anti-h4-1BB antibodies 54-1A11, 55-1E3, 55-8H5, and 56-2A6.
Figure 21:
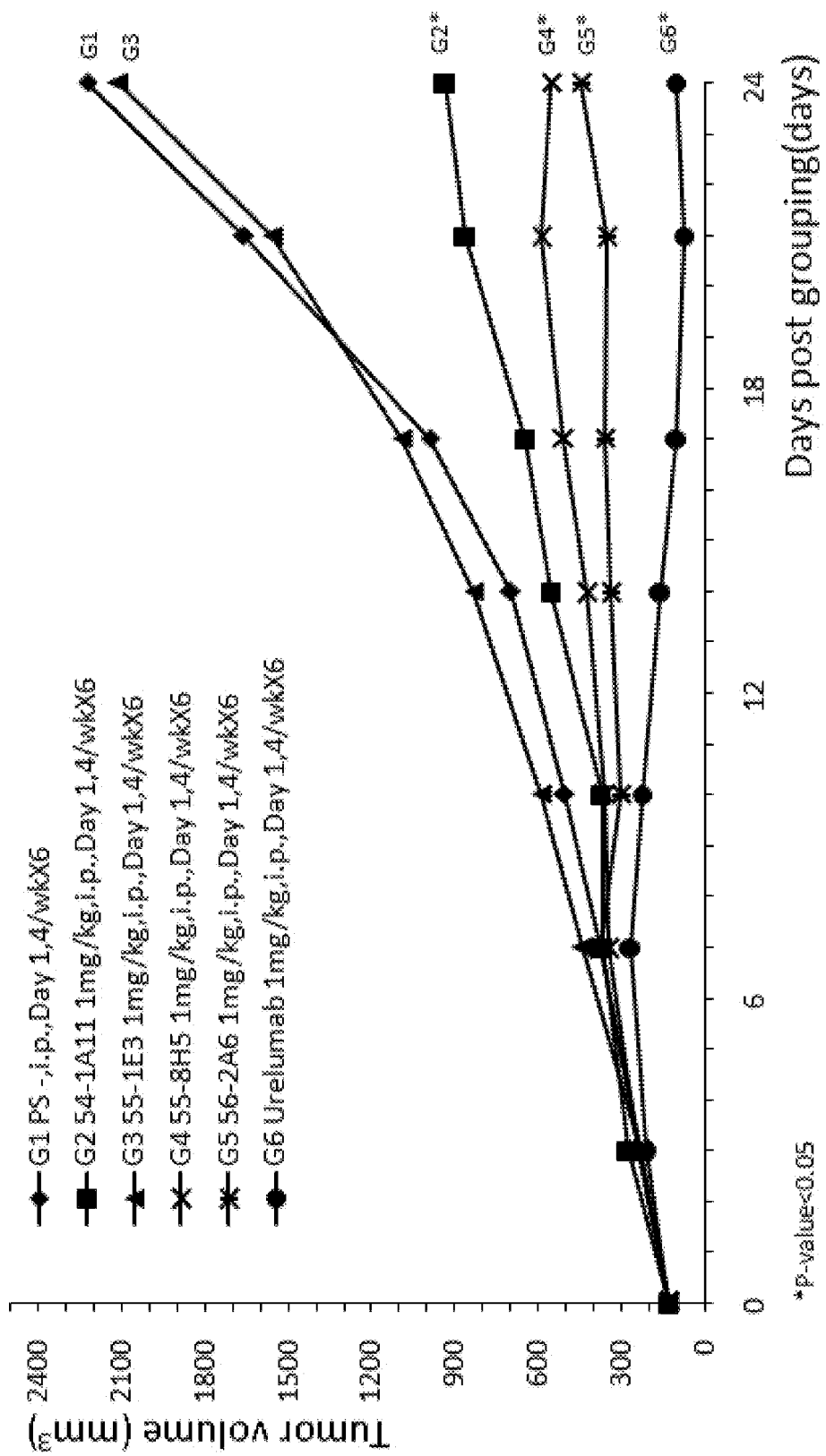
FIG. 21 is a graph showing tumor size over time in humanized 4-1BB mice (B-h4-1BB) with MC-38 tumor cells treated with urelumab and mouse anti-h4-1BB antibodies 54-1A11, 55-1E3, 55-8H5, and 56-2A6.

The weight of the mice was monitored during the entire treatment period. The average weight of mice in different groups all increased at the end of the treatment period (FIG. 19, and FIG. 20). No obvious difference in weight was observed among different groups. The results showed that these anti-h4-1BB antibodies were well tolerated and were not obviously toxic to the mice. The tumor size for each group is shown in FIG. 21.

The TGI % at day 24 (24 days after grouping) was also calculated as shown in the table below.

TABLE 17

| | | Tumor volume (mm³) | | | | | | P value | |
|---|---|---|---|---|---|---|---|---|---|
| | | Day 0 | Day 10 | Day 17 | Day 24 | Survival | TGI % | Body weight | Tumor Volume |
| Control | G1 | 131 ± 5 | 505 ± 92 | 991 ± 162 | 2226 ± 264 | 5/5 | n.a. | n.a. | n.a. |
| Treat | G2 | 132 ± 6 | 371 ± 42 | 646 ± 85 | 936 ± 190 | 5/5 | 61.6% | 0.419 | 0.004 |
| | G3 | 131 ± 10 | 590 ± 121 | 1091 ± 195 | 2113 ± 331 | 5/5 | 5.4% | 0.542 | 0.796 |
| | G4 | 132 ± 9 | 359 ± 120 | 510 ± 149 | 556 ± 159 | 5/5 | 79.7% | 0.155 | 6.3E-04 |
| | G5 | 131 ± 5 | 307 ± 28 | 364 ± 41 | 447 ± 132 | 5/5 | 84.9% | 0.247 | 0.008 |
| | G6 | 131 ± 8 | 222 ± 21 | 105 ± 18 | 102 ± 44 | 5/5 | 101.4% | 0.065 | 0.002 |

The results showed that anti-h4-1BB antibodies 54-1A11, 55-8H5, and 56-2A6 all significantly inhibited tumor growth. 55-1E3 was not effective in inhibiting tumor growth.

In Vivo Results for Mouse Anti-h4-1BB Antibodies 58-4B8 ("4B8"), 69-3C2 ("3C2"), and 69-4B11 ("4B11")

B-h4-1BB mice were injected with physiological saline (PS) (G1), 1 mg/kg 58-4B8 (G2), 1 mg/kg 69-3C2 (G3), and 1 mg/kg 69-4B11 (G4). 1 mg/kg Urelumab was also administered to the mice for comparison purpose (G5).

TABLE 18

| Group | No. of mice | Anti-bodies | Dosage (mg/kg) | Route | Frequency | Total No. of administration |
|---|---|---|---|---|---|---|
| G1 | 5 | PS (control) | — | i.p. | Day 1, 4/wk | 6 |
| G2 | 5 | 58-4B8 | 1 mg/kg | i.p. | Day 1, 4/wk | 6 |
| G3 | 5 | 69-3C2 | 1 mg/kg | i.p. | Day 1, 4/wk | 6 |
| G4 | 5 | 69-4B11 | 1 mg/kg | i.p. | Day 1, 4/wk | 6 |
| G5 | 5 | Urelumab | 1 mg/kg | i.p. | Day 1, 4/wk | 6 |

Figure 22:
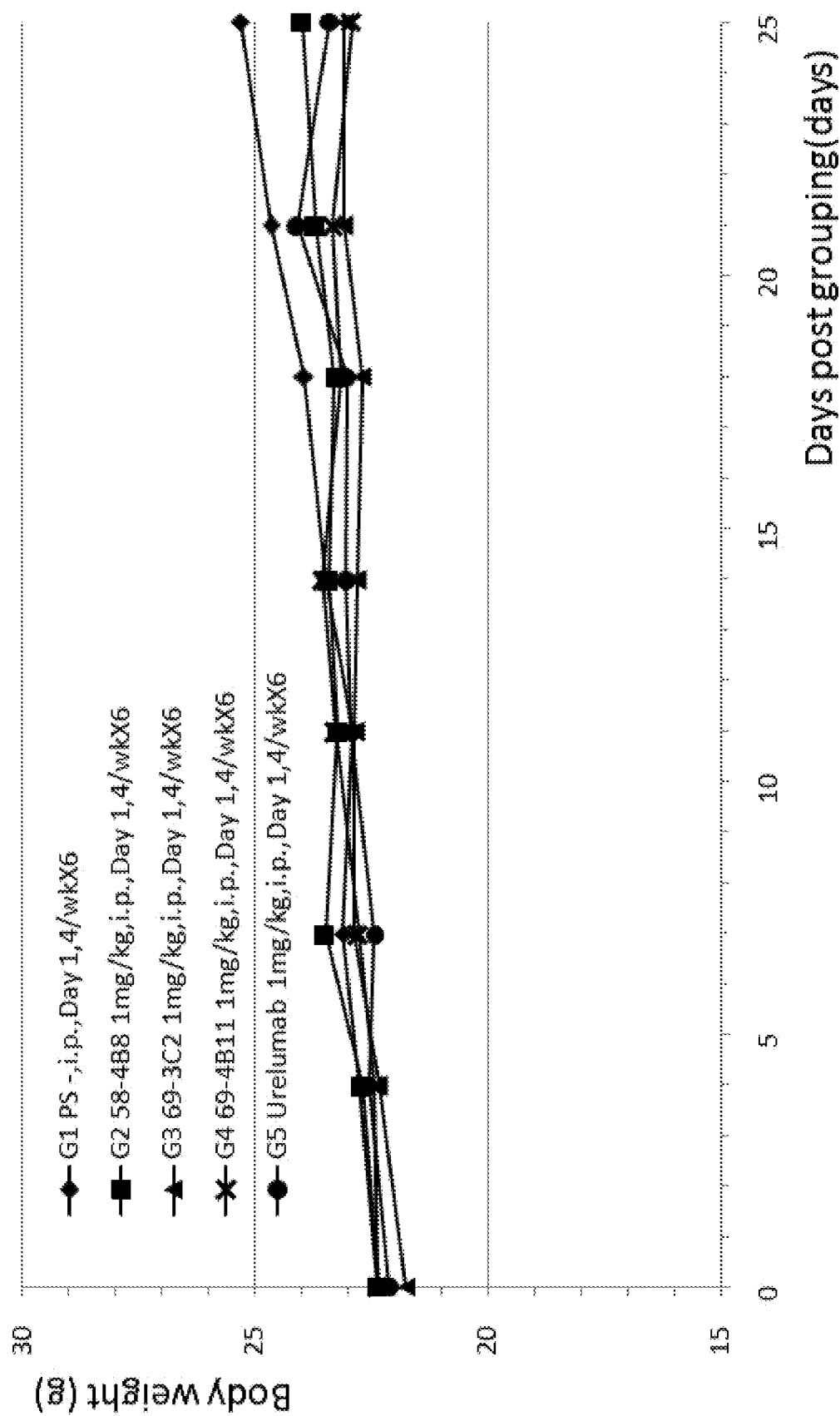
FIG. 22 is a graph showing body weight over time of humanized 4-1BB mice (B-h4-1BB) with MC-38 tumor cells treated with urelumab and mouse anti-h4-1BB antibodies 58-4B8, 69-3C2, and 69-4B11.
Figure 23:
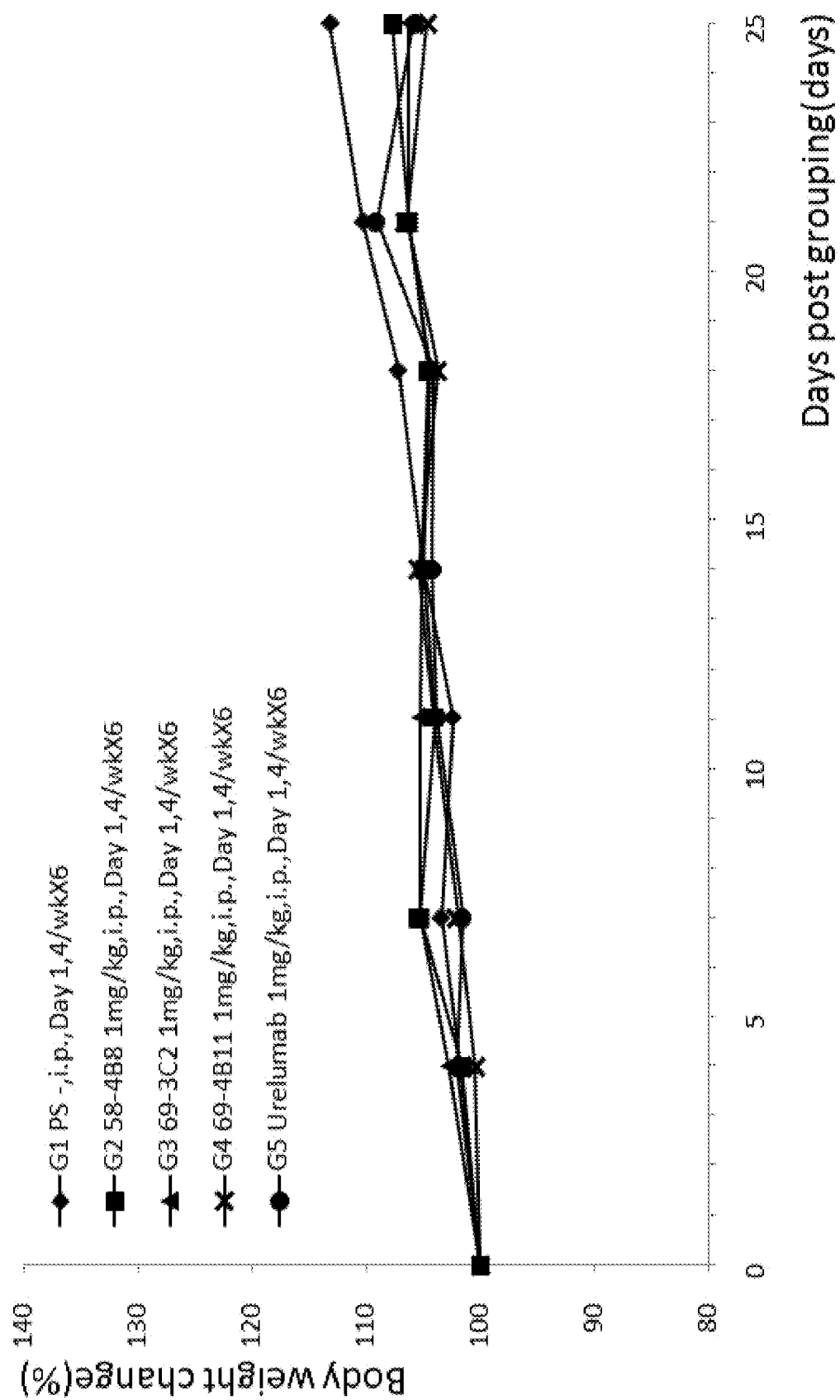
FIG. 23 is a graph showing percentage change of body weight over time of humanized 4-1BB mice (B-h4-1BB) with MC-38 tumor cells treated with urelumab and mouse anti-h4-1BB antibodies 58-4B8, 69-3C2, and 69-4B11.
Figure 24:
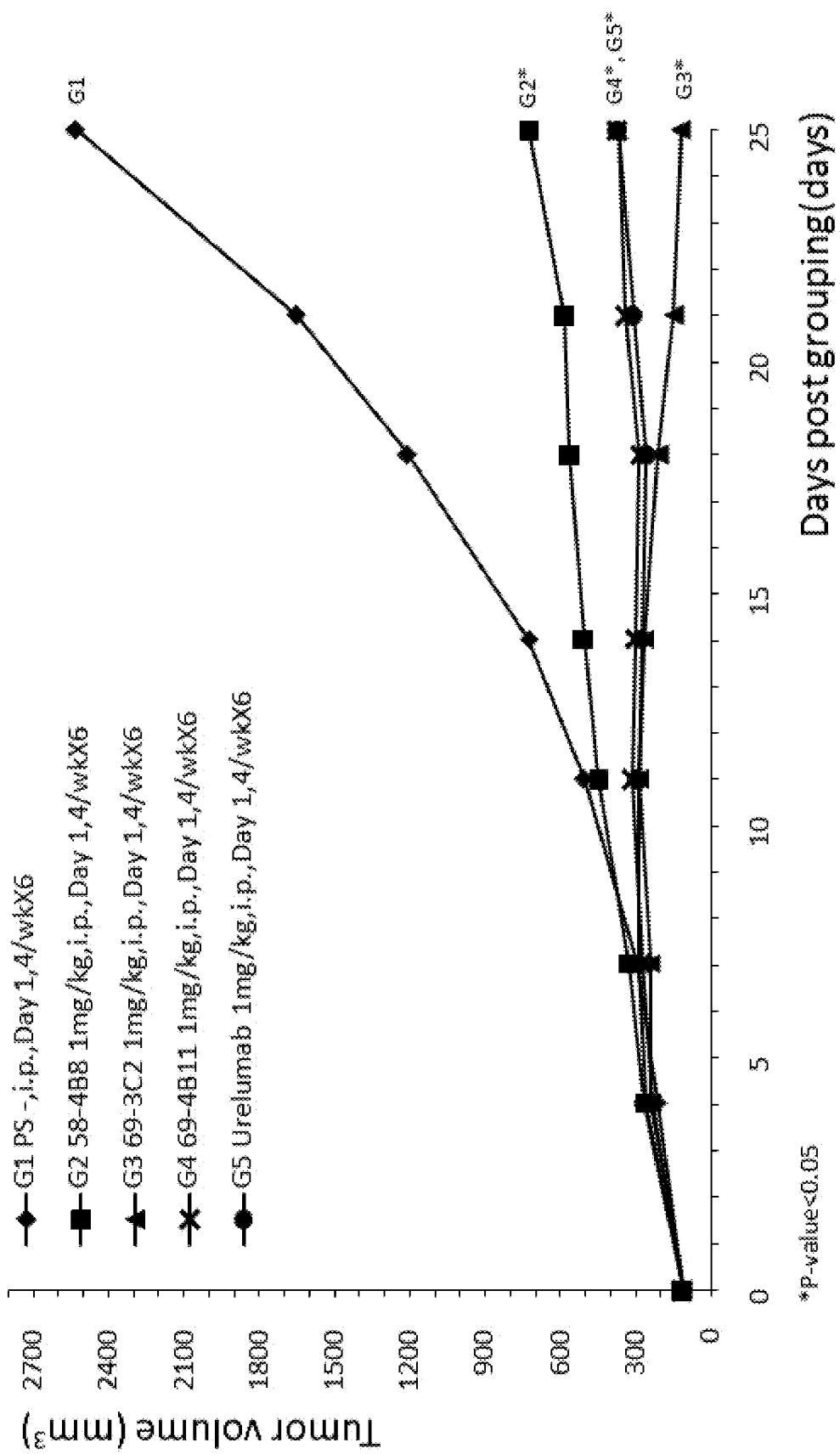
FIG. 24 is a graph showing tumor size over time in humanized 4-1BB mice (B-h4-1BB) with MC-38 tumor cells treated with urelumab and mouse anti-h4-1BB antibodies 58-4B8, 69-3C2, and 69-4B11.

The weight of the mice was monitored during the entire treatment period. The weight of mice in different groups all increased (FIG. 22, and FIG. 23). No obvious difference in weight was observed among different groups. The results showed that these anti-h4-1BB antibodies were well tolerated and were not obviously toxic to the mice. The tumor size for each group is shown in FIG. 24.

The TGI % at day 25 (25 days after grouping) was also calculated as shown in the table below.

TABLE 19

| | | Tumor volume (mm³) | | | | | | P value | |
|---|---|---|---|---|---|---|---|---|---|
| | | Day 0 | Day 11 | Day 18 | Day 25 | Survival | TGI % | Body weight | Tumor Volume |
| Control | G1 | 111 ± 7 | 505 ± 65 | 1212 ± 119 | 2535 ± 230 | 5/5 | n.a. | n.a. | n.a. |
| Treat | G2 | 111 ± 8 | 448 ± 100 | 562 ± 158 | 728 ± 228 | 5/5 | 74.6% | 0.244 | 5.2E-04 |
| | G3 | 112 ± 9 | 286 ± 104 | 209 ± 112 | 118 ± 76 | 5/5 | 99.8% | 0.052 | 8.7E-06 |
| | G4 | 111 ± 6 | 311 ± 102 | 286 ± 169 | 369 ± 295 | 5/5 | 89.4% | 0.120 | 6.1E-04 |
| | G5 | 112 ± 7 | 289 ± 84 | 257 ± 109 | 371 ± 221 | 5/5 | 89.3% | 0.111 | 1.4E-04 |

The results showed that anti-h4-1BB antibodies 58-4B8, 69-3C2, and 69-4B11 all significantly inhibited tumor growth.

Example 8. In Vivo Testing of Chimeric Anti-h4-1BB Antibodies

The chimeric anti-h4-1BB antibodies were tested in 4-1BB humanized mice (B-h4-1BB) to determine their effect on tumor growth in vivo. MC-38 cancer tumor cells (colon adenocarcinoma cell) were injected subcutaneously in B-h4-1BB mice. When the tumors in the mice reached a volume of 150±50 mm³, the mice were randomly placed into different groups based on the volume of the tumor.

In Vivo Results for 30-5F9-mHvKv-IgG2, 30-5F9-mHvKv-IgG4, 16-1C4-mHvKv-IgG2, 16-1C4-mHvKv-IgG4, 16-1C4-mHvKv-IgG1

B-h4-1BB mice were injected with physiological saline (PS) (G1), 30-5F9-mHvKv-IgG2 (G2), 30-5F9-mHvKv-IgG4 (G3), 16-1C4-mHvKv-IgG2 (G4), 16-1C4-mHvKv-IgG4 (G5), 16-1C4-mHvKv-IgG1 (G6), 30-5F9 (G7), 16-1C4 (G8), utomilumab (G9), and urelumab (G10).

TABLE 20

| Group | No. of mice | Antibodies | Dosage (mg/kg) | Route | Frequency | Total No. of administration |
|---|---|---|---|---|---|---|
| G1 | 5 | PS (control) | — | i.p. | Day 1, 4/wk | 6 |
| G2 | 5 | 30-5F9-mHvKv-IgG2 | 1 mg/kg | i.p. | Day 1, 4/wk | 6 |
| G3 | 5 | 30-5F9-mHvKv-IgG4 | 1 mg/kg | i.p. | Day 1, 4/wk | 6 |
| G4 | 5 | 16-1C4-mHvKv-IgG2 | 1 mg/kg | i.p. | Day 1, 4/wk | 6 |
| G5 | 5 | 16-1C4-mHvKv-IgG4 | 1 mg/kg | i.p. | Day 1, 4/wk | 6 |
| G6 | 5 | 16-1C4-mHvKv-IgG1 | 1 mg/kg | i.p. | Day 1, 5/wk | 6 |
| G7 | 5 | 30-5F9 | 1 mg/kg | i.p. | Day 1, 4/wk | 6 |
| G8 | 5 | 16-1C4 | 1 mg/kg | i.p. | Day 1, 4/wk | 6 |
| G9 | 5 | Utomilumab | 1 mg/kg | i.p. | Day 1, 4/wk | 6 |
| G10 | 5 | Urelumab | 1 mg/kg | i.p. | Day 1, 4/wk | 6 |

Figure 25:
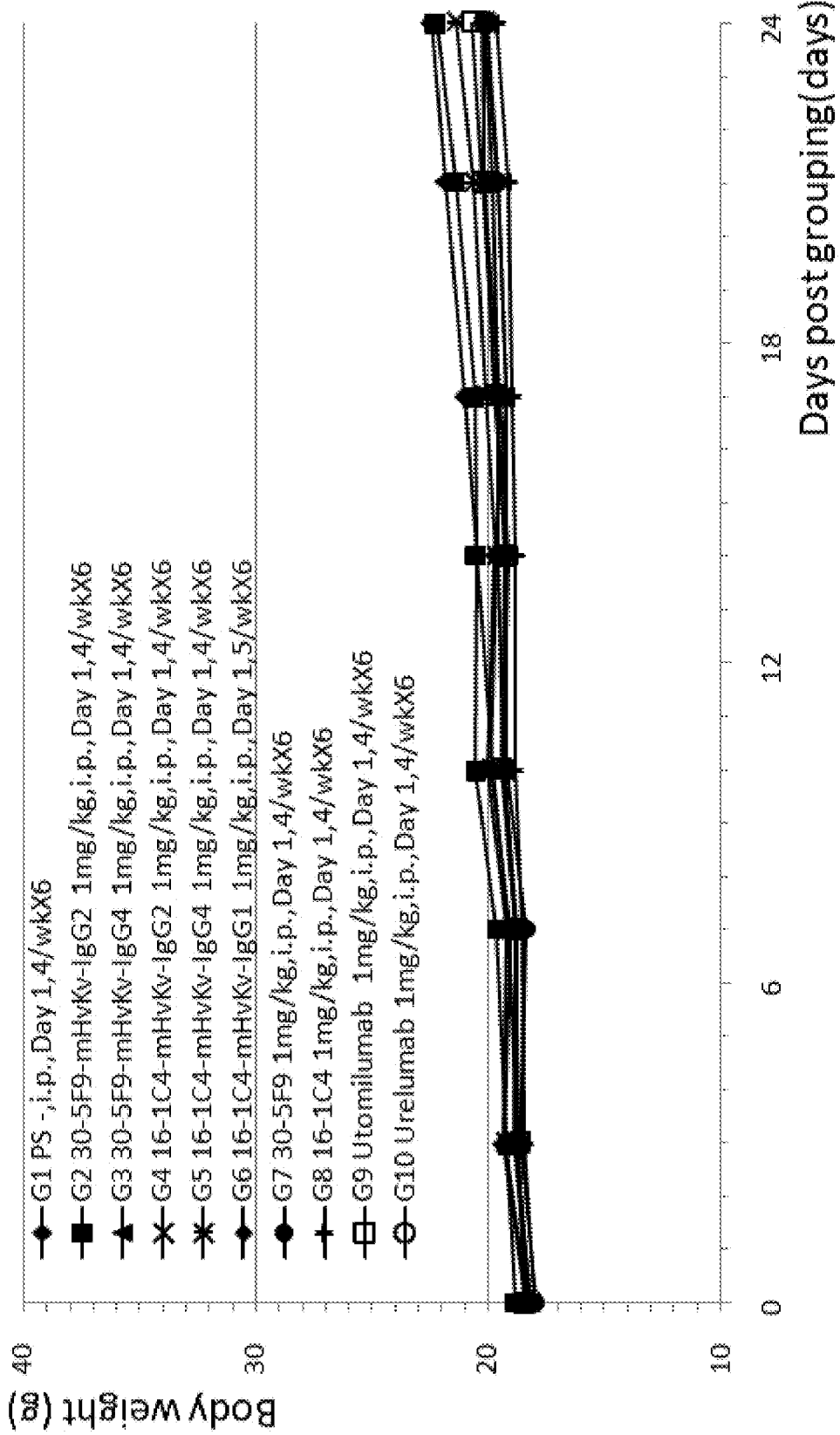
FIG. 25 is a graph showing body weight over time of humanized 4-1BB mice (B-h4-1BB) with MC-38 tumor cells treated with anti-h4-1BB antibodies 30-5F9-mHvKv-IgG2, 30-5F9-mHvKv-IgG4, 16-1C4-mHvKv-IgG2, 16-1C4-mHvKv-IgG4, 16-1C4-mHvKv-IgG1, 30-5F9, 16-1C4, utomilumab, and urelumab
Figure 26:
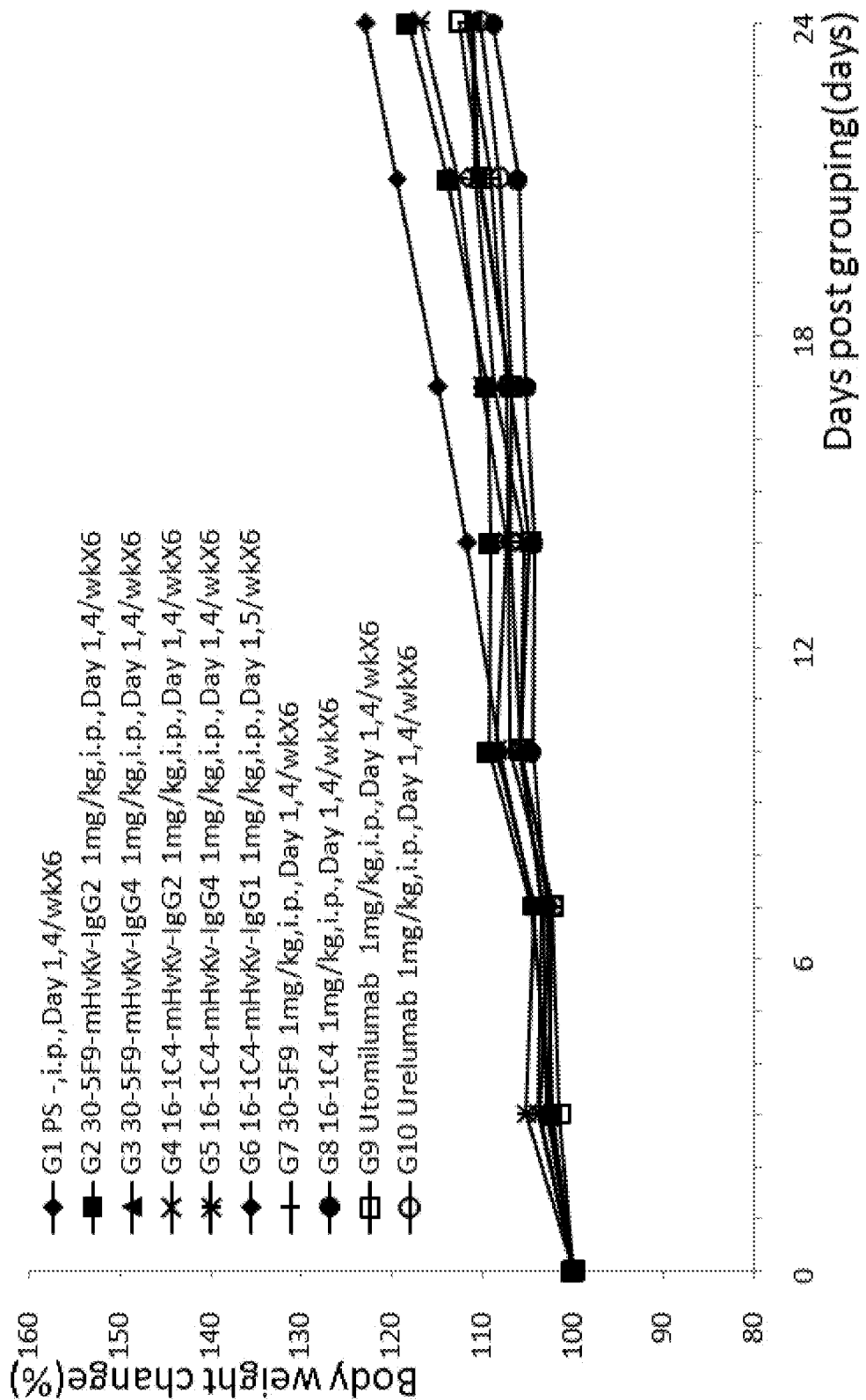
FIG. 26 is a graph showing percentage change of body weight over time of humanized 4-1BB mice (B-h4-1BB) with MC-38 tumor cells treated with anti-h4-1BB antibodies 30-5F9-mHvKv-IgG2, 30-5F9-mHvKv-IgG4, 16-1C4-mHvKv-IgG2, 16-1C4-mHvKv-IgG4, 16-1C4-mHvKv-IgG1, 30-5F9, 16-1C4, utomilumab, and urelumab
Figure 27:
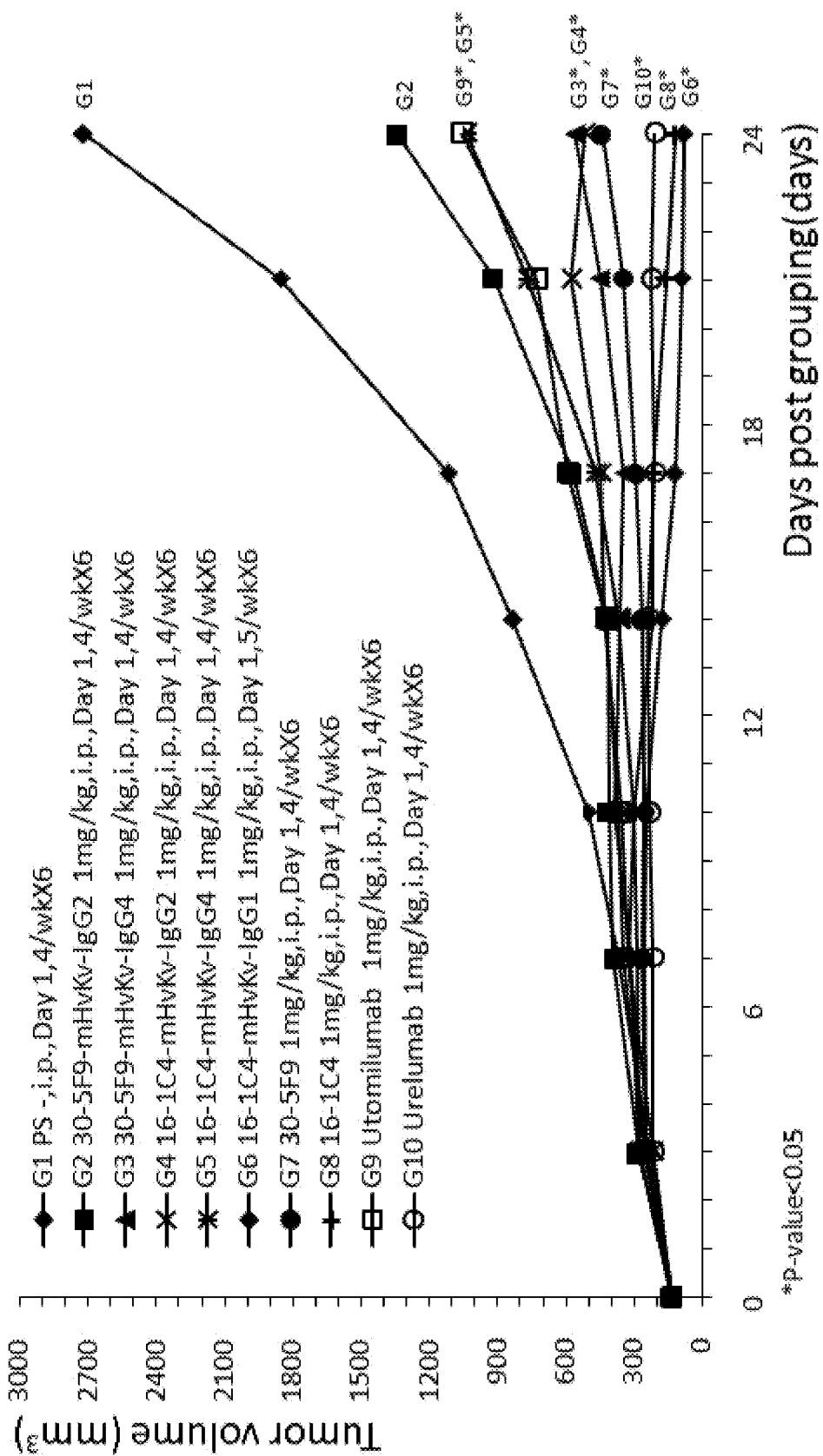
FIG. 27 is a graph showing tumor size over time in humanized 4-1BB mice (B-h4-1BB) with MC-38 tumor cells treated with anti-h4-1BB antibodies 30-5F9-mHvKv-IgG2, 30-5F9-mHvKv-IgG4, 16-1C4-mHvKv-IgG2, 16-1C4-mHvKv-IgG4, 16-1C4-mHvKv-IgG1, 30-5F9, 16-1C4, utomilumab, and urelumab

The weight of the mice was monitored during the entire treatment period. The average weight of mice in different groups all increased at the end of the treatment period (FIG. 25, and FIG. 26). No obvious difference in weight was observed among different groups. The results showed that these anti-h4-1BB antibodies were well tolerated and were not obviously toxic to the mice. The tumor size for each group is shown in FIG. 27.

The TGI % at day 24 (24 days after grouping) was also calculated as shown in the table below.

TABLE 21

| | | Tumor volume(mm$^3$) | | | | | | P value | |
|---|---|---|---|---|---|---|---|---|---|
| | | Day 0 | Day 10 | Day 17 | Day 24 | Survival | TGI % | Body weight | Tumor Volume |
| Control | G1 | 138 ± 6 | 503 ± 87 | 1122 ± 225 | 2723 ± 546 | 5/5 | n.a. | n.a. | n.a. |
| Treat | G2 | 138 ± 14 | 411 ± 187 | 571 ± 368 | 1342 ± 1063 | 5/5 | 53.4% | 0.756 | 0.281 |
| | G3 | 138 ± 12 | 391 ± 31 | 347 ± 73 | 560 ± 257 | 5/5 | 83.7% | 0.075 | 0.007 |
| | G4 | 138 ± 9 | 354 ± 167 | 445 ± 259 | 517 ± 267 | 5/5 | 85.3% | 0.024 | 0.007 |
| | G5 | 138 ± 6 | 302 ± 60 | 472 ± 173 | 1036 ± 458 | 5/5 | 65.3% | 0.398 | 0.045 |
| | G6 | 138 ± 8 | 253 ± 40 | 122 ± 42 | 85 ± 30 | 5/5 | 102.0% | 0.036 | 0.001 |
| | G7 | 138 ± 12 | 255 ± 30 | 294 ± 87 | 442 ± 182 | 5/5 | 88.2% | 0.004 | 0.004 |
| | G8 | 138 ± 9 | 300 ± 117 | 217 ± 120 | 123 ± 70 | 5/5 | 100.6% | 0.020 | 0.001 |
| | G9 | 138 ± 7 | 372 ± 33 | 595 ± 18 | 1062 ± 98 | 5/5 | 64.3% | 0.019 | 0.017 |
| | G10 | 138 ± 8 | 235 ± 53 | 211 ± 125 | 210 ± 169 | 5/5 | 97.2% | 0.044 | 0.002 |

The results showed that all of these anti-h4-1BB antibodies can inhibit tumor growth. Particularly, The IgG1 subclass of 16-1C4-mHvKv (G6) had a higher TGI % than the IgG2 subclass (G4) and the IgG4 subclass (G5).

In Vivo Results for 16-IC4-mHvKv-IgG2, 29-6A5-mHvKv-IgG2, 30-5F9-mHvKv-IgG2, 45-2B3-mHvKv-IgG2, 45-7E9-mHvKv-IgG2, 45-7G9-mHvKv-IgG2, 45-8E2-mHvKv-IgG2, and 45-8F1-mHvKv-IgG2

B-h4-1BB mice were injected with physiological saline (PS) (G1), 16-1C4-mHvKv-IgG2 (G2), 29-6A5-mHvKv-IgG2 (G3), 30-5F9-mHvKv-IgG2 (G4), 45-2B3-mHvKv-IgG2 (G5), 45-7E9-mHvKv-IgG2 (G6), 45-7G9-mHvKv-IgG2 (G7), 45-8E2-mHvKv-IgG2 (G8), 45-8F1-mHvKv-IgG2 (G9), and Urelumab (G10).

TABLE 22

| Group | No. of mice | Antibodies | Dosage (mg/kg) | Route | Frequency | Total No. of administration |
|---|---|---|---|---|---|---|
| G1 | 5 | PS (control) | — | i.p. | Day 2, 5/wk | 6 |
| G2 | 5 | 16-1C4-mHvKv-IgG2 | 1 mg/kg | i.p. | Day 2, 5/wk | 6 |
| G3 | 5 | 29-6A5-mHvKv-IgG2 | 1 mg/kg | i.p. | Day 2, 5/wk | 6 |
| G4 | 5 | 30-5F9-mHvKv-IgG2 | 1 mg/kg | i.p. | Day 2, 5/wk | 6 |
| G5 | 5 | 45-2B3-mHvKv-IgG2 | 1 mg/kg | i.p. | Day 2, 5/wk | 6 |
| G6 | 5 | 45-7E9-mHvKv-IgG2 | 1 mg/kg | i.p. | Day 2, 5/wk | 6 |
| G7 | 5 | 45-7G9-mHvKv-IgG2 | 1 mg/kg | i.p. | Day 2, 5/wk | 6 |
| G8 | 5 | 45-8E2-mHvKv-IgG2 | 1 mg/kg | i.p. | Day 2, 5/wk | 6 |
| G9 | 5 | 45-8F1-mHvKv-IgG2 | 1 mg/kg | i.p. | Day 2, 5/wk | 6 |
| G10 | 5 | Urelumab | 1 mg/kg | i.p. | Day 2, 5/wk | 6 |

Figure 28:
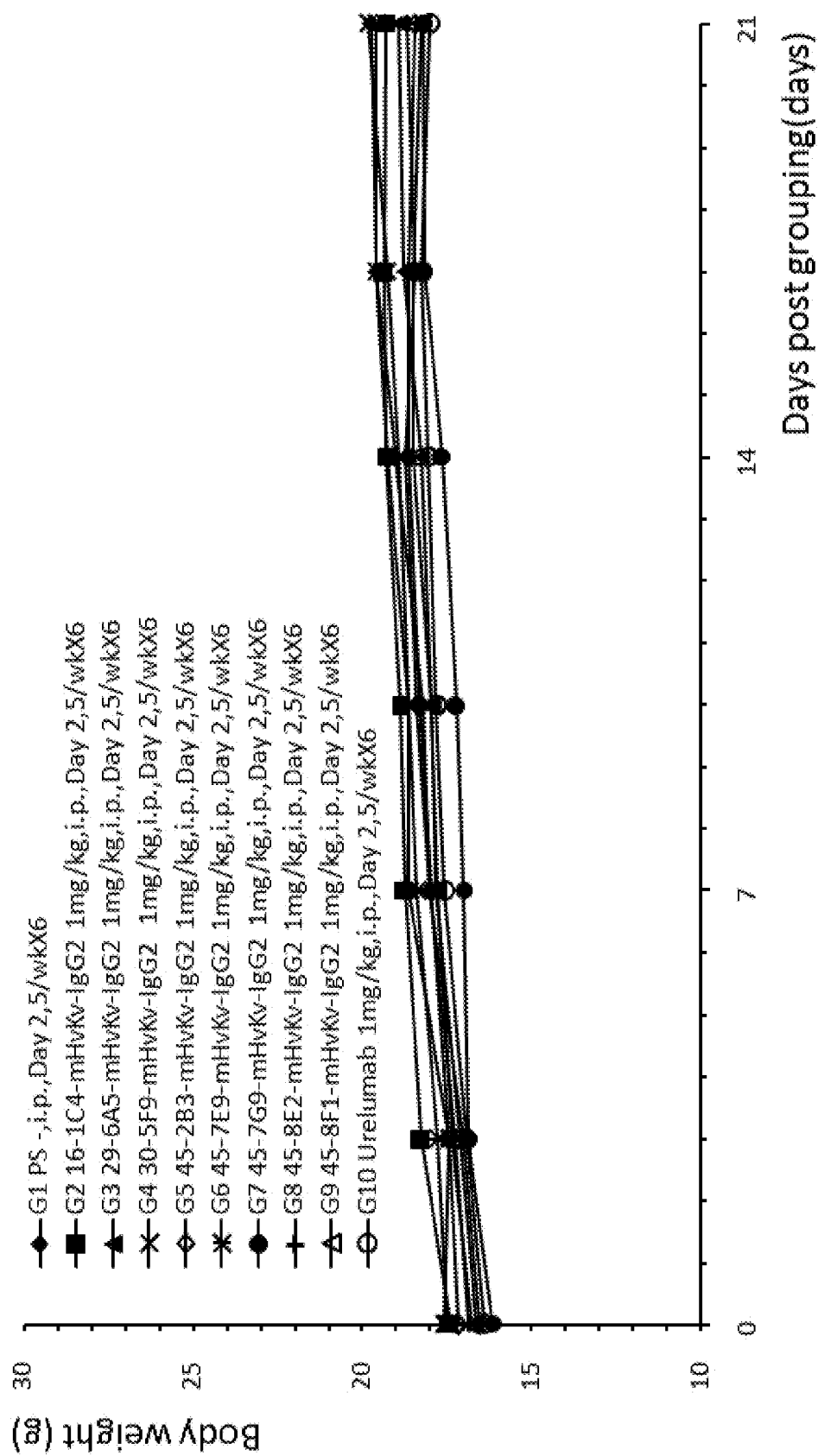
FIG. 28 is a graph showing body weight over time of humanized 4-1BB mice (B-h4-1BB) with MC-38 tumor cells treated with anti-h4-1BB antibodies 16-1C4-mHvKv-IgG2, 29-6A5-mHvKv-IgG2, 30-5F9-mHvKv-IgG2, 45-2B3-mHvKv-IgG2, 45-7E9-mHvKv-IgG2, 45-7G9-mHvKv-IgG2, 45-8E2-mHvKv-IgG2, 45-8F1-mHvKv-IgG2, and urelumab.
Figure 29:
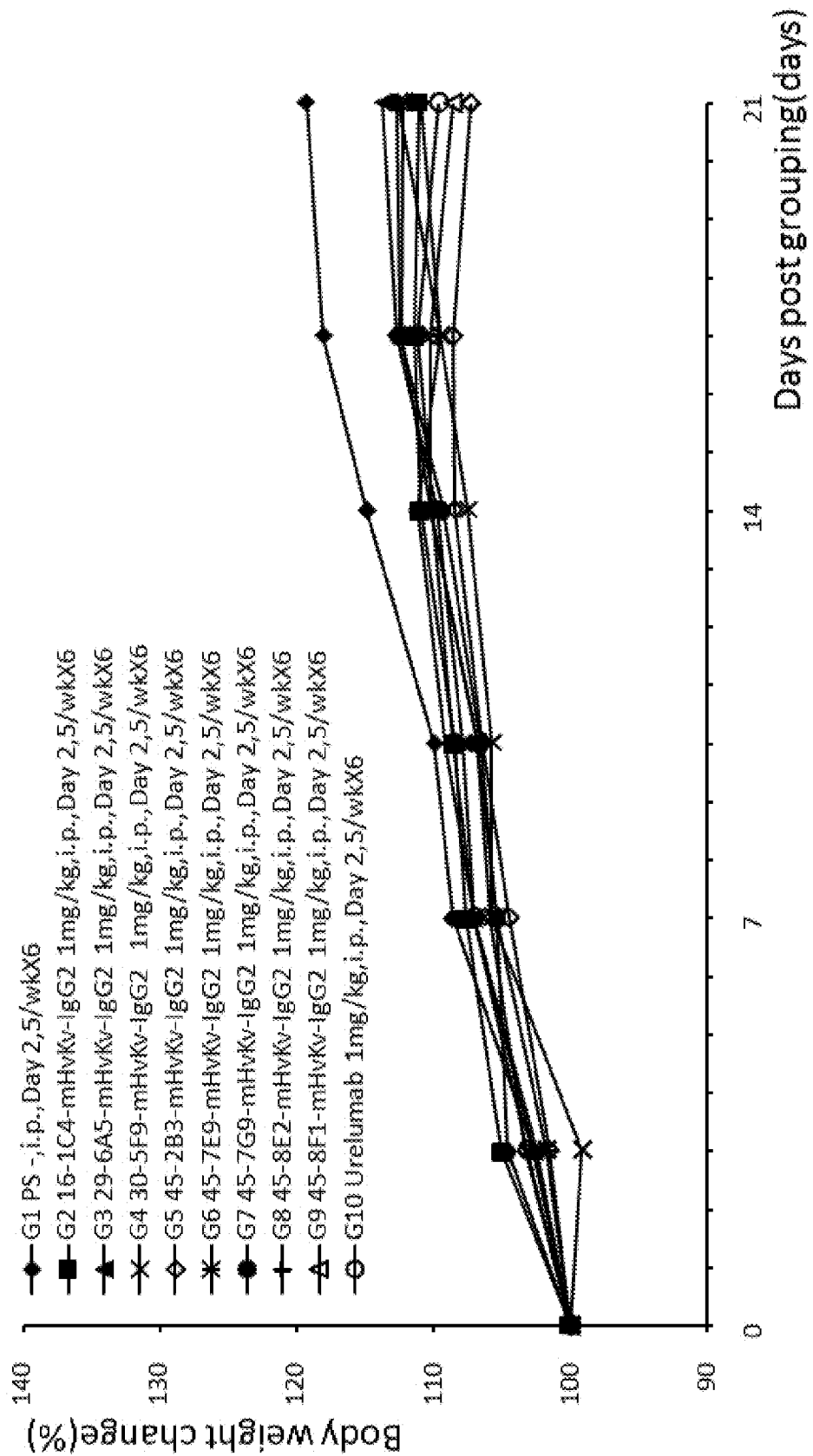
FIG. 29 is a graph showing percentage change of body weight over time of humanized 4-1BB mice (B-h4-1BB) with MC-38 tumor cells treated with anti-h4-1BB antibodies 16-1C4-mHvKv-IgG2, 29-6A5-mHvKv-IgG2, 30-5F9-mHvKv-IgG2, 45-2B3-mHvKv-IgG2, 45-7E9-mHvKv-IgG2, 45-7G9-mHvKv-IgG2, 45-8E2-mHvKv-IgG2, 45-8F1-mHvKv-IgG2, and urelumab.
Figure 30:
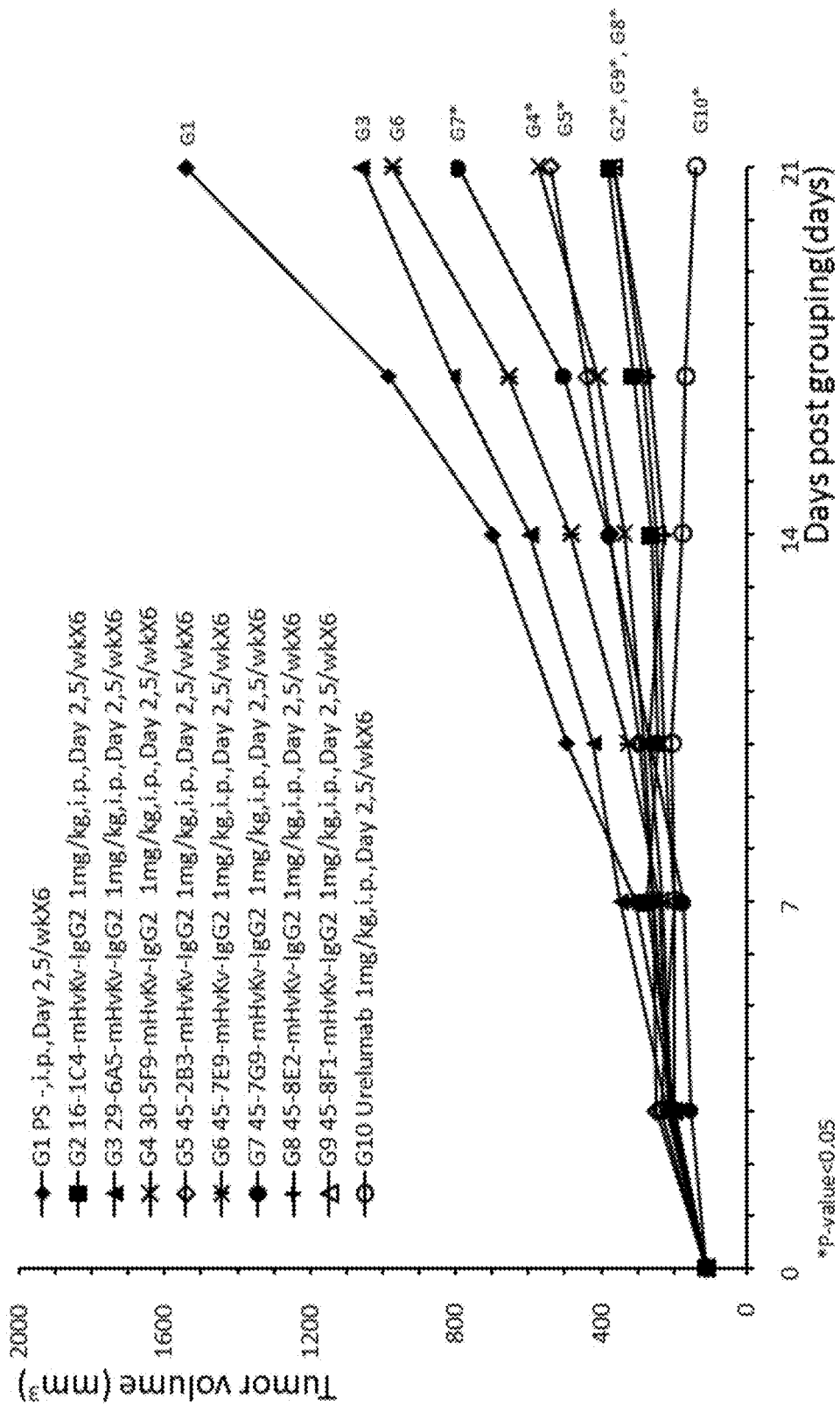
FIG. 30 is a graph showing tumor size over time in humanized 4-1BB mice (B-h4-1BB) with MC-38 tumor cells treated with anti-h4-1BB antibodies 16-1C4-mHvKv-IgG2, 29-6A5-mHvKv-IgG2, 30-5F9-mHvKv-IgG2, 45-2B3-mHvKv-IgG2, 45-7E9-mHvKv-IgG2, 45-7G9-mHvKv-IgG2, 45-8E2-mHvKv-IgG2, 45-8F1-mHvKv-IgG2, and urelumab.

The weight of the mice was monitored during the entire treatment period. The average weight of mice in different groups all increased at the end of the treatment period (FIG. 28, and FIG. 29). No obvious difference in weight was observed among different groups. The results showed that these anti-h4-1BB antibodies were well tolerated and were not obviously toxic to the mice. The tumor size for each group is shown in FIG. 30.

The TGI % at day 21 (21 days after grouping) was also calculated as shown in the table below.

TABLE 23

|  |  | Tumor volume(mm$^3$) | | | | Survival | TGI % | P value | |
|---|---|---|---|---|---|---|---|---|---|
|  |  | Day 0 | Day 7 | Day 14 | Day 21 |  |  | Body weight | Tumor Volume |
| Control | G1 | 111 ± 4 | 308 ± 41 | 698 ± 95 | 1543 ± 239 | 5/5 | n.a. | n.a. | n.a. |
| Treat | G2 | 111 ± 8 | 275 ± 43 | 262 ± 91 | 381 ± 195 | 5/5 | 75.3% | 0.586 | 0.006 |
|  | G3 | 111 ± 6 | 348 ± 59 | 596 ± 122 | 1060 ± 194 | 5/5 | 31.3% | 0.423 | 0.156 |
|  | G4 | 111 ± 8 | 258 ± 37 | 338 ± 39 | 574 ± 94 | 5/5 | 62.8% | 0.960 | 0.005 |
|  | G5 | 111 ± 6 | 258 ± 27 | 378 ± 59 | 539 ± 107 | 5/5 | 65.1% | 0.332 | 0.005 |
|  | G6 | 111 ± 7 | 241 ± 51 | 487 ± 245 | 974 ± 598 | 5/5 | 36.9% | 0.869 | 0.403 |
|  | G7 | 111 ± 5 | 175 ± 24 | 382 ± 82 | 794 ± 194 | 5/5 | 48.6% | 0.233 | 0.041 |
|  | G8 | 111 ± 8 | 233 ± 33 | 229 ± 63 | 366 ± 181 | 5/5 | 76.3% | 0.345 | 0.004 |
|  | G9 | 111 ± 7 | 201 ± 33 | 252 ± 106 | 367 ± 227 | 5/5 | 76.2% | 0.173 | 0.007 |
|  | G10 | 111 ± 7 | 198 ± 49 | 180 ± 72 | 140 ± 76 | 5/5 | 90.9% | 0.104 | 0.001 |

The results showed that all of these chimeric antibodies can inhibit tumor growth to different extents.

Example 9. In Vivo Testing of Humanized Anti-h4-1BB Antibodies

The humanized anti-h4-1BB antibodies were tested in 4-1BB humanized mice (B-h4-1BB) to demonstrate their effect on tumor growth in vivo. MC-38 cancer tumor cells (colon adenocarcinoma cell) were injected subcutaneously in B-h4-1BB mice. When the tumors in the mice reached a volume of 150±50 mm$^3$, the mice were randomly placed into different groups based on the volume of the tumor.
In Vivo Results for Humanized Anti-4-1BB Antibodies 6A5-H1K2-IgG2, 6A5-H1K3-IgG2, and 6A5-H2K2-IgG2

In G1 group, B-h4-1BB mice were injected with physiological saline (PS) as a control. In the treatment groups, 6A5-H1K2-IgG2 (G2), 6A5-H1K3-IgG2 (G3), 6A5-H2K2-IgG2 (G4), 6A5 (G5), and urelumab (G6) were administered to the mice.

TABLE 24

| Group | No. of mice | Antibodies | Dosage (mg/kg) | Route | Frequency | Total No. of administration |
|---|---|---|---|---|---|---|
| G1 | 9 | PS (control) | — | i.p. | Day 1, 4/wk | 6 |
| G2 | 9 | 6A5-H1K2-IgG2 | 1 mg/kg | i.p. | Day 1, 4/wk | 6 |
| G3 | 9 | 6A5-H1K3-IgG2 | 1 mg/kg | i.p. | Day 1, 4/wk | 6 |
| G4 | 9 | 6A5-H2K2-IgG2 | 1 mg/kg | i.p. | Day 1, 4/wk | 6 |
| G5 | 9 | 29-6A5 | 1 mg/kg | i.p. | Day 1, 4/wk | 6 |
| G6 | 9 | Urelumab | 1 mg/kg | i.p. | Day 1, 4/wk | 6 |

Figure 31:
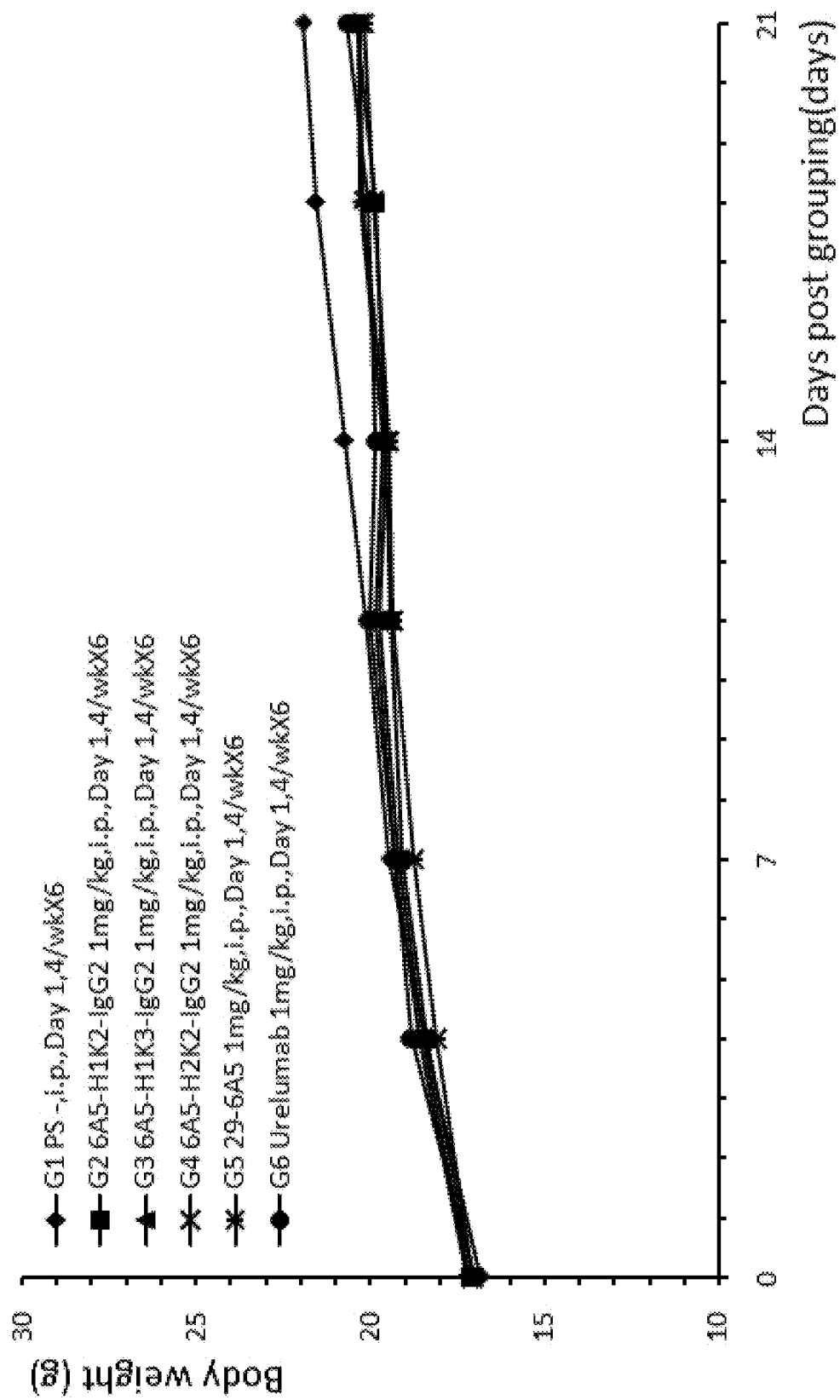
FIG. 31 is a graph showing body weight over time of humanized 4-1BB mice (B-h4-1BB) with MC-38 tumor cells treated with anti-h4-1BB antibodies 6A5-H1K2-IgG2, 6A5-H1K3-IgG2, 6A5-H2K2-IgG2, 6A5, and urelumab.
Figure 32:
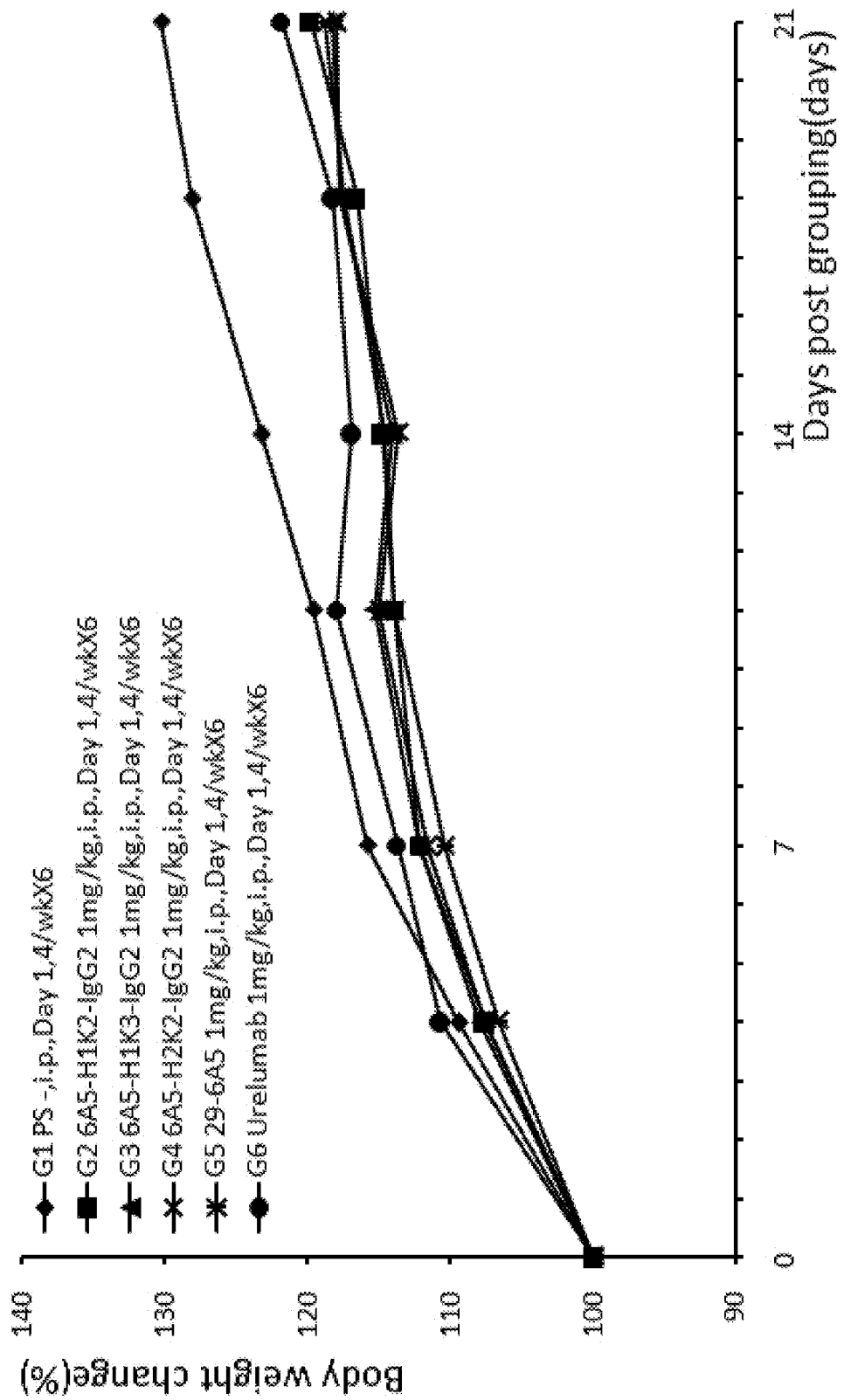
FIG. 32 is a graph showing percentage change of body weight over time of humanized 4-1BB mice (B-h4-1BB) with MC-38 tumor cells treated with anti-h4-1BB antibodies 6A5-H1K2-IgG2, 6A5-H1K3-IgG2, 6A5-H2K2-IgG2, 6A5, and urelumab.
Figure 33:
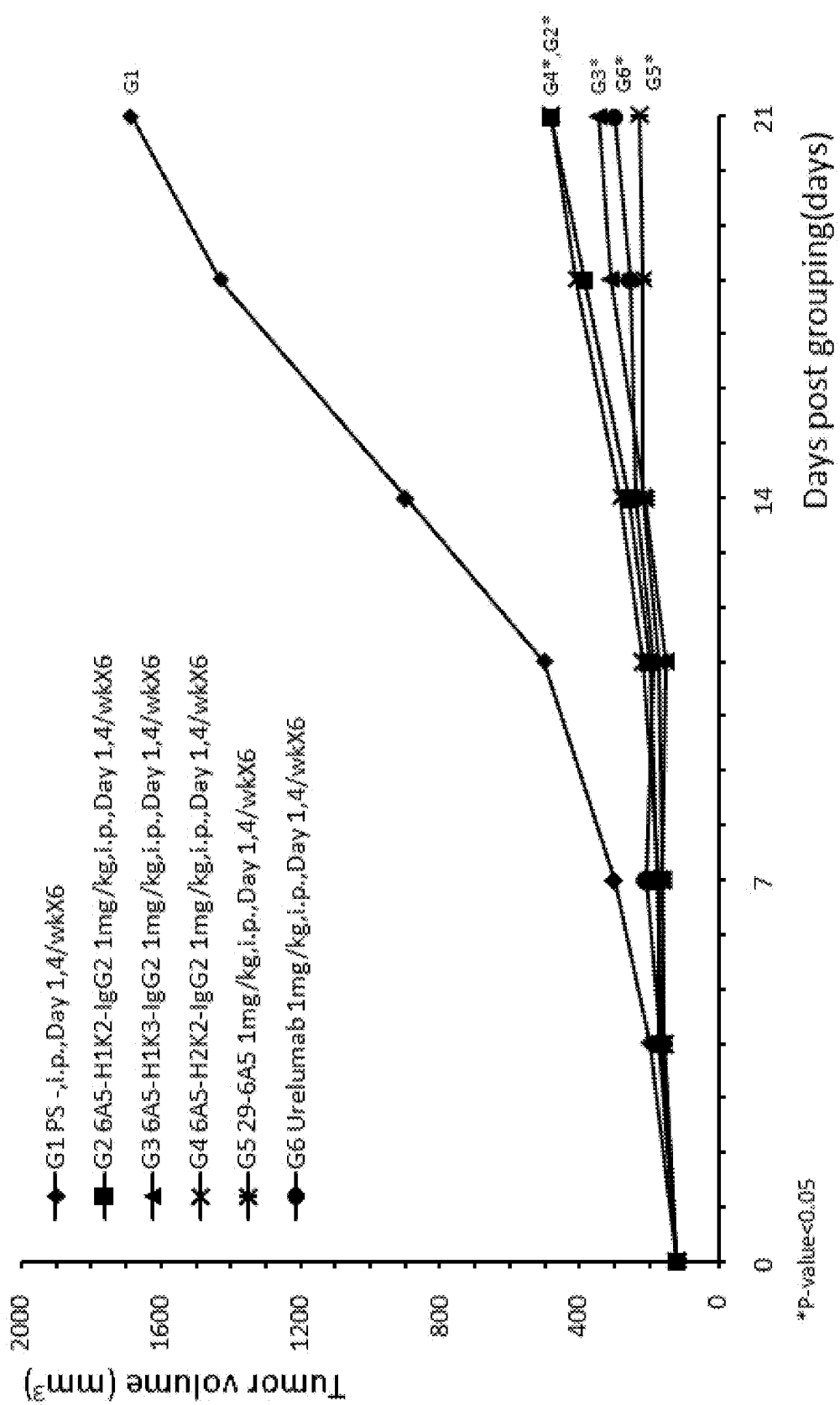
FIG. 33 is a graph showing tumor size over time in humanized 4-1BB mice (B-h4-1BB) with MC-38 tumor cells treated with anti-h4-1BB antibodies 6A5-H1K2-IgG2, 6A5-H1K3-IgG2, 6A5-H2K2-IgG2, 6A5, and urelumab.

The weight of the mice was monitored during the entire treatment period. The average weight of mice in different groups all increased at the end of the treatment period (FIG. 31, and FIG. 32). No obvious difference in weight was observed among different groups. The results showed that these anti-h4-1BB antibodies were well tolerated and were not obviously toxic to the mice. The tumor size for each group is shown in FIG. 33.

The TGI % at day 21 (21 days after grouping) was also calculated as shown in the table below.

TABLE 25

| | | Tumor volume(mm³) | | | | | P value | |
|---|---|---|---|---|---|---|---|---|---|
| | | Day 0 | Day 7 | Day 14 | Day 21 | Survival | TGI % | Body weight | Tumor Volume |
| Control | G1 | 119 ± 6 | 300 ± 52 | 900 ± 202 | 1688 ± 341 | 9/9 | n.a. | n.a. | n.a. |
| Treat | G2 | 119 ± 7 | 179 ± 18 | 257 ± 49 | 480 ± 132 | 9/9 | 71.6% | 0.086 | 0.005 |
| | G3 | 119 ± 7 | 160 ± 20 | 211 ± 29 | 346 ± 61 | 9/9 | 79.5% | 0.084 | 1.4E−03 |
| | G4 | 119 ± 7 | 172 ± 26 | 284 ± 56 | 480 ± 118 | 9/9 | 71.6% | 0.111 | 0.004 |
| | G5 | 119 ± 6 | 160 ± 29 | 219 ± 66 | 227 ± 97 | 9/9 | 86.6% | 0.065 | 8.1E−04 |
| | G6 | 119 ± 7 | 210 ± 29 | 239 ± 65 | 298 ± 130 | 9/9 | 82.3% | 0.131 | 0.002 |

The results showed that all of these humanized anti-h4-1BB antibodies (G2, G3, and G4) can inhibit tumor growth.

In Vivo Results for Humanized Anti-4-1BB Antibodies 1C4-H1K1-IgG4, 1C4-H1K2-IgG4, 5F9-H1K1-IgG4, and 30-5F9-H1K2-IgG4

In G1 group, B-h4-1BB mice were injected with physiological saline (PS) as a control. In treatment groups, 1C4-H1K1-IgG4 (G2), 1C4-H1K2-IgG4 (G3), 5F9-H1K1-IgG4 (G4), 5F9-H1K2-IgG4 (G5), 16-1C4 (G6), 30-5F9 (G7) and urelumab (G8) were administered to the mice.

TABLE 26

| Group | No. of mice | Antibodies | Dosage (mg/kg) | Route | Frequency | Total No. of administration |
|---|---|---|---|---|---|---|
| G1 | 5 | PS (control) | — | i.p. | Day 1, 4/wk | 6 |
| G2 | 5 | 1C4-H1K1-IgG4 | 1 mg/kg | i.p. | Day 2, 5/wk | 6 |
| G3 | 5 | 1C4-H1K2-IgG4 | 1 mg/kg | i.p. | Day 2, 5/wk | 6 |
| G4 | 5 | 5F9-H1K1-IgG4 | 1 mg/kg | i.p. | Day 2, 5/wk | 6 |
| G5 | 5 | 5F9-H1K2-IgG4 | 1 mg/kg | i.p. | Day 2, 5/wk | 6 |
| G6 | 5 | 16-1C4 | 1 mg/kg | i.p. | Day 2, 5/wk | 6 |
| G7 | 5 | 30-5F9 | 1 mg/kg | i.p. | Day 2, 5/wk | 6 |
| G8 | 5 | Urelumab | 1 mg/kg | i.p. | Day 2, 5/wk | 6 |

Figure 34:
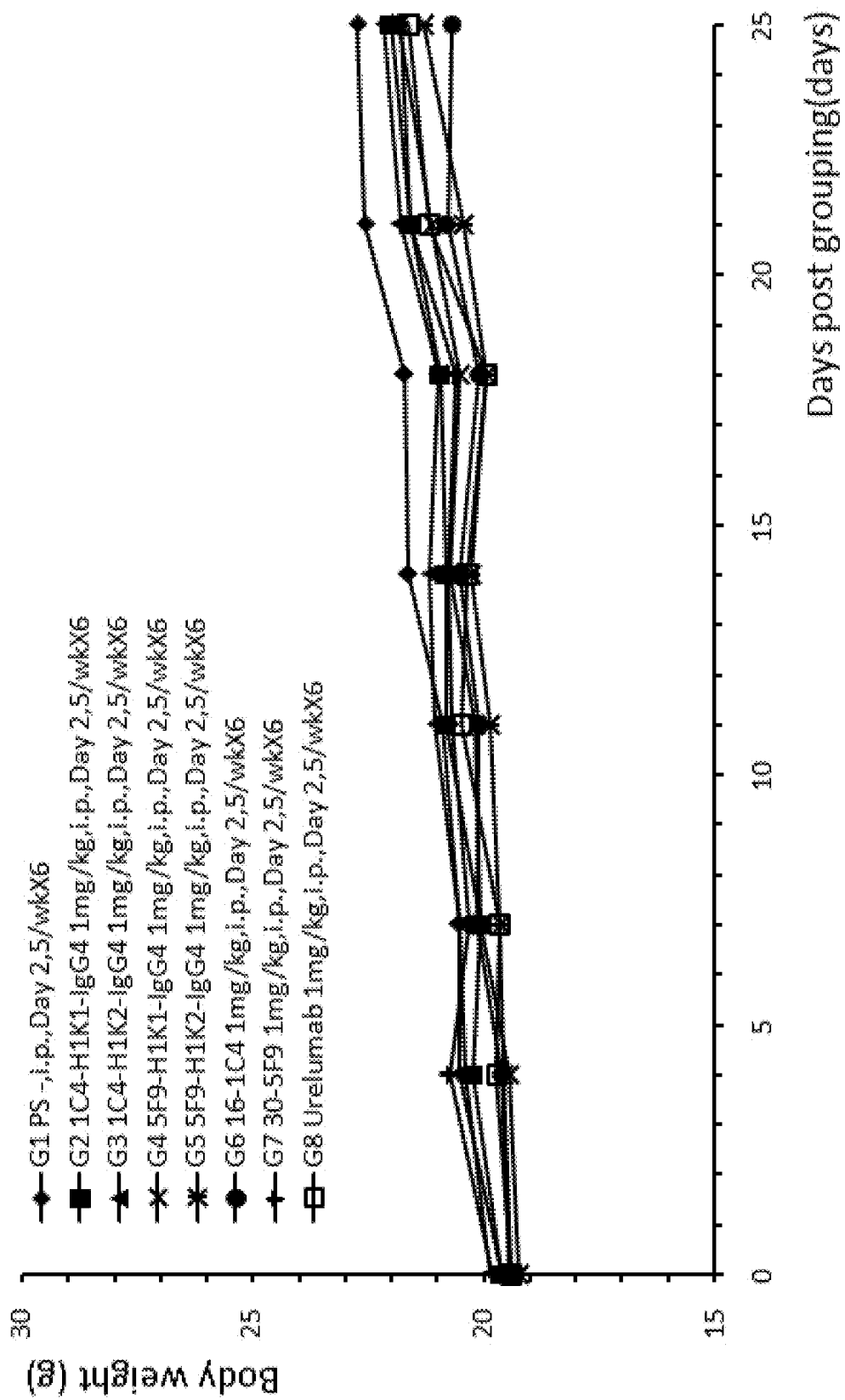
FIG. 34 is a graph showing body weight over time of humanized 4-1BB mice (B-h4-1BB) with MC-38 tumor cells treated with anti-h4-1BB antibodies 1C4-H1K1-IgG4, 1C4-H1K2-IgG4, 5F9-H1K1-IgG4, 5F9-H1K2-IgG4, 16-1C4, 30-5F9, and urelumab.
Figure 35:
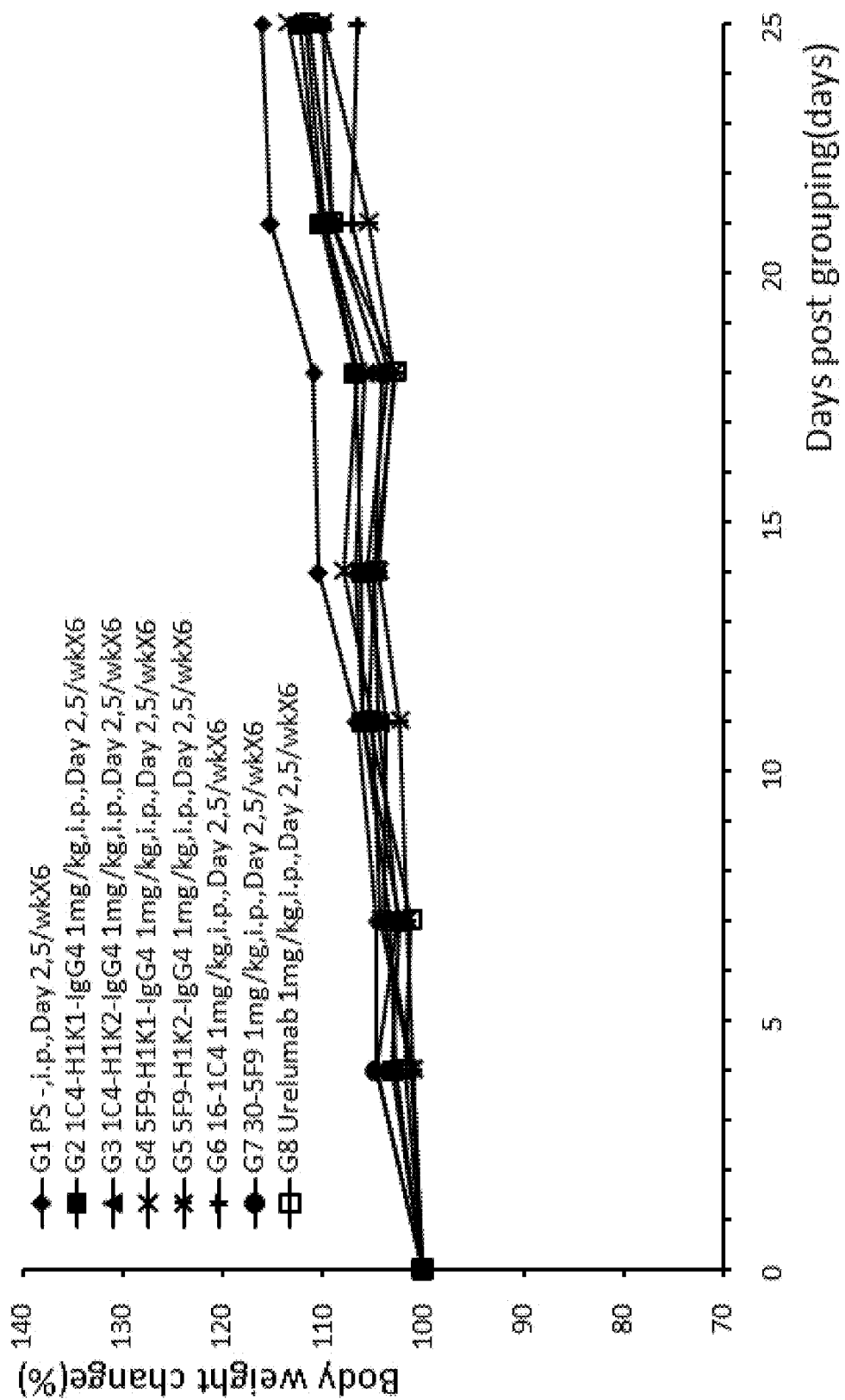
FIG. 35 is a graph showing percentage change of body weight over time of humanized 4-1BB mice (B-h4-1BB) with MC-38 tumor cells treated with anti-h4-1BB antibodies 1C4-H1K1-IgG4, 1C4-H1K2-IgG4, 5F9-H1K1-IgG4, 5F9-H1K2-IgG4, 16-1C4, 30-5F9, and urelumab.
Figure 36:
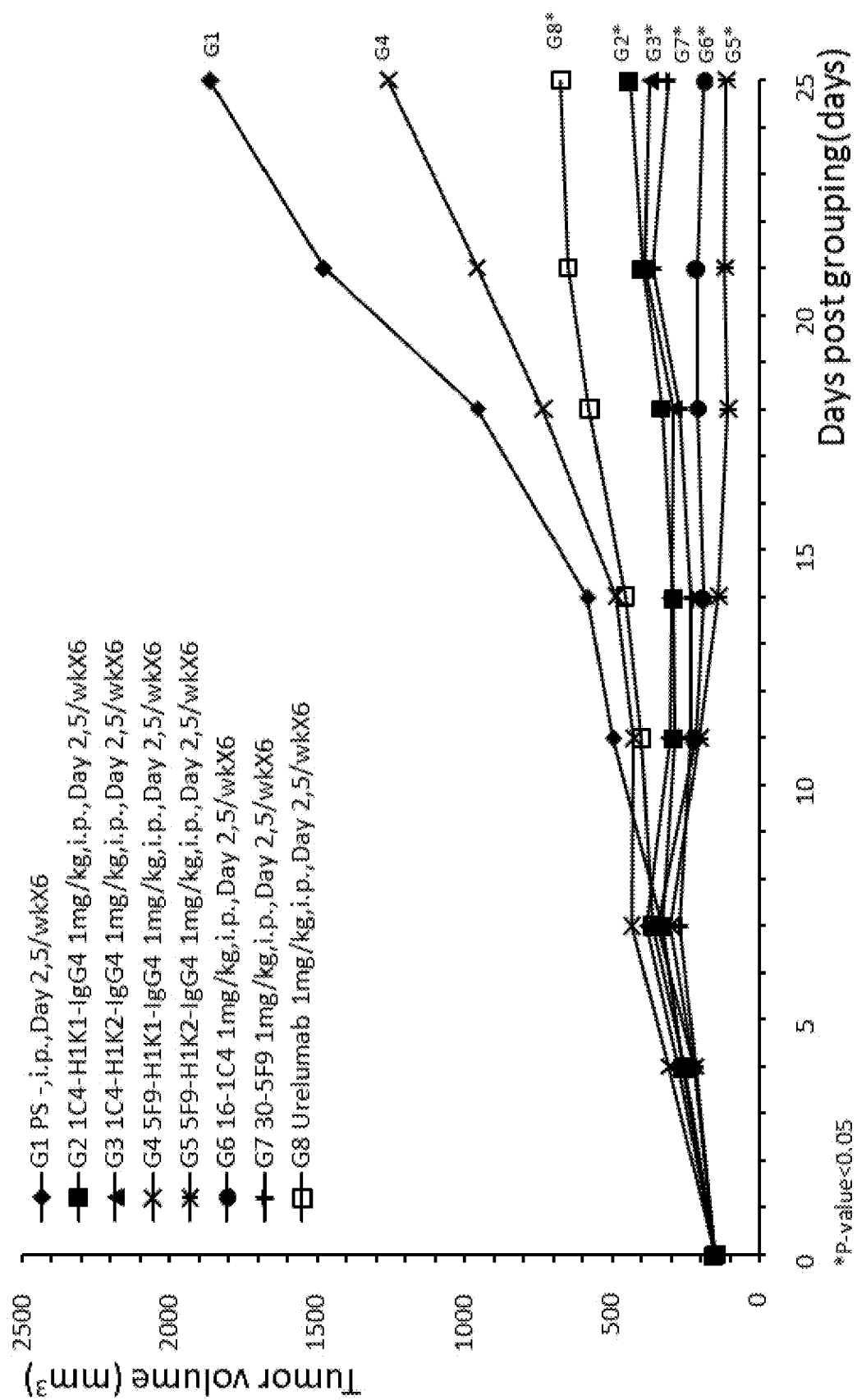
FIG. 36 is a graph showing tumor size over time in humanized 4-1BB mice (B-h4-1BB) with MC-38 tumor cells treated with anti-h4-1BB antibodies 1C4-H1K1-IgG4, 1C4-H1K2-IgG4, 5F9-H1K1-IgG4, -5F9-H1K2-IgG4, 16-1C4, 30-5F9, and urelumab.

The weight of the mice was monitored during the entire treatment period. The average weight of mice in different groups all increased at the end of the treatment period (FIG. 34, and FIG. 35). No obvious difference in weight was observed among different groups. The results showed that these anti-h4-1BB antibodies were well tolerated and were not obviously toxic to the mice. The tumor size for each group is shown in FIG. 36.

The TGI % at day 25 (25 days after grouping) was also calculated as shown in the table below.

The results showed that these humanized anti-h4-1BB antibodies have different tumor inhibitory effects.

Example 10. In Vivo Testing of IgG1, IgG2, and IgG4 Antibodies

MC-38 cancer tumor cells (colon adenocarcinoma cell) were injected subcutaneously in B-h4-1BB mice. When the tumors in the mice reached a volume of 150±50 mm³, the mice were randomly placed into different groups based on the volume of the tumor.

In G1 group, B-h4-1BB mice were injected with physiological saline (PS) as a control. Chimeric anti-h4-1BB antibodies 16-1C4-mHvKv-IgG1 (G2), 16-1C4-mHvKv-IgG2 (G3), 16-1C4-mHvKv-IgG4 (G4), mouse anti-h4-1BB antibodies 16-1C4 (G5), and urelumab (G6) were administered to the mice.

TABLE 27

| | | Tumor volume(mm³) | | | | | | P value | |
|---|---|---|---|---|---|---|---|---|---|
| | | Day 0 | Day 11 | Day 18 | Day 25 | Survival | TGI % | Body weight | Tumor Volume |
| Control | G1 | 150 ± 5 | 495 ± 88 | 955 ± 236 | 1863 ± 340 | 5/5 | n.a. | n.a. | n.a. |
| Treat | G2 | 150 ± 6 | 287 ± 20 | 330 ± 86 | 436 ± 166 | 5/5 | 76.6% | 0.579 | 0.005 |
| | G3 | 150 ± 6 | 302 ± 22 | 289 ± 57 | 371 ± 115 | 5/5 | 80.1% | 0.640 | 0.003 |
| | G4 | 150 ± 6 | 426 ± 91 | 733 ± 268 | 1259 ± 609 | 5/5 | 32.4% | 0.538 | 0.412 |
| | G5 | 150 ± 6 | 201 ± 46 | 107 ± 65 | 109 ± 83 | 5/5 | 94.2% | 0.270 | 1.0E−03 |
| | G6 | 150 ± 6 | 214 ± 28 | 208 ± 38 | 186 ± 70 | 5/5 | 90.0% | 0.117 | 1.3E−03 |
| | G7 | 150 ± 5 | 232 ± 28 | 266 ± 79 | 307 ± 140 | 5/5 | 83.5% | 0.456 | 0.003 |
| | G8 | 150 ± 7 | 400 ± 89 | 576 ± 171 | 672 ± 294 | 5/5 | 63.9% | 0.381 | 0.029 |

TABLE 28

| Group | No. of mice | Antibodies | Dosage (mg/kg) | Route | Frequency | Total No. of administration |
|---|---|---|---|---|---|---|
| G1 | 7 | PS (control) | — | i.p. | Day 1, 4/wk | 6 |
| G2 | 7 | 16-1C4-mHvKv-IgG1 | 1 mg/kg | i.p. | Day 1, 4/wk | 6 |
| G3 | 7 | 16-1C4-mHvKv-IgG2 | 1 mg/kg | i.p. | Day 1, 4/wk | 6 |
| G4 | 7 | 16-1C4-mHvKv-IgG4 | 1 mg/kg | i.p. | Day 1, 4/wk | 6 |
| G5 | 7 | 16-1C4 | 1 mg/kg | i.p. | Day 1, 4/wk | 6 |
| G6 | 7 | Urelumab | 1 mg/kg | i.p. | Day 1, 4/wk | 6 |

Figure 37:
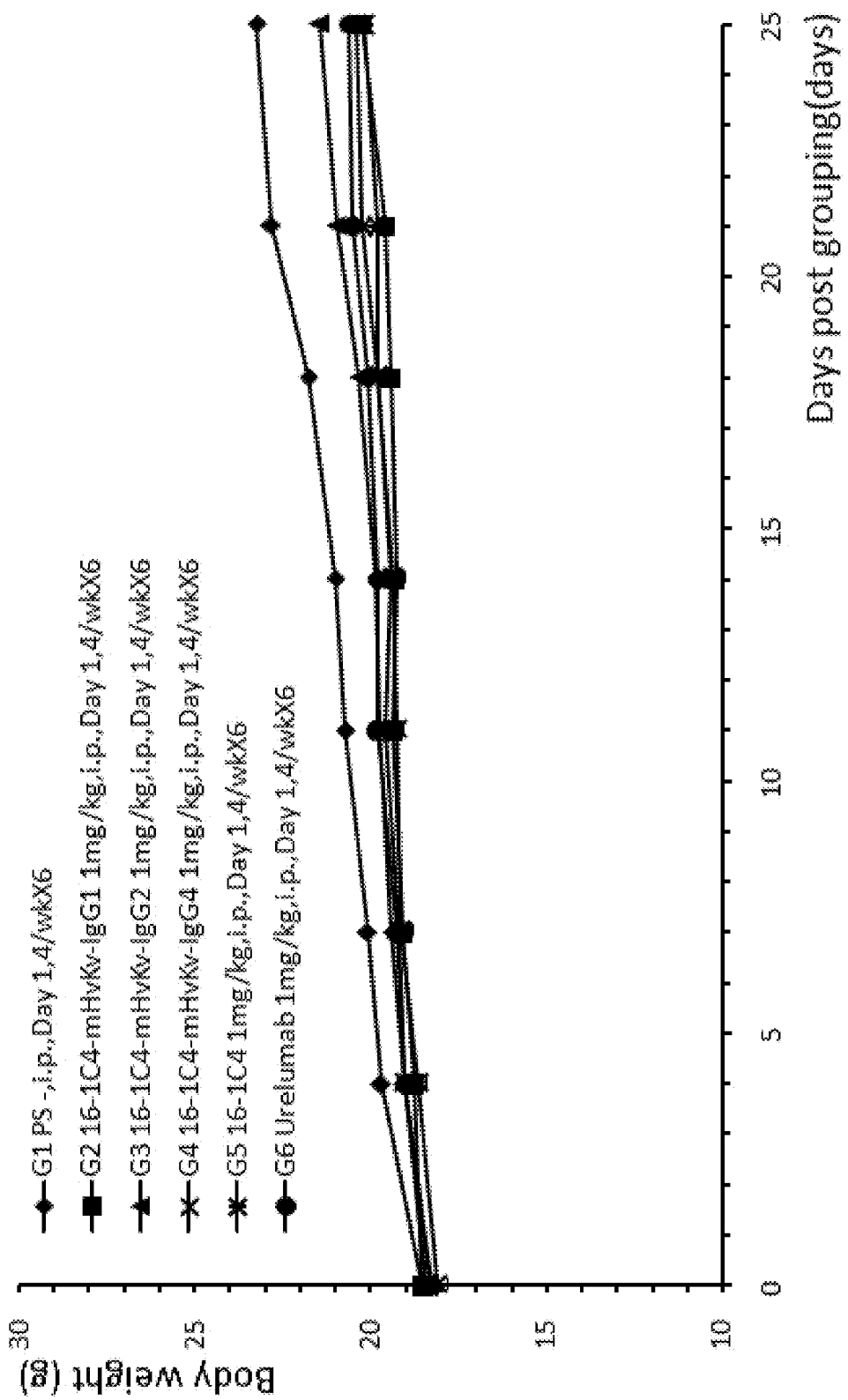
FIG. 37 is a graph showing body weight over time of humanized 4-1BB mice (B-h4-1BB) with MC-38 tumor cells treated with anti-h4-1BB antibodies 16-1C4-mHvKv-IgG1 (G2), 16-1C4-mHvKv-IgG2 (G3), 16-1C4-mHvKv-IgG4 (G4), 16-1C4 (G5), and urelumab (G6).
Figure 38:
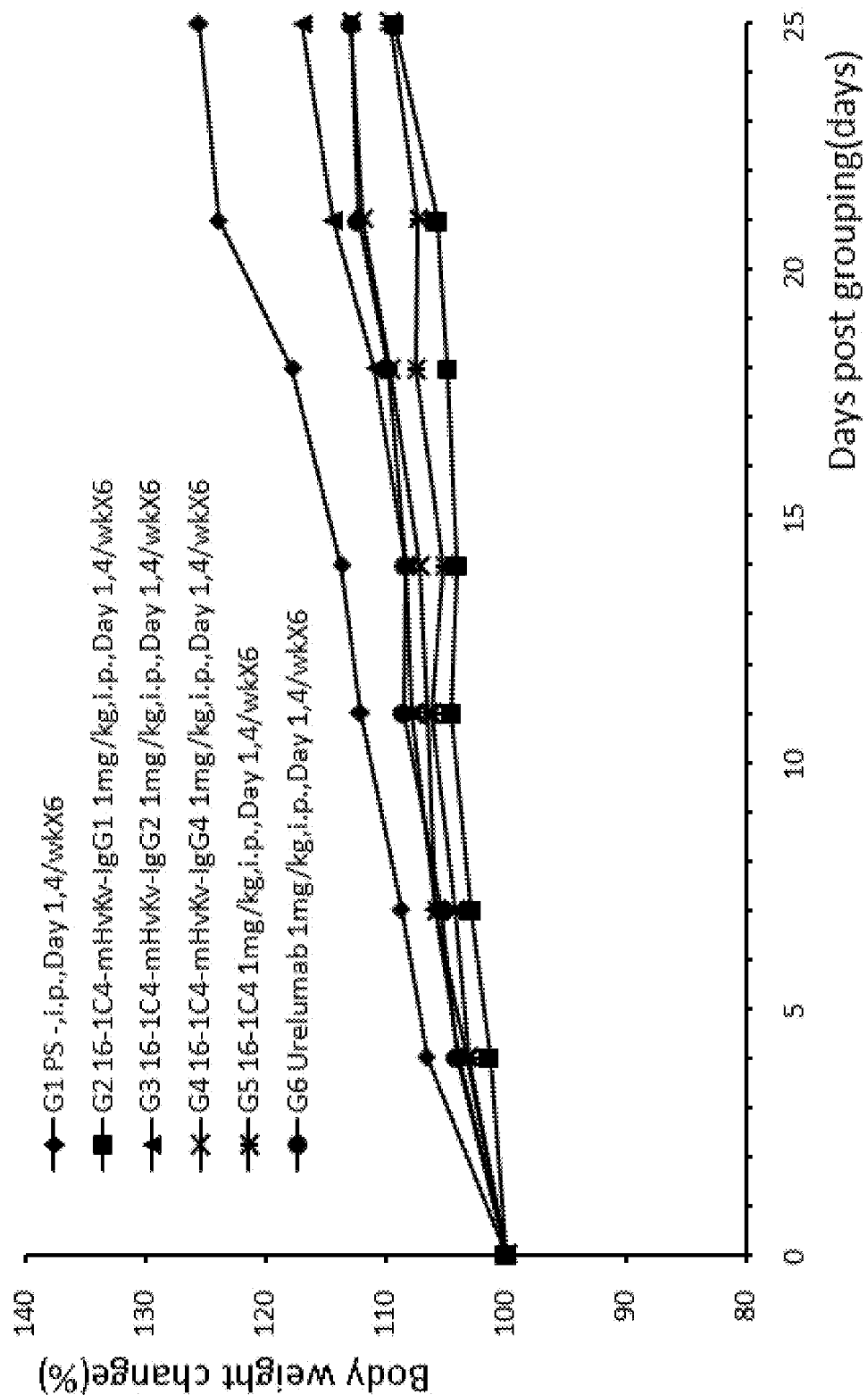
FIG. 38 is a graph showing percentage change of body weight over time of humanized 4-1BB mice (B-h4-1BB) with MC-38 tumor cells treated with anti-h4-1BB antibodies 16-1C4-mHvKv-IgG1 (G2), 16-1C4-mHvKv-IgG2 (G3), 16-1C4-mHvKv-IgG4 (G4), 16-1C4 (G5), and urelumab (G6).
Figure 39:
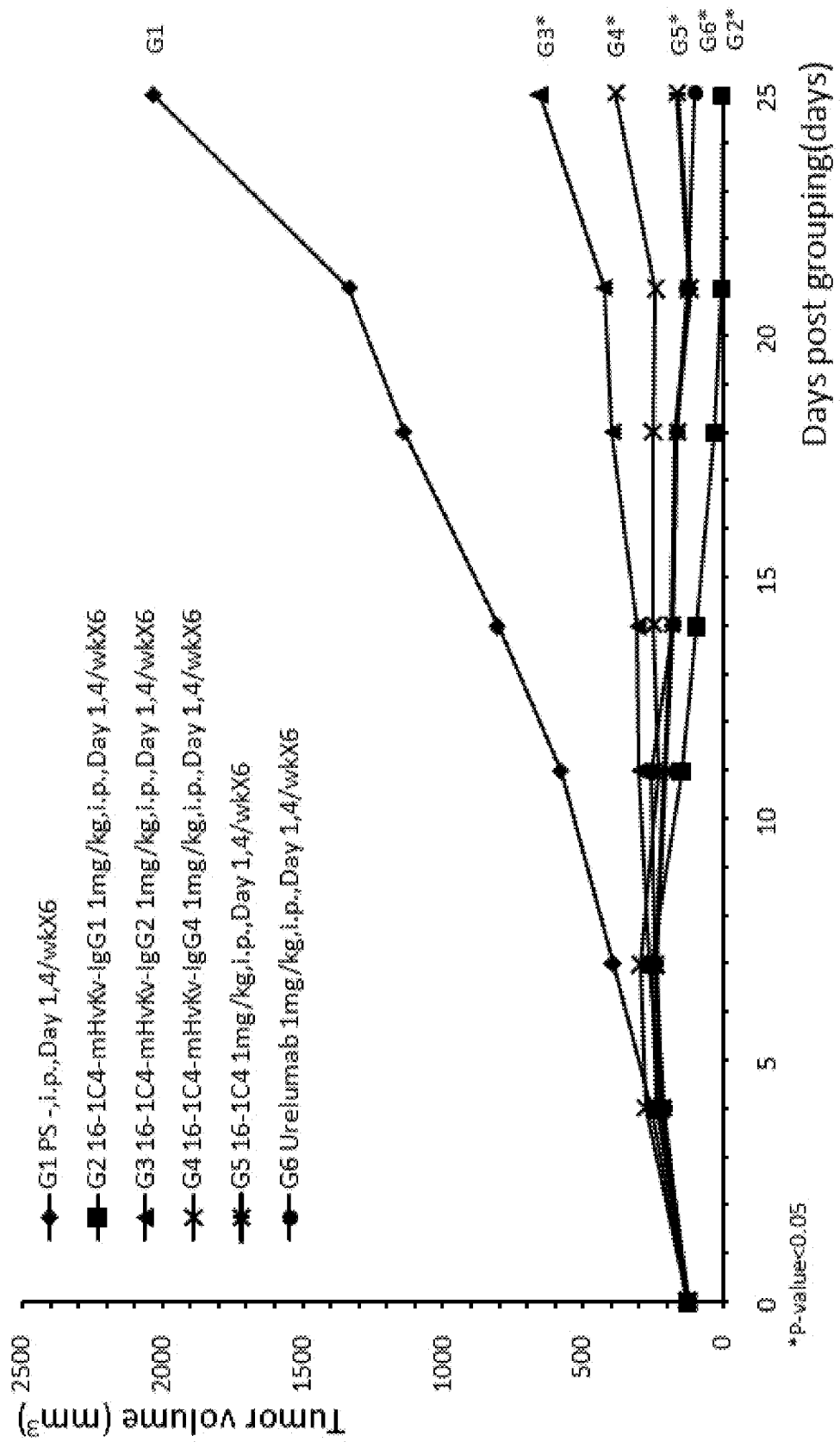
FIG. 39 is a graph showing tumor size over time in humanized 4-1BB mice (B-h4-1BB) with MC-38 tumor cells treated with anti-h4-1BB antibodies 16-1C4-mHvKv-IgG1 (G2), 16-1C4-mHvKv-IgG2 (G3), 16-1C4-mHvKv-IgG4 (G4), 16-1C4 (G5), and urelumab (G6).

The weight of the mice was monitored during the entire treatment period. The average weight of mice in different groups all increased at the end of the treatment period (FIG. 37, and FIG. 38). No obvious difference in weight was observed among different groups. The results showed that these anti-h4-1BB antibodies were well tolerated and were not obviously toxic to the mice. The tumor size for each group is shown in FIG. 39.

The TGI % at day 25 (25 days after grouping) was also calculated as shown in the table below.

TABLE 29

| | | Tumor volume(mm$^3$) | | | | | P value | |
|---|---|---|---|---|---|---|---|---|
| | | Day 0 | Day 11 | Day 18 | Day 25 | Survival | TGI % | Body weight | Tumor Volume |
| Control | G1 | 124 ± 7 | 580 ± 74 | 1139 ± 121 | 2035 ± 176 | 7/7 | n.a. | n.a. | n.a. |
| Treat | G2 | 125 ± 7 | 147 ± 34 | 28 ± 14 | 0 ± 0 | 7/7 | 100.0% | 0.001 | 7.4E−08 |
| | G3 | 125 ± 6 | 297 ± 75 | 396 ± 148 | 655 ± 250 | 7/7 | 67.8% | 0.052 | 7.1E−04 |
| | G4 | 125 ± 6 | 230 ± 42 | 247 ± 73 | 383 ± 150 | 7/7 | 81.2% | 0.001 | 1.2E−05 |
| | G5 | 124 ± 7 | 205 ± 52 | 166 ± 92 | 164 ± 109 | 7/7 | 91.9% | 0.001 | 1.1E−06 |
| | G6 | 124 ± 7 | 254 ± 89 | 167 ± 102 | 102 ± 63 | 7/7 | 95.0% | 0.001 | 2.5E−07 |

The results showed that all of these anti-h4-1BB antibodies inhibited tumor growth. Particularly, IgG1 subclass had higher TGI % than the IgG2 and IgG4 subclasses.

Example 11. In Vivo Testing of Chimeric Anti-4-1BB IgG2 Antibodies

MC-38 cancer tumor cells (colon adenocarcinoma cell) were injected subcutaneously in B-h4-1BB mice. When the tumors in the mice reached a volume of 150±50 mm$^3$, the mice were randomly placed into different groups based on the volume of the tumor.

In G1 group, B-h4-1BB mice were injected with physiological saline (PS) as a control. In treatment groups, chimeric anti-h4-1BB antibodies 54-8B11-mHvKv-IgG2 (G2), 55-8F6-mHvKv-IgG2 (G3), 56-2A6-mHvKv-IgG2 (G4), 69-3C2-mHvKv-IgG2 (G5), 61-6A7-mHvKv-IgG2 (G6), 70-6F10-mHvKv-IgG2 (G7), 70-3F9-mHvKv-IgG2 (G8), 45-4B9-mHvkv-IgG2 (G9), and also urelumab (G10) were administered to the mice through intraperitoneal (i.p.) injection.

TABLE 30

| Group | No. of mice | Antibodies | Dosage (mg/kg) | Route | Frequency | Total No. of administration |
|---|---|---|---|---|---|---|
| G1 | 5 | PS (control) | — | i.p. | Day 2, 5/wk | 6 |
| G2 | 5 | 54-8B11-mHvKv-IgG2 | 1 mg/kg | i.p. | Day 2, 5/wk | 6 |
| G3 | 5 | 55-8F6-mHvKv-IgG2 | 1 mg/kg | i.p. | Day 2, 5/wk | 6 |
| G4 | 5 | 56-2A6-mHvKv-IgG2 | 1 mg/kg | i.p. | Day 2, 5/wk | 6 |
| G5 | 5 | 69-3C2-mHvKv-IgG2 | 1 mg/kg | i.p. | Day 2, 5/wk | 6 |
| G6 | 5 | 61-6A7-mHvKv-IgG2 | 1 mg/kg | i.p. | Day 2, 5/wk | 6 |
| G7 | 5 | 70-6F10-mHvKv-IgG2 | 1 mg/kg | i.p. | Day 2, 5/wk | 6 |
| G8 | 5 | 70-3F9-mHvKv-IgG2 | 1 mg/kg | i.p. | Day 2, 5/wk | 6 |
| G9 | 5 | 45-4B9-mHvkv-IgG2 | 1 mg/kg | i.p. | Day 2, 5/wk | 6 |
| G10 | 5 | Urelumab | 1 mg/kg | i.p. | Day 2, 5/wk | 6 |

Figure 40:
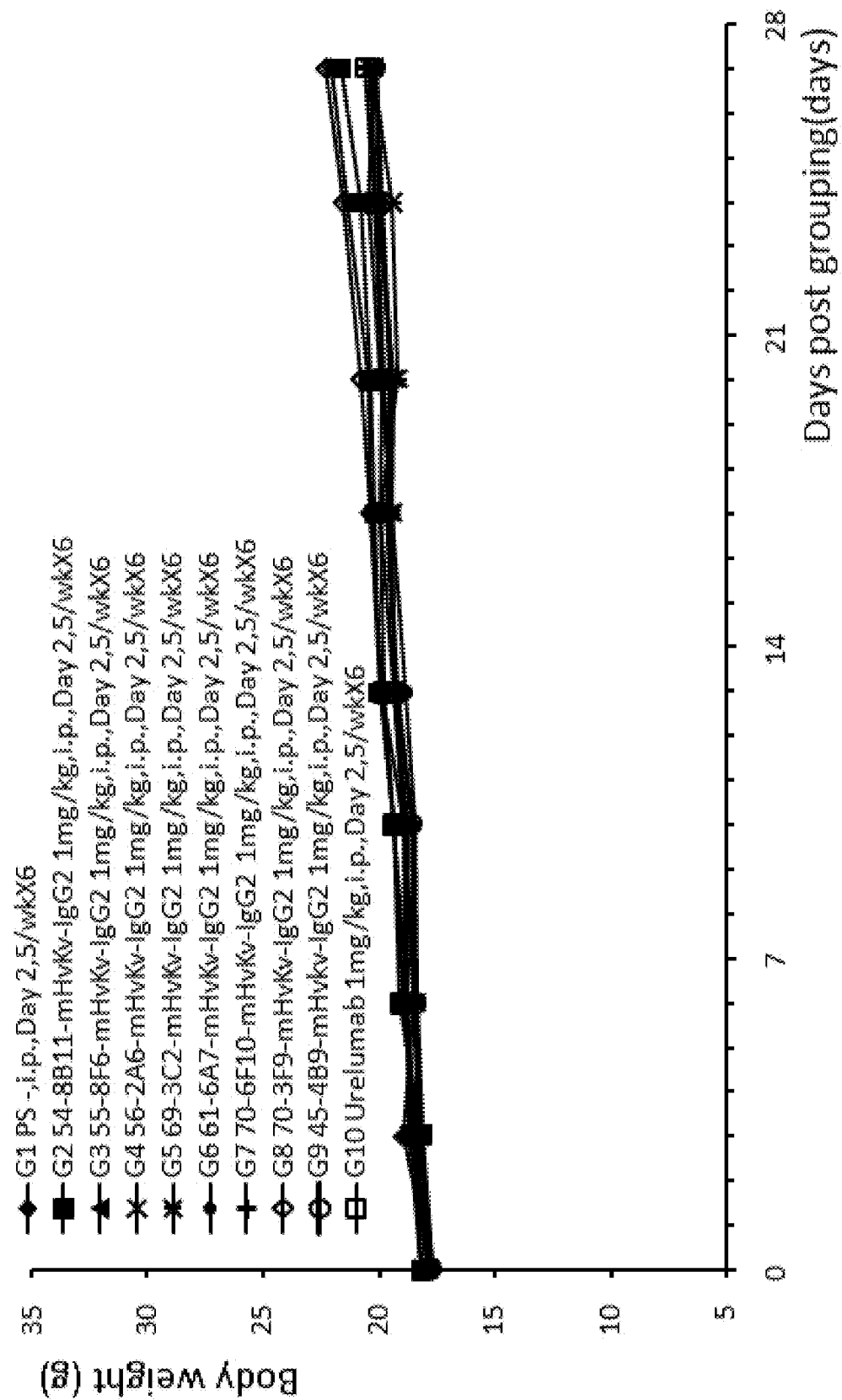
FIG. 40 is a graph showing body weight over time of humanized 4-1BB mice (B-h4-1BB) with MC-38 tumor cells treated with anti-h4-1BB antibodies 54-8B11-mHvKv-IgG2 (G2), 55-8F6-mHvKv-IgG2 (G3), 56-2A6-mHvKv-IgG2 (G4), 69-3C2-mHvKv-IgG2 (G5), 61-6A7-mHvKv-IgG2 (G6), 70-6F10-mHvKv-IgG2 (G7), 70-3F9-mHvKv-IgG2 (G8), 45-4B9-mHvkv-IgG2 (G9), and also urelumab (G10).
Figure 41:
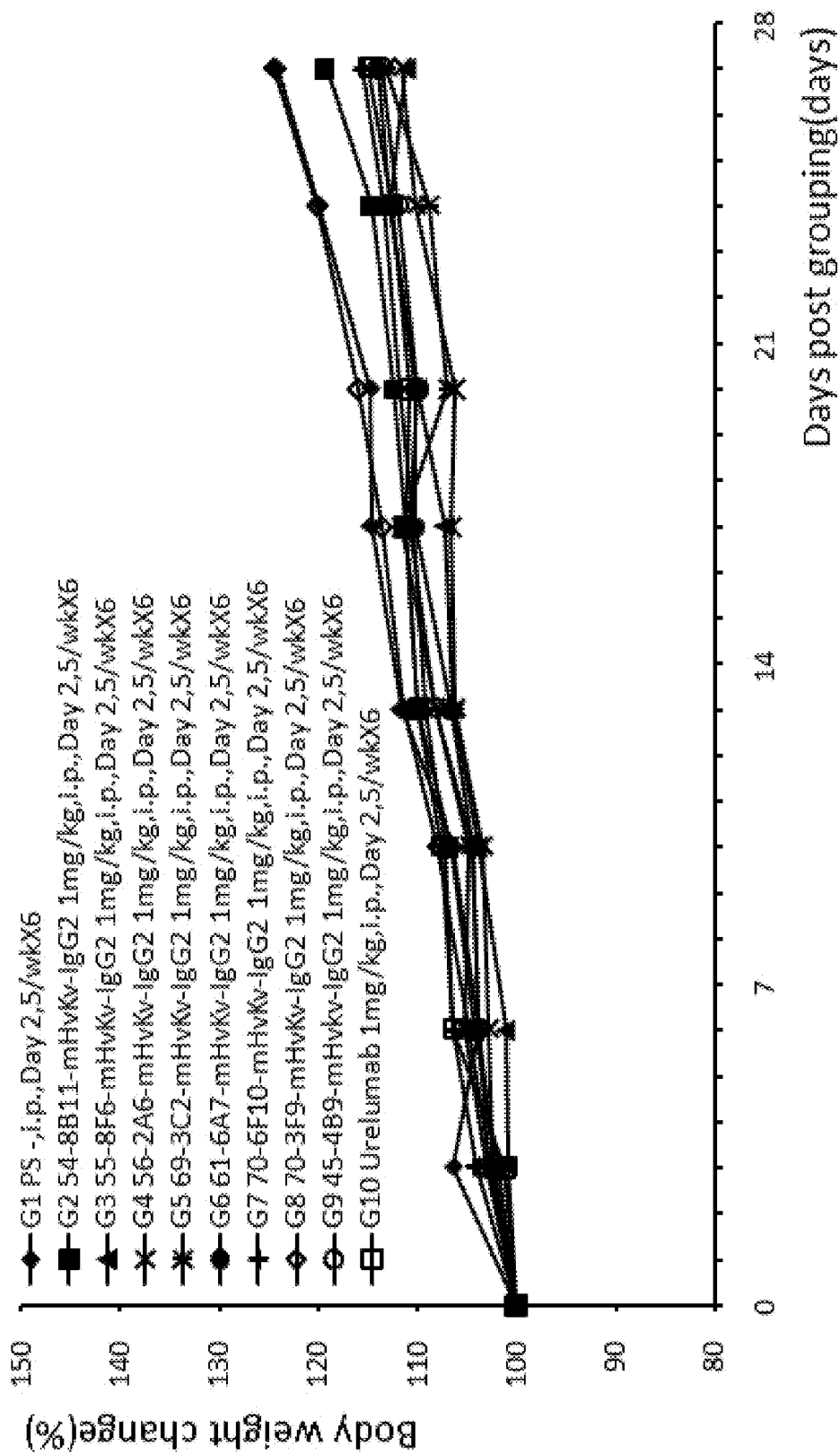
FIG. 41 is a graph showing percentage change of body weight over time of humanized 4-1BB mice (B-h4-1BB) with MC-38 tumor cells treated with anti-h4-1BB antibodies 54-8B11-mHvKv-IgG2 (G2), 55-8F6-mHvKv-IgG2 (G3), 56-2A6-mHvKv-IgG2 (G4), 69-3C2-mHvKv-IgG2 (G5), 61-6A7-mHvKv-IgG2 (G6), 70-6F10-mHvKv-IgG2 (G7), 70-3F9-mHvKv-IgG2 (G8), 45-4B9-mHvkv-IgG2 (G9), and also urelumab (G10).
Figure 42:
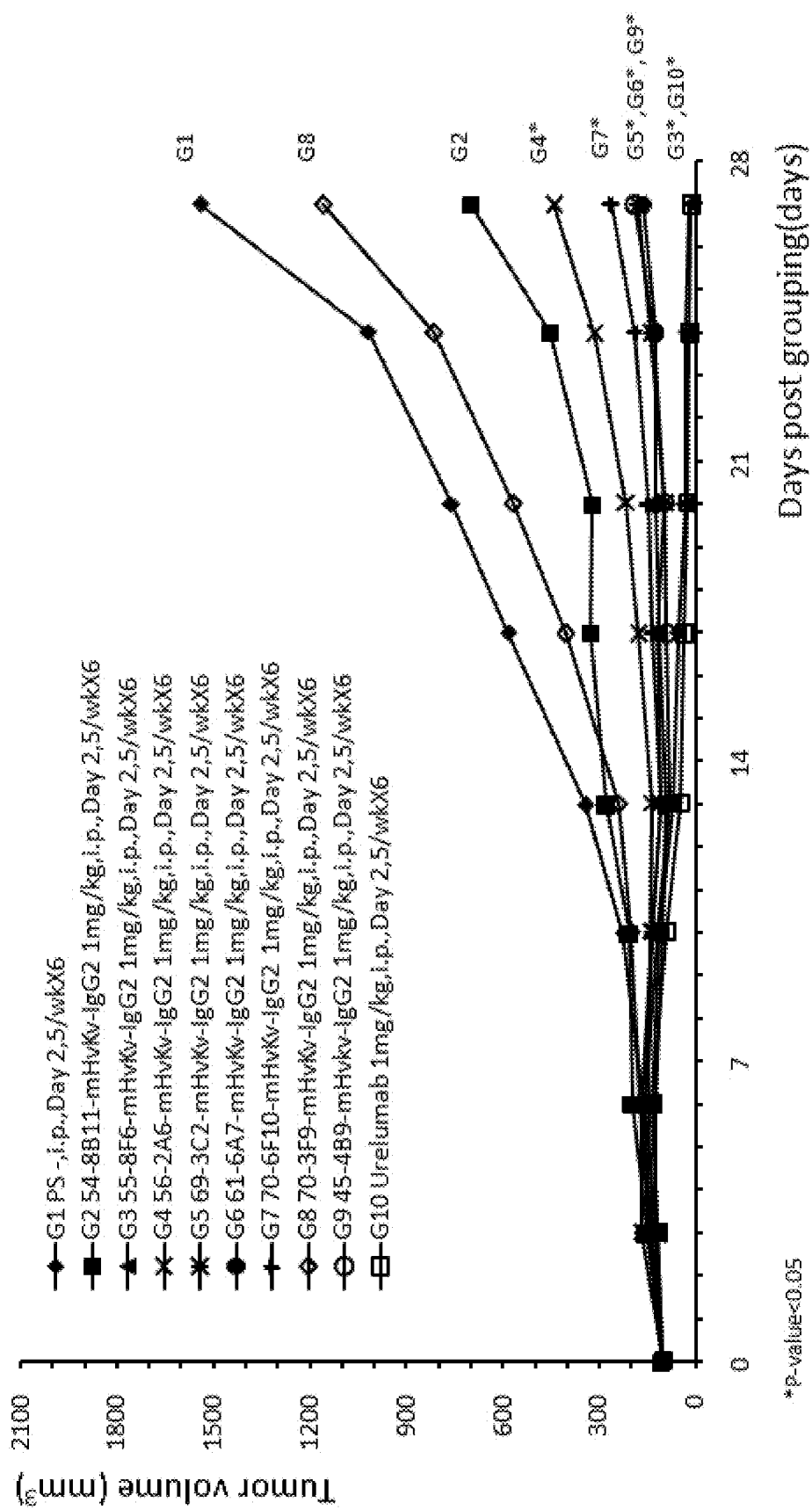
FIG. 42 is a graph showing tumor size over time in humanized 4-1BB mice (B-h4-1BB) with MC-38 tumor cells treated with anti-h4-1BB antibodies 54-8B11-mHvKv-IgG2 (G2), 55-8F6-mHvKv-IgG2 (G3), 56-2A6-mHvKv-IgG2 (G4), 69-3C2-mHvKv-IgG2 (G5), 61-6A7-mHvKv-IgG2 (G6), 70-6F10-mHvKv-IgG2 (G7), 70-3F9-mHvKv-IgG2 (G8), 45-4B9-mHvkv-IgG2 (G9), and also urelumab (G10).

The weight of the mice was monitored during the entire treatment period. The average weight of mice in different groups all increased at the end of the treatment period (FIG. 40, and FIG. 41). No obvious difference in weight was observed among the different groups. The results showed that these anti-h4-1BB antibodies were well tolerated and were not obviously toxic to the mice. The tumor size for each group is shown in FIG. 42.

The TGI % at day 27 (27 days after grouping) was also calculated as shown in the table below.

TABLE 31

| | | Tumor volume(mm³) | | | | | | P value | |
|---|---|---|---|---|---|---|---|---|---|
| | | Day 0 | Day 10 | Day 20 | Day 27 | Survival | TGI % | Body weight | Tumor Volume |
| Control | G1 | 105 ± 4 | 229 ± 46 | 760 ± 219 | 1542 ± 477 | 5/5 | n.a. | n.a. | n.a. |
| Treat | G2 | 105 ± 9 | 207 ± 40 | 320 ± 111 | 699 ± 221 | 5/5 | 58.7% | 0.610 | 0.147 |
| | G3 | 105 ± 5 | 114 ± 8 | 32 ± 15 | 18 ± 18 | 5/5 | 106.0% | 0.084 | 0.013 |
| | G4 | 105 ± 9 | 141 ± 36 | 217 ± 123 | 444 ± 305 | 5/5 | 76.4% | 0.021 | 0.088 |
| | G5 | 105 ± 6 | 138 ± 49 | 100 ± 64 | 178 ± 128 | 5/5 | 94.9% | 0.072 | 0.025 |
| | G6 | 105 ± 9 | 105 ± 10 | 123 ± 38 | 164 ± 63 | 5/5 | 95.9% | 0.016 | 0.021 |
| | G7 | 105 ± 11 | 135 ± 39 | 148 ± 65 | 262 ± 117 | 5/5 | 89.1% | 0.217 | 0.031 |
| | G8 | 105 ± 3 | 203 ± 45 | 569 ± 265 | 1160 ± 440 | 5/5 | 26.6% | 0.765 | 0.572 |
| | G9 | 105 ± 7 | 120 ± 48 | 96 ± 78 | 189 ± 180 | 5/5 | 94.2% | 0.070 | 0.029 |
| | G10 | 105 ± 6 | 90 ± 19 | 29 ± 12 | 17 ± 11 | 5/5 | 106.1% | 0.056 | 0.007 |

The results showed that these chimeric anti-h4-1BB antibodies had different tumor inhibitory effects.

Example 12. In Vivo Testing of Humanized and Chimeric Anti-4-1BB IgG2 Antibodies MC-38 Cancer Tumor Cells were Injected Subcutaneously in B-h4-1BB Mice. When the tumors in the mice reached a volume of 150±50 mm³, the mice were randomly placed into different groups based on the volume of the tumor, and were administered with different antibodies as shown in the table below.

TABLE 32

| Group | No. of mice | Antibodies | Dosage (mg/kg) | Route | Frequency | Total No. of administration |
|---|---|---|---|---|---|---|
| G1 | 8 | PS (control) | — | i.p. | Day 1, 4/wk | 6 |
| G2 | 8 | 6A5-H1K2-IgG2 | 1 mg/kg | i.p. | Day 1, 4/wk | 6 |
| G3 | 8 | 6A5-H1K3-IgG2 | 1 mg/kg | i.p. | Day 1, 4/wk | 6 |
| G4 | 8 | 1C4-H1K1-IgG2 | 1 mg/kg | i.p. | Day 1, 4/wk | 6 |
| G5 | 8 | 1C4-H1K2-IgG2 | 1 mg/kg | i.p. | Day 1, 4/wk | 6 |
| G6 | 8 | 5F9-H1K1-IgG2 | 1 mg/kg | i.p. | Day 1, 4/wk | 6 |
| G7 | 8 | 5F9-H1K2-IgG2 | 1 mg/kg | i.p. | Day 1, 4/wk | 6 |
| G8 | 8 | 16-1C4-mHvKv-IgG2 | 1 mg/kg | i.p. | Day 1, 4/wk | 6 |
| G9 | 8 | 29-6A5-mHvKv-IgG2 | 1 mg/kg | i.p. | Day 1, 4/wk | 6 |
| G10 | 8 | 30-5F9-mHvKv-IgG2 | 1 mg/kg | i.p. | Day 1, 4/wk | 6 |
| G11 | 8 | Urelumab | 1 mg/kg | i.p. | Day 1, 4/wk | 6 |

Figure 43:
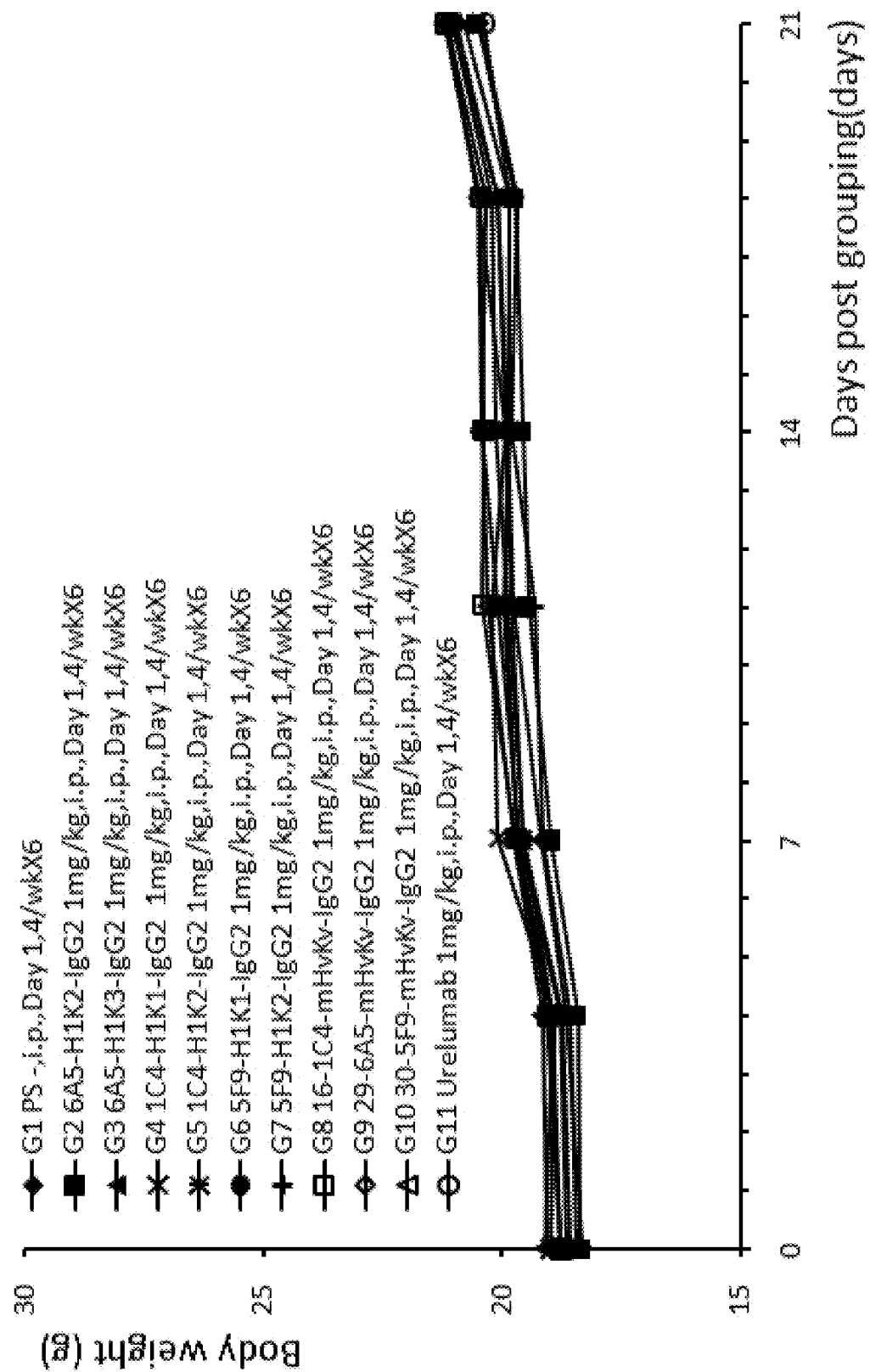
FIG. 43 is a graph showing body weight over time of humanized 4-1BB mice (B-h4-1BB) with MC-38 tumor cells treated with anti-h4-1BB antibodies 6A5-H1K2-IgG2, 6A5-H1K3-IgG2, 1C4-H1K1-IgG2, 1C4-H1K2-IgG2, 5F9-H1K1-IgG2, 5F9-H1K2-IgG2, 16-1C4-mHvKv-IgG2, 29-6A5-mHvKv-IgG2, 30-5F9-mHvKv-IgG2, and urelumab.
Figure 44:
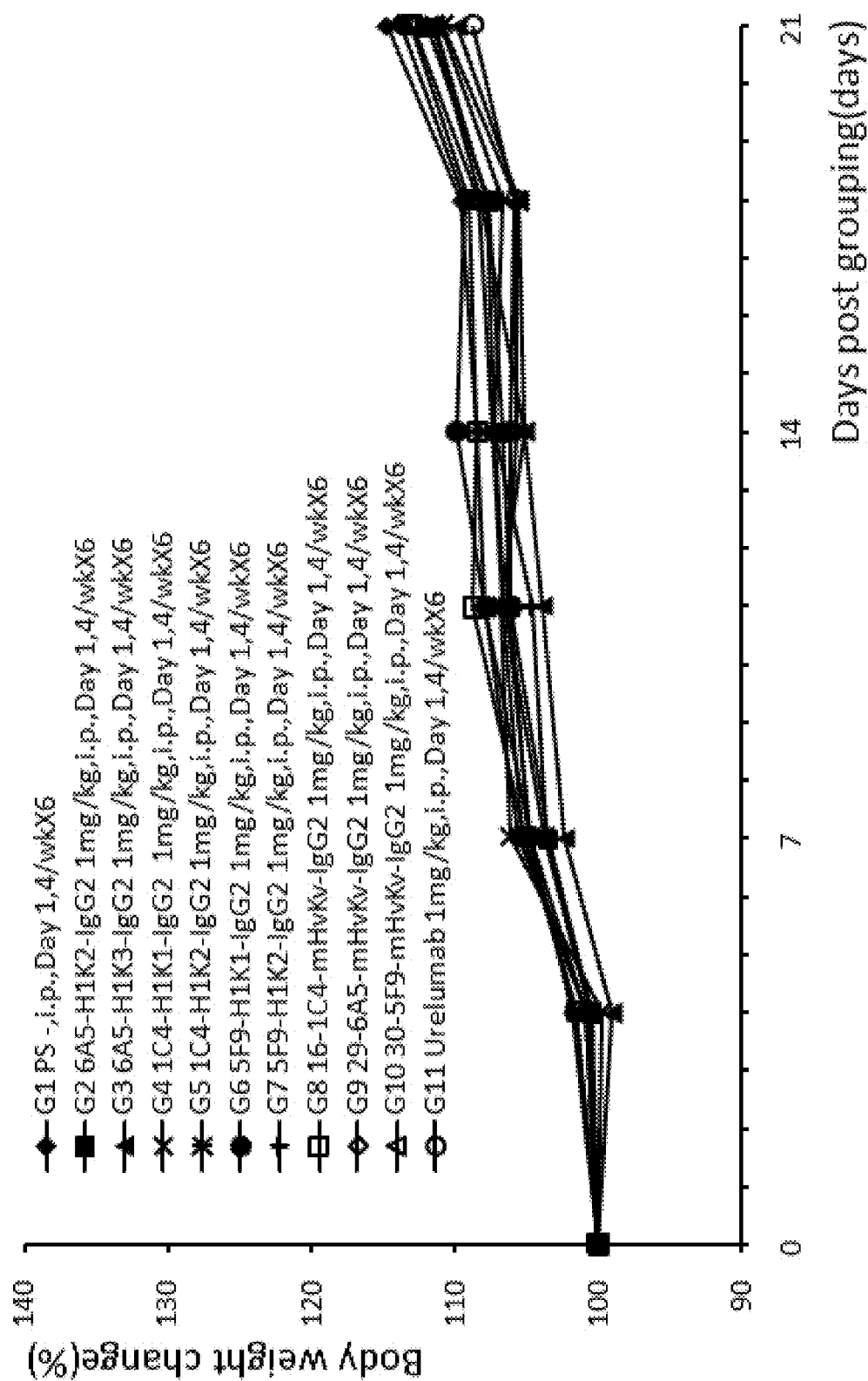
FIG. 44 is a graph showing percentage change of body weight over time of humanized 4-1BB mice (B-h4-1BB) with MC-38 tumor cells treated with anti-h4-1BB antibodies 6A5-H1K2-IgG2, 6A5-H1K3-IgG2, 1C4-H1K1-IgG2, 1C4-H1K2-IgG2, 5F9-H1K1-IgG2, 5F9-H1K2-IgG2, 16-1C4-mHvKv-IgG2, 29-6A5-mHvKv-IgG2, 30-5F9-mHvKv-IgG2, and urelumab.
Figure 45:
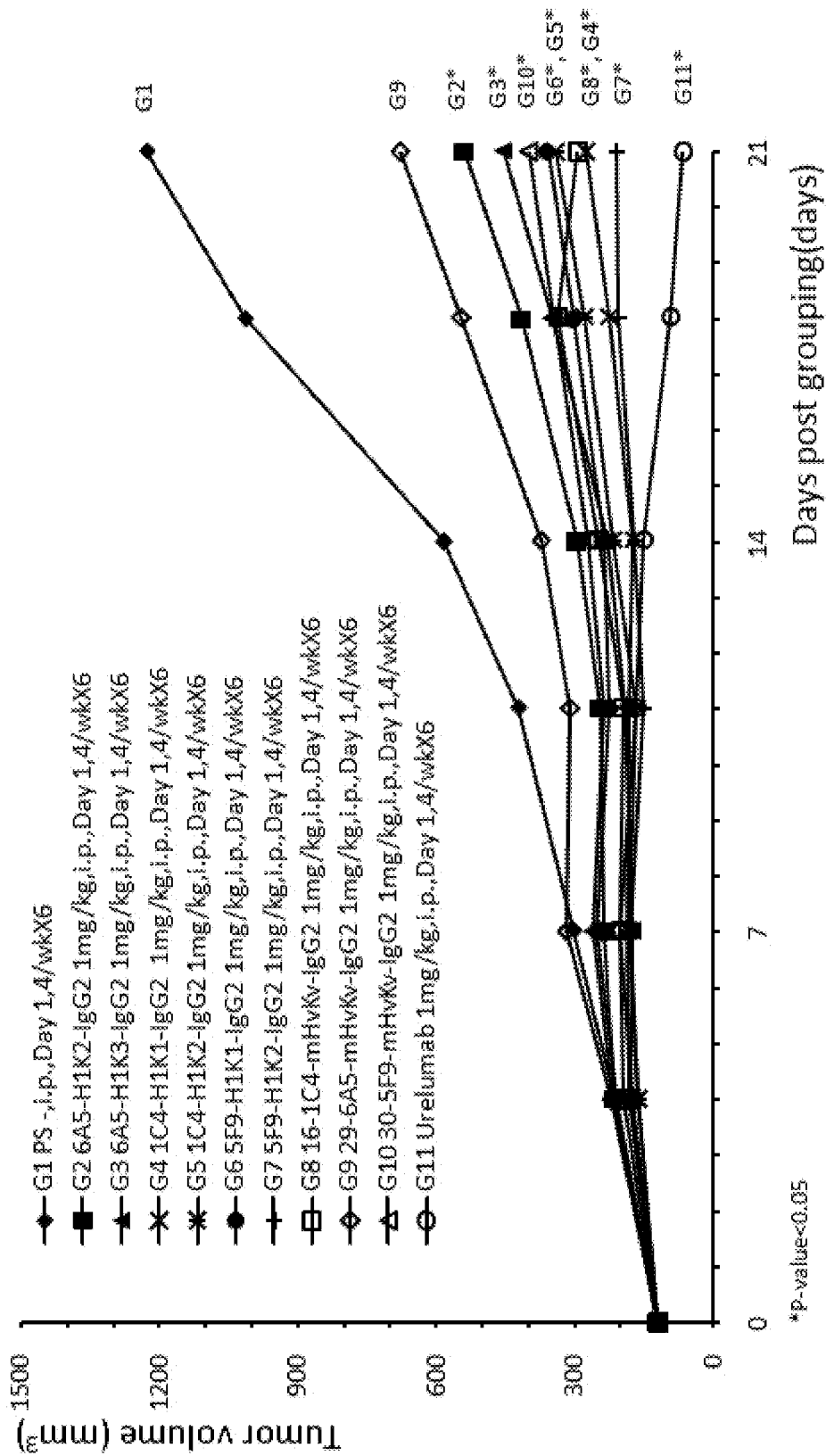
FIG. 45 is a graph showing tumor size over time in humanized 4-1BB mice (B-h4-1BB) with MC-38 tumor cells treated with anti-h4-1BB antibodies 6A5-H1K2-IgG2, 6A5-H1K3-IgG2, 1C4-H1K1-IgG2, 1C4-H1K2-IgG2, 5F9-H1K1-IgG2, 5F9-H1K2-IgG2, 16-1C4-mHvKv-IgG2, 29-6A5-mHvKv-IgG2, 30-5F9-mHvKv-IgG2, and urelumab.

The weight of the mice was monitored during the entire treatment period. The average weight of mice in different groups all increased at the end of the treatment period (FIG. 43, and FIG. 44). No obvious difference in weight was observed among different groups. The results showed that these anti-h4-1BB antibodies were well tolerated and were not obviously toxic to the mice. The tumor size for each group is shown in FIG. 45.

The TGI % at day 21 (21 days after grouping) was also calculated as shown in the table below.

TABLE 33

|  |  | Tumor volume(mm³) | | | | Survival | TGI % | P value | |
|---|---|---|---|---|---|---|---|---|---|
|  |  | Day 0 | Day 6 | Day 13 | Day 17 | | | Body weight | Tumor Volume |
| Control | G1 | 121 ± 6 | 301 ± 27 | 585 ± 111 | 1227 ± 198 | 8/8 | n.a. | n.a. | n.a. |
| Treat | G2 | 121 ± 8 | 236 ± 27 | 296 ± 31 | 540 ± 89 | 8/8 | 62.1% | 0.458 | 0.007 |
|  | G3 | 121 ± 7 | 176 ± 28 | 230 ± 81 | 455 ± 222 | 8/8 | 69.8% | 0.981 | 0.021 |
|  | G4 | 121 ± 7 | 188 ± 28 | 177 ± 31 | 275 ± 75 | 8/8 | 86.1% | 0.897 | 5.1E−04 |
|  | G5 | 121 ± 8 | 184 ± 27 | 216 ± 50 | 340 ± 92 | 8/8 | 80.2% | 0.772 | 1.2E−03 |
|  | G6 | 121 ± 7 | 251 ± 26 | 237 ± 43 | 359 ± 89 | 8/8 | 78.5% | 0.868 | 1.3E−03 |
|  | G7 | 121 ± 6 | 180 ± 16 | 171 ± 37 | 210 ± 49 | 8/8 | 92.0% | 0.461 | 2.0E−04 |
|  | G8 | 121 ± 7 | 203 ± 25 | 248 ± 72 | 296 ± 116 | 8/8 | 84.2% | 0.806 | 1.2E−03 |
|  | G9 | 121 ± 7 | 319 ± 55 | 374 ± 100 | 680 ± 232 | 8/8 | 49.5% | 0.910 | 0.094 |
|  | G10 | 121 ± 7 | 262 ± 26 | 273 ± 43 | 399 ± 101 | 8/8 | 74.8% | 0.803 | 0.002 |
|  | G11 | 121 ± 8 | 202 ± 29 | 152 ± 41 | 67 ± 26 | 8/8 | 104.9% | 0.353 | 4.6E−05 |

The results showed that these humanized and chimeric antibodies had different tumor inhibitory effects.

Example 13. Human Anti-4-1BB IgG1 Antibodies have Better Efficacy than Other IgG Subclasses Based on results from 16-1C4-mHvKv-IgG1 as described above, it was hypothesized that for the same VH and VL, the IgG1 subclass have better tumor inhibitory effects than the other IgG subclasses. Different subclasses of anti-h4-1BB IgG antibodies were tested in 4-1BB humanized mice (B-h4-1BB) to determine their effect on tumor growth in vivo. Furthermore, IgG1 antibodies with N297A (EU numbering) mutation, IgG1 antibodies with FC-SI mutations (EU Numbering: F243L/R292P/Y300L/V305I/P396L), and IgG1 antibodies with FC-V11 mutations (G237D/P238D/H268D/P271G/A330R) were also tested. The N297A mutation can reduce ADCC effects. The FC-SI mutations can increase the binding affinities with almost all Fc receptors, particularly FcγRIIIA/IIA, and may increase ADCC effects. And the FC-V11 mutation can increase the binding affinity with FcγRIIB, but will not increase the binding affinity with FcγRIIA, and thus will reduce the binding affinity with FcγRIIIA MC-38 cancer tumor cells (colon adenocarcinoma cell) were injected subcutaneously in B-h4-1BB mice. When the tumors in the mice reached a volume of 150±50 mm³, the mice were randomly placed into different groups based on the volume of the tumor, and were administered with different antibodies as shown in the table below. Urelumab is a fully human IgG4 monoclonal antibody. The antibody urelumab-IgG1 has VH and VL from urelumab, and the constant domains are from IgG1 subclass. Similarly, the antibody urelumab-IgG2 has VH and VL form urelumab, and the constant domains are from IgG2 subclass. The antibody urelumab-IgG4 has constant domains from human IgG4.

TABLE 34

| Group | No. of mice | Antibodies | Dosage (mg/kg) | Route | Frequency | Total No. of administration |
|---|---|---|---|---|---|---|
| G1 | 7 | PS (control) | — | i.p. | Day 2, 5/wk | 4 |
| G2 | 7 | Urelumab-IgG1 | 1 mg/kg | i.p. | Day 2, 5/wk | 4 |
| G3 | 7 | Urelumab-IgG2 | 1 mg/kg | i.p. | Day 2, 5/wk | 4 |
| G4 | 7 | Urelumab-IgG4 | 1 mg/kg | i.p. | Day 2, 5/wk | 4 |
| G5 | 7 | Urelumab-IgG1-N297A | 1 mg/kg | i.p. | Day 2, 5/wk | 4 |
| G6 | 7 | Urelumab-IgG1-FC-SI | 1 mg/kg | i.p. | Day 2, 5/wk | 4 |
| G7 | 7 | Urelumab-IgG1-FC-V11 | 1 mg/kg | i.p. | Day 2, 5/wk | 4 |

Figure 46:
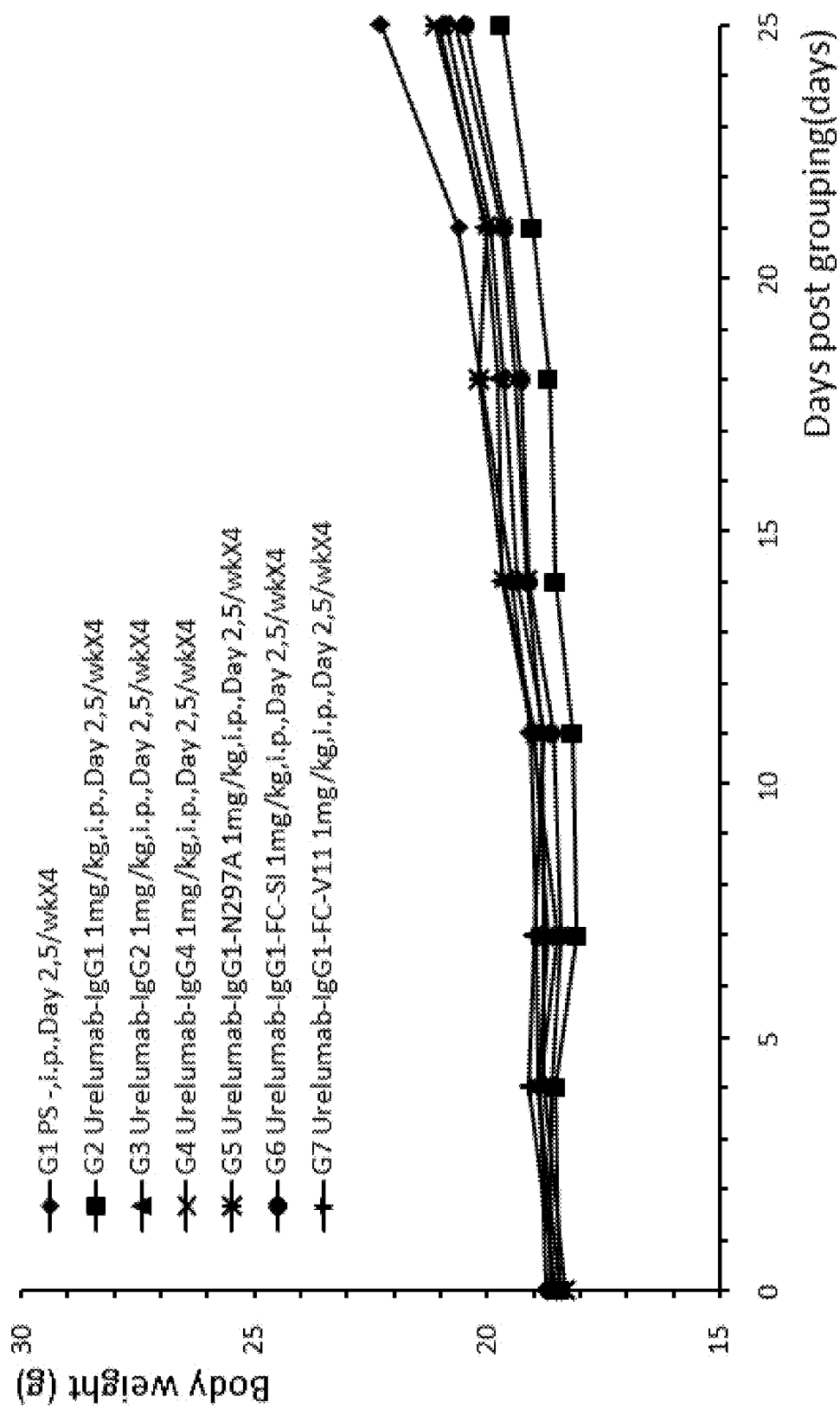
FIG. 46 is a graph showing body weight over time of humanized 4-1BB mice (B-h4-1BB) with MC-38 tumor cells treated with anti-h4-1BB antibodies urelumab-IgG1, urelumab-IgG2, urelumab-IgG4, urelumab-IgG1-N297A, urelumab-IgG1-FC-SI, and urelumab-IgG1-FC-V11.
Figure 47:
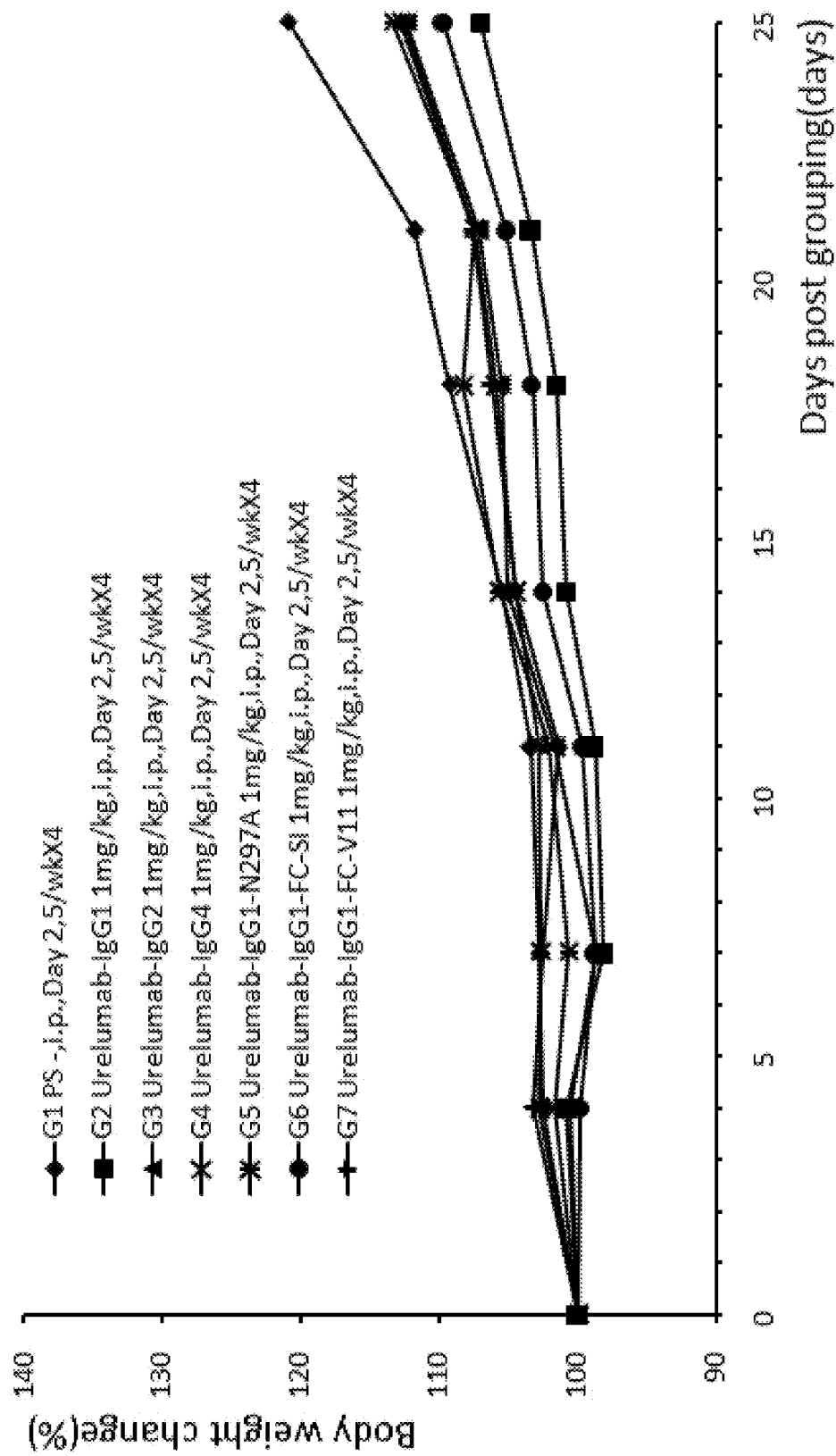
FIG. 47 is a graph showing percentage change of body weight over time of humanized 4-1BB mice (B-h4-1BB) with MC-38 tumor cells treated with anti-h4-1BB antibodies urelumab-IgG1, urelumab-IgG2, urelumab-IgG4, urelumab-IgG1-N297A, urelumab-IgG1-FC-SI, and urelumab-IgG1-FC-V11.
Figure 48:
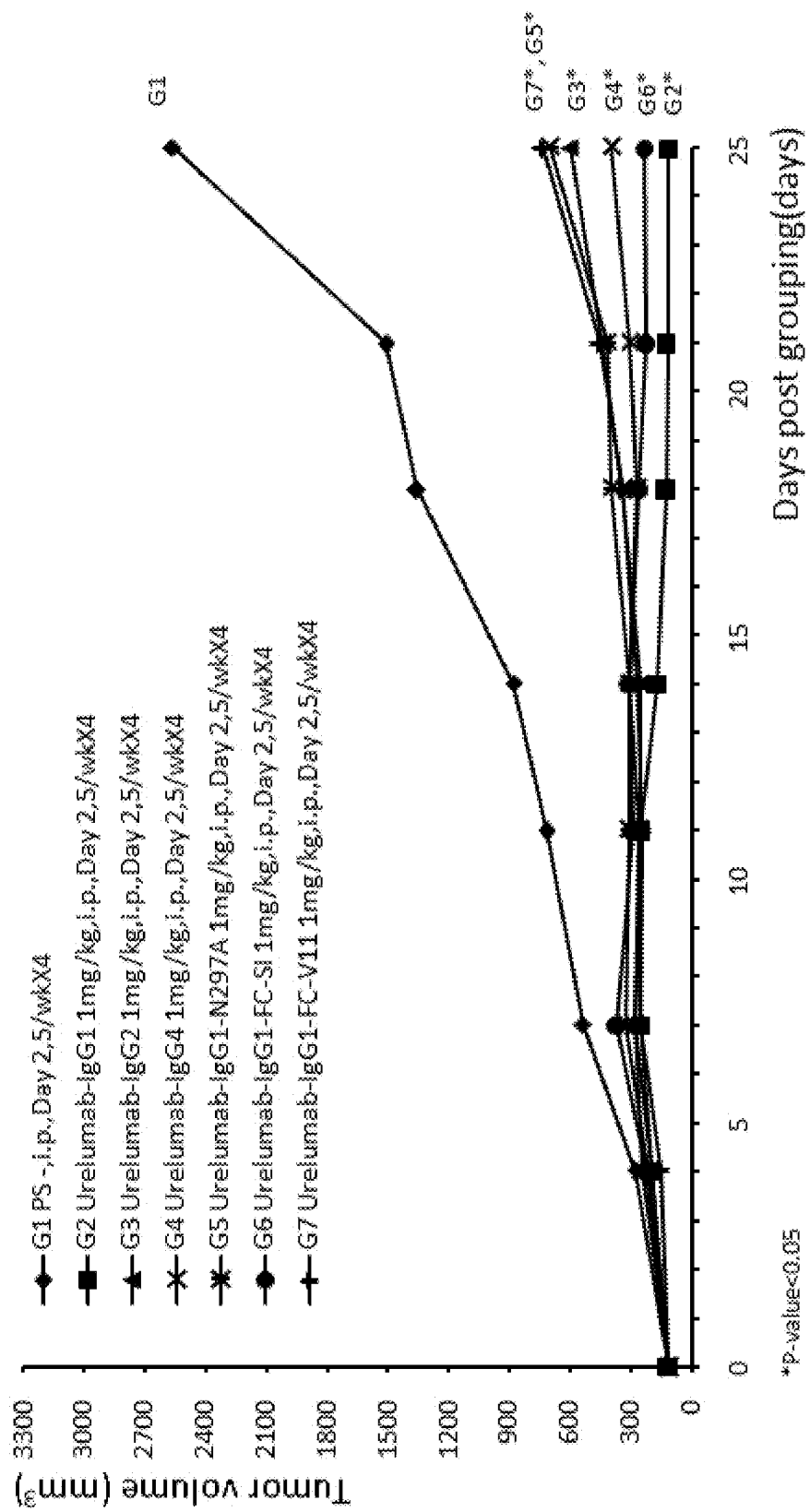
FIG. 48 is a graph showing tumor size over time in humanized 4-1BB mice (B-h4-1BB) with MC-38 tumor cells treated with anti-h4-1BB antibodies urelumab-IgG1, urelumab-IgG2, urelumab-IgG4, urelumab-IgG1-N297A, urelumab-IgG1-FC-SI, and urelumab-IgG1-FC-V11.

The weight of the mice was monitored during the entire treatment period. The average weight of mice in different groups all increased at the end of the treatment period (FIG. 46, and FIG. 47). No obvious difference in weight was observed among the different groups. The results showed that these anti-h4-1BB antibodies were well tolerated and were not obviously toxic to the mice. The tumor size for each group is shown in FIG. 48.

The TGI % at day 25 (25 days after grouping) was also calculated as shown in the table below.

TABLE 35

| | | Tumor volume(mm³) | | | | | P value | |
|---|---|---|---|---|---|---|---|---|
| | | Day 0 | Day 11 | Day 18 | Day 25 | Survival | TGI % | Body weight | Tumor Volume |
| Control | G1 | 119 ± 5 | 718 ± 97 | 1358 ± 338 | 2562 ± 477 | 7/7 | n.a. | n.a. | n.a. |
| Treat | G2 | 119 ± 6 | 249 ± 40 | 128 ± 38 | 116 ± 50 | 7/7 | 100.1% | 0.007 | 2.6E−04 |
| | G3 | 119 ± 6 | 256 ± 48 | 340 ± 110 | 604 ± 195 | 7/7 | 80.1% | 0.071 | 0.003 |
| | G4 | 119 ± 7 | 262 ± 58 | 276 ± 64 | 398 ± 111 | 7/7 | 88.6% | 0.074 | 8.3E−04 |
| | G5 | 119 ± 5 | 305 ± 44 | 399 ± 91 | 697 ± 181 | 7/7 | 76.3% | 0.294 | 0.003 |
| | G6 | 119 ± 6 | 293 ± 65 | 258 ± 111 | 232 ± 138 | 7/7 | 95.4% | 0.004 | 5.2E−04 |
| | G7 | 119 ± 5 | 240 ± 31 | 347 ± 67 | 740 ± 188 | 7/7 | 74.6% | 0.078 | 0.004 |

The results confirmed that anti-h4-1BB IgG1 subclasses had higher tumor inhibitory effects as compared to IgG2 and IgG4 subclasses.

Example 14. Chimeric Anti-4-1BB IgG1 Antibodies have Better Efficacy than Other IgG Subclasses Experiments were repeated to test different subclasses of anti-h4-1BB IgG antibodies. MC-38 cancer tumor cells (colon adenocarcinoma cell) were injected subcutaneously in B-h4-1BB mice. When the tumors in the mice reached a volume of 150±50 mm³, the mice were randomly placed into different groups based on the volume of the tumor, and were administered with different antibodies once a week (QW) as shown in the table below.

TABLE 36

| Group | No. of mice | Antibodies | Dosage (mg/kg) | Route | Frequency | Total No. of administration |
|---|---|---|---|---|---|---|
| G1 | 8 | PS (control) | — | i.p. | QW | 4 |
| G2 | 8 | 16-1C4-mHvKv-IgG1 | 1 mg/kg | i.p. | QW | 4 |
| G3 | 8 | 16-1C4-mHvKv-IgG2 | 1 mg/kg | i.p. | QW | 4 |
| G4 | 8 | 16-1C4-mHvKv-IgG4 | 1 mg/kg | i.p. | QW | 4 |
| G5 | 8 | 16-1C4-mHvKv-IgG1-FC-V11 | 1 mg/kg | i.p. | QW | 4 |
| G6 | 8 | 16-1C4-mHvKv-IgG1-FC-SI | 1 mg/kg | i.p. | QW | 4 |
| G7 | 8 | 16-1C4 | 1 mg/kg | i.p. | QW | 4 |
| G8 | 8 | Urelumab | 1 mg/kg | i.p. | QW | 4 |

Figure 49:
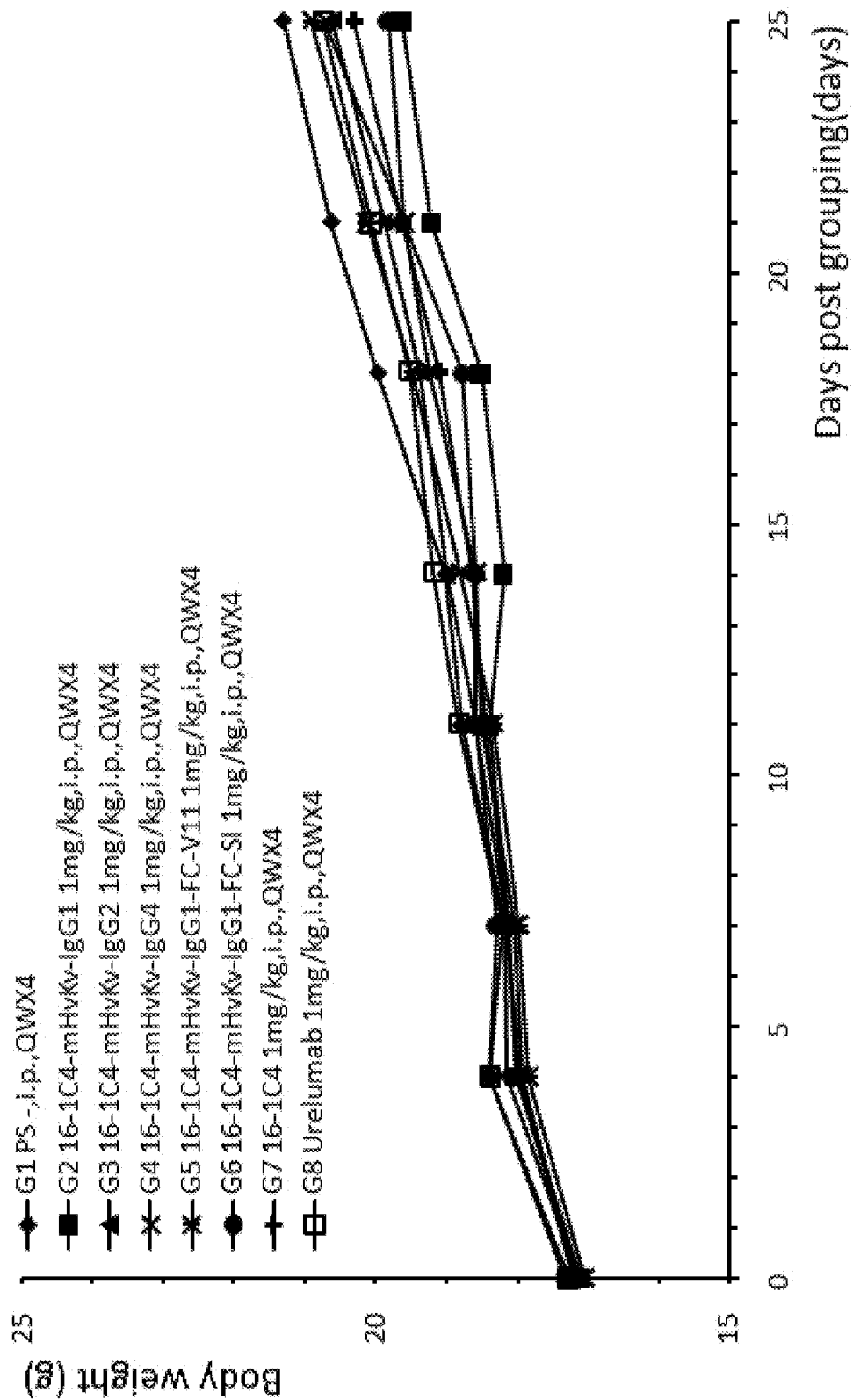
FIG. 49 is a graph showing body weight over time of humanized 4-1BB mice (B-h4-1BB) with MC-38 tumor cells treated with anti-h4-1BB antibodies 16-1C4-mHvKv-IgG1, 16-1C4-mHvKv-IgG2, 16-1C4-mHvKv-IgG4, 16-1C4-mHvKv-IgG1-FC-V11, 16-1C4-mHvKv-IgG1-FC-SI, 16-1C4, and urelumab.
Figure 50:
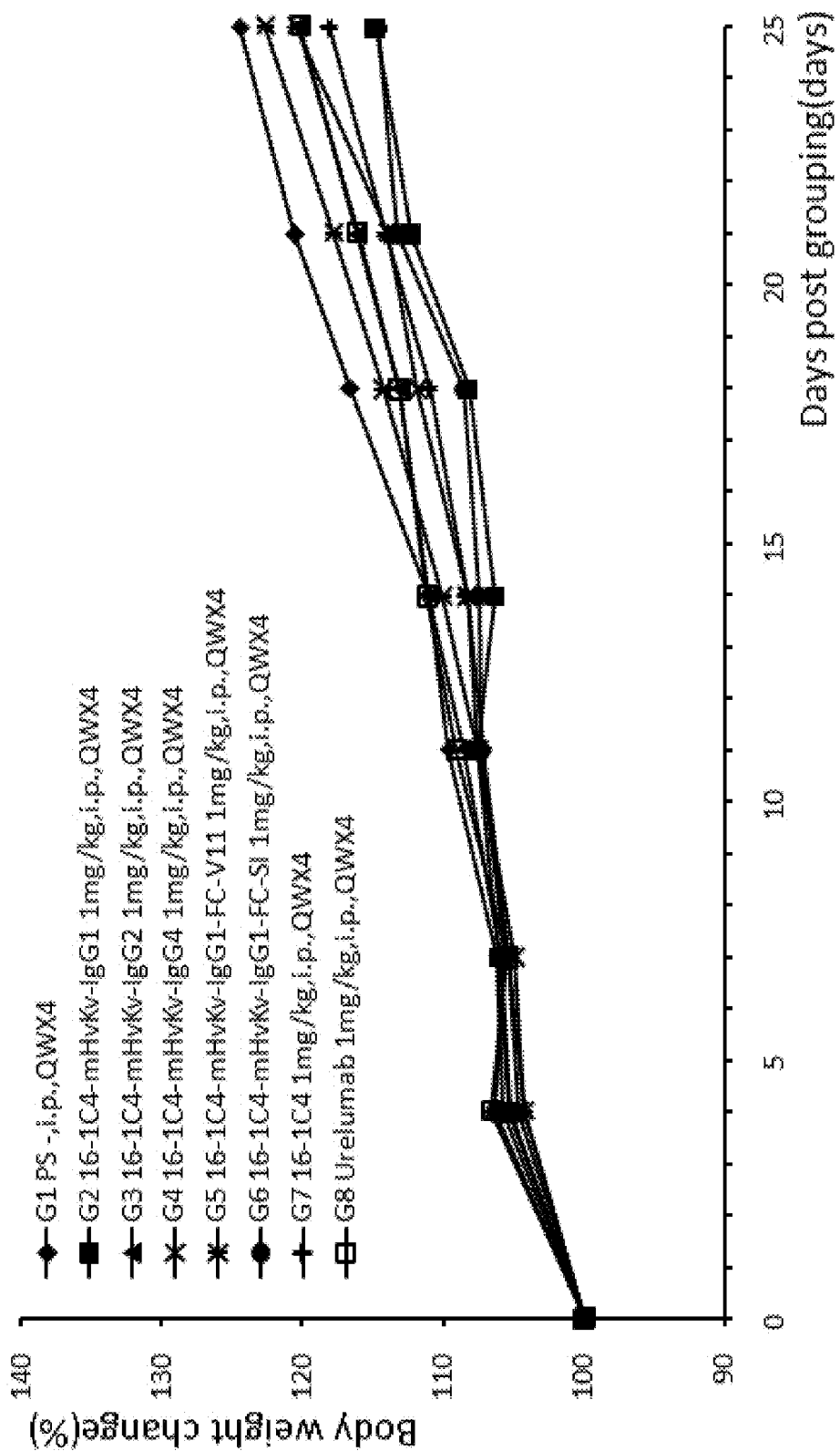
FIG. 50 is a graph showing percentage change of body weight over time of humanized 4-1BB mice (B-h4-1BB) with MC-38 tumor cells treated with anti-h4-1BB antibodies 16-1C4-mHvKv-IgG1, 16-1C4-mHvKv-IgG2, 16-1C4-mHvKv-IgG4, 16-1C4-mHvKv-IgG1-FC-V11, 16-1C4-mHvKv-IgG1-FC-SI, 16-1C4, and urelumab.
Figure 51:
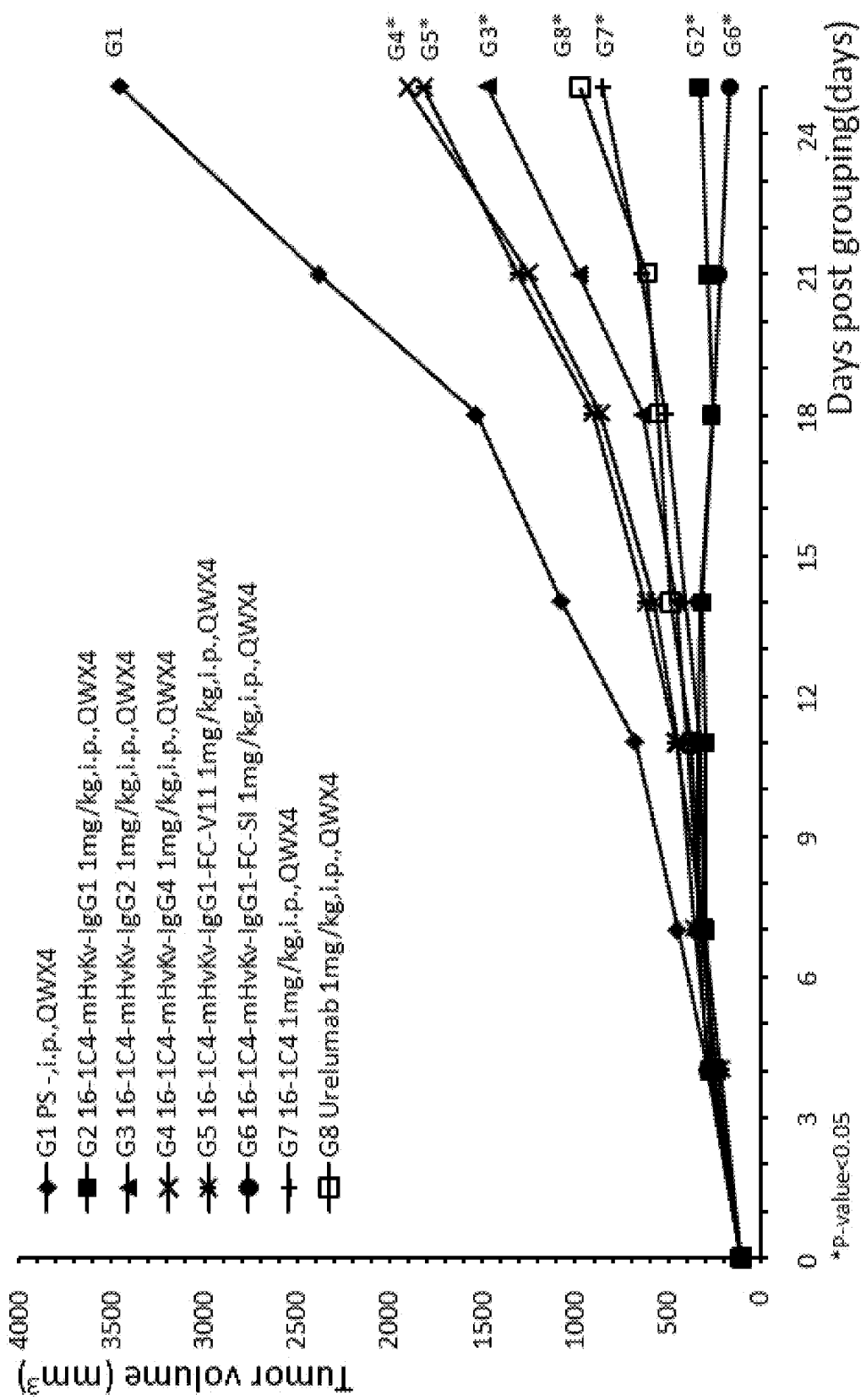
FIG. 51 is a graph showing tumor size over time in humanized 4-1BB mice (B-h4-1BB) with MC-38 tumor cells treated with anti-h4-1BB antibodies 16-1C4-mHvKv-IgG1, 16-1C4-mHvKv-IgG2, 16-1C4-mHvKv-IgG4, 16-1C4-mHvKv-IgG1-FC-V11, 16-1C4-mHvKv-IgG1-FC-SI, 16-1C4, and urelumab.

The weight of the mice was monitored during the entire treatment period. The average weight of mice in different groups all increased at the end of treatment period (FIG. 49, and FIG. 50). No obvious difference in weight was observed among the different groups. The results showed that these anti-h4-1BB antibodies were well tolerated and were not obviously toxic to the mice. The tumor size for each group is shown in FIG. 51.

The TGI % at day 25 (25 days after grouping) was also calculated as shown in the table below.

TABLE 37

| | | Tumor volume(mm³) | | | | | | P value | |
|---|---|---|---|---|---|---|---|---|---|
| | | Day 0 | Day 11 | Day 18 | Day 25 | Survival | TGI % | Body weight | Tumor Volume |
| Control | G1 | 111 ± 7 | 678 ± 151 | 1533 ± 293 | 3455 ± 435 | 8/8 | n.a. | n.a. | n.a. |
| Treat | G2 | 111 ± 6 | 299 ± 21 | 262 ± 62 | 328 ± 204 | 8/8 | 93.5% | 0.030 | 1.4E−05 |
| | G3 | 111 ± 7 | 396 ± 77 | 640 ± 170 | 1474 ± 414 | 8/8 | 59.3% | 0.378 | 0.005 |

TABLE 37-continued

|  | Tumor volume(mm³) | | | | | | P value | |
|---|---|---|---|---|---|---|---|---|
|  | Day 0 | Day 11 | Day 18 | Day 25 | Survival | TGI % | Body weight | Tumor Volume |
| G4 | 112 ± 5 | 445 ± 61 | 867 ± 165 | 1912 ± 452 | 8/8 | 46.2% | 0.454 | 0.027 |
| G5 | 111 ± 6 | 454 ± 74 | 903 ± 176 | 1822 ± 352 | 8/8 | 48.8% | 0.570 | 0.011 |
| G6 | 111 ± 6 | 337 ± 44 | 263 ± 52 | 164 ± 41 | 8/8 | 98.4% | 0.032 | 2.7E−06 |
| G7 | 111 ± 7 | 330 ± 36 | 519 ± 133 | 860 ± 247 | 8/8 | 77.6% | 0.126 | 1.4E−04 |
| G8 | 111 ± 5 | 380 ± 59 | 560 ± 132 | 970 ± 271 | 8/8 | 74.3% | 0.383 | 2.6E−04 |

The results again confirmed that IgG1 subclasses had higher tumor inhibitory effects as compared to IgG2 and IgG4 subclasses.

Example 15. Chimeric and Human Anti-4-1BB IgG1 Antibodies have Better Efficacy than Other IgG Subclasses Experiments were repeated to test different subclasses of chimeric and human anti-h4-1BB IgG antibodies. mIgG2A and human IgG1 have better ADCC effects, and mIgG1 and human IgG4 have weaker or no ADCC effects, MC-38 cancer tumor cells (colon adenocarcinoma cell) were injected subcutaneously in B-h4-1BB mice. When the tumors in the mice reached a volume of 150±50 mm³, the mice were randomly placed into different groups based on the volume of the tumor, and were administered with different antibodies once a week (QW) as shown in the table below.

TABLE 38

| Group | No. of mice | Antibodies | Dosage (mg/kg) | Route | Frequency | Total No. of administration |
|---|---|---|---|---|---|---|
| G1 | 8 | PS (control) | — | i.p. | QW | 3 |
| G2 | 8 | Urelumab-mIgG1 | 1 mg/kg | i.p. | QW | 3 |
| G3 | 8 | Urelumab-mIgG2A | 1 mg/kg | i.p. | QW | 3 |
| G4 | 8 | 16-1C4-mHvKv-mIgG1 | 1 mg/kg | i.p. | QW | 3 |
| G5 | 8 | 16-1C4-mHvKv-mIgG2A | 1 mg/kg | i.p. | QW | 3 |
| G6 | 8 | Urelumab | 1 mg/kg | i.p. | QW | 3 |
| G7 | 8 | Urelumab-IgG1 | 1 mg/kg | i.p. | QW | 3 |
| G8 | 8 | 16-1C4-mHvKv-IgG1 | 1 mg/kg | i.p. | QW | 3 |
| G9 | 8 | 16-1C4-mHvKv-IgG4 | 1 mg/kg | i.p. | QW | 3 |

Figure 59:
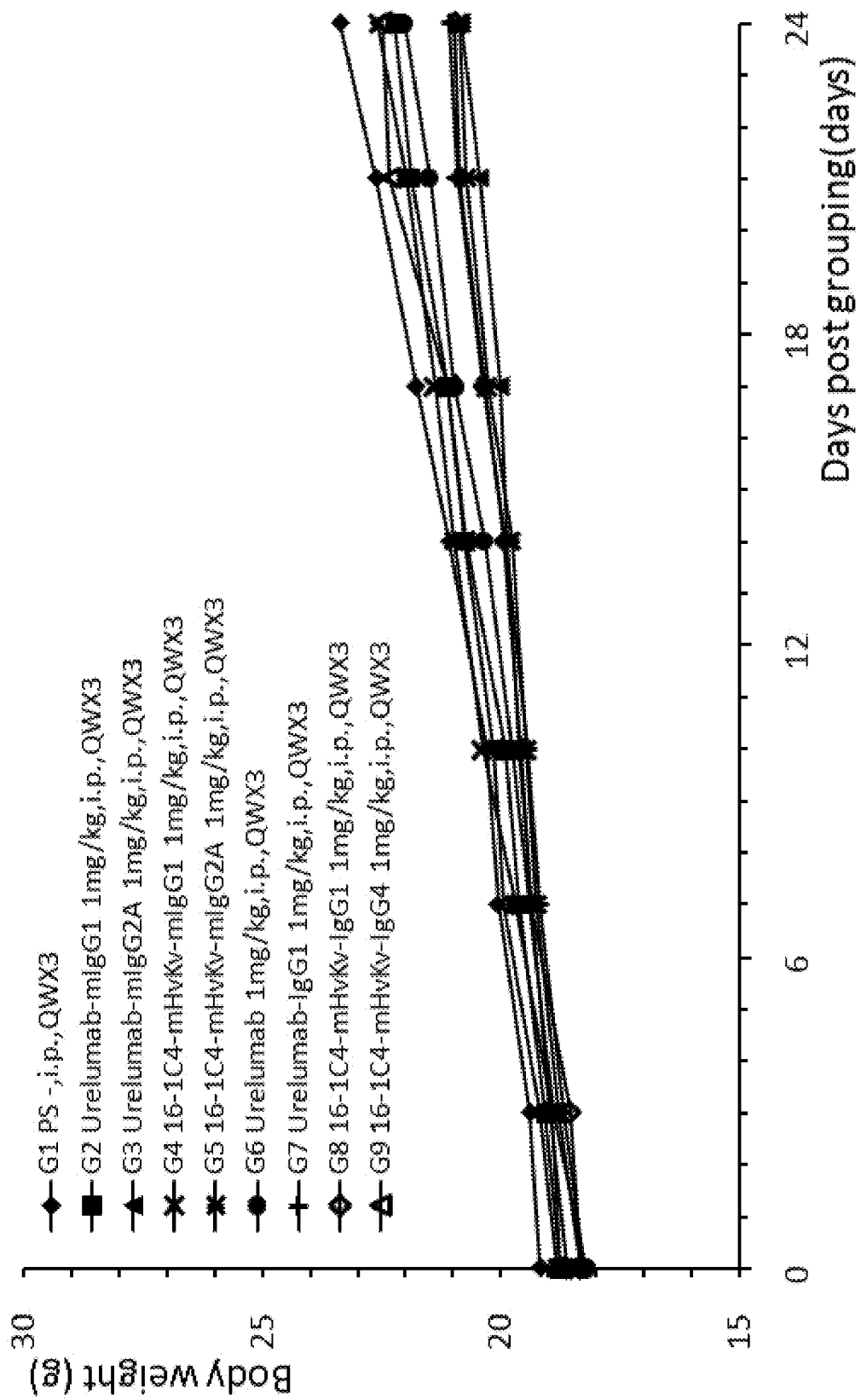
FIG. 59 is a graph showing body weight over time of humanized 4-1BB mice (B-h4-1BB) with MC-38 tumor cells treated with anti-h4-1BB antibodies Urelumab-mIgG1 (G2), Urelumab-mIgG2A (G3), 16-1C4-mHvKv-mIgG1 (G4), 16-1C4-mHvKv-mIgG2A (G5), Urelumab (G6), Urelumab-IgG1 (G7), 16-1C4-mHvKv-IgG1(G8) and 16-1C4-mHvKv-IgG4 (G9).
Figure 60:
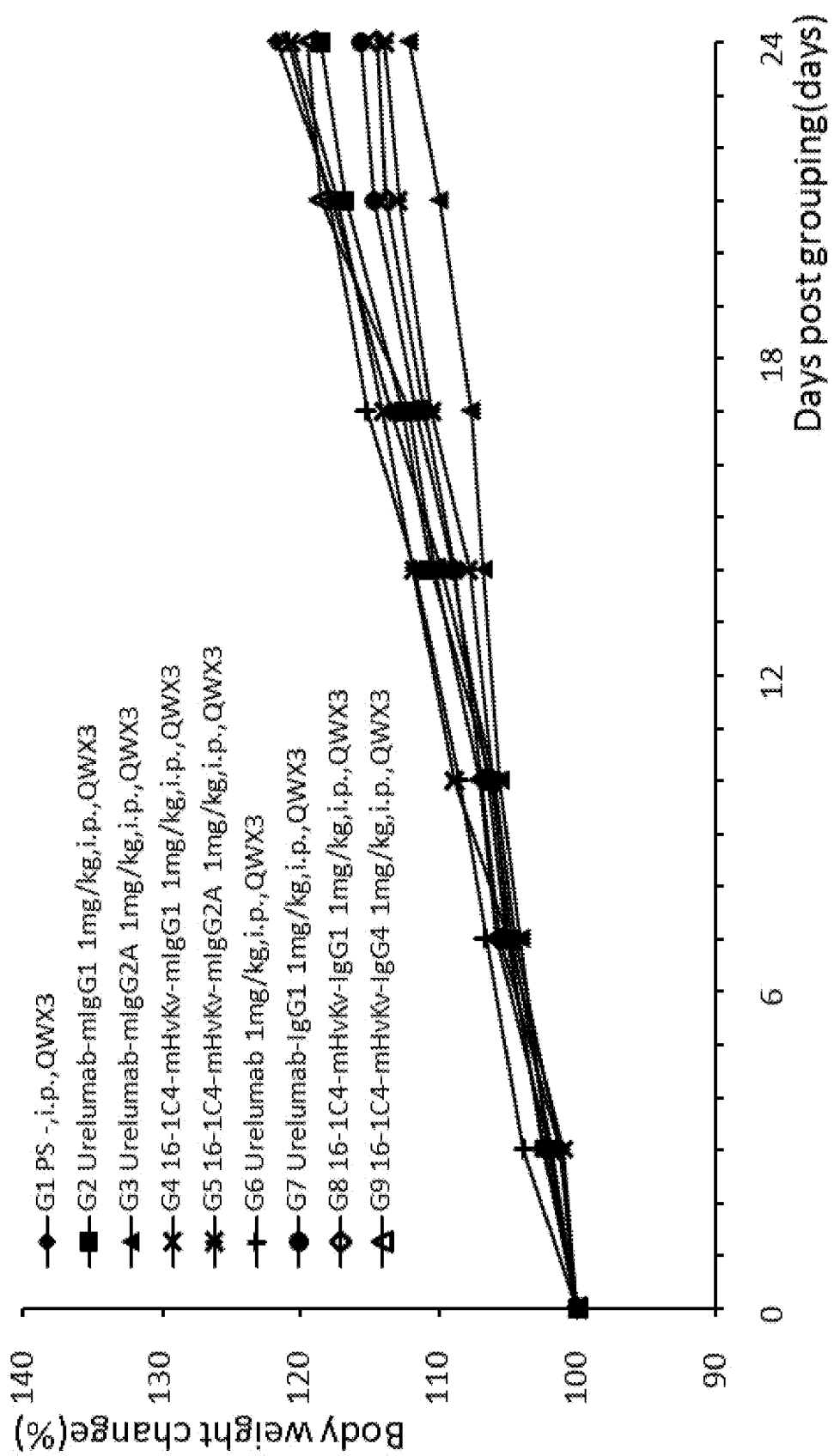
FIG. 60 is a graph showing percentage change of body weight over time of humanized 4-1BB mice (B-h4-1BB) with MC-38 tumor cells treated with anti-h4-1BB antibodies Urelumab-mIgG1 (G2), Urelumab-mIgG2A (G3), 16-1C4-mHvKv-mIgG1 (G4), 16-1C4-mHvKv-mIgG2A (G5), Urelumab (G6), Urelumab-IgG1 (G7), 16-1C4-mHvKv-IgG1 (G8) and 16-1C4-mHvKv-IgG4 (G9).
Figure 61:
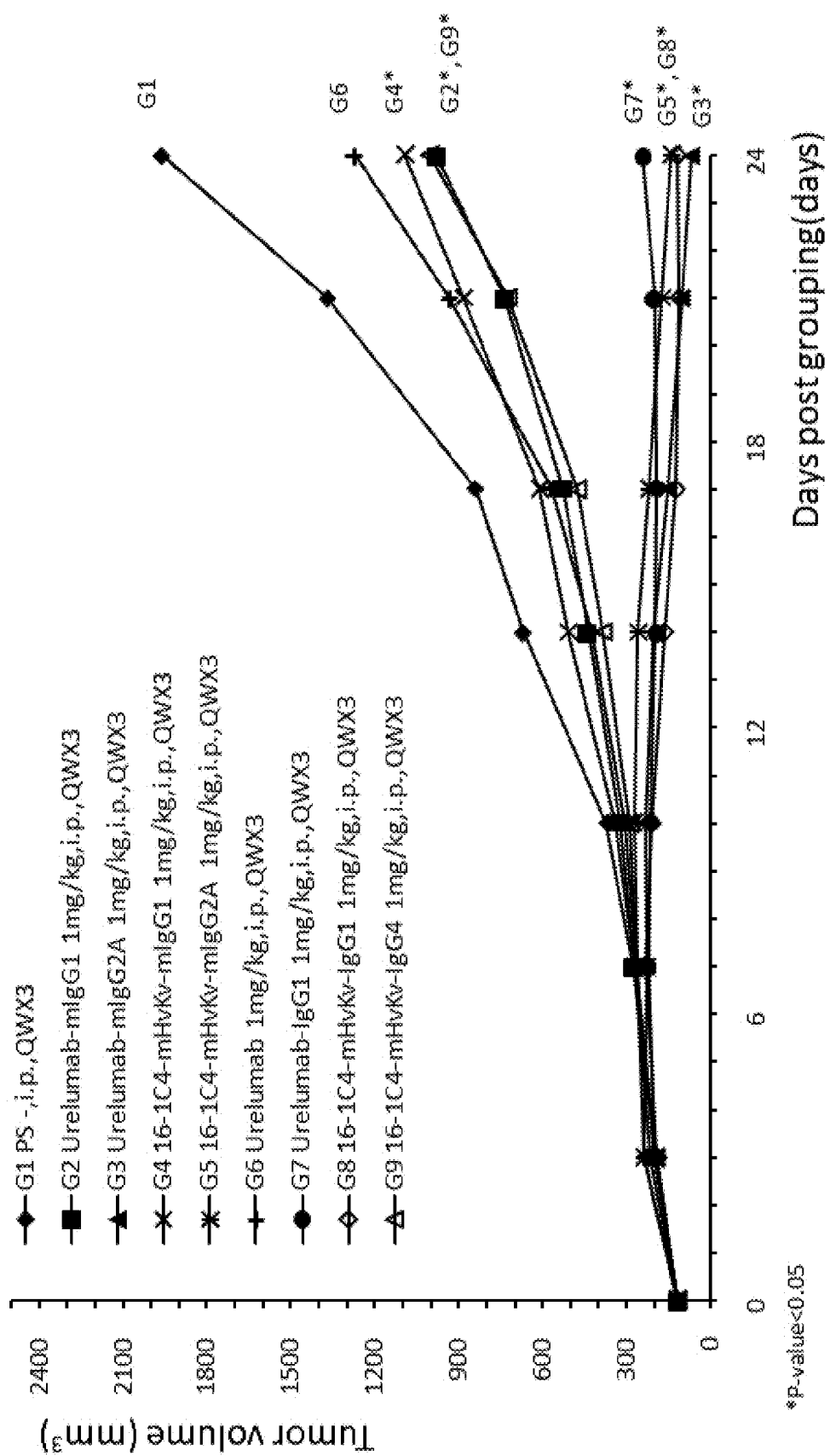
FIG. 61 is a graph showing tumor size over time in humanized 4-1BB mice (B-h4-1BB) with MC-38 tumor cells treated with anti-h4-1BB antibodies Urelumab-mIgG1 (G2), Urelumab-mIgG2A (G3), 16-1C4-mHvKv-mIgG1 (G4), 16-1C4-mHvKv-mIgG2A (G5), Urelumab (G6), Urelumab-IgG1 (G7), 16-1C4-mHvKv-IgG1(G8) and 16-1C4-mHvKv-IgG4 (G9).

The weight of the mice was monitored during the entire treatment period. The average weight of mice in different groups all increased at the end of treatment period (FIG. 59, and FIG. 60). No obvious difference in weight was observed among the different groups. The results showed that these anti-h4-1BB antibodies were well tolerated and were not obviously toxic to the mice. The tumor size for each group is shown in FIG. 61

The TGI % at day 24 (24 days after grouping) was also calculated as shown in the table below.

TABLE 39

| | | Tumor volume(mm³) | | | | | | P value | |
|---|---|---|---|---|---|---|---|---|---|
| | | Day 0 | Day 10 | Day 17 | Day 24 | Survival | TGI % | Body weight | Tumor Volume |
| Control | G1 | 117 ± 4 | 374 ± 30 | 841 ± 104 | 1964 ± 149 | 8/8 | n.a. | n.a. | n.a. |
| Treat | G2 | 117 ± 4 | 321 ± 34 | 525 ± 87 | 979 ± 171 | 8/8 | 53.3% | 0.353 | 6.7E−04 |
| | G3 | 117 ± 4 | 234 ± 21 | 153 ± 29 | 70 ± 21 | 8/8 | 102.5% | 0.018 | 5.3E−09 |
| | G4 | 117 ± 4 | 341 ± 41 | 611 ± 91 | 1094 ± 183 | 8/8 | 47.1% | 0.429 | 0.002 |
| | G5 | 117 ± 4 | 274 ± 70 | 219 ± 53 | 139 ± 171 | 8/8 | 98.8% | 0.036 | 2.0E−08 |
| | G6 | 117 ± 5 | 306 ± 40 | 570 ± 122 | 1273 ± 312 | 8/8 | 37.4% | 0.249 | 0.065 |
| | G7 | 117 ± 6 | 213 ± 34 | 190 ± 51 | 243 ± 88 | 8/8 | 93.1% | 0.037 | 1.0E−07 |
| | G8 | 117 ± 11 | 208 ± 28 | 126 ± 38 | 116 ± 87 | 8/8 | 100.0% | 0.041 | 4.1E−08 |
| | G9 | 117 ± 15 | 287 ± 28 | 475 ± 76 | 1003 ± 215 | 8/8 | 52.0% | 0.414 | 0.003 |

The results again confirmed that mIgG2A or human IgG1 subclasses had higher tumor inhibitory effects as compared to mIgG1 or human IgG4 subclasses. Thus, the results show that anti-4-1BB antibodies inhibit tumor growth primarily through ADCC.

Example 16. Anti-4-1BB IgG1 Antibodies had a Higher Tumor Inhibitory Effect as Compared to Anti-4-1BB IgG4 Antibodies MC-38 cancer tumor cells (colon adenocarcinoma cell) were injected subcutaneously in B-h4-1BB mice. When the tumors in the mice reached a volume of 100~150 mm$^3$, the mice were randomly placed into different groups based on the volume of the tumor, and were administered with different antibodies as shown in the table below. As discussed above, Urelumab is a fully human IgG4 monoclonal antibody. The antibody urelumab-IgG1 has VH and VL from urelumab, and the constant domains are from IgG1 subclass.

The results confirmed that urelumab-IgG1 antibodies had higher tumor inhibitory effects as compared to urelumab (IgG4); 16-1C4-mHvKv-IgG1 antibodies had higher tumor inhibitory effects as compared to 16-1C4-mHvKv-IgG4 antibodies; 1C4-H1K1-IgG1 antibodies had higher tumor inhibitory effects as compared to 1C4-H1K1-IgG4 antibodies; 1C4-H1K2-IgG1 antibodies had higher tumor inhibitory effects as compared to 1C4-H1K2-IgG4 antibodies. In summary, the result showed that for the same antigen binding domains, IgG1 antibodies had a higher tumor inhibitory effect as compared to IgG4 antibodies.

Example 17. Anti-h4-1BB Antibody Combination Therapies

MC-38 cancer tumor cells (colon adenocarcinoma cell) expressing human PD-L1 were injected subcutaneously in B-h4-1BB mice. When the tumors in the mice reached a volume of about 400 mm$^3$, the mice were randomly placed into different groups based on the volume of the tumor, and were administered with different antibodies as shown in the table below. Keytruda (Pembrolizumab) is a humanized anti-PD-1 IgG4 antibody.

TABLE 40

| Group | No. of mice | Antibodies | Dosage (mg/kg) | Route | Frequency | Total No. of administration |
|---|---|---|---|---|---|---|
| G1 | 8 | PS (control) | — | i.p. | QW | 3 |
| G2 | 8 | Urelumab | 1 mg/kg | i.p. | QW | 3 |
| G3 | 8 | Urelumab-IgG1 | 1 mg/kg | i.p. | QW | 3 |
| G4 | 8 | 16-1C4-mHvKv-IgG1 | 1 mg/kg | i.p. | QW | 3 |
| G5 | 8 | 16-1C4-mHvKv-IgG4 | 1 mg/kg | i.p. | QW | 3 |
| G6 | 8 | 1C4-H1K1-IgG1 | 1 mg/kg | i.p. | QW | 3 |
| G7 | 8 | 1C4-H1K1-IgG4 | 1 mg/kg | i.p. | QW | 3 |
| G8 | 8 | 1C4-H1K2-IgG1 | 1 mg/kg | i.p. | QW | 3 |
| G9 | 8 | 1C4-H1K2-IgG4 | 1 mg/kg | i.p. | QW | 3 |
| G10 | 8 | 6A5-H1K2-IgG1 | 1 mg/kg | i.p. | QW | 3 |
| G11 | 8 | 5F9-H1K1-IgG1 | 1 mg/kg | i.p. | QW | 3 |
| G12 | 8 | 16-1C4-mHvKv-IgG1-FC-V11 | 1 mg/kg | i.p. | QW | 3 |

Figure 62:
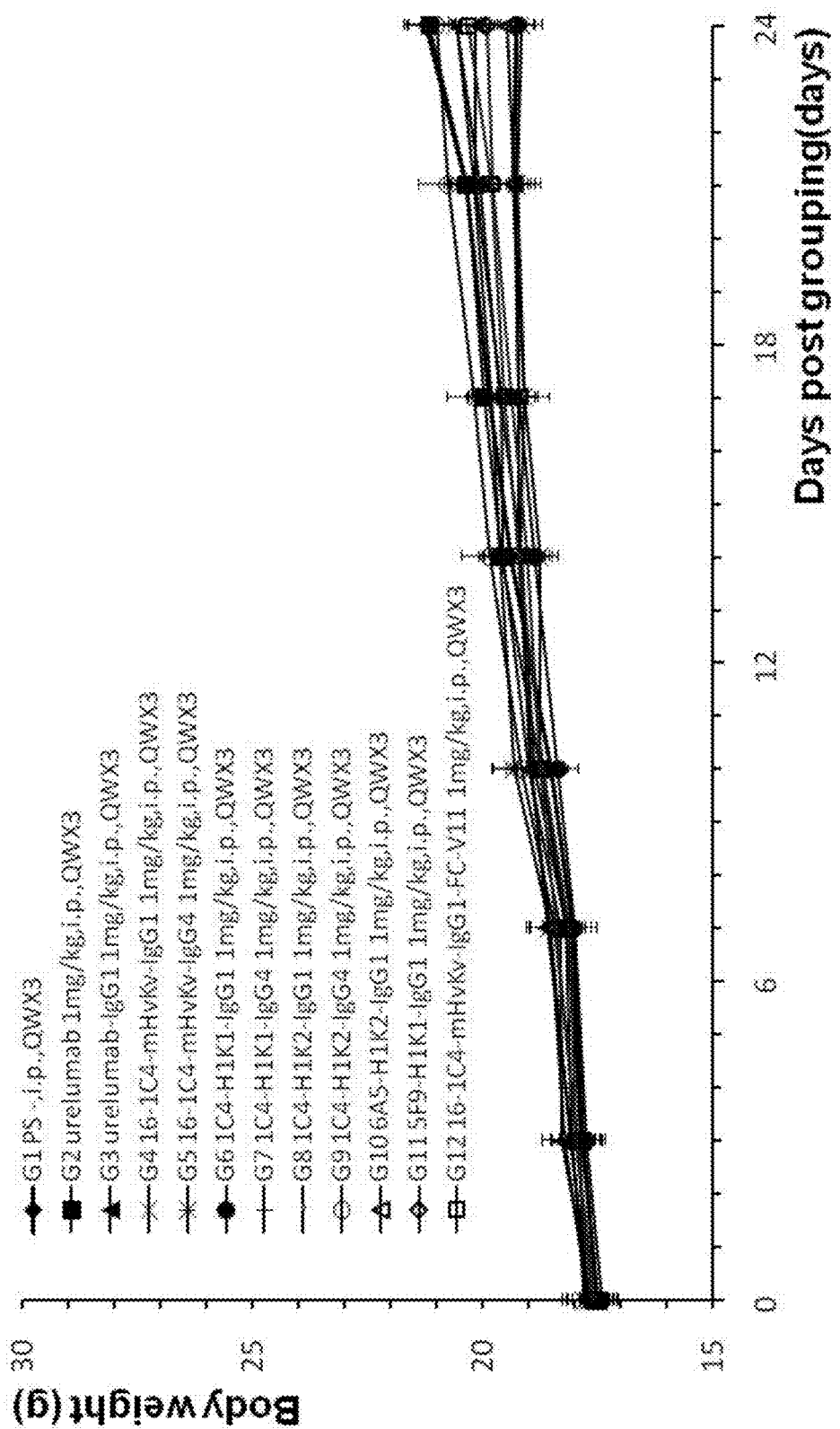
FIG. 62 is a graph showing body weight over time of humanized 4-1BB mice (B-h4-1BB) with MC-38 tumor cells treated with anti-h4-1BB antibodies urelumab, urelumab-IgG1, 1C4-mHvKv-IgG1, 1C4-mHvKv-IgG4, 1C4-H1K1-IgG1, 1C4-H1K1-IgG4, 1C4-H1K2-IgG1, 1C4-H1K2-IgG4, 6A5-H1K2-IgG1, 5F9-H1K1-IgG1 and 1C4-mHvKv-IgG1-FC-V11.
Figure 63:
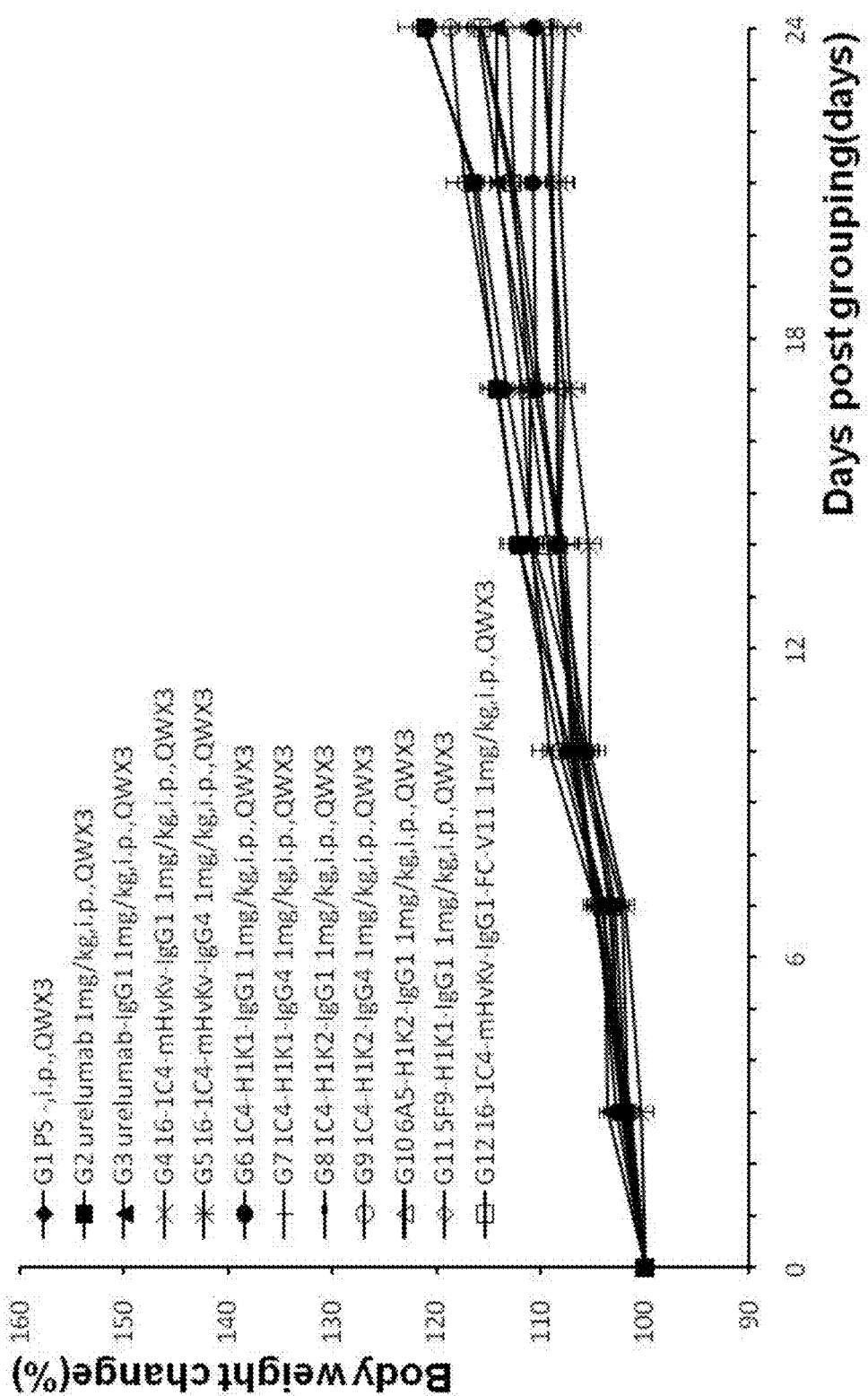
FIG. 63 is a graph showing percentage change of body weight over time of humanized 4-1BB mice (B-h4-1BB) with MC-38 tumor cells treated with anti-h4-1BB antibodies urelumab, urelumab-IgG1, 1C4-mHvKv-IgG1, 1C4-mHvKv-IgG4, 1C4-H1K1-IgG1, 1C4-H1K1-IgG4, 1C4-H1K2-IgG1, 1C4-H1K2-IgG4, 6A5-H1K2-IgG1, 5F9-H1K1-IgG1 and 1C4-mHvKv-IgG1-FC-V11.
Figure 64:
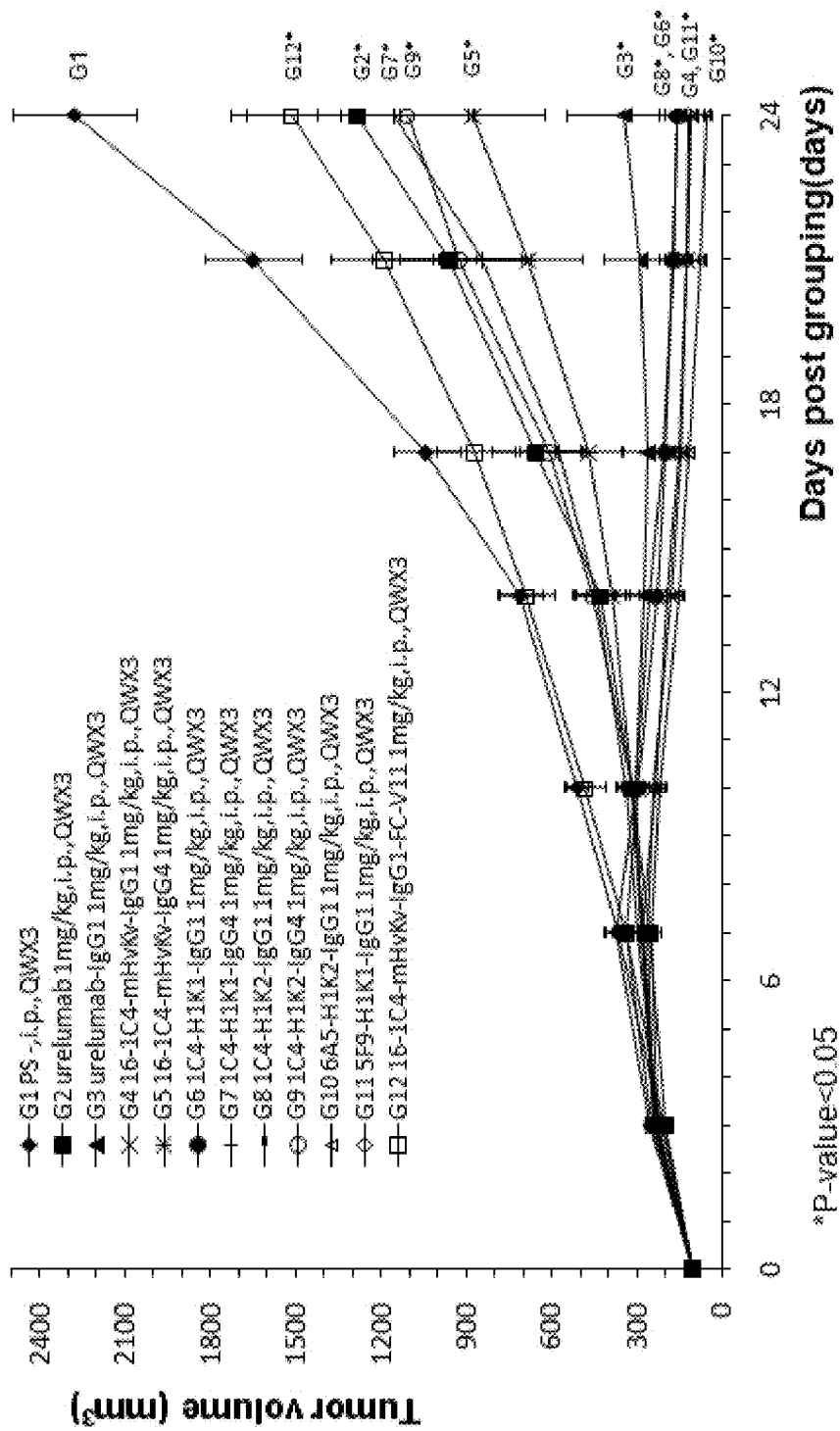
FIG. 64 is a graph showing tumor size over time in humanized 4-1BB mice (B-h4-1BB) with MC-38 tumor cells treated with anti-h4-1BB antibodies urelumab, urelumab-IgG1, 1C4-mHvKv-IgG1, 1C4-mHvKv-IgG4, 1C4-H1K1-IgG1, 1C4-H1K1-IgG4, 1C4-H1K2-IgG1, 1C4-H1K2-IgG4, 6A5-H1K2-IgG1, 5F9-H1K1-IgG1 and 1C4-mHvKv-IgG1-FC-V11.

The weight of the mice was monitored during the entire treatment period. The average weight of mice in different groups all increased at the end of the treatment period (FIG. 62 and FIG. 63). No obvious differences in weight were observed among the different groups. The results showed that these anti-h4-1BB antibodies were well tolerated and were not obviously toxic to the mice. The tumor size for each group is shown in FIG. 64.

The TGI % at day 24 (24 days after grouping) was also calculated as shown in the table below.

TABLE 41

| | | Tumor volume(mm)$^3$ | | | | | | P value | |
|---|---|---|---|---|---|---|---|---|---|
| | | Day 0 | Day 10 | Day 17 | Day 24 | Survival | TGI % | Body weight | Tumor Volume |
| Control | G1 | 107 ± 3 | 512 ± 36 | 1042 ± 115 | 2283 ± 217 | 8/8 | n.a. | n.a. | n.a. |
| Treat | G2 | 107 ± 4 | 318 ± 55 | 655 ± 160 | 1289 ± 390 | 8/8 | 45.7% | 0.902 | 0.043 |
| | G3 | 107 ± 4 | 306 ± 47 | 267 ± 88 | 344 ± 205 | 8/8 | 89.1% | 0.133 | <0.001 |
| | G4 | 107 ± 4 | 240 ± 21 | 150 ± 21 | 109 ± 23 | 8/8 | 99.9% | 0.002 | <0.001 |
| | G5 | 107 ± 4 | 321 ± 59 | 471 ± 120 | 882 ± 254 | 8/8 | 64.4% | 0.439 | 0.001 |
| | G6 | 107 ± 3 | 296 ± 62 | 202 ± 54 | 161 ± 64 | 8/8 | 97.5% | 0.006 | <0.001 |
| | G7 | 107 ± 4 | 337 ± 42 | 577 ± 97 | 1157 ± 273 | 8/8 | 51.8% | 0.301 | 0.006 |
| | G8 | 107 ± 4 | 305 ± 30 | 209 ± 29 | 160 ± 48 | 8/8 | 97.6% | 0.020 | <0.001 |
| | G9 | 107 ± 3 | 322 ± 30 | 607 ± 107 | 1110 ± 235 | 8/8 | 53.9% | 0.770 | 0.003 |
| | G10 | 107 ± 3 | 221 ± 21 | 116 ± 12 | 58 ± 9 | 8/8 | 102.3% | 0.007 | <0.001 |
| | G11 | 107 ± 3 | 239 ± 22 | 157 ± 27 | 117 ± 33 | 8/8 | 99.6% | 0.109 | <0.001 |
| | G12 | 107 ± 2 | 484 ± 71 | 869 ± 137 | 1518 ± 217 | 8/8 | 35.2% | 0.151 | 0.026 |

TABLE 42

| Group | No. of mice | Antibodies | Dosage (mg/kg) | Route | Frequency | Total No. of administration |
|---|---|---|---|---|---|---|
| G1 | 8 | PS (control) | — | i.p. | BIW | 6 |
| G2 | 8 | 1C4-H1K1-IgG1 | 0.3 mg/kg | i.p. | BIW | 6 |
| G3 | 8 | 1C4-H1K1-IgG4 | 0.3 mg/kg | i.p. | BIW | 6 |
| G4 | 8 | urelumab-IgG1 | 0.3 mg/kg | i.p. | BIW | 6 |
| G5 | 8 | urelumab-IgG4 | 0.3 mg/kg | i.p. | BIW | 6 |
| G6 | 8 | Keytruda-IgG4 | 0.3 mg/kg | i.p. | BIW | 6 |
| G7 | 8 | 1C4-H1K1-IgG1 + Keytruda-IgG4 | 0.3 mg/kg + 0.3 mg/kg | i.p. | BIW | 6 |
| G8 | 8 | 1C4-H1K1-IgG4 + Keytruda-IgG4 | 0.3 mg/kg + 0.3 mg/kg | i.p. | BIW | 6 |
| G9 | 8 | urelumab-IgG1 + Keytruda-IgG4 | 0.3 mg/kg + 0.3 mg/kg | i.p. | BIW | 6 |
| G10 | 8 | urelumab-IgG4 + Keytruda-IgG4 | 0.3 mg/kg + 0.3 mg/kg | i.p. | BIW | 6 |

Figure 65:
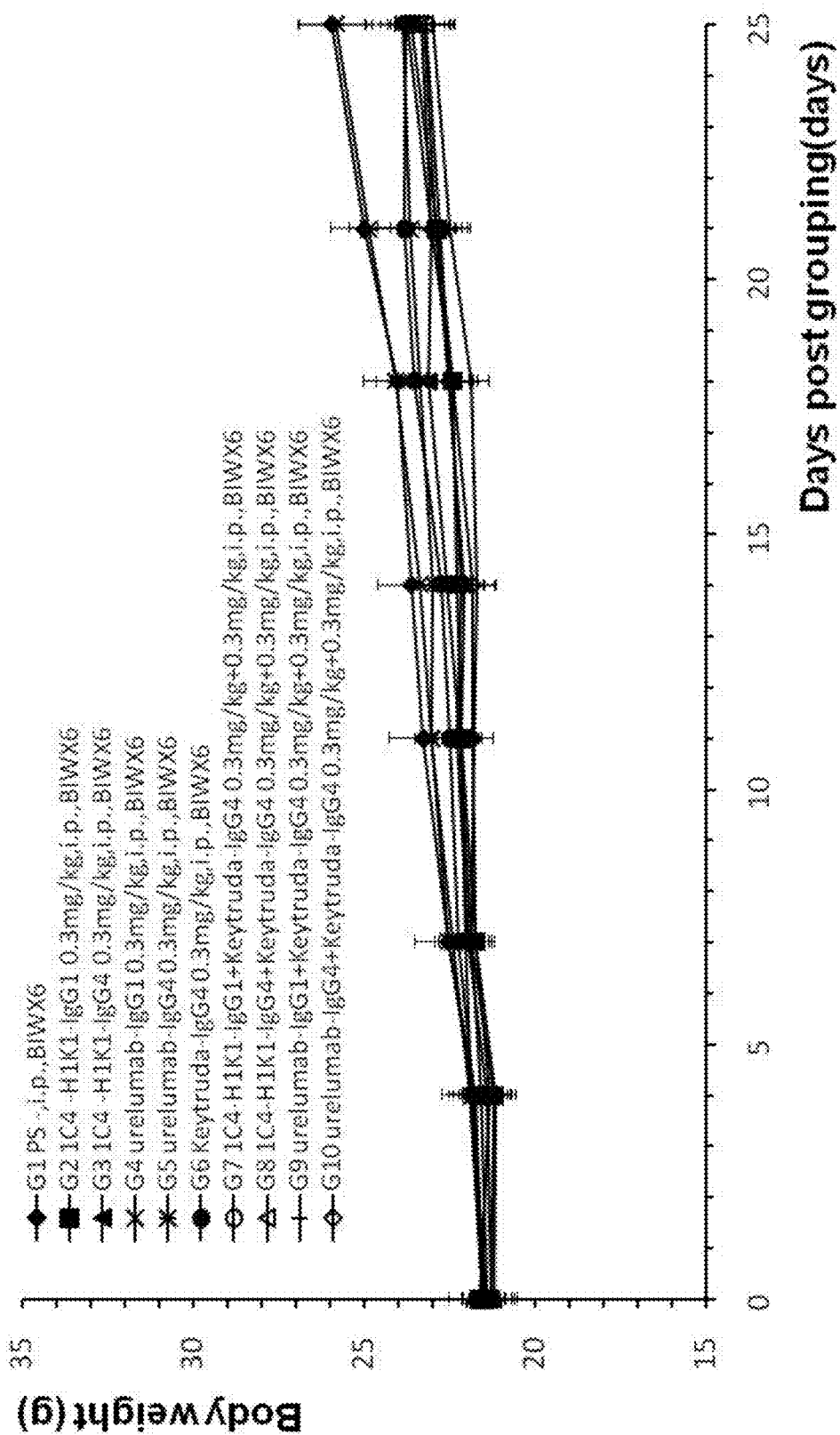
FIG. 65 is a graph showing body weight over time of humanized 4-1BB mice (B-h4-1BB) with MC-38 tumor cells treated with anti-h4-1BB antibodies 1C4-IgG1-H1K1, 1C4-IgG4-H1K1, urelumab-IgG1, urelumab-IgG4, Keytruda-IgG4, 1C4-IgG1-H1K1+Keytruda®-IgG4, 1C4-IgG4-H1K1+Keytruda®-IgG4, urelumab-IgG1+Keytruda®-IgG4 and urelumab-IgG4+Keytruda®-IgG4.
Figure 66:
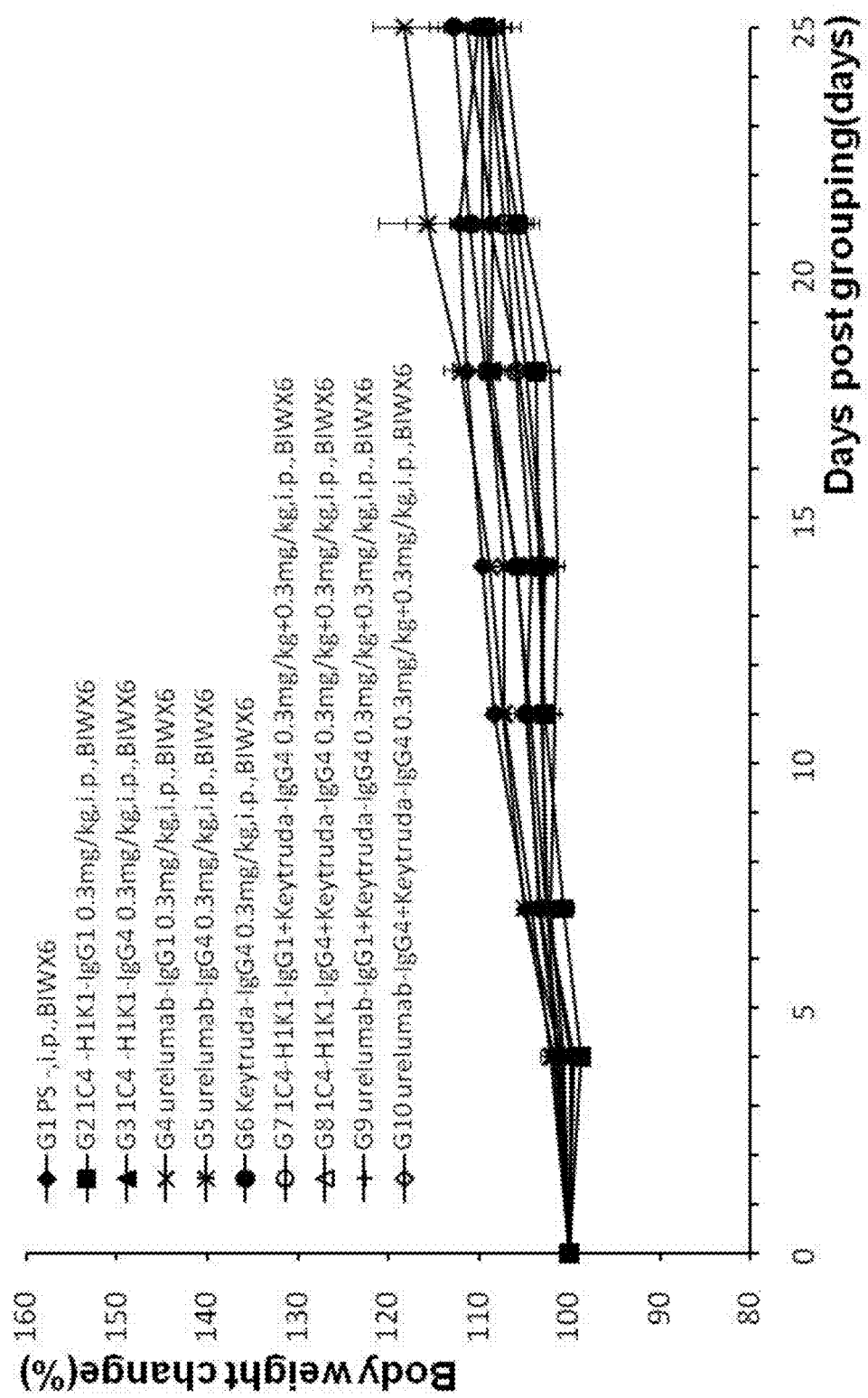
FIG. 66 is a graph showing percentage change of body weight over time of humanized 4-1BB mice (B-h4-1BB) with MC-38 tumor cells treated with anti-h4-1BB antibodies 1C4-IgG1-H1K1, 1C4-IgG4-H1K1, urelumab-IgG1, urelumab-IgG4, Keytruda®-IgG4, 1C4-IgG1-H1K1+Keytruda®-IgG4, 1C4-IgG4-H1K1+Keytruda®-IgG4, urelumab-IgG1+Keytruda®-IgG4 and urelumab-IgG4+Keytruda®-IgG4.
Figure 67:
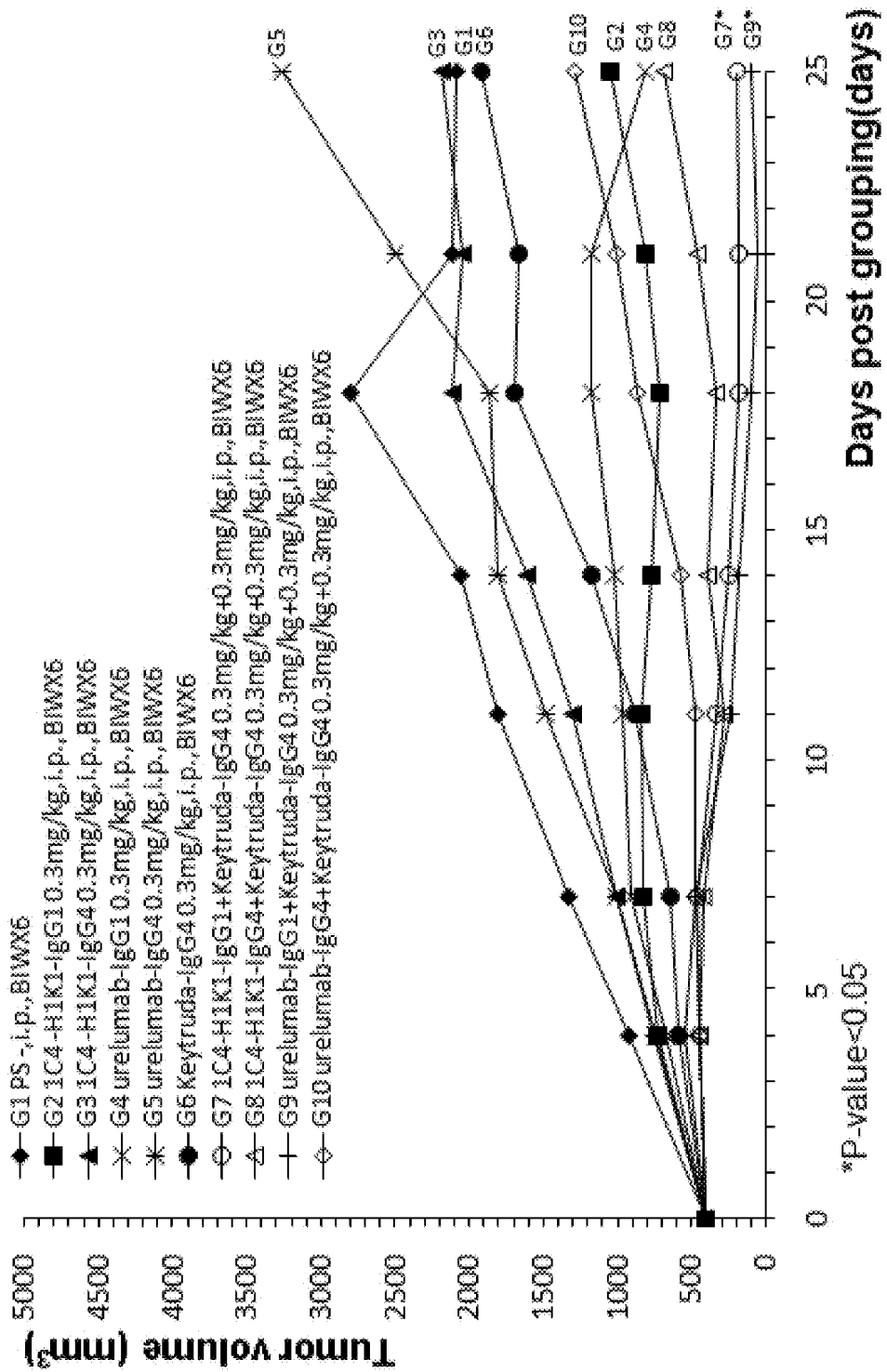
FIG. 67 is a graph showing tumor size over time in humanized 4-1BB mice (B-h4-1BB) with MC-38 tumor cells treated with anti-h4-1BB antibodies 1C4-IgG1-H1K1, 1C4-IgG4-H1K1, urelumab-IgG1, urelumab-IgG4, Keytruda®-IgG4, 1C4-IgG1-H1K1+Keytruda®-IgG4, 1C4-IgG4-H1K1+Keytruda®-IgG4, urelumab-IgG1+Keytruda®-IgG4 and urelumab-IgG4+Keytruda®-IgG4.

The weight of the mice was monitored during the entire treatment period. The average weight of mice in different groups all increased at the end of the treatment period (FIG. 65 and FIG. 66). No obvious differences in weight were observed among the different groups. The results showed that these anti-h4-1BB antibodies were well tolerated and were not obviously toxic to the mice. The tumor size for each group is shown in FIG. 67.

The TGI % at day 25 (25 days after grouping) was also calculated as shown in the table below.

TABLE 43

| | | Tumor volume(mm$^3$) | | | | | | P value | |
|---|---|---|---|---|---|---|---|---|---|
| | | Day 0 | Day 11 | Day 18 | Day 25 | Survival | TGI % | Body weight | Tumor Volume |
| Control | G1 | 399 ± 20 | 1811 ± 275 | 2803 ± 508 | 2092 ± 769 | 2/8 | n.a. | n.a. | n.a. |
| Treat | G2 | 400 ± 23 | 840 ± 104 | 710 ± 187 | 1051 ± 471 | 8/8 | 61.5% | 0.124 | 0.342 |
| | G3 | 400 ± 22 | 1301 ± 202 | 2117 ± 452 | 2182 ± 578 | 4/8 | −5.3% | 0.317 | 0.932 |
| | G4 | 400 ± 24 | 972 ± 239 | 1175 ± 441 | 810 ± 366 | 6/8 | 75.8% | 0.147 | 0.142 |
| | G5 | 399 ± 29 | 1482 ± 228 | 1858 ± 257 | 3266 ± 554 | 5/8 | −69.3% | 0.953 | 0.299 |
| | G6 | 400 ± 29 | 882 ± 188 | 1692 ± 515 | 1916 ± 538 | 6/8 | 10.4% | 0.084 | 0.872 |
| | G7 | 399 ± 24 | 337 ± 51 | 175 ± 65 | 190 ± 125 | 8/8 | 112.4% | 0.166 | 0.001 |
| | G8 | 400 ± 22 | 284 ± 76 | 330 ± 155 | 691 ± 341 | 8/8 | 82.8% | 0.060 | 0.108 |
| | G9 | 400 ± 27 | 243 ± 65 | 93 ± 53 | 95 ± 95 | 8/8 | 118.0% | 0.043 | 0.001 |
| | G10 | 400 ± 24 | 475 ± 151 | 868 ± 379 | 1284 ± 705 | 7/8 | 47.8% | 0.139 | 0.588 |

The results confirmed that 1C4-H1K1-IgG1 antibodies had higher tumor inhibitory effects as compared to 1C4-H1K1-IgG4; and urelumab-IgG1 antibodies had higher tumor inhibitory effects as compared to urelumab-IgG4 antibodies. Furthermore, the results showed that the combination of anti-4-1BB antibodies with anti-PD-1 antibodies had higher tumor inhibitory effects as compared to the treatment using an anti-4-1 antibody alone or using an anti-PD-1 antibody alone. In addition, the combination of an anti-4-1BB IgG1 antibody with an anti-PD-1 antibody had higher tumor inhibitory effects as compared to the combination of an anti-4-1BB IgG4 antibody with an anti-PD-1 antibody.

Example 18. In Vivo Testing with Melanoma Cancer Cells

B16-F10 cells (melanoma cell line) expressing human PD-L1 were injected subcutaneously in B-h4-1BB mice. When the tumors in the mice reached a volume of 100-150 mm$^3$, the mice were randomly placed into different groups based on the volume of the tumor, and were administered with different antibodies as shown in the table below.

TABLE 44

| Group | No. of mice | Antibodies | Dosage (mg/kg) | Route | Frequency | Total No. of administration |
|---|---|---|---|---|---|---|
| G1 | 8 | PS (control) | — | i.p. | BIW | 4 |
| G2 | 8 | 1C4-H1K1IgG1 | 3 mg/kg | i.p. | BIW | 4 |

TABLE 44-continued

| Group | No. of mice | Antibodies | Dosage (mg/kg) | Route | Frequency | Total No. of administration |
|---|---|---|---|---|---|---|
| G3 | 8 | Keytruda-IgG4 | 3 mg/kg | i.p. | BIW | 4 |
| G4 | 8 | 1C4-H1K1-IgG1 + Keytruda-IgG4 | 3 mg/kg + 3 mg/kg | i.p. | BIW | 4 |

Figure 68:
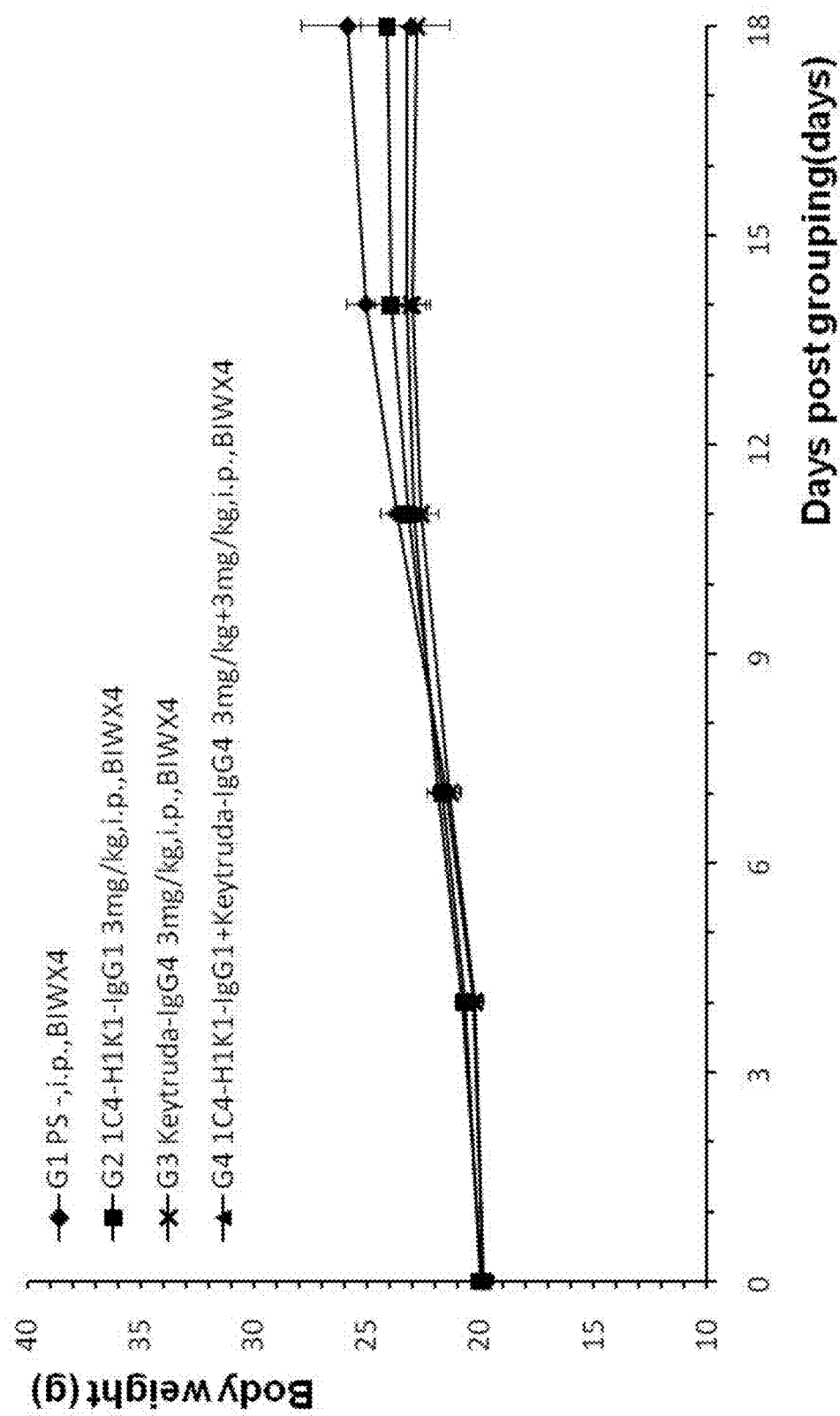
FIG. 68 is a graph showing body weight over time of humanized 4-1BB mice (B-h4-1BB) with B16-F10 cancer cells treated with different anti-h4-1BB antibodies.
Figure 69:
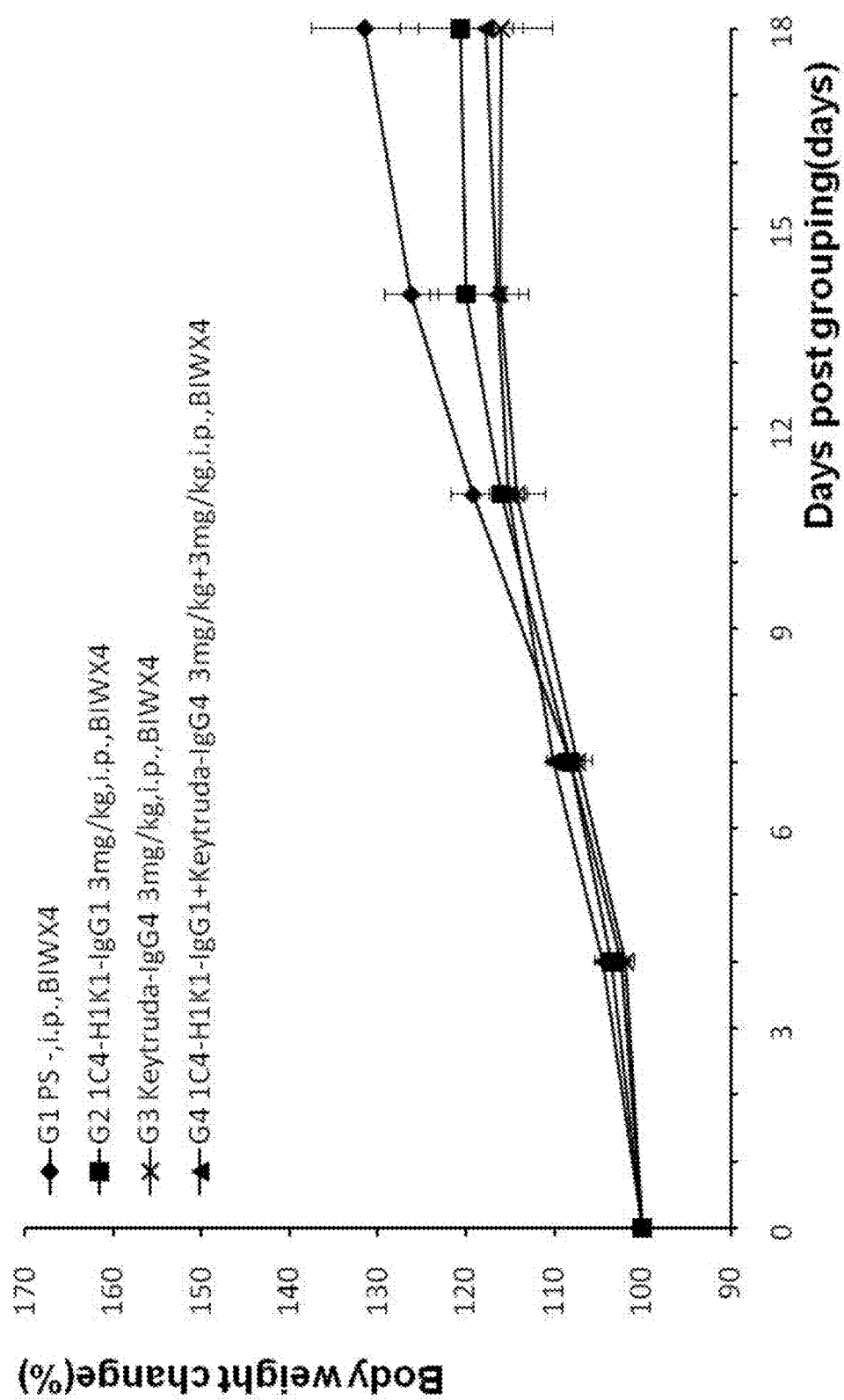
FIG. 69 is a graph showing percentage change of body weight over time of humanized 4-1BB mice (B-h4-1BB) with B16-F10 cancer cells treated with different anti-h4-1BB antibodies.
Figure 70:
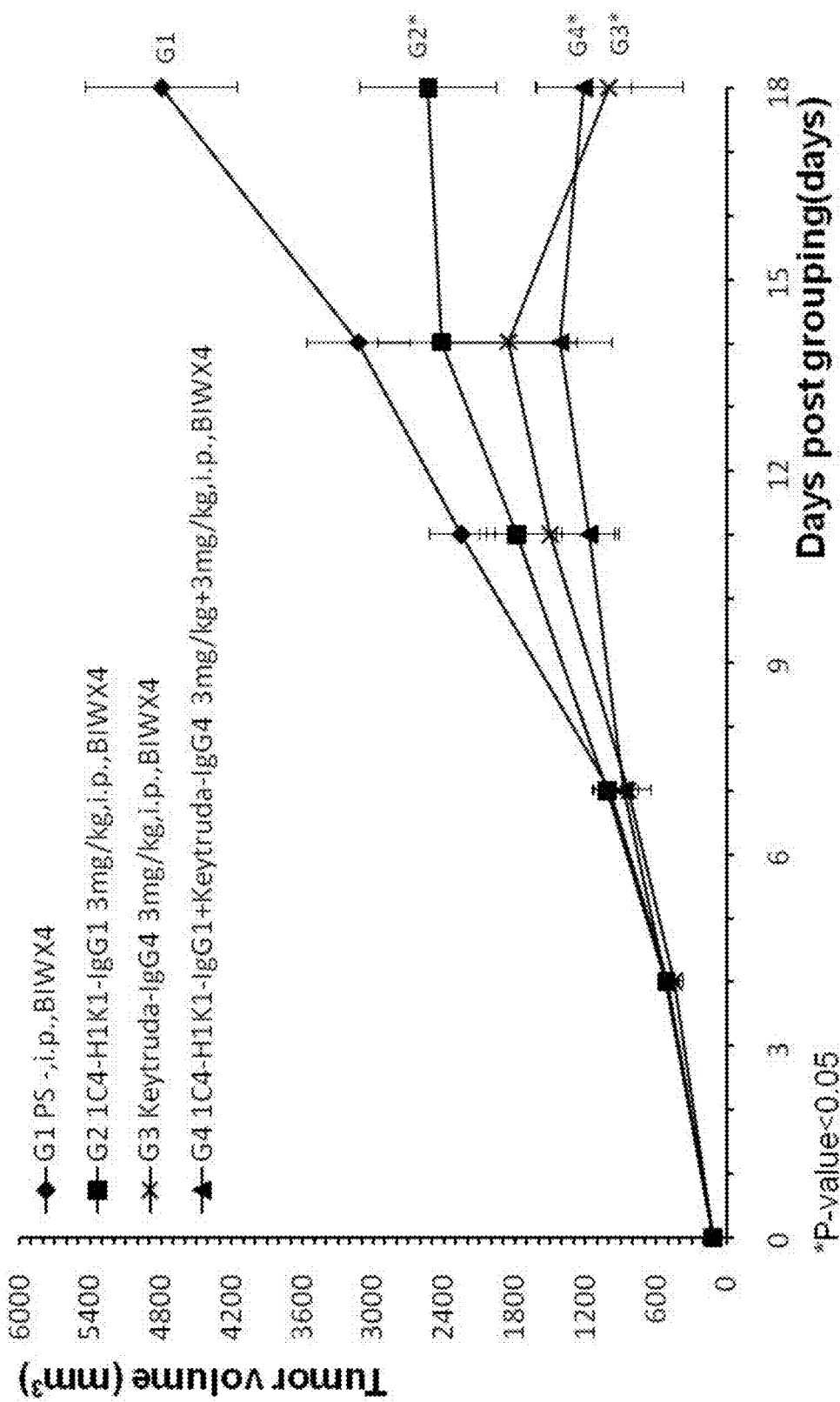
FIG. 70 is a graph showing tumor size over time in humanized 4-1BB mice (B-h4-1BB) with B16-F10 cancer cells treated with different anti-h4-1BB antibodies.

The weight of the mice was monitored during the entire treatment period. The average weight of mice in different groups all increased at the end of the treatment period (FIG. 68, and FIG. 69). No obvious differences in weight were observed among the different groups. The results showed that these anti-h4-1BB antibodies were well tolerated and were not obviously toxic to the mice. The tumor size for each group is shown in FIG. 70.

The TGI % at day 18 (18 days after grouping) was also calculated as shown in the table below.

TABLE 45

| | | Tumor volume(mm$^3$) | | | | | | P value | |
|---|---|---|---|---|---|---|---|---|---|
| | | Day 0 | Day 4 | Day 11 | Day 18 | Survival | TGI % | Body weight | Tumor Volume |
| Control | G1 | 112 ± 5 | 503 ± 85 | 2252 ± 280 | 4801 ± 643 | 4/8 | n.a. | n.a. | n.a. |
| Treat | G2 | 112 ± 6 | 522 ± 60 | 1779 ± 323 | 2543 ± 578 | 5/8 | 48.1% | 0.450 | 0.035 |
| | G3 | 112 ± 5 | 445 ± 73 | 1497 ± 545 | 1003 ± 622 | 4/8 | 81.0% | 0.257 | 0.005 |
| | G4 | 112 ± 5 | 521 ± 55 | 1166 ± 243 | 1216 ± 401 | 7/8 | 76.5% | 0.144 | 0.001 |

The results showed that anti-h4-1BB IgG1 antibodies had excellent tumor inhibitory effects against melanoma cancer cells, and the combination with anti-h4-1BB IgG1 antibodies with anti-PD-1 antibody can further improve tumor inhibitory effects. While TGI % in G3 was 81.0%, the TGI % was calculated based on the only 4 surviving mice and the survival rate in G3 was only 4/8. In contrast, the survival rate in G4 was 7/8. The results showed that the combination treatment significantly improved the survival rate.

Example 19. In Vivo Testing with Lymphoma Cancer Cells

EL4 cells (lymphoma cancer cells) were injected subcutaneously in B-h4-1BB mice. When the tumors in the mice reached a volume of 100~150 mm$^3$, the mice were randomly placed into different groups based on the volume of the tumor, and were administered with different antibodies as shown in the table below.

TABLE 46

| Group | No. of mice | Antibodies | Dosage (mg/kg) | Route | Frequency | Total No. of administration |
|---|---|---|---|---|---|---|
| G1 | 8 | PS (control) | — | i.p. | BIW | 6 |
| G2 | 8 | 1C4-H1K1-IgG1 | 3 mg/kg | i.p. | BIW | 6 |
| G3 | 8 | Keytruda-IgG4 | 3 mg/kg | i.p. | BIW | 6 |
| G4 | 8 | 1C4-H1K1-IgG1 + Keytruda-IgG4 | 3 mg/kg + 3 mg/kg | i.p. | BIW | 6 |

Figure 71:
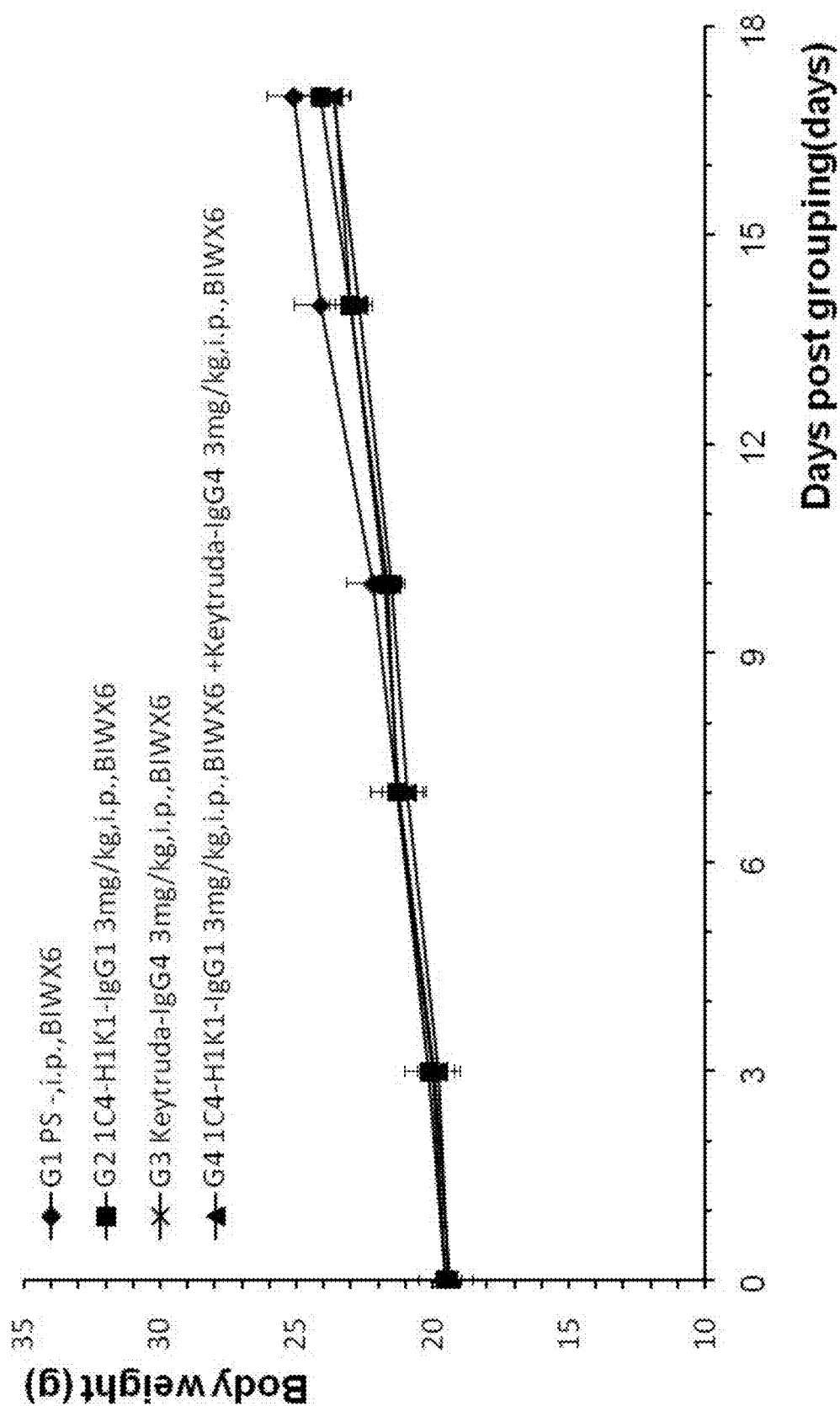
FIG. 71 is a graph showing body weight over time of humanized 4-1BB mice (B-h4-1BB) with EL4 cancer cells treated with different anti-h4-1BB antibodies.
Figure 72:
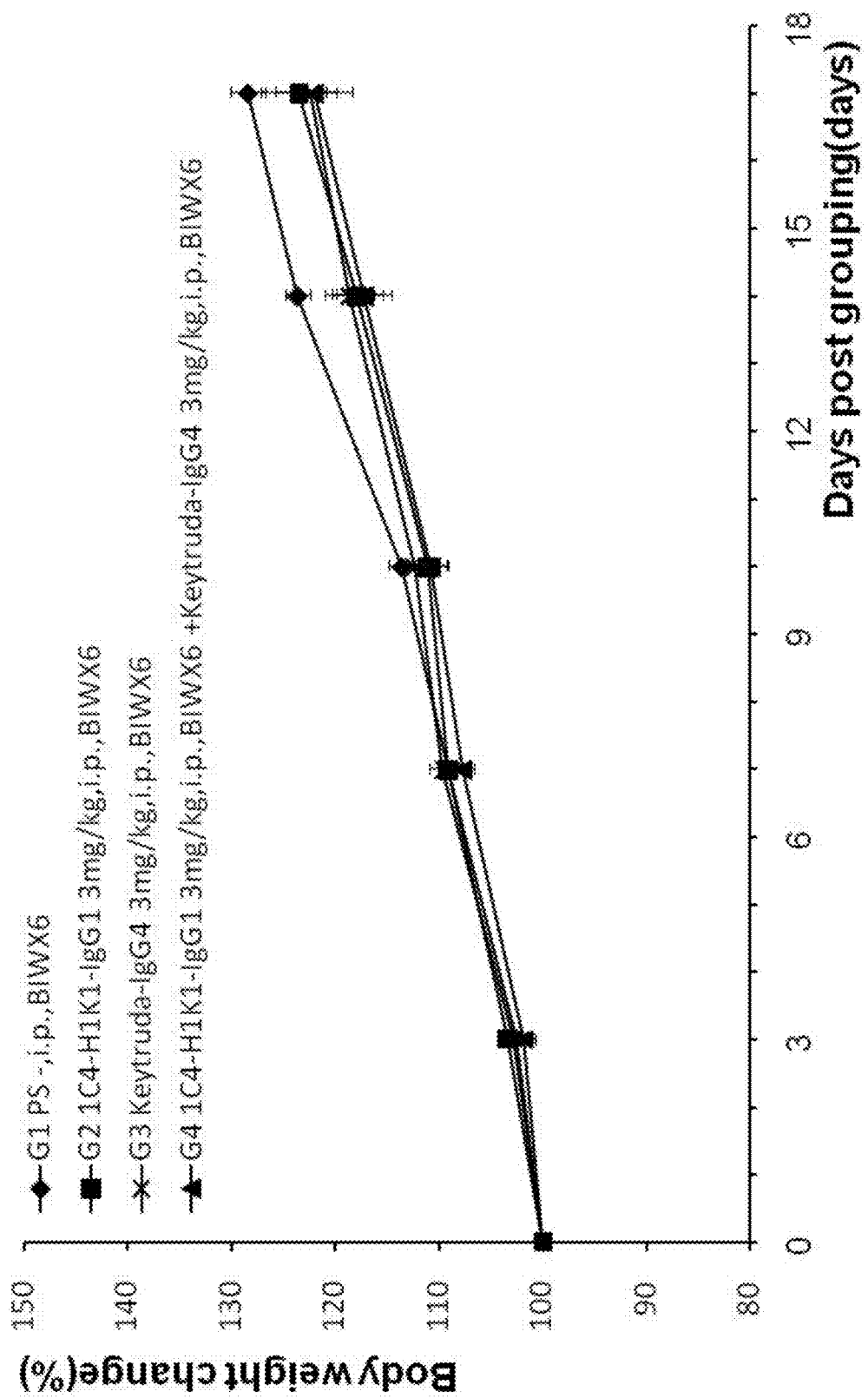
FIG. 72 is a graph showing percentage change of body weight over time of humanized 4-1BB mice (B-h4-1BB) with EL4 cancer cells treated with different anti-h4-1BB antibodies.
Figure 73:
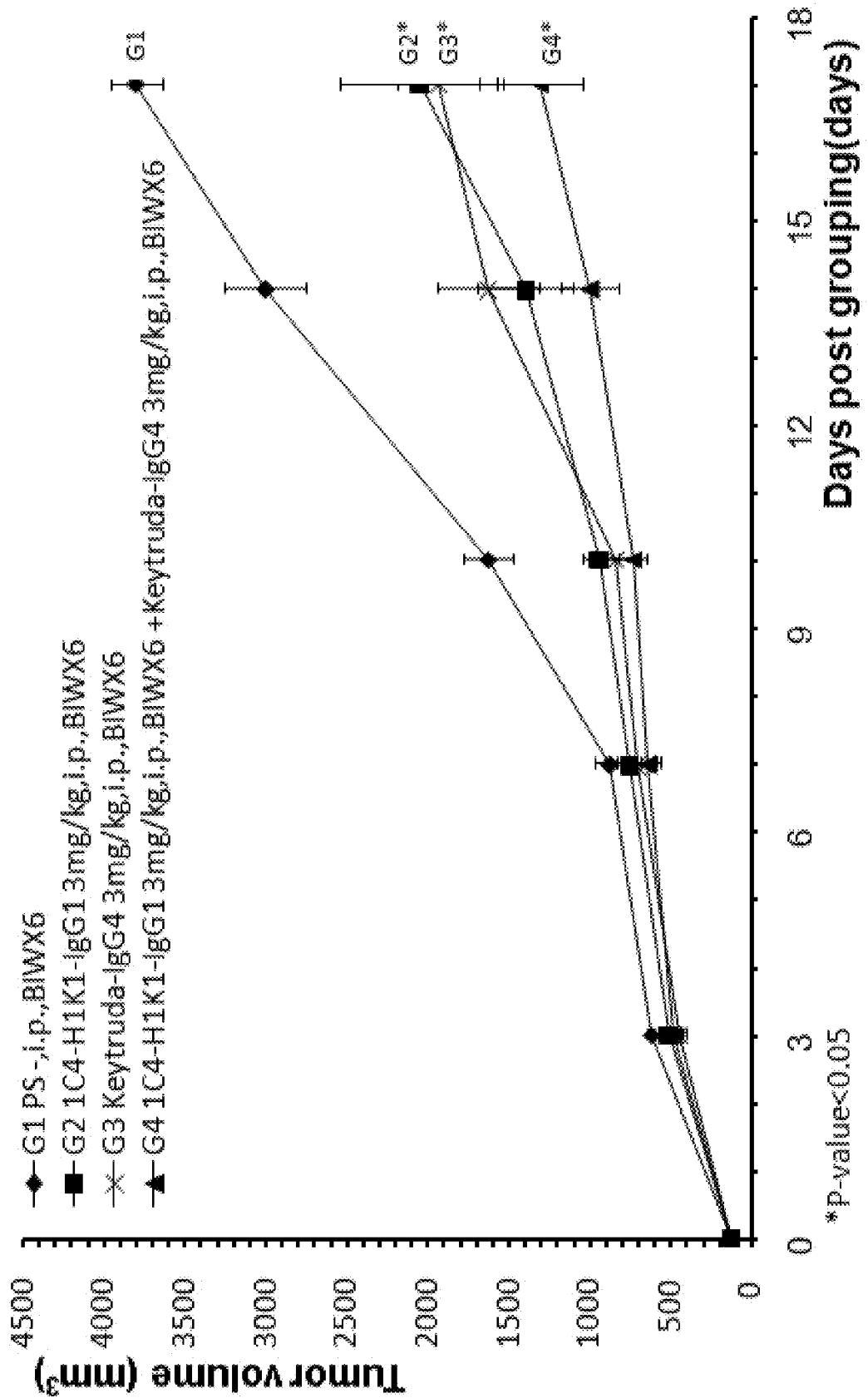
FIG. 73 is a graph showing tumor size over time in humanized 4-1BB mice (B-h4-1BB) with EL4 cancer cells treated with different anti-h4-1BB antibodies.

The weight of the mice was monitored during the entire treatment period. The average weight of mice in different groups all increased at the end of the treatment period (FIG. 71, and FIG. 72). No obvious difference in weight was observed among the different groups. The results showed that these anti-h4-1BB antibodies were well tolerated and were not obviously toxic to the mice. The tumor size for each group is shown in FIG. 73.

The TGI % at day 17 (17 days after grouping) was also calculated as shown in the table below.

TABLE 47

| | | Tumor volume(mm$^3$) | | | | | P value | |
|---|---|---|---|---|---|---|---|---|
| | | Day 0 | Day 3 | Day 10 | Day 17 | Survival | TGI % | Body weight | Tumor Volume |
| Control | G1 | 129 ± 1 | 622 ± 23 | 1626 ± 158 | 3799 ± 157 | 5/8 | n.a. | n.a. | n.a. |
| Treat | G2 | 129 ± 2 | 502 ± 54 | 931 ± 115 | 2038 ± 507 | 8/8 | 48.0% | 0.379 | 0.022 |
| | G3 | 129 ± 2 | 445 ± 42 | 842 ± 127 | 1933 ± 256 | 7/8 | 50.8% | 0.123 | <0.001 |
| | G4 | 129 ± 1 | 477 ± 52 | 733 ± 85 | 1306 ± 264 | 8/8 | 67.9% | 0.134 | <0.001 |

The results showed that anti-h4-1BB IgG1 antibodies had excellent tumor inhibitory effects against lymphoma cancer cells, and the combination with anti-h4-1BB IgG1 antibodies with anti-PD-1 antibody can further improve tumor inhibitor effects.

Example 20. Further Analysis of Effects of Humanized Anti-4-1BB Antibodies

MC-38 cancer tumor cells (colon adenocarcinoma cell) were injected subcutaneously in B-h4-1BB mice. When the tumors in the mice reached a volume of about 200±50 mm$^3$, the mice were randomly placed into different groups based on the volume of the tumor, and were administered with different antibodies as shown in the table below.

TABLE 48

| Group | No. of mice | Antibodies | Dosage (mg/kg) | Route | Frequency | Total No. of administration |
|---|---|---|---|---|---|---|
| G1 | 5 | PS (control) | — | i.p. | QD | 1 |
| G2 | 5 | 1C4-H1K1-IgG1 | 3 mg/kg | i.p. | QD | 1 |
| G3 | 5 | 1C4-H1K1-IgG4 | 3 mg/kg | i.p. | QD | 1 |
| G4 | 5 | Urelumab-IgG1 | 3 mg/kg | i.p. | QD | 1 |
| G5 | 5 | Urelumab-IgG4 | 3 mg/kg | i.p. | QD | 1 |

Two days after the administration, the mice were sacrificed. The tumor samples and the spleen samples were collected for further analysis. The weight of the mice was also recorded as shown in the table below. No obvious differences in weight were observed among the different groups.

TABLE 49

| | | Body weight (g) | | | P value |
|---|---|---|---|---|---|
| | | Day 0 | Day 2 | Survival | Body weight |
| Control | G1 | 19.4 ± 0.5 | 19.7 ± 0.5 | 5/5 | n.a. |
| Treat | G2 | 19.6 ± 0.5 | 19.4 ± 0.5 | 5/5 | 0.699 |
| | G3 | 19.1 ± 0.3 | 19.7 ± 0.3 | 5/5 | 1.000 |
| | G4 | 18.8 ± 0.5 | 19.0 ± 0.6 | 5/5 | 0.408 |
| | G5 | 20.0 ± 0.5 | 20.0 ± 0.5 | 5/5 | 0.684 |

The collected tumor and spleen samples were grinded and treated with digestive enzymes. The mixture was incubated at 37° C. for 60 minutes, filtered, washed, and re-suspended as a single-cell suspension.

Figure 74:
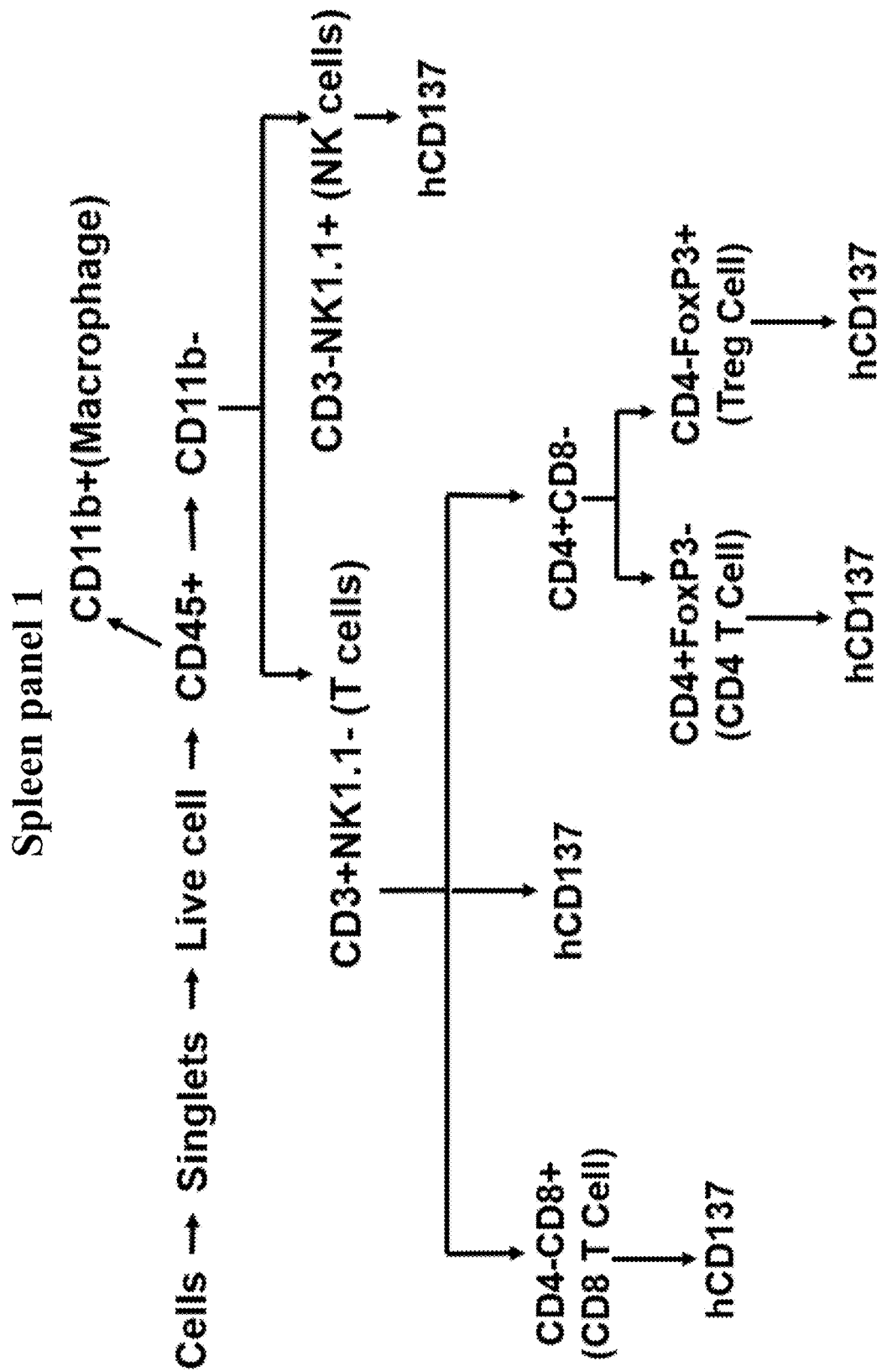
FIGS. 74-75 are diagrams showing two fluorescence activated cell sorting (FACS) procedures for analyzing spleen samples.
Figure 75:
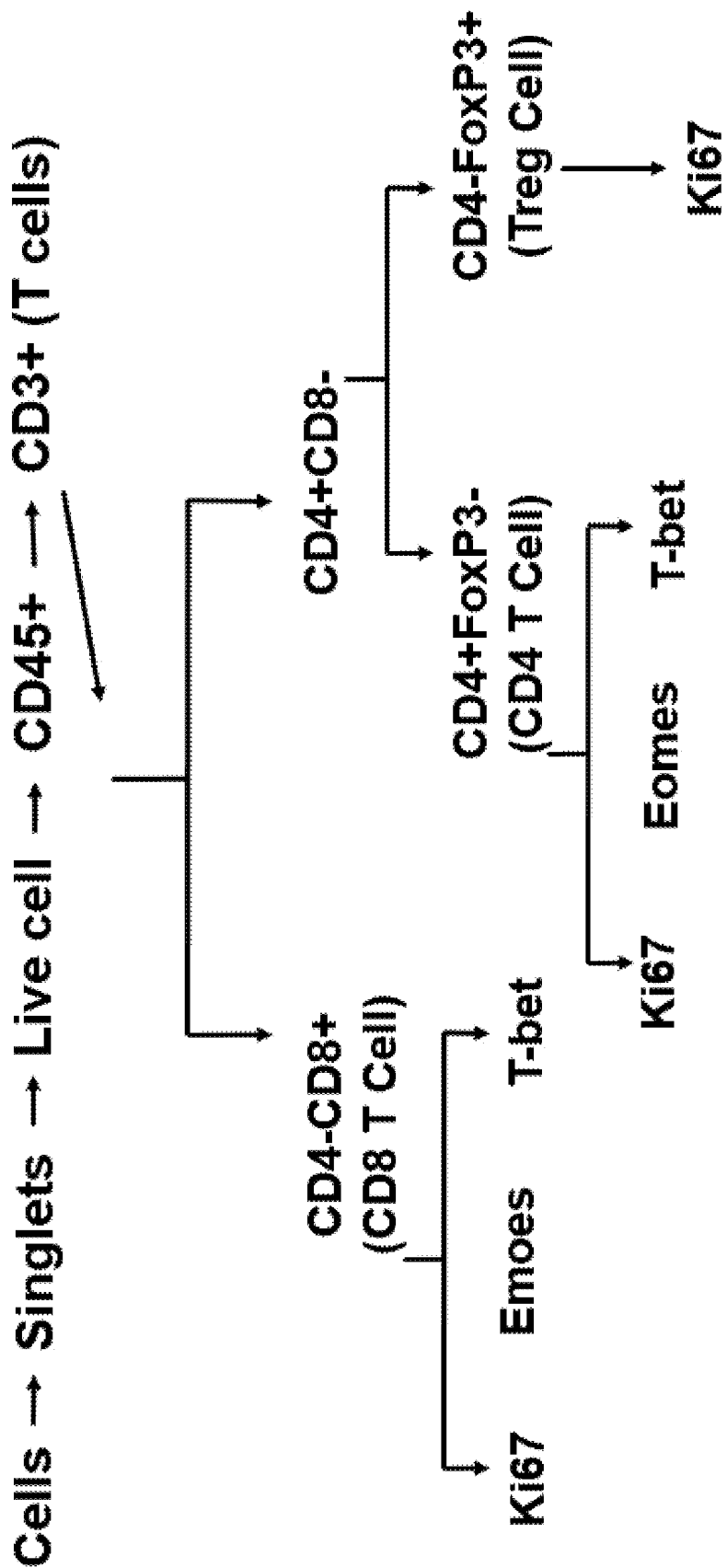
Figure 76:
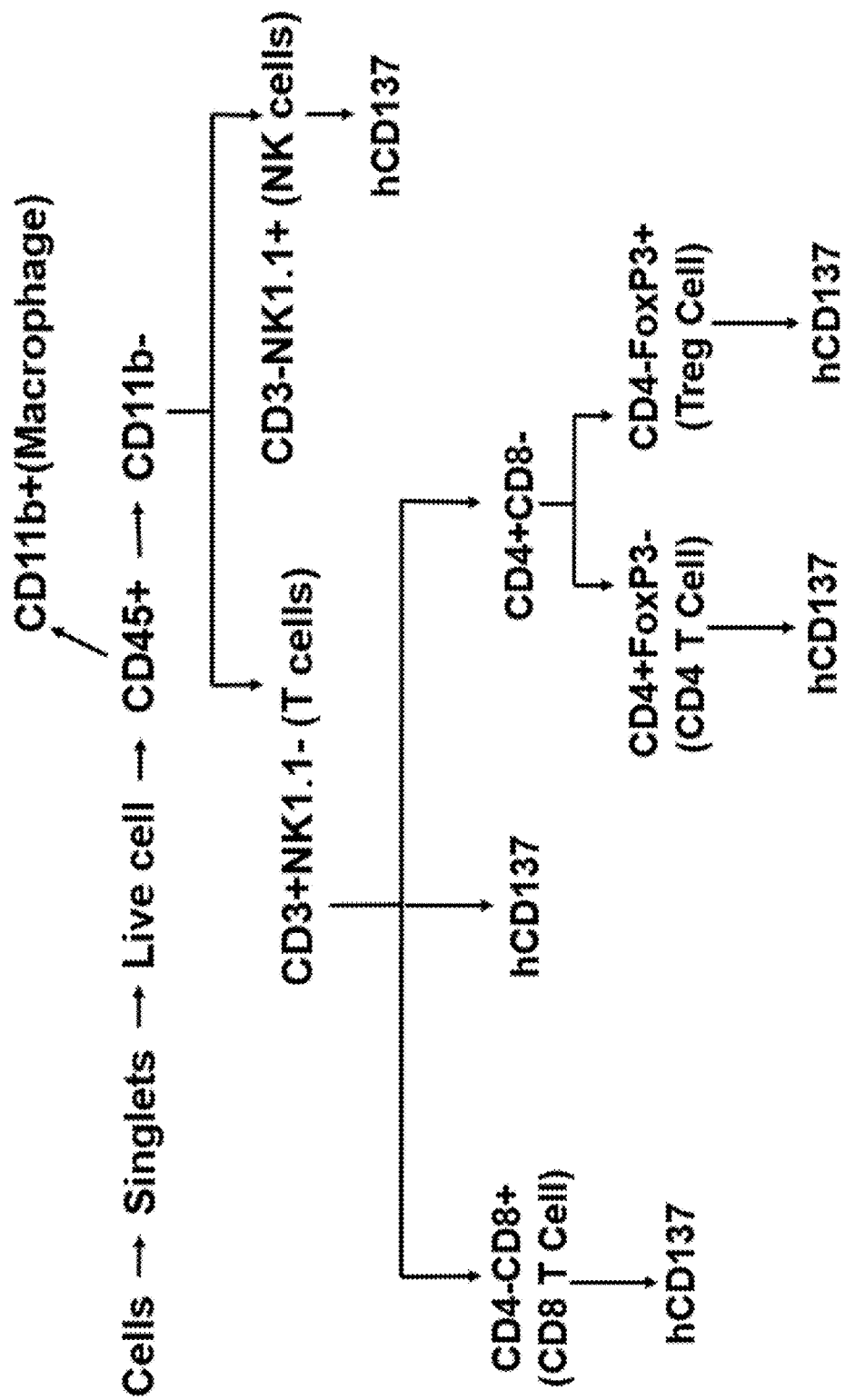
FIGS. 76-77 are diagrams showing two FACS procedures for analyzing tumor samples
Figure 77:
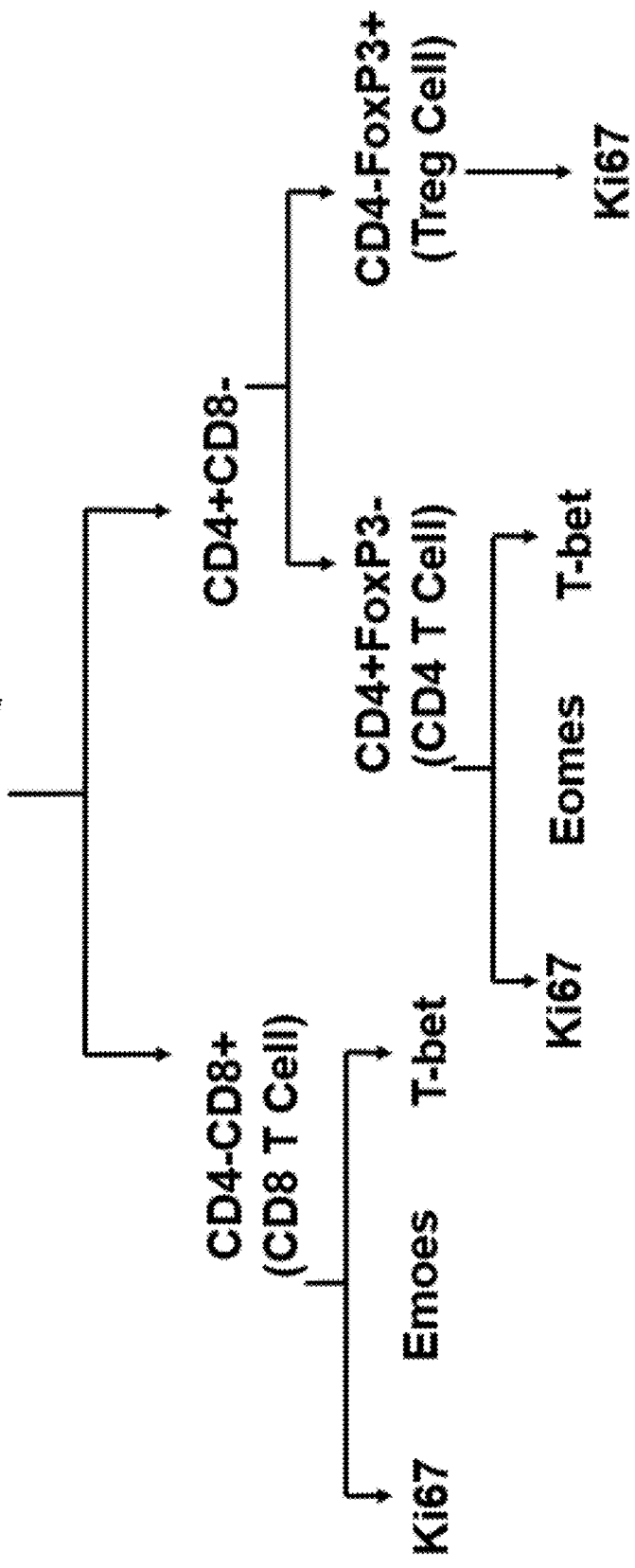
Figures 78A, 78B, 78C, 78D:
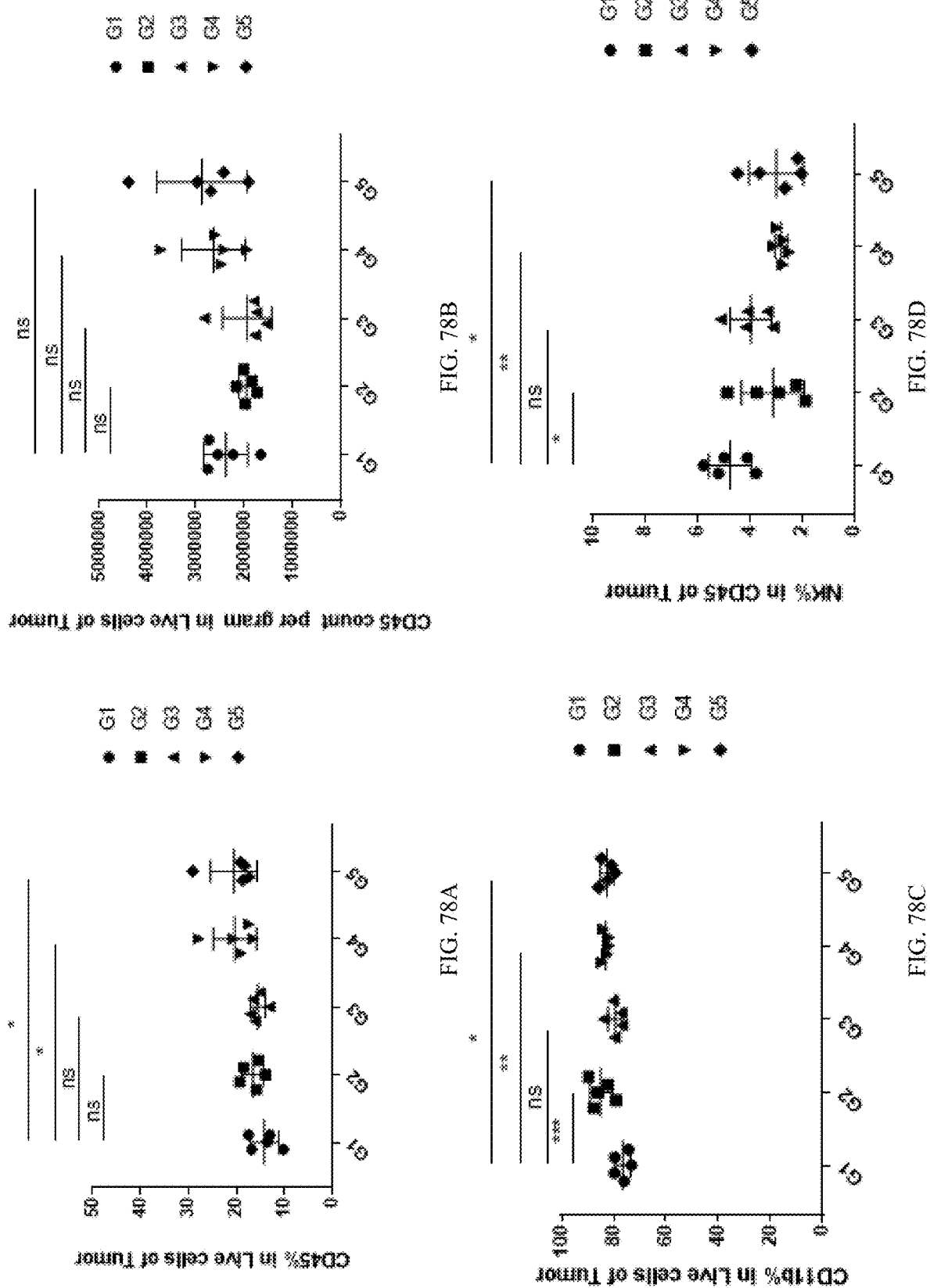
FIG. 78A is a graph showing percentage of CD45+ cells in tumor cells.
FIG. 78B is a graph showing counts of CD45+ cells in tumor cells.
FIG. 78C is a graph showing percentage of CD11b+ cells in tumor cells.
FIG. 78D is a graph showing percentage of NK cells in CD45+ cells in tumor sample.
Figure 79A:
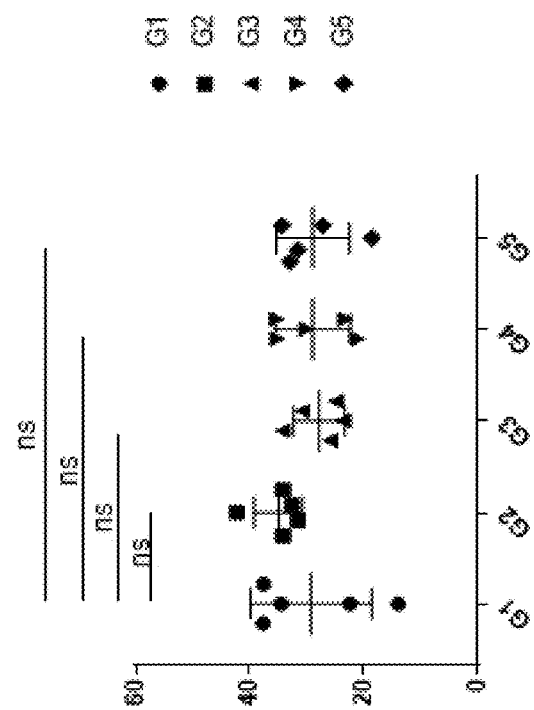
FIG. 79A is a graph showing percentage of CD3+ cells in CD45+ cells in tumor sample.
Figure 79B:
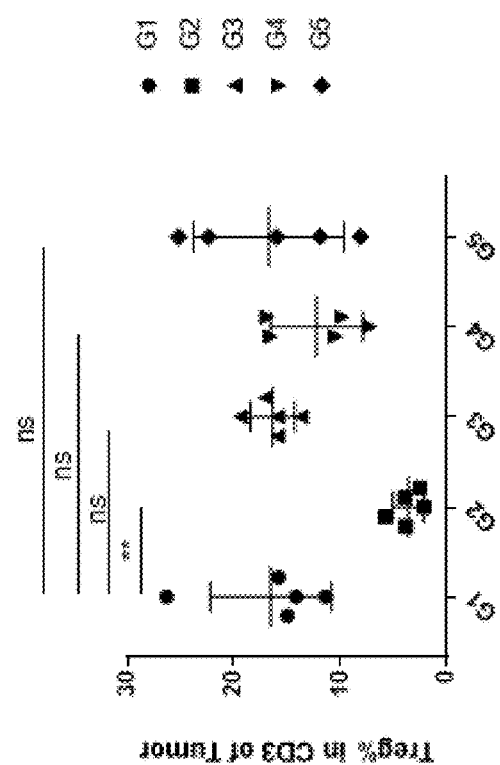
FIG. 79B is a graph showing percentage of CD8+ cells in CD3+ cells in tumor sample.
Figure 79C:
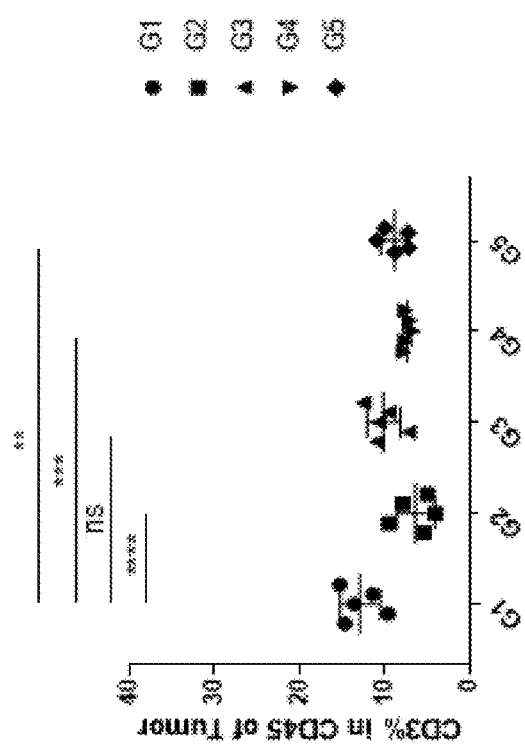
FIG. 79C is a graph showing percentage of CD4+FoxP3− cells in CD3+ cells in tumor sample.
Figure 79D:
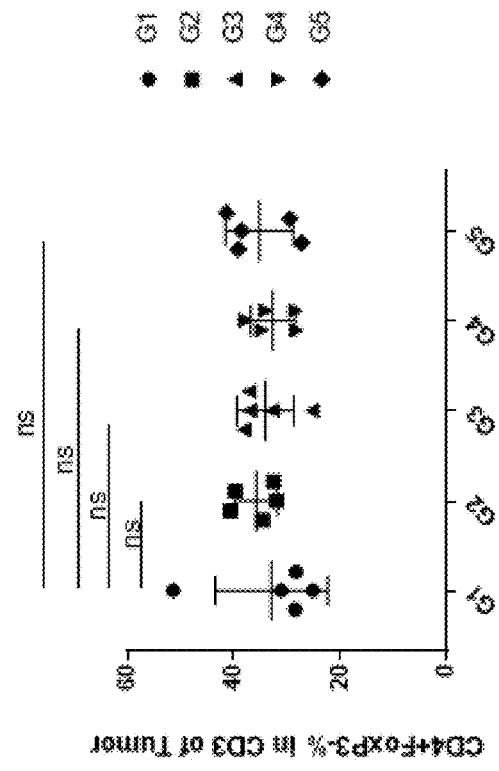
FIG. 79D is a graph showing percentage of Treg cells in CD3+ cells in tumor sample.
Figure 80B:
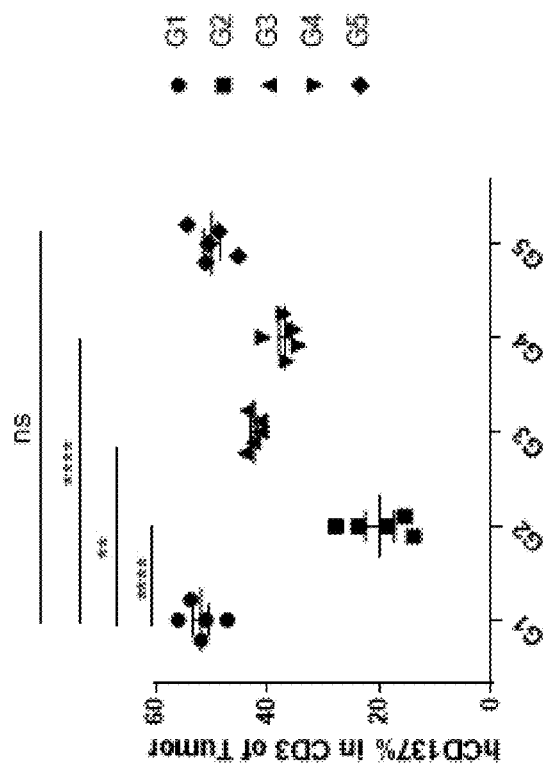
FIG. 80B is a graph showing percentage of hCD137+ cells in CD3+ cells in tumor sample.
Figure 80D:
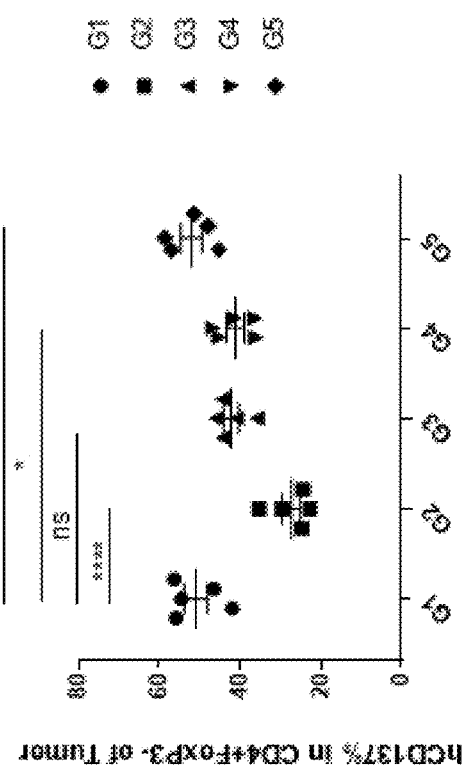
FIG. 80D is a graph showing percentage of hCD137+ cells in CD4+FoxP3− cells in tumor sample.
Figure 80A:
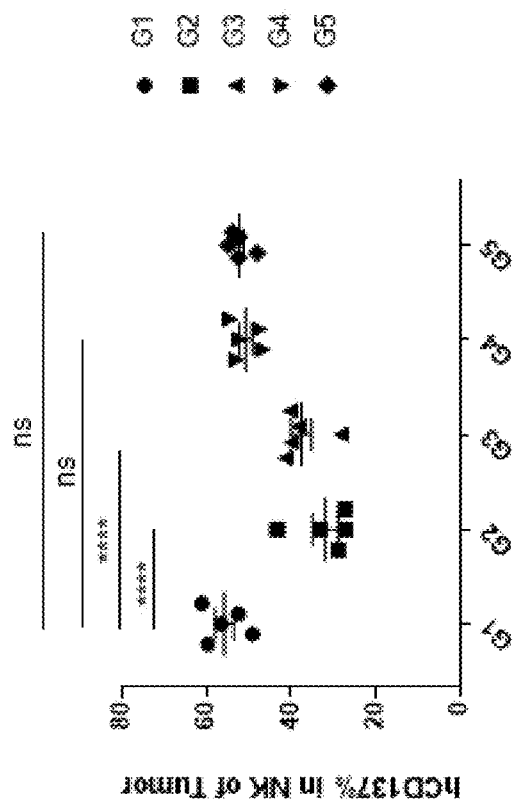
FIG. 80A is a graph showing percentage of hCD137+ cells in NK cells in tumor sample.
Figure 80C:
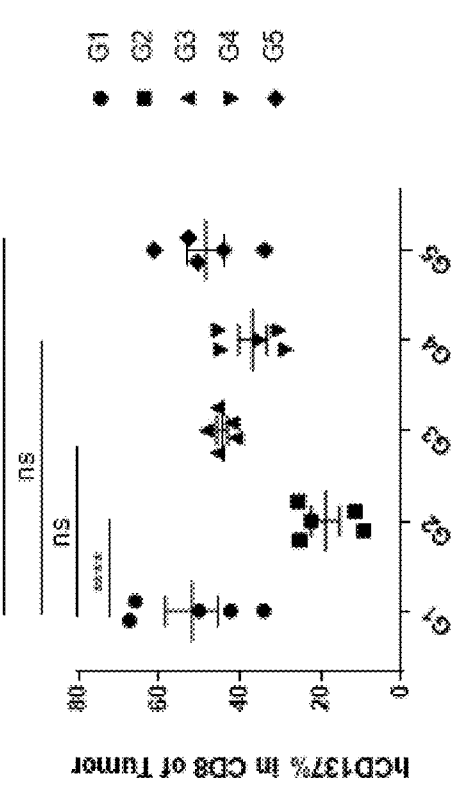
FIG. 80C is a graph showing percentage of hCD137+ cells in CD8+ cells in tumor sample.
Figure 83A:
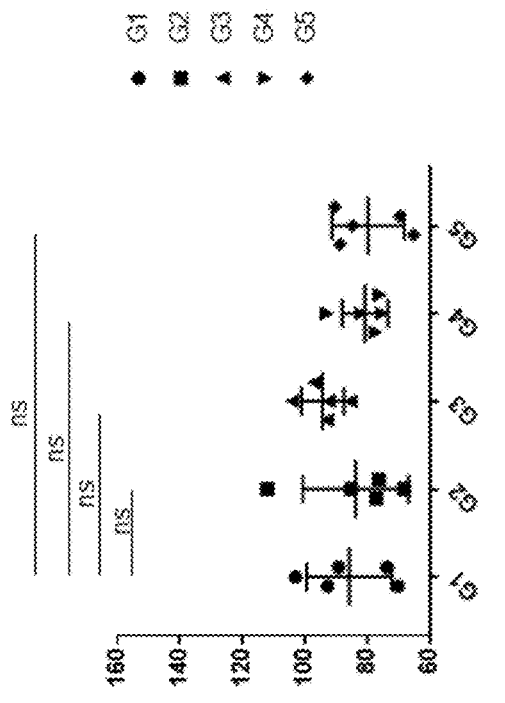
FIG. 83A is a graph showing counts of Eomes+ cells in CD8+ cells in tumor sample.
Figure 83B:
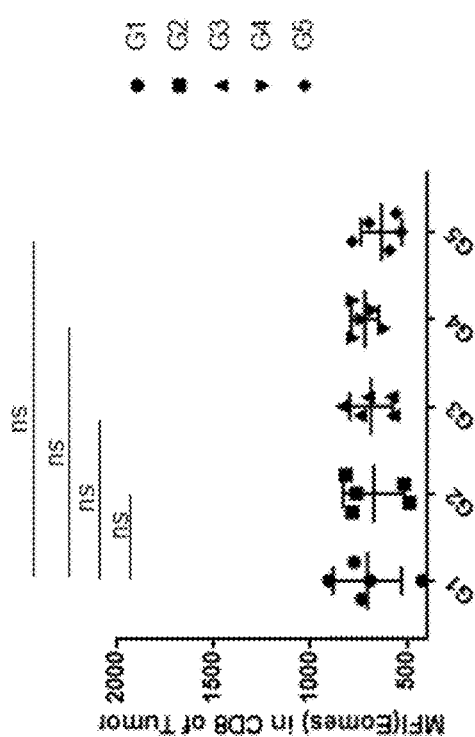
FIG. 83B is a graph showing counts of Eomes+ cells in CD4+FoxP3+ cells in tumor sample.
Figure 83C:
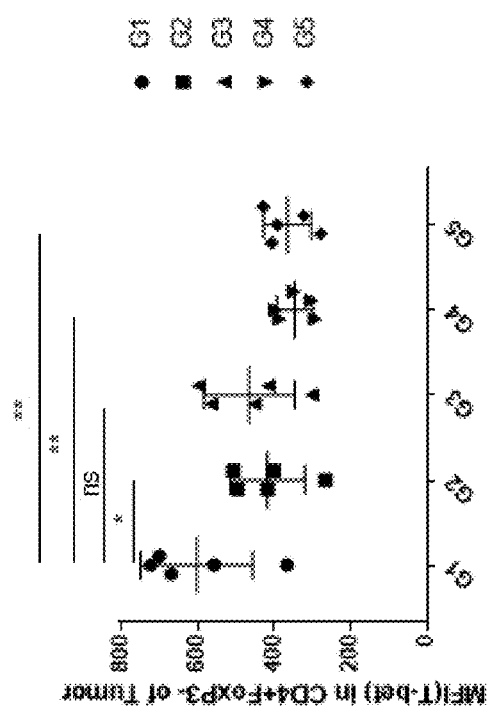
FIG. 83C is a graph showing counts of T-bet+ cells in CD8+ cells in tumor sample.
Figure 83D:
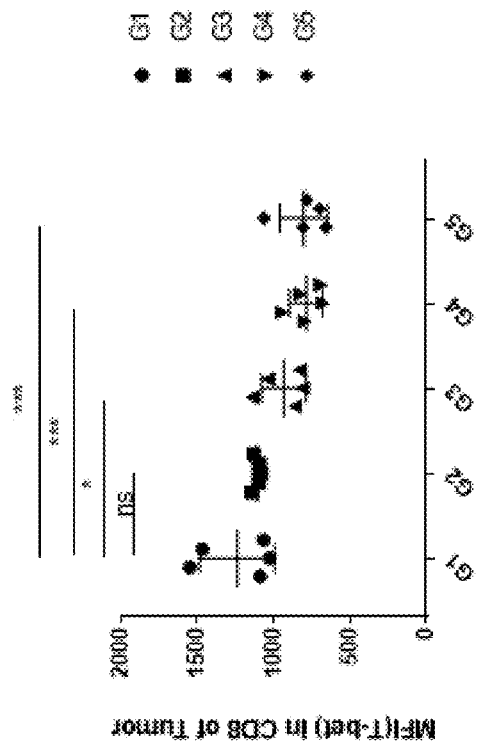
FIG. 83D is a graph showing counts of T-bet+ cells in CD4+FoxP3− cells in tumor sample.

The cells were incubated with fluorescent-labeled antibodies and were analyzed by flow cytometry. The spleen samples were processed by the procedures as shown in FIG. 74 and FIG. 75. The tumor samples were processed by the procedures as shown in FIG. 76 and FIG. 77.

The results are shown in FIGS. 78-83. As shown in FIG. 79D, anti-4-1BB IgG1 antibodies can effectively decrease the percentage of Treg cells in tumors, thereby increasing immune response. The result is also consistent with the result in FIG. 82A, wherein a lower ratio of CD8 to Treg is associated with an unfavorable outcome. In addition, the results in FIG. 82A also explain that the 1C4 anti-4-1BB antibody has a higher tumor inhibitory effects as compared to Urelumab.

Example 21. More Testing on Anti-h4-1BB IgG1 Antibodies

Experiments are repeated to test different subclasses of anti-h4-1BB IgG antibodies.

MC-38 cancer tumor cells (colon adenocarcinoma cell) are injected subcutaneously in B-h4-1BB mice. When the tumors in the mice reach a volume of 150±50 mm$^3$, the mice are randomly placed into different groups based on the volume of the tumor (e.g., n=5), and are administered with IgG1, IgG2, and IgG4 versions of antibodies selected from Table 1, Table 2, and/or Table 4 through i.p. administration twice a week with 1 mg/kg or 3 mg/kg dosage. A total number of 6 administrations is performed. Physiological saline (PS) is administered to one group of mice as a control.

The weight of the mice and the tumor size are monitored during the entire treatment period. The TGI % at the end of the treatment period is calculated.

It is expected that anti-h4-1BB IgG1 subclasses have higher TGI %, thus better tumor inhibitory effects as compared to IgG2 and IgG4 subclasses.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody or antigen-binding fragment thereof that specifically binds to 4-1BB (TNF Receptor Superfamily Member 9) comprising:
a heavy chain variable region (VH) comprising complementarity determining regions (CDRs) 1, 2, and 3, wherein the VH CDR1 region comprises an amino acid sequence that is identical to a selected VH CDR1 amino acid sequence, the VH CDR2 region comprises an amino acid sequence that is identical to a selected VH CDR2 amino acid sequence, and the VH CDR3 region comprises an amino acid sequence that is identical to a selected VH CDR3 amino acid sequence; and
a light chain variable region (VL) comprising CDRs 1, 2, and 3, wherein the VL CDR1 region comprises an amino acid sequence that is identical to a selected VL CDR1 amino acid sequence, the VL CDR2 region comprises an amino acid sequence that is identical to a selected VL CDR2 amino acid sequence, and the VL CDR3 region comprises an amino acid sequence that is identical to a selected VL CDR3 amino acid sequence,
wherein the selected VH CDRs 1, 2, and 3 amino acid sequences and the selected VL CDRs, 1, 2, and 3 amino acid sequences are one of the following:
(1) the selected VH CDRs 1, 2, 3 amino acid sequences are set forth in SEQ ID NOs: 1, 2, 3, respectively, and the selected VL CDRs 1, 2, 3 amino acid sequences are set forth in SEQ ID NOs: 4, 5, 6, respectively; and
(2) the selected VH CDRs 1, 2, 3 amino acid sequences are set forth in SEQ ID NOs: 109, 110, 111, respectively, and the selected VL CDRs 1, 2, 3 amino acid sequences are set forth in SEQ ID NOs: 112, 113, 114, respectively.

2. The antibody or antigen-binding fragment thereof of claim 1, wherein the VH comprises CDRs 1, 2, 3 with the amino acid sequences set forth in SEQ ID NOs: 1, 2, and 3 respectively, and the VL comprises CDRs 1, 2, 3 with the amino acid sequences set forth in SEQ ID NOs: 4, 5, and 6, respectively, wherein the VH CDRs 1, 2, 3 and VL CDRs 1, 2, 3 are determined according to Kabat definition.

3. The antibody or antigen-binding fragment thereof of claim 1, wherein the VH comprises CDRs 1, 2, 3 with the amino acid sequences set forth in SEQ ID NOs: 109, 110, and 111, respectively, and the VL comprises CDRs 1, 2, 3 with the amino acid sequences set forth in SEQ ID NOs: 112, 113, and 114, respectively, wherein the VH CDRs 1, 2, 3 and VL CDRs 1, 2, 3 are determined according to Chothia definition.

4. The antibody or antigen-binding fragment thereof of claim 1, wherein the antibody or antigen-binding fragment specifically binds to human 4-1BB.

5. The antibody or antigen-binding fragment thereof claim 1, wherein the antibody or antigen-binding fragment is a humanized antibody or antigen-binding fragment thereof.

6. The antibody or antigen-binding fragment thereof claim 1, wherein the antibody or antigen-binding fragment is a single-chain variable fragment (scFv) or a bispecific antibody.

7. An antibody-drug conjugate comprising the antibody or antigen-binding fragment thereof of claim 1 covalently bound to a therapeutic agent.

8. A pharmaceutical composition comprising the antibody or antigen-binding fragment thereof of claim 1, and a pharmaceutically acceptable carrier.

9. A nucleic acid comprising a polynucleotide encoding a polypeptide comprising:

(1) an immunoglobulin heavy chain or a fragment thereof comprising a heavy chain variable region (VH) comprising complementarity determining regions (CDRs) 1, 2, and 3 comprising the amino acid sequences set forth in SEQ ID NOs: 1, 2, and 3, respectively, and wherein the VH, when paired with a light chain variable region (VL) comprising the amino acid sequence set forth in SEQ ID NO: 225, 226, 227, 228, or 244 binds to 4-1BB; or (2) an immunoglobulin light chain or a fragment thereof comprising a VL comprising CDRs 1, 2, and 3 comprising the amino acid sequences set forth in SEQ ID NOs: 4, 5, and 6, respectively, and wherein the VL, when paired with a VH comprising the amino acid sequence set forth in SEQ ID NO: 221, 222, 223, 224, or 243 binds to 4-1BB.

10. A vector comprising one or more of the nucleic acids of claim 9.

11. An isolated cell comprising one or more of the nucleic acids of claim 9.

12. A method of producing an antibody or an antigen-binding fragment thereof, the method comprising
culturing the isolated cell of claim 11 under conditions sufficient for the cell to produce the immunoglobulin heavy chain or a fragment thereof comprising a VH and the immunoglobulin light chain or a fragment thereof comprising a VL, wherein the VH and the VL can associate with each other and bind to 4-1BB.

13. An antibody or antigen-binding fragment thereof that specifically binds to 4-1BB comprising
a heavy chain variable region (VH) comprising an amino acid sequence that is identical to a selected VH sequence, and a light chain variable region (VL) comprising an amino acid sequence that is identical to a selected VL sequence, wherein
the selected VH sequence is SEQ ID NO: 221, 222, 223, 224, or 243, and the selected VL sequence is SEQ ID NO: 225, 226, 227, 228, or 244.

14. The antibody or antigen-binding fragment thereof of claim 13, wherein the selected VH sequence is SEQ ID NO: 221 and the selected VL sequence is SEQ ID NO: 225.

15. The antibody or antigen-binding fragment thereof of claim 13, wherein the selected VH sequence is SEQ ID NO: 221 and the selected VL sequence is SEQ ID NO: 226.

16. The antibody or antigen-binding fragment thereof of claim 13, wherein the selected VH sequence is SEQ ID NO: 222 and the selected VL sequence is SEQ ID NO: 228.

17. The antibody or antigen-binding fragment thereof of claim 13, wherein the selected VH sequence is SEQ ID NO: 221 and the selected VL sequence is SEQ ID NO: 227.

18. The antibody or antigen-binding fragment thereof of claim 13, wherein the selected VH sequence is SEQ ID NO: 221 and the selected VL sequence is SEQ ID NO: 228.

19. The antibody or antigen-binding fragment thereof of claim 13, wherein the selected VH sequence is SEQ ID NO: 222 and the selected VL sequence is SEQ ID NO: 225.

20. The antibody or antigen-binding fragment thereof of claim 13, wherein the selected VH sequence is SEQ ID NO: 222 and the selected VL sequence is SEQ ID NO: 226.

21. The antibody or antigen-binding fragment thereof of claim 13, wherein the selected VH sequence is SEQ ID NO: 222 and the selected VL sequence is SEQ ID NO: 227.

22. The antibody or antigen-binding fragment thereof of claim 13, wherein the selected VH sequence is SEQ ID NO: 223 and the selected VL sequence is SEQ ID NO: 225.

23. The antibody or antigen-binding fragment thereof of claim 13, wherein the selected VH sequence is SEQ ID NO: 223 and the selected VL sequence is SEQ ID NO: 226.

24. The antibody or antigen-binding fragment thereof of claim 13, wherein the selected VH sequence is SEQ ID NO: 223 and the selected VL sequence is SEQ ID NO: 227.

25. The antibody or antigen-binding fragment thereof of claim 13, wherein the selected VH sequence is SEQ ID NO: 223 and the selected VL sequence is SEQ ID NO: 228.

26. The antibody or antigen-binding fragment thereof of claim 13, wherein the selected VH sequence is SEQ ID NO: 224 and the selected VL sequence is SEQ ID NO: 225.

27. The antibody or antigen-binding fragment thereof of claim 13, wherein the selected VH sequence is SEQ ID NO: 224 and the selected VL sequence is SEQ ID NO: 226.

28. The antibody or antigen-binding fragment thereof of claim 13, wherein the selected VH sequence is SEQ ID NO: 224 and the selected VL sequence is SEQ ID NO: 227.

29. The antibody or antigen-binding fragment thereof of claim 13, wherein the selected VH sequence is SEQ ID NO: 224 and the selected VL sequence is SEQ ID NO: 228.

30. A method of treating a subject having cancer, the method comprising administering a therapeutically effective amount of a composition comprising the antibody or antigen-binding fragment thereof of claim 1 to the subject.

31. The method of claim 30, wherein the subject has a solid tumor, breast cancer, oropharyngeal cancer, ovarian cancer, B cell lymphoma, Non-Hodgkin's lymphoma, non-small cell lung cancer (NSCLC), melanoma, B-cell non-Hodgkin lymphoma, colorectal cancer, hematologic malignancy, head and neck cancer, bladder cancer, or multiple myeloma.

32. A method of decreasing the rate of tumor growth, the method comprising administering to a subject in need thereof an effective amount of a composition comprising an antibody or antigen-binding fragment thereof of claim 1.

33. A method of killing a tumor cell, the method comprising administering to a subject in need thereof an effective amount of a composition comprising the antibody or antigen-binding fragment thereof of claim 1.

* * * * *

UNITED STATES PATENT AND TRADEMARK OFFICE
CERTIFICATE OF CORRECTION

PATENT NO. : 11,292,849 B2
APPLICATION NO. : 17/200021
DATED : April 5, 2022
INVENTOR(S) : Yi Yang et al.

It is certified that error appears in the above-identified patent and that said Letters Patent is hereby corrected as shown below:

In the Claims

Claim 5: In Column 320, Line 52, please delete "thereof" and insert -- thereof of --, therefor.

Claim 6: In Column 320, Line 56, please delete "thereof" and insert -- thereof of --, therefor.

Signed and Sealed this
Thirty-first Day of May, 2022

Katherine Kelly Vidal
*Director of the United States Patent and Trademark Office*

SEQUENCE LISTING

<160> NUMBER OF SEQ ID NOS: 518

<210> SEQ ID NO 1
<211> LENGTH: 5
<212> TYPE: PRT
<213> ORGANISM: Artificial Sequence
<220> FEATURE:
<223> OTHER INFORMATION: CDR sequence

<400> SEQUENCE: 1

Ser Ser Tyr Ile Asn
1               5

<210> SEQ ID NO 2
<211> LENGTH: 17
<212> TYPE: PRT
<213> ORGANISM: Artificial Sequence
<220> FEATURE:
<223> OTHER INFORMATION: CDR sequence

<400> SEQUENCE: 2

Trp Ile Phe Ala Gly Thr Gly Gly Thr Tyr Tyr Asn Gln Lys Phe Thr
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: CDR sequence

<400> SEQUENCE: 3

His Ser Pro Arg Ala Thr Leu Phe Asp Phe
1               5                   10

<210> SEQ ID NO 4
<211> LENGTH: 10
<212> TYPE: PRT
<213> ORGANISM: Artificial Sequence
<220> FEATURE:
<223> OTHER INFORMATION: CDR sequence

<400> SEQUENCE: 4

Arg Ala Ser Ser Ser Val Asn His Met His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDR sequence

<400> SEQUENCE: 5

Ala Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR sequence

<400> SEQUENCE: 6

```
Gln Gln Trp Ser Ser Asn Pro Tyr Thr
1               5

<210> SEQ ID NO 7
<211> LENGTH: 5
<212> TYPE: PRT
<213> ORGANISM: Artificial Sequence
<220> FEATURE:
<223> OTHER INFORMATION: CDR sequence

<400> SEQUENCE: 7

Ser Tyr Trp Ile Asn
1               5

<210> SEQ ID NO 8
<211> LENGTH: 17
<212> TYPE: PRT
<213> ORGANISM: Artificial Sequence
<220> FEATURE:
<223> OTHER INFORMATION: CDR sequence

<400> SEQUENCE: 8

Asn Ile Tyr Pro Ser Asp Ser Tyr Thr Asn Tyr Asn Gln Lys Phe Lys
1               5                   10                  15

Asp

<210> SEQ ID NO 9
<211> LENGTH: 12
<212> TYPE: PRT
<213> ORGANISM: Artificial Sequence
<220> FEATURE:
<223> OTHER INFORMATION: CDR sequence

<400> SEQUENCE: 9

Thr Trp Glu Phe Tyr Tyr Asp Ser Val Phe Asp Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: CDR sequence

<400> SEQUENCE: 10

Lys Ala Ser Gln Asp Ile Asn Ser Tyr Leu Ser
1               5                   10

<210> SEQ ID NO 11
<211> LENGTH: 7
<212> TYPE: PRT
<213> ORGANISM: Artificial Sequence
<220> FEATURE:
<223> OTHER INFORMATION: CDR sequence

<400> SEQUENCE: 11

Arg Ala Asn Arg Leu Val Asp
1               5

<210> SEQ ID NO 12
<211> LENGTH: 9
<212> TYPE: PRT
<213> ORGANISM: Artificial Sequence
<220> FEATURE:
<223> OTHER INFORMATION: CDR sequence

<400> SEQUENCE: 12
```

Leu Gln Tyr Asp Glu Leu Pro Pro Thr
1               5

<210> SEQ ID NO 13
<211> LENGTH: 5
<212> TYPE: PRT
<213> ORGANISM: Artificial Sequence
<220> FEATURE:
<223> OTHER INFORMATION: CDR sequence

<400> SEQUENCE: 13

Thr Tyr Asp Ile Ser
1               5

<210> SEQ ID NO 14
<211> LENGTH: 16
<212> TYPE: PRT
<213> ORGANISM: Artificial Sequence
<220> FEATURE:
<223> OTHER INFORMATION: CDR sequence

<400> SEQUENCE: 14

Val Ile Trp Thr Gly Gly Gly Thr Asn Tyr Asn Ser Ser Phe Met Ser
1               5                   10                  15

<210> SEQ ID NO 15
<211> LENGTH: 3
<212> TYPE: PRT
<213> ORGANISM: Artificial Sequence
<220> FEATURE:
<223> OTHER INFORMATION: CDR sequence

<400> SEQUENCE: 15

Val Asp Tyr
1

<210> SEQ ID NO 16
<211> LENGTH: 16
<212> TYPE: PRT
<213> ORGANISM: Artificial Sequence
<220> FEATURE:
<223> OTHER INFORMATION: CDR sequence

<400> SEQUENCE: 16

Arg Ser Ser Gln Ser Leu Val His Ser Asn Gly Asn Thr Tyr Leu His
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: CDR sequence

<400> SEQUENCE: 17

Lys Val Ser Asn Arg Phe Ser
1               5

<210> SEQ ID NO 18
<211> LENGTH: 9
<212> TYPE: PRT
<213> ORGANISM: Artificial Sequence
<220> FEATURE:
<223> OTHER INFORMATION: CDR sequence

<400> SEQUENCE: 18

```
Ser Gln Asn Thr His Val Pro Trp Thr
1               5
```

<210> SEQ ID NO 19
<211> LENGTH: 5
<212> TYPE: PRT
<213> ORGANISM: Artificial Sequence
<220> FEATURE:
<223> OTHER INFORMATION: CDR sequence

<400> SEQUENCE: 19

```
Thr Ser Trp Met Asn
1               5
```

<210> SEQ ID NO 20
<211> LENGTH: 17
<212> TYPE: PRT
<213> ORGANISM: Artificial Sequence
<220> FEATURE:
<223> OTHER INFORMATION: CDR sequence

<400> SEQUENCE: 20

```
Arg Ile Tyr Pro Gly Asp Gly Asp Thr Asp Tyr Asn Gly Arg Phe Lys
1               5                   10                  15
Gly
```

<210> SEQ ID NO 21
<211> LENGTH: 12
<212> TYPE: PRT
<213> ORGANISM: Artificial Sequence
<220> FEATURE:
<223> OTHER INFORMATION: CDR sequence

<400> SEQUENCE: 21

```
Leu Asp Gly Tyr Tyr Glu Val Phe Tyr Phe Asp Tyr
1               5                   10
```

<210> SEQ ID NO 22
<211> LENGTH: 16
<212> TYPE: PRT
<213> ORGANISM: Artificial Sequence
<220> FEATURE:
<223> OTHER INFORMATION: CDR sequence

<400> SEQUENCE: 22

```
Lys Ser Ser Gln Ser Leu Leu Tyr Ser Asn Gly Lys Thr Tyr Leu Asn
1               5                   10                  15
```

<210> SEQ ID NO 23
<211> LENGTH: 7
<212> TYPE: PRT
<213> ORGANISM: Artificial Sequence
<220> FEATURE:
<223> OTHER INFORMATION: CDR sequence

<400> SEQUENCE: 23

```
Leu Val Ser Lys Leu Asp Ser
1               5
```

<210> SEQ ID NO 24
<211> LENGTH: 9
<212> TYPE: PRT
<213> ORGANISM: Artificial Sequence
<220> FEATURE:
<223> OTHER INFORMATION: CDR sequence

<400> SEQUENCE: 24

```
Phe Gln Gly Thr His Phe Pro Trp Thr
1               5

<210> SEQ ID NO 25
<211> LENGTH: 5
<212> TYPE: PRT
<213> ORGANISM: Artificial Sequence
<220> FEATURE:
<223> OTHER INFORMATION: CDR sequence

<400> SEQUENCE: 25

Thr Tyr Val Met Tyr
1               5

<210> SEQ ID NO 26
<211> LENGTH: 17
<212> TYPE: PRT
<213> ORGANISM: Artificial Sequence
<220> FEATURE:
<223> OTHER INFORMATION: CDR sequence

<400> SEQUENCE: 26

Tyr Ile Asn Pro Tyr Asn Asp Asp Ile Arg Tyr Asn Glu Lys Phe Lys
1               5                   10                  15

Gly

<210> SEQ ID NO 27
<211> LENGTH: 5
<212> TYPE: PRT
<213> ORGANISM: Artificial Sequence
<220> FEATURE:
<223> OTHER INFORMATION: CDR sequence

<400> SEQUENCE: 27

Gln Gly Gly Asp Tyr
1               5

<210> SEQ ID NO 28
<211> LENGTH: 11
<212> TYPE: PRT
<213> ORGANISM: Artificial Sequence
<220> FEATURE:
<223> OTHER INFORMATION: CDR sequence

<400> SEQUENCE: 28

Arg Ala Ser Lys Asn Ile Asn Lys Tyr Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: CDR sequence

<400> SEQUENCE: 29

Ser Gly Ser Thr Leu Gln Ser
1               5

<210> SEQ ID NO 30
<211> LENGTH: 9
<212> TYPE: PRT
<213> ORGANISM: Artificial Sequence
<220> FEATURE:
<223> OTHER INFORMATION: CDR sequence
```

```
<400> SEQUENCE: 30

Gln Gln Tyr Asn Glu Tyr Pro Leu Thr
1               5

<210> SEQ ID NO 31
<211> LENGTH: 5
<212> TYPE: PRT
<213> ORGANISM: Artificial Sequence
<220> FEATURE:
<223> OTHER INFORMATION: CDR sequence

<400> SEQUENCE: 31

Thr Tyr Gly Val His
1               5

<210> SEQ ID NO 32
<211> LENGTH: 16
<212> TYPE: PRT
<213> ORGANISM: Artificial Sequence
<220> FEATURE:
<223> OTHER INFORMATION: CDR sequence

<400> SEQUENCE: 32

Val Ile Trp Ser Asp Gly Asn Thr Asp Tyr Asn Asp Ala Phe Ile Ser
1               5                   10                  15

<210> SEQ ID NO 33
<211> LENGTH: 10
<212> TYPE: PRT
<213> ORGANISM: Artificial Sequence
<220> FEATURE:
<223> OTHER INFORMATION: CDR sequence

<400> SEQUENCE: 33

Asn Ser Ile Thr Ser Val Ser Phe Asp Cys
1               5                   10

<210> SEQ ID NO 34
<211> LENGTH: 11
<212> TYPE: PRT
<213> ORGANISM: Artificial Sequence
<220> FEATURE:
<223> OTHER INFORMATION: CDR sequence

<400> SEQUENCE: 34

Lys Ala Ser Gln Asn Val Gly Thr Thr Val Ala
1               5                   10

<210> SEQ ID NO 35
<211> LENGTH: 7
<212> TYPE: PRT
<213> ORGANISM: Artificial Sequence
<220> FEATURE:
<223> OTHER INFORMATION: CDR sequence

<400> SEQUENCE: 35

Ser Ala Ser Tyr Arg Tyr Ser
1               5

<210> SEQ ID NO 36
<211> LENGTH: 9
<212> TYPE: PRT
<213> ORGANISM: Artificial Sequence
<220> FEATURE:
<223> OTHER INFORMATION: CDR sequence

<400> SEQUENCE: 36
```

Gln Gln Tyr Asn Ser Tyr Pro Leu Thr
1               5

<210> SEQ ID NO 37
<211> LENGTH: 5
<212> TYPE: PRT
<213> ORGANISM: Artificial Sequence
<220> FEATURE:
<223> OTHER INFORMATION: CDR sequence

<400> SEQUENCE: 37

Asn Tyr Trp Ile His
1               5

<210> SEQ ID NO 38
<211> LENGTH: 17
<212> TYPE: PRT
<213> ORGANISM: Artificial Sequence
<220> FEATURE:
<223> OTHER INFORMATION: CDR sequence

<400> SEQUENCE: 38

Asn Ile Tyr Pro Ala Ser Asp Tyr Thr Asn Tyr Asp Glu Lys Phe Lys
1               5                   10                  15

Asn

<210> SEQ ID NO 39
<211> LENGTH: 8
<212> TYPE: PRT
<213> ORGANISM: Artificial Sequence
<220> FEATURE:
<223> OTHER INFORMATION: CDR sequence

<400> SEQUENCE: 39

Gly Tyr Phe Gly Ser Leu Asp Tyr
1               5

<210> SEQ ID NO 40
<211> LENGTH: 11
<212> TYPE: PRT
<213> ORGANISM: Artificial Sequence
<220> FEATURE:
<223> OTHER INFORMATION: CDR sequence

<400> SEQUENCE: 40

Arg Ala Ser Gln Pro Ile Gly Thr Gly Ile His
1               5                   10

<210> SEQ ID NO 41
<211> LENGTH: 7
<212> TYPE: PRT
<213> ORGANISM: Artificial Sequence
<220> FEATURE:
<223> OTHER INFORMATION: CDR sequence

<400> SEQUENCE: 41

Ser Ala Ser Glu Ser Ile Ser
1               5

<210> SEQ ID NO 42
<211> LENGTH: 9
<212> TYPE: PRT
<213> ORGANISM: Artificial Sequence
<220> FEATURE:
<223> OTHER INFORMATION: CDR sequence

```
<400> SEQUENCE: 42

Gln Gln Ser Tyr Ser Trp Pro Thr Thr
1               5

<210> SEQ ID NO 43
<211> LENGTH: 5
<212> TYPE: PRT
<213> ORGANISM: Artificial Sequence
<220> FEATURE:
<223> OTHER INFORMATION: CDR sequence

<400> SEQUENCE: 43

Ser Asn Trp Met His
1               5

<210> SEQ ID NO 44
<211> LENGTH: 17
<212> TYPE: PRT
<213> ORGANISM: Artificial Sequence
<220> FEATURE:
<223> OTHER INFORMATION: CDR sequence

<400> SEQUENCE: 44

Val Ile Tyr Pro Gly Asn Ser Asp Thr Ser Tyr Asn Gln Lys Phe Lys
1               5                   10                  15

Gly

<210> SEQ ID NO 45
<211> LENGTH: 8
<212> TYPE: PRT
<213> ORGANISM: Artificial Sequence
<220> FEATURE:
<223> OTHER INFORMATION: CDR sequence

<400> SEQUENCE: 45

Gly Ile Thr Thr Ala Pro Glu Tyr
1               5

<210> SEQ ID NO 46
<211> LENGTH: 11
<212> TYPE: PRT
<213> ORGANISM: Artificial Sequence
<220> FEATURE:
<223> OTHER INFORMATION: CDR sequence

<400> SEQUENCE: 46

Lys Ala Ser Glu Asn Val Gly Ile Tyr Val Ser
1               5                   10

<210> SEQ ID NO 47
<211> LENGTH: 7
<212> TYPE: PRT
<213> ORGANISM: Artificial Sequence
<220> FEATURE:
<223> OTHER INFORMATION: CDR sequence

<400> SEQUENCE: 47

Gly Ala Ser Asn Arg Tyr Thr
1               5

<210> SEQ ID NO 48
<211> LENGTH: 9
<212> TYPE: PRT
<213> ORGANISM: Artificial Sequence
<220> FEATURE:
<223> OTHER INFORMATION: CDR sequence
```

<400> SEQUENCE: 48

Gly His Thr Tyr Asn Tyr Pro Phe Thr
1               5

<210> SEQ ID NO 49
<211> LENGTH: 5
<212> TYPE: PRT
<213> ORGANISM: Artificial Sequence
<220> FEATURE:
<223> OTHER INFORMATION: CDR sequence

<400> SEQUENCE: 49

Arg Tyr Trp Met Ser
1               5

<210> SEQ ID NO 50
<211> LENGTH: 17
<212> TYPE: PRT
<213> ORGANISM: Artificial Sequence
<220> FEATURE:
<223> OTHER INFORMATION: CDR sequence

<400> SEQUENCE: 50

Glu Ile His Pro Asp Ser Ser Ala Ile Asn Tyr Thr Pro Ser Leu Lys
1               5                   10                  15

Asp

<210> SEQ ID NO 51
<211> LENGTH: 9
<212> TYPE: PRT
<213> ORGANISM: Artificial Sequence
<220> FEATURE:
<223> OTHER INFORMATION: CDR sequence

<400> SEQUENCE: 51

Ser Tyr Tyr Gly Arg Val Phe Asp Tyr
1               5

<210> SEQ ID NO 52
<211> LENGTH: 11
<212> TYPE: PRT
<213> ORGANISM: Artificial Sequence
<220> FEATURE:
<223> OTHER INFORMATION: CDR sequence

<400> SEQUENCE: 52

Arg Ala Ser Gln Ser Ile Ser Asp Tyr Leu His
1               5                   10

<210> SEQ ID NO 53
<211> LENGTH: 7
<212> TYPE: PRT
<213> ORGANISM: Artificial Sequence
<220> FEATURE:
<223> OTHER INFORMATION: CDR sequence

<400> SEQUENCE: 53

Tyr Ala Ser Gln Ser Ile Ser
1               5

<210> SEQ ID NO 54
<211> LENGTH: 9
<212> TYPE: PRT
<213> ORGANISM: Artificial Sequence
<220> FEATURE:

<223> OTHER INFORMATION: CDR sequence

<400> SEQUENCE: 54

Gln Asp Gly His Ser Phe Pro Pro Thr
1               5

<210> SEQ ID NO 55
<211> LENGTH: 5
<212> TYPE: PRT
<213> ORGANISM: Artificial Sequence
<220> FEATURE:
<223> OTHER INFORMATION: CDR sequence

<400> SEQUENCE: 55

Ser Tyr Trp Met His
1               5

<210> SEQ ID NO 56
<211> LENGTH: 17
<212> TYPE: PRT
<213> ORGANISM: Artificial Sequence
<220> FEATURE:
<223> OTHER INFORMATION: CDR sequence

<400> SEQUENCE: 56

Val Ile Tyr Pro Gly Asn Ser Asp Thr Ser Tyr Asn Gln Lys Phe Lys
1               5                   10                  15

Gly

<210> SEQ ID NO 57
<211> LENGTH: 8
<212> TYPE: PRT
<213> ORGANISM: Artificial Sequence
<220> FEATURE:
<223> OTHER INFORMATION: CDR sequence

<400> SEQUENCE: 57

Gly Ile Thr Thr Ala Pro Asp Tyr
1               5

<210> SEQ ID NO 58
<211> LENGTH: 11
<212> TYPE: PRT
<213> ORGANISM: Artificial Sequence
<220> FEATURE:
<223> OTHER INFORMATION: CDR sequence

<400> SEQUENCE: 58

Lys Ala Ser Glu Asn Val Gly Ile His Val Ser
1               5                   10

<210> SEQ ID NO 59
<211> LENGTH: 7
<212> TYPE: PRT
<213> ORGANISM: Artificial Sequence
<220> FEATURE:
<223> OTHER INFORMATION: CDR sequence

<400> SEQUENCE: 59

Gly Ala Ser Ser Gly Tyr Asn
1               5

<210> SEQ ID NO 60
<211> LENGTH: 9
<212> TYPE: PRT
<213> ORGANISM: Artificial Sequence

```
<220> FEATURE:
<223> OTHER INFORMATION: CDR sequence

<400> SEQUENCE: 60

Gly Gln Thr Tyr Ser Tyr Pro Phe Thr
1               5

<210> SEQ ID NO 61
<211> LENGTH: 5
<212> TYPE: PRT
<213> ORGANISM: Artificial Sequence
<220> FEATURE:
<223> OTHER INFORMATION: CDR sequence

<400> SEQUENCE: 61

Asn Tyr Gly Met Asn
1               5

<210> SEQ ID NO 62
<211> LENGTH: 17
<212> TYPE: PRT
<213> ORGANISM: Artificial Sequence
<220> FEATURE:
<223> OTHER INFORMATION: CDR sequence

<400> SEQUENCE: 62

Trp Ile Asn Thr Tyr Thr Gly Glu Pro Thr Tyr Ala Asp Asp Phe Lys
1               5                   10                  15

Gly

<210> SEQ ID NO 63
<211> LENGTH: 10
<212> TYPE: PRT
<213> ORGANISM: Artificial Sequence
<220> FEATURE:
<223> OTHER INFORMATION: CDR sequence

<400> SEQUENCE: 63

Arg Glu Tyr Tyr Pro Trp Val Phe Val Tyr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: CDR sequence

<400> SEQUENCE: 64

Ser Ala Ser Ser Ser Val Ser Tyr Met His
1               5                   10

<210> SEQ ID NO 65
<211> LENGTH: 7
<212> TYPE: PRT
<213> ORGANISM: Artificial Sequence
<220> FEATURE:
<223> OTHER INFORMATION: CDR sequence

<400> SEQUENCE: 65

Asp Thr Ser Lys Leu Ala Ser
1               5

<210> SEQ ID NO 66
<211> LENGTH: 9
<212> TYPE: PRT
```

```
<213> ORGANISM: Artificial Sequence
<220> FEATURE:
<223> OTHER INFORMATION: CDR sequence

<400> SEQUENCE: 66

Phe Gln Gly Ser Gly Tyr Pro Leu Thr
1               5

<210> SEQ ID NO 67
<211> LENGTH: 5
<212> TYPE: PRT
<213> ORGANISM: Artificial Sequence
<220> FEATURE:
<223> OTHER INFORMATION: CDR sequence

<400> SEQUENCE: 67

Ser Tyr Trp Ile Asn
1               5

<210> SEQ ID NO 68
<211> LENGTH: 17
<212> TYPE: PRT
<213> ORGANISM: Artificial Sequence
<220> FEATURE:
<223> OTHER INFORMATION: CDR sequence

<400> SEQUENCE: 68

Asn Ile Tyr Pro Ser Asp Ser Tyr Thr Asn Tyr Asn Gln Lys Phe Lys
1               5                   10                  15

Asp

<210> SEQ ID NO 69
<211> LENGTH: 10
<212> TYPE: PRT
<213> ORGANISM: Artificial Sequence
<220> FEATURE:
<223> OTHER INFORMATION: CDR sequence

<400> SEQUENCE: 69

Phe His Tyr Gly Ser Ser Pro Phe Asp Asn
1               5                   10

<210> SEQ ID NO 70
<211> LENGTH: 11
<212> TYPE: PRT
<213> ORGANISM: Artificial Sequence
<220> FEATURE:
<223> OTHER INFORMATION: CDR sequence

<400> SEQUENCE: 70

Arg Ala Ser Gln Asp Ile Ser His Tyr Leu Asn
1               5                   10

<210> SEQ ID NO 71
<211> LENGTH: 7
<212> TYPE: PRT
<213> ORGANISM: Artificial Sequence
<220> FEATURE:
<223> OTHER INFORMATION: CDR sequence

<400> SEQUENCE: 71

Tyr Thr Ser Arg Leu His Ser
1               5

<210> SEQ ID NO 72
<211> LENGTH: 9
```

```
<212> TYPE: PRT
<213> ORGANISM: Artificial Sequence
<220> FEATURE:
<223> OTHER INFORMATION: CDR sequence

<400> SEQUENCE: 72

Gln Gln Gly His Thr Leu Pro Arg Thr
1               5

<210> SEQ ID NO 73
<211> LENGTH: 5
<212> TYPE: PRT
<213> ORGANISM: Artificial Sequence
<220> FEATURE:
<223> OTHER INFORMATION: CDR sequence

<400> SEQUENCE: 73

Asn Tyr Gly Met Asn
1               5

<210> SEQ ID NO 74
<211> LENGTH: 17
<212> TYPE: PRT
<213> ORGANISM: Artificial Sequence
<220> FEATURE:
<223> OTHER INFORMATION: CDR sequence

<400> SEQUENCE: 74

Trp Ile Asn Thr Tyr Thr Gly Glu Pro Thr Tyr Ala Asp Asp Phe Lys
1               5                   10                  15

Gly

<210> SEQ ID NO 75
<211> LENGTH: 9
<212> TYPE: PRT
<213> ORGANISM: Artificial Sequence
<220> FEATURE:
<223> OTHER INFORMATION: CDR sequence

<400> SEQUENCE: 75

Arg Asp Tyr Leu Gly Ala Met Asp Tyr
1               5

<210> SEQ ID NO 76
<211> LENGTH: 12
<212> TYPE: PRT
<213> ORGANISM: Artificial Sequence
<220> FEATURE:
<223> OTHER INFORMATION: CDR sequence

<400> SEQUENCE: 76

Arg Ala Ser Ser Ser Val Ser Ser Ser Tyr Leu His
1               5                   10

<210> SEQ ID NO 77
<211> LENGTH: 7
<212> TYPE: PRT
<213> ORGANISM: Artificial Sequence
<220> FEATURE:
<223> OTHER INFORMATION: CDR sequence

<400> SEQUENCE: 77

Ser Thr Ser Asn Leu Ala Ser
1               5

<210> SEQ ID NO 78
```

```
<211> LENGTH: 9
<212> TYPE: PRT
<213> ORGANISM: Artificial Sequence
<220> FEATURE:
<223> OTHER INFORMATION: CDR sequence

<400> SEQUENCE: 78

Gln Gln Tyr Ser Ala Tyr Leu Tyr Thr
1               5

<210> SEQ ID NO 79
<211> LENGTH: 5
<212> TYPE: PRT
<213> ORGANISM: Artificial Sequence
<220> FEATURE:
<223> OTHER INFORMATION: CDR sequence

<400> SEQUENCE: 79

Thr Tyr Trp Ile Asn
1               5

<210> SEQ ID NO 80
<211> LENGTH: 17
<212> TYPE: PRT
<213> ORGANISM: Artificial Sequence
<220> FEATURE:
<223> OTHER INFORMATION: CDR sequence

<400> SEQUENCE: 80

Asn Ile Tyr Pro Ser Asp Ser Tyr Thr Asn Tyr Asn Gln Lys Phe Lys
1               5                   10                  15

Asp

<210> SEQ ID NO 81
<211> LENGTH: 13
<212> TYPE: PRT
<213> ORGANISM: Artificial Sequence
<220> FEATURE:
<223> OTHER INFORMATION: CDR sequence

<400> SEQUENCE: 81

Glu Ala Gly Asp Gly Thr His Tyr Tyr Ala Ile Asp Tyr
1               5                   10

<210> SEQ ID NO 82
<211> LENGTH: 11
<212> TYPE: PRT
<213> ORGANISM: Artificial Sequence
<220> FEATURE:
<223> OTHER INFORMATION: CDR sequence

<400> SEQUENCE: 82

Lys Ala Ser Glu Asn Val Gly Thr Tyr Val Ser
1               5                   10

<210> SEQ ID NO 83
<211> LENGTH: 7
<212> TYPE: PRT
<213> ORGANISM: Artificial Sequence
<220> FEATURE:
<223> OTHER INFORMATION: CDR sequence

<400> SEQUENCE: 83

Gly Ala Ser Asn Arg Tyr Pro
1               5
```

```
<210> SEQ ID NO 84
<211> LENGTH: 9
<212> TYPE: PRT
<213> ORGANISM: Artificial Sequence
<220> FEATURE:
<223> OTHER INFORMATION: CDR sequence

<400> SEQUENCE: 84

Gly Gln Gly Tyr Ser Tyr Leu Arg Thr
1               5

<210> SEQ ID NO 85
<211> LENGTH: 5
<212> TYPE: PRT
<213> ORGANISM: Artificial Sequence
<220> FEATURE:
<223> OTHER INFORMATION: CDR sequence

<400> SEQUENCE: 85

Asp Tyr Tyr Met His
1               5

<210> SEQ ID NO 86
<211> LENGTH: 17
<212> TYPE: PRT
<213> ORGANISM: Artificial Sequence
<220> FEATURE:
<223> OTHER INFORMATION: CDR sequence

<400> SEQUENCE: 86

Trp Ile Asp Pro Glu Asn Gly Asn Thr Ile Tyr Asp Pro Lys Phe Gln
1               5                   10                  15

Asp

<210> SEQ ID NO 87
<211> LENGTH: 8
<212> TYPE: PRT
<213> ORGANISM: Artificial Sequence
<220> FEATURE:
<223> OTHER INFORMATION: CDR sequence

<400> SEQUENCE: 87

Gly Leu Pro Trp Tyr Phe Asp Tyr
1               5

<210> SEQ ID NO 88
<211> LENGTH: 10
<212> TYPE: PRT
<213> ORGANISM: Artificial Sequence
<220> FEATURE:
<223> OTHER INFORMATION: CDR sequence

<400> SEQUENCE: 88

Ser Ala Ser Ser Ser Val Ser Asp Met Asn
1               5                   10

<210> SEQ ID NO 89
<211> LENGTH: 7
<212> TYPE: PRT
<213> ORGANISM: Artificial Sequence
<220> FEATURE:
<223> OTHER INFORMATION: CDR sequence

<400> SEQUENCE: 89

Leu Thr Ser Asn Leu Ser Ser
1               5
```

<210> SEQ ID NO 90
<211> LENGTH: 9
<212> TYPE: PRT
<213> ORGANISM: Artificial Sequence
<220> FEATURE:
<223> OTHER INFORMATION: CDR sequence

<400> SEQUENCE: 90

Gln Gln Trp Ser Gly Asn Pro Leu Thr
1               5

<210> SEQ ID NO 91
<211> LENGTH: 5
<212> TYPE: PRT
<213> ORGANISM: Artificial Sequence
<220> FEATURE:
<223> OTHER INFORMATION: CDR sequence

<400> SEQUENCE: 91

Ser Phe Gly Met His
1               5

<210> SEQ ID NO 92
<211> LENGTH: 17
<212> TYPE: PRT
<213> ORGANISM: Artificial Sequence
<220> FEATURE:
<223> OTHER INFORMATION: CDR sequence

<400> SEQUENCE: 92

Tyr Ile Ser Ser Gly Ser Ser Ala Ile Tyr Tyr Ala Asp Thr Val Lys
1               5                   10                  15

Gly

<210> SEQ ID NO 93
<211> LENGTH: 5
<212> TYPE: PRT
<213> ORGANISM: Artificial Sequence
<220> FEATURE:
<223> OTHER INFORMATION: CDR sequence

<400> SEQUENCE: 93

Asp Trp Val Asp Tyr
1               5

<210> SEQ ID NO 94
<211> LENGTH: 11
<212> TYPE: PRT
<213> ORGANISM: Artificial Sequence
<220> FEATURE:
<223> OTHER INFORMATION: CDR sequence

<400> SEQUENCE: 94

Arg Ala Ser Glu Asn Ile Tyr Ser Asn Leu Val
1               5                   10

<210> SEQ ID NO 95
<211> LENGTH: 7
<212> TYPE: PRT
<213> ORGANISM: Artificial Sequence
<220> FEATURE:
<223> OTHER INFORMATION: CDR sequence

<400> SEQUENCE: 95

Thr Ala Thr Lys Leu Thr Asn
1               5

```
<210> SEQ ID NO 96
<211> LENGTH: 9
<212> TYPE: PRT
<213> ORGANISM: Artificial Sequence
<220> FEATURE:
<223> OTHER INFORMATION: CDR sequence

<400> SEQUENCE: 96

Gln His Phe Trp Asp Thr Pro Tyr Thr
1               5

<210> SEQ ID NO 97
<211> LENGTH: 5
<212> TYPE: PRT
<213> ORGANISM: Artificial Sequence
<220> FEATURE:
<223> OTHER INFORMATION: CDR sequence

<400> SEQUENCE: 97

Ser Tyr Trp Ile Asn
1               5

<210> SEQ ID NO 98
<211> LENGTH: 17
<212> TYPE: PRT
<213> ORGANISM: Artificial Sequence
<220> FEATURE:
<223> OTHER INFORMATION: CDR sequence

<400> SEQUENCE: 98

Asn Ile Phe Pro Ser Asp Ser Tyr Thr Asn Tyr Asn Gln Lys Phe Lys
1               5                   10                  15

Asp

<210> SEQ ID NO 99
<211> LENGTH: 14
<212> TYPE: PRT
<213> ORGANISM: Artificial Sequence
<220> FEATURE:
<223> OTHER INFORMATION: CDR sequence

<400> SEQUENCE: 99

Phe Gly Ser Ser Gly Tyr Pro Asp Tyr Tyr Thr Met Glu Tyr
1               5                   10

<210> SEQ ID NO 100
<211> LENGTH: 11
<212> TYPE: PRT
<213> ORGANISM: Artificial Sequence
<220> FEATURE:
<223> OTHER INFORMATION: CDR sequence

<400> SEQUENCE: 100

Arg Ala Ser Gly Asn Ile Asp Asn Tyr Leu Ala
1               5                   10

<210> SEQ ID NO 101
<211> LENGTH: 7
<212> TYPE: PRT
<213> ORGANISM: Artificial Sequence
<220> FEATURE:
<223> OTHER INFORMATION: CDR sequence

<400> SEQUENCE: 101

Asn Ala Lys Thr Leu Ala Glu
```

<210> SEQ ID NO 102
<211> LENGTH: 9
<212> TYPE: PRT
<213> ORGANISM: Artificial Sequence
<220> FEATURE:
<223> OTHER INFORMATION: CDR sequence

<400> SEQUENCE: 102

Gln Gln Tyr Trp Thr Ile Pro Tyr Thr
1               5

<210> SEQ ID NO 103
<211> LENGTH: 5
<212> TYPE: PRT
<213> ORGANISM: Artificial Sequence
<220> FEATURE:
<223> OTHER INFORMATION: CDR sequence

<400> SEQUENCE: 103

Asn Ser Trp Met Asn
1               5

<210> SEQ ID NO 104
<211> LENGTH: 17
<212> TYPE: PRT
<213> ORGANISM: Artificial Sequence
<220> FEATURE:
<223> OTHER INFORMATION: CDR sequence

<400> SEQUENCE: 104

Arg Ile Tyr Pro Gly Asp Gly Asp Thr Asp Tyr Asn Gly Lys Phe Lys
1               5                   10                  15

Gly

<210> SEQ ID NO 105
<211> LENGTH: 12
<212> TYPE: PRT
<213> ORGANISM: Artificial Sequence
<220> FEATURE:
<223> OTHER INFORMATION: CDR sequence

<400> SEQUENCE: 105

Leu Asp Gly Asn Tyr Tyr Tyr Trp Tyr Phe Asp Val
1               5                   10

<210> SEQ ID NO 106
<211> LENGTH: 16
<212> TYPE: PRT
<213> ORGANISM: Artificial Sequence
<220> FEATURE:
<223> OTHER INFORMATION: CDR sequence

<400> SEQUENCE: 106

Lys Ser Ser Gln Ser Leu Leu Asp Ser Asp Gly Lys Thr Tyr Leu Asn
1               5                   10                  15

<210> SEQ ID NO 107
<211> LENGTH: 7
<212> TYPE: PRT
<213> ORGANISM: Artificial Sequence
<220> FEATURE:
<223> OTHER INFORMATION: CDR sequence

<400> SEQUENCE: 107

```
Leu Val Ser Lys Leu Asp Ser
1               5
```

<210> SEQ ID NO 108
<211> LENGTH: 9
<212> TYPE: PRT
<213> ORGANISM: Artificial Sequence
<220> FEATURE:
<223> OTHER INFORMATION: CDR sequence

<400> SEQUENCE: 108

```
Trp Gln Gly Thr His Phe Pro Gln Thr
1               5
```

<210> SEQ ID NO 109
<211> LENGTH: 10
<212> TYPE: PRT
<213> ORGANISM: Artificial Sequence
<220> FEATURE:
<223> OTHER INFORMATION: CDR sequence

<400> SEQUENCE: 109

```
Gly Phe Thr Phe Ser Ser Ser Tyr Ile Asn
1               5                   10
```

<210> SEQ ID NO 110
<211> LENGTH: 6
<212> TYPE: PRT
<213> ORGANISM: Artificial Sequence
<220> FEATURE:
<223> OTHER INFORMATION: CDR sequence

<400> SEQUENCE: 110

```
Phe Ala Gly Thr Gly Gly
1               5
```

<210> SEQ ID NO 111
<211> LENGTH: 10
<212> TYPE: PRT
<213> ORGANISM: Artificial Sequence
<220> FEATURE:
<223> OTHER INFORMATION: CDR sequence

<400> SEQUENCE: 111

```
His Ser Pro Arg Ala Thr Leu Phe Asp Phe
1               5                   10
```

<210> SEQ ID NO 112
<211> LENGTH: 10
<212> TYPE: PRT
<213> ORGANISM: Artificial Sequence
<220> FEATURE:
<223> OTHER INFORMATION: CDR sequence

<400> SEQUENCE: 112

```
Arg Ala Ser Ser Ser Val Asn His Met His
1               5                   10
```

<210> SEQ ID NO 113
<211> LENGTH: 7
<212> TYPE: PRT
<213> ORGANISM: Artificial Sequence
<220> FEATURE:
<223> OTHER INFORMATION: CDR sequence

<400> SEQUENCE: 113

Ala Thr Ser Asn Leu Ala Ser

```
1               5

<210> SEQ ID NO 114
<211> LENGTH: 9
<212> TYPE: PRT
<213> ORGANISM: Artificial Sequence
<220> FEATURE:
<223> OTHER INFORMATION: CDR sequence

<400> SEQUENCE: 114

Gln Gln Trp Ser Ser Asn Pro Tyr Thr
1               5

<210> SEQ ID NO 115
<211> LENGTH: 10
<212> TYPE: PRT
<213> ORGANISM: Artificial Sequence
<220> FEATURE:
<223> OTHER INFORMATION: CDR sequence

<400> SEQUENCE: 115

Gly Tyr Thr Phe Ser Ser Tyr Trp Ile Asn
1               5                   10

<210> SEQ ID NO 116
<211> LENGTH: 6
<212> TYPE: PRT
<213> ORGANISM: Artificial Sequence
<220> FEATURE:
<223> OTHER INFORMATION: CDR sequence

<400> SEQUENCE: 116

Tyr Pro Ser Asp Ser Tyr
1               5

<210> SEQ ID NO 117
<211> LENGTH: 12
<212> TYPE: PRT
<213> ORGANISM: Artificial Sequence
<220> FEATURE:
<223> OTHER INFORMATION: CDR sequence

<400> SEQUENCE: 117

Thr Trp Glu Phe Tyr Tyr Asp Ser Val Phe Asp Tyr
1               5                   10

<210> SEQ ID NO 118
<211> LENGTH: 11
<212> TYPE: PRT
<213> ORGANISM: Artificial Sequence
<220> FEATURE:
<223> OTHER INFORMATION: CDR sequence

<400> SEQUENCE: 118

Lys Ala Ser Gln Asp Ile Asn Ser Tyr Leu Ser
1               5                   10

<210> SEQ ID NO 119
<211> LENGTH: 7
<212> TYPE: PRT
<213> ORGANISM: Artificial Sequence
<220> FEATURE:
<223> OTHER INFORMATION: CDR sequence

<400> SEQUENCE: 119

Arg Ala Asn Arg Leu Val Asp
1               5
```

```
<210> SEQ ID NO 120
<211> LENGTH: 9
<212> TYPE: PRT
<213> ORGANISM: Artificial Sequence
<220> FEATURE:
<223> OTHER INFORMATION: CDR sequence

<400> SEQUENCE: 120

Leu Gln Tyr Asp Glu Leu Pro Pro Thr
1               5

<210> SEQ ID NO 121
<211> LENGTH: 10
<212> TYPE: PRT
<213> ORGANISM: Artificial Sequence
<220> FEATURE:
<223> OTHER INFORMATION: CDR sequence

<400> SEQUENCE: 121

Gly Phe Ser Leu Thr Thr Tyr Asp Ile Ser
1               5                   10

<210> SEQ ID NO 122
<211> LENGTH: 5
<212> TYPE: PRT
<213> ORGANISM: Artificial Sequence
<220> FEATURE:
<223> OTHER INFORMATION: CDR sequence

<400> SEQUENCE: 122

Trp Thr Gly Gly Gly
1               5

<210> SEQ ID NO 123
<211> LENGTH: 3
<212> TYPE: PRT
<213> ORGANISM: Artificial Sequence
<220> FEATURE:
<223> OTHER INFORMATION: CDR sequence

<400> SEQUENCE: 123

Val Asp Tyr
1

<210> SEQ ID NO 124
<211> LENGTH: 16
<212> TYPE: PRT
<213> ORGANISM: Artificial Sequence
<220> FEATURE:
<223> OTHER INFORMATION: CDR sequence

<400> SEQUENCE: 124

Arg Ser Ser Gln Ser Leu Val His Ser Asn Gly Asn Thr Tyr Leu His
1               5                   10                  15

<210> SEQ ID NO 125
<211> LENGTH: 7
<212> TYPE: PRT
<213> ORGANISM: Artificial Sequence
<220> FEATURE:
<223> OTHER INFORMATION: CDR sequence

<400> SEQUENCE: 125

Lys Val Ser Asn Arg Phe Ser
1               5
```

```
<210> SEQ ID NO 126
<211> LENGTH: 9
<212> TYPE: PRT
<213> ORGANISM: Artificial Sequence
<220> FEATURE:
<223> OTHER INFORMATION: CDR sequence

<400> SEQUENCE: 126

Ser Gln Asn Thr His Val Pro Trp Thr
1               5

<210> SEQ ID NO 127
<211> LENGTH: 10
<212> TYPE: PRT
<213> ORGANISM: Artificial Sequence
<220> FEATURE:
<223> OTHER INFORMATION: CDR sequence

<400> SEQUENCE: 127

Gly Tyr Ala Phe Ser Thr Ser Trp Met Asn
1               5                   10

<210> SEQ ID NO 128
<211> LENGTH: 6
<212> TYPE: PRT
<213> ORGANISM: Artificial Sequence
<220> FEATURE:
<223> OTHER INFORMATION: CDR sequence

<400> SEQUENCE: 128

Tyr Pro Gly Asp Gly Asp
1               5

<210> SEQ ID NO 129
<211> LENGTH: 12
<212> TYPE: PRT
<213> ORGANISM: Artificial Sequence
<220> FEATURE:
<223> OTHER INFORMATION: CDR sequence

<400> SEQUENCE: 129

Leu Asp Gly Tyr Tyr Glu Val Phe Tyr Phe Asp Tyr
1               5                   10

<210> SEQ ID NO 130
<211> LENGTH: 16
<212> TYPE: PRT
<213> ORGANISM: Artificial Sequence
<220> FEATURE:
<223> OTHER INFORMATION: CDR sequence

<400> SEQUENCE: 130

Lys Ser Ser Gln Ser Leu Leu Tyr Ser Asn Gly Lys Thr Tyr Leu Asn
1               5                   10                  15

<210> SEQ ID NO 131
<211> LENGTH: 7
<212> TYPE: PRT
<213> ORGANISM: Artificial Sequence
<220> FEATURE:
<223> OTHER INFORMATION: CDR sequence

<400> SEQUENCE: 131

Leu Val Ser Lys Leu Asp Ser
1               5
```

```
<210> SEQ ID NO 132
<211> LENGTH: 9
<212> TYPE: PRT
<213> ORGANISM: Artificial Sequence
<220> FEATURE:
<223> OTHER INFORMATION: CDR sequence

<400> SEQUENCE: 132

Phe Gln Gly Thr His Phe Pro Trp Thr
1               5

<210> SEQ ID NO 133
<211> LENGTH: 10
<212> TYPE: PRT
<213> ORGANISM: Artificial Sequence
<220> FEATURE:
<223> OTHER INFORMATION: CDR sequence

<400> SEQUENCE: 133

Gly Tyr Thr Phe Thr Thr Tyr Val Met Tyr
1               5                   10

<210> SEQ ID NO 134
<211> LENGTH: 6
<212> TYPE: PRT
<213> ORGANISM: Artificial Sequence
<220> FEATURE:
<223> OTHER INFORMATION: CDR sequence

<400> SEQUENCE: 134

Asn Pro Tyr Asn Asp Asp
1               5

<210> SEQ ID NO 135
<211> LENGTH: 5
<212> TYPE: PRT
<213> ORGANISM: Artificial Sequence
<220> FEATURE:
<223> OTHER INFORMATION: CDR sequence

<400> SEQUENCE: 135

Gln Gly Gly Asp Tyr
1               5

<210> SEQ ID NO 136
<211> LENGTH: 11
<212> TYPE: PRT
<213> ORGANISM: Artificial Sequence
<220> FEATURE:
<223> OTHER INFORMATION: CDR sequence

<400> SEQUENCE: 136

Arg Ala Ser Lys Asn Ile Asn Lys Tyr Leu Ala
1               5                   10

<210> SEQ ID NO 137
<211> LENGTH: 7
<212> TYPE: PRT
<213> ORGANISM: Artificial Sequence
<220> FEATURE:
<223> OTHER INFORMATION: CDR sequence

<400> SEQUENCE: 137

Ser Gly Ser Thr Leu Gln Ser
1               5

<210> SEQ ID NO 138
```

```
<211> LENGTH: 9
<212> TYPE: PRT
<213> ORGANISM: Artificial Sequence
<220> FEATURE:
<223> OTHER INFORMATION: CDR sequence

<400> SEQUENCE: 138

Gln Gln Tyr Asn Glu Tyr Pro Leu Thr
1               5

<210> SEQ ID NO 139
<211> LENGTH: 10
<212> TYPE: PRT
<213> ORGANISM: Artificial Sequence
<220> FEATURE:
<223> OTHER INFORMATION: CDR sequence

<400> SEQUENCE: 139

Gly Phe Ser Leu Thr Thr Tyr Gly Val His
1               5                   10

<210> SEQ ID NO 140
<211> LENGTH: 5
<212> TYPE: PRT
<213> ORGANISM: Artificial Sequence
<220> FEATURE:
<223> OTHER INFORMATION: CDR sequence

<400> SEQUENCE: 140

Trp Ser Asp Gly Asn
1               5

<210> SEQ ID NO 141
<211> LENGTH: 10
<212> TYPE: PRT
<213> ORGANISM: Artificial Sequence
<220> FEATURE:
<223> OTHER INFORMATION: CDR sequence

<400> SEQUENCE: 141

Asn Ser Ile Thr Ser Val Ser Phe Asp Cys
1               5                   10

<210> SEQ ID NO 142
<211> LENGTH: 11
<212> TYPE: PRT
<213> ORGANISM: Artificial Sequence
<220> FEATURE:
<223> OTHER INFORMATION: CDR sequence

<400> SEQUENCE: 142

Lys Ala Ser Gln Asn Val Gly Thr Thr Val Ala
1               5                   10

<210> SEQ ID NO 143
<211> LENGTH: 7
<212> TYPE: PRT
<213> ORGANISM: Artificial Sequence
<220> FEATURE:
<223> OTHER INFORMATION: CDR sequence

<400> SEQUENCE: 143

Ser Ala Ser Tyr Arg Tyr Ser
1               5

<210> SEQ ID NO 144
<211> LENGTH: 9
```

```
<212> TYPE: PRT
<213> ORGANISM: Artificial Sequence
<220> FEATURE:
<223> OTHER INFORMATION: CDR sequence

<400> SEQUENCE: 144

Gln Gln Tyr Asn Ser Tyr Pro Leu Thr
1               5

<210> SEQ ID NO 145
<211> LENGTH: 10
<212> TYPE: PRT
<213> ORGANISM: Artificial Sequence
<220> FEATURE:
<223> OTHER INFORMATION: CDR sequence

<400> SEQUENCE: 145

Gly Tyr Thr Phe Ser Asn Tyr Trp Ile His
1               5                   10

<210> SEQ ID NO 146
<211> LENGTH: 6
<212> TYPE: PRT
<213> ORGANISM: Artificial Sequence
<220> FEATURE:
<223> OTHER INFORMATION: CDR sequence

<400> SEQUENCE: 146

Tyr Pro Ala Ser Asp Tyr
1               5

<210> SEQ ID NO 147
<211> LENGTH: 8
<212> TYPE: PRT
<213> ORGANISM: Artificial Sequence
<220> FEATURE:
<223> OTHER INFORMATION: CDR sequence

<400> SEQUENCE: 147

Gly Tyr Phe Gly Ser Leu Asp Tyr
1               5

<210> SEQ ID NO 148
<211> LENGTH: 11
<212> TYPE: PRT
<213> ORGANISM: Artificial Sequence
<220> FEATURE:
<223> OTHER INFORMATION: CDR sequence

<400> SEQUENCE: 148

Arg Ala Ser Gln Pro Ile Gly Thr Gly Ile His
1               5                   10

<210> SEQ ID NO 149
<211> LENGTH: 7
<212> TYPE: PRT
<213> ORGANISM: Artificial Sequence
<220> FEATURE:
<223> OTHER INFORMATION: CDR sequence

<400> SEQUENCE: 149

Ser Ala Ser Glu Ser Ile Ser
1               5

<210> SEQ ID NO 150
<211> LENGTH: 9
<212> TYPE: PRT
```

```
<213> ORGANISM: Artificial Sequence
<220> FEATURE:
<223> OTHER INFORMATION: CDR sequence

<400> SEQUENCE: 150

Gln Gln Ser Tyr Ser Trp Pro Thr Thr
1               5

<210> SEQ ID NO 151
<211> LENGTH: 10
<212> TYPE: PRT
<213> ORGANISM: Artificial Sequence
<220> FEATURE:
<223> OTHER INFORMATION: CDR sequence

<400> SEQUENCE: 151

Gly Tyr Ser Phe Thr Ser Asn Trp Met His
1               5                   10

<210> SEQ ID NO 152
<211> LENGTH: 6
<212> TYPE: PRT
<213> ORGANISM: Artificial Sequence
<220> FEATURE:
<223> OTHER INFORMATION: CDR sequence

<400> SEQUENCE: 152

Tyr Pro Gly Asn Ser Asp
1               5

<210> SEQ ID NO 153
<211> LENGTH: 8
<212> TYPE: PRT
<213> ORGANISM: Artificial Sequence
<220> FEATURE:
<223> OTHER INFORMATION: CDR sequence

<400> SEQUENCE: 153

Gly Ile Thr Thr Ala Pro Glu Tyr
1               5

<210> SEQ ID NO 154
<211> LENGTH: 11
<212> TYPE: PRT
<213> ORGANISM: Artificial Sequence
<220> FEATURE:
<223> OTHER INFORMATION: CDR sequence

<400> SEQUENCE: 154

Lys Ala Ser Glu Asn Val Gly Ile Tyr Val Ser
1               5                   10

<210> SEQ ID NO 155
<211> LENGTH: 7
<212> TYPE: PRT
<213> ORGANISM: Artificial Sequence
<220> FEATURE:
<223> OTHER INFORMATION: CDR sequence

<400> SEQUENCE: 155

Gly Ala Ser Asn Arg Tyr Thr
1               5

<210> SEQ ID NO 156
<211> LENGTH: 9
<212> TYPE: PRT
<213> ORGANISM: Artificial Sequence
```

```
<220> FEATURE:
<223> OTHER INFORMATION: CDR sequence

<400> SEQUENCE: 156

Gly His Thr Tyr Asn Tyr Pro Phe Thr
1               5

<210> SEQ ID NO 157
<211> LENGTH: 10
<212> TYPE: PRT
<213> ORGANISM: Artificial Sequence
<220> FEATURE:
<223> OTHER INFORMATION: CDR sequence

<400> SEQUENCE: 157

Gly Phe Asp Phe Ser Arg Tyr Trp Met Ser
1               5                   10

<210> SEQ ID NO 158
<211> LENGTH: 6
<212> TYPE: PRT
<213> ORGANISM: Artificial Sequence
<220> FEATURE:
<223> OTHER INFORMATION: CDR sequence

<400> SEQUENCE: 158

His Pro Asp Ser Ser Ala
1               5

<210> SEQ ID NO 159
<211> LENGTH: 9
<212> TYPE: PRT
<213> ORGANISM: Artificial Sequence
<220> FEATURE:
<223> OTHER INFORMATION: CDR sequence

<400> SEQUENCE: 159

Ser Tyr Tyr Gly Arg Val Phe Asp Tyr
1               5

<210> SEQ ID NO 160
<211> LENGTH: 11
<212> TYPE: PRT
<213> ORGANISM: Artificial Sequence
<220> FEATURE:
<223> OTHER INFORMATION: CDR sequence

<400> SEQUENCE: 160

Arg Ala Ser Gln Ser Ile Ser Asp Tyr Leu His
1               5                   10

<210> SEQ ID NO 161
<211> LENGTH: 7
<212> TYPE: PRT
<213> ORGANISM: Artificial Sequence
<220> FEATURE:
<223> OTHER INFORMATION: CDR sequence

<400> SEQUENCE: 161

Tyr Ala Ser Gln Ser Ile Ser
1               5

<210> SEQ ID NO 162
<211> LENGTH: 9
<212> TYPE: PRT
<213> ORGANISM: Artificial Sequence
<220> FEATURE:
```

<223> OTHER INFORMATION: CDR sequence

<400> SEQUENCE: 162

Gln Asp Gly His Ser Phe Pro Pro Thr
1               5

<210> SEQ ID NO 163
<211> LENGTH: 10
<212> TYPE: PRT
<213> ORGANISM: Artificial Sequence
<220> FEATURE:
<223> OTHER INFORMATION: CDR sequence

<400> SEQUENCE: 163

Gly Tyr Ser Phe Thr Ser Tyr Trp Met His
1               5                   10

<210> SEQ ID NO 164
<211> LENGTH: 6
<212> TYPE: PRT
<213> ORGANISM: Artificial Sequence
<220> FEATURE:
<223> OTHER INFORMATION: CDR sequence

<400> SEQUENCE: 164

Tyr Pro Gly Asn Ser Asp
1               5

<210> SEQ ID NO 165
<211> LENGTH: 8
<212> TYPE: PRT
<213> ORGANISM: Artificial Sequence
<220> FEATURE:
<223> OTHER INFORMATION: CDR sequence

<400> SEQUENCE: 165

Gly Ile Thr Thr Ala Pro Asp Tyr
1               5

<210> SEQ ID NO 166
<211> LENGTH: 11
<212> TYPE: PRT
<213> ORGANISM: Artificial Sequence
<220> FEATURE:
<223> OTHER INFORMATION: CDR sequence

<400> SEQUENCE: 166

Lys Ala Ser Glu Asn Val Gly Ile His Val Ser
1               5                   10

<210> SEQ ID NO 167
<211> LENGTH: 7
<212> TYPE: PRT
<213> ORGANISM: Artificial Sequence
<220> FEATURE:
<223> OTHER INFORMATION: CDR sequence

<400> SEQUENCE: 167

Gly Ala Ser Ser Gly Tyr Asn
1               5

<210> SEQ ID NO 168
<211> LENGTH: 9
<212> TYPE: PRT
<213> ORGANISM: Artificial Sequence
<220> FEATURE:
<223> OTHER INFORMATION: CDR sequence

<400> SEQUENCE: 168

Gly Gln Thr Tyr Ser Tyr Pro Phe Thr
1               5

<210> SEQ ID NO 169
<211> LENGTH: 10
<212> TYPE: PRT
<213> ORGANISM: Artificial Sequence
<220> FEATURE:
<223> OTHER INFORMATION: CDR sequence

<400> SEQUENCE: 169

Lys Phe Thr Phe Thr Asn Tyr Gly Met Asn
1               5                   10

<210> SEQ ID NO 170
<211> LENGTH: 6
<212> TYPE: PRT
<213> ORGANISM: Artificial Sequence
<220> FEATURE:
<223> OTHER INFORMATION: CDR sequence

<400> SEQUENCE: 170

Asn Thr Tyr Thr Gly Glu
1               5

<210> SEQ ID NO 171
<211> LENGTH: 10
<212> TYPE: PRT
<213> ORGANISM: Artificial Sequence
<220> FEATURE:
<223> OTHER INFORMATION: CDR sequence

<400> SEQUENCE: 171

Arg Glu Tyr Tyr Pro Trp Val Phe Val Tyr
1               5                   10

<210> SEQ ID NO 172
<211> LENGTH: 10
<212> TYPE: PRT
<213> ORGANISM: Artificial Sequence
<220> FEATURE:
<223> OTHER INFORMATION: CDR sequence

<400> SEQUENCE: 172

Ser Ala Ser Ser Ser Val Ser Tyr Met His
1               5                   10

<210> SEQ ID NO 173
<211> LENGTH: 7
<212> TYPE: PRT
<213> ORGANISM: Artificial Sequence
<220> FEATURE:
<223> OTHER INFORMATION: CDR sequence

<400> SEQUENCE: 173

Asp Thr Ser Lys Leu Ala Ser
1               5

<210> SEQ ID NO 174
<211> LENGTH: 9
<212> TYPE: PRT
<213> ORGANISM: Artificial Sequence
<220> FEATURE:
<223> OTHER INFORMATION: CDR sequence

```
<400> SEQUENCE: 174

Phe Gln Gly Ser Gly Tyr Pro Leu Thr
1               5

<210> SEQ ID NO 175
<211> LENGTH: 10
<212> TYPE: PRT
<213> ORGANISM: Artificial Sequence
<220> FEATURE:
<223> OTHER INFORMATION: CDR sequence

<400> SEQUENCE: 175

Gly Tyr Ile Phe Thr Ser Tyr Trp Ile Asn
1               5                   10

<210> SEQ ID NO 176
<211> LENGTH: 6
<212> TYPE: PRT
<213> ORGANISM: Artificial Sequence
<220> FEATURE:
<223> OTHER INFORMATION: CDR sequence

<400> SEQUENCE: 176

Tyr Pro Ser Asp Ser Tyr
1               5

<210> SEQ ID NO 177
<211> LENGTH: 10
<212> TYPE: PRT
<213> ORGANISM: Artificial Sequence
<220> FEATURE:
<223> OTHER INFORMATION: CDR sequence

<400> SEQUENCE: 177

Phe His Tyr Gly Ser Ser Pro Phe Asp Asn
1               5                   10

<210> SEQ ID NO 178
<211> LENGTH: 11
<212> TYPE: PRT
<213> ORGANISM: Artificial Sequence
<220> FEATURE:
<223> OTHER INFORMATION: CDR sequence

<400> SEQUENCE: 178

Arg Ala Ser Gln Asp Ile Ser His Tyr Leu Asn
1               5                   10

<210> SEQ ID NO 179
<211> LENGTH: 7
<212> TYPE: PRT
<213> ORGANISM: Artificial Sequence
<220> FEATURE:
<223> OTHER INFORMATION: CDR sequence

<400> SEQUENCE: 179

Tyr Thr Ser Arg Leu His Ser
1               5

<210> SEQ ID NO 180
<211> LENGTH: 9
<212> TYPE: PRT
<213> ORGANISM: Artificial Sequence
<220> FEATURE:
<223> OTHER INFORMATION: CDR sequence

<400> SEQUENCE: 180
```

Gln Gln Gly His Thr Leu Pro Arg Thr
1               5

<210> SEQ ID NO 181
<211> LENGTH: 10
<212> TYPE: PRT
<213> ORGANISM: Artificial Sequence
<220> FEATURE:
<223> OTHER INFORMATION: CDR sequence

<400> SEQUENCE: 181

Gly Tyr Thr Phe Thr Asn Tyr Gly Met Asn
1               5                   10

<210> SEQ ID NO 182
<211> LENGTH: 6
<212> TYPE: PRT
<213> ORGANISM: Artificial Sequence
<220> FEATURE:
<223> OTHER INFORMATION: CDR sequence

<400> SEQUENCE: 182

Asn Thr Tyr Thr Gly Glu
1               5

<210> SEQ ID NO 183
<211> LENGTH: 9
<212> TYPE: PRT
<213> ORGANISM: Artificial Sequence
<220> FEATURE:
<223> OTHER INFORMATION: CDR sequence

<400> SEQUENCE: 183

Arg Asp Tyr Leu Gly Ala Met Asp Tyr
1               5

<210> SEQ ID NO 184
<211> LENGTH: 12
<212> TYPE: PRT
<213> ORGANISM: Artificial Sequence
<220> FEATURE:
<223> OTHER INFORMATION: CDR sequence

<400> SEQUENCE: 184

Arg Ala Ser Ser Ser Val Ser Ser Ser Tyr Leu His
1               5                   10

<210> SEQ ID NO 185
<211> LENGTH: 7
<212> TYPE: PRT
<213> ORGANISM: Artificial Sequence
<220> FEATURE:
<223> OTHER INFORMATION: CDR sequence

<400> SEQUENCE: 185

Ser Thr Ser Asn Leu Ala Ser
1               5

<210> SEQ ID NO 186
<211> LENGTH: 9
<212> TYPE: PRT
<213> ORGANISM: Artificial Sequence
<220> FEATURE:
<223> OTHER INFORMATION: CDR sequence

<400> SEQUENCE: 186

```
Gln Gln Tyr Ser Ala Tyr Leu Tyr Thr
1               5

<210> SEQ ID NO 187
<211> LENGTH: 10
<212> TYPE: PRT
<213> ORGANISM: Artificial Sequence
<220> FEATURE:
<223> OTHER INFORMATION: CDR sequence

<400> SEQUENCE: 187

Gly Tyr Thr Phe Thr Thr Tyr Trp Ile Asn
1               5                   10

<210> SEQ ID NO 188
<211> LENGTH: 6
<212> TYPE: PRT
<213> ORGANISM: Artificial Sequence
<220> FEATURE:
<223> OTHER INFORMATION: CDR sequence

<400> SEQUENCE: 188

Tyr Pro Ser Asp Ser Tyr
1               5

<210> SEQ ID NO 189
<211> LENGTH: 13
<212> TYPE: PRT
<213> ORGANISM: Artificial Sequence
<220> FEATURE:
<223> OTHER INFORMATION: CDR sequence

<400> SEQUENCE: 189

Glu Ala Gly Asp Gly Thr His Tyr Tyr Ala Ile Asp Tyr
1               5                   10

<210> SEQ ID NO 190
<211> LENGTH: 11
<212> TYPE: PRT
<213> ORGANISM: Artificial Sequence
<220> FEATURE:
<223> OTHER INFORMATION: CDR sequence

<400> SEQUENCE: 190

Lys Ala Ser Glu Asn Val Gly Thr Tyr Val Ser
1               5                   10

<210> SEQ ID NO 191
<211> LENGTH: 7
<212> TYPE: PRT
<213> ORGANISM: Artificial Sequence
<220> FEATURE:
<223> OTHER INFORMATION: CDR sequence

<400> SEQUENCE: 191

Gly Ala Ser Asn Arg Tyr Pro
1               5

<210> SEQ ID NO 192
<211> LENGTH: 9
<212> TYPE: PRT
<213> ORGANISM: Artificial Sequence
<220> FEATURE:
<223> OTHER INFORMATION: CDR sequence

<400> SEQUENCE: 192

Gly Gln Gly Tyr Ser Tyr Leu Arg Thr
```

<210> SEQ ID NO 193
<211> LENGTH: 10
<212> TYPE: PRT
<213> ORGANISM: Artificial Sequence
<220> FEATURE:
<223> OTHER INFORMATION: CDR sequence

<400> SEQUENCE: 193

Gly Phe Asn Ile Lys Asp Tyr Tyr Met His
1               5                   10

<210> SEQ ID NO 194
<211> LENGTH: 6
<212> TYPE: PRT
<213> ORGANISM: Artificial Sequence
<220> FEATURE:
<223> OTHER INFORMATION: CDR sequence

<400> SEQUENCE: 194

Asp Pro Glu Asn Gly Asn
1               5

<210> SEQ ID NO 195
<211> LENGTH: 8
<212> TYPE: PRT
<213> ORGANISM: Artificial Sequence
<220> FEATURE:
<223> OTHER INFORMATION: CDR sequence

<400> SEQUENCE: 195

Gly Leu Pro Trp Tyr Phe Asp Tyr
1               5

<210> SEQ ID NO 196
<211> LENGTH: 10
<212> TYPE: PRT
<213> ORGANISM: Artificial Sequence
<220> FEATURE:
<223> OTHER INFORMATION: CDR sequence

<400> SEQUENCE: 196

Ser Ala Ser Ser Ser Val Ser Asp Met Asn
1               5                   10

<210> SEQ ID NO 197
<211> LENGTH: 7
<212> TYPE: PRT
<213> ORGANISM: Artificial Sequence
<220> FEATURE:
<223> OTHER INFORMATION: CDR sequence

<400> SEQUENCE: 197

Leu Thr Ser Asn Leu Ser Ser
1               5

<210> SEQ ID NO 198
<211> LENGTH: 9
<212> TYPE: PRT
<213> ORGANISM: Artificial Sequence
<220> FEATURE:
<223> OTHER INFORMATION: CDR sequence

<400> SEQUENCE: 198

Gln Gln Trp Ser Gly Asn Pro Leu Thr
1               5

```
<210> SEQ ID NO 199
<211> LENGTH: 10
<212> TYPE: PRT
<213> ORGANISM: Artificial Sequence
<220> FEATURE:
<223> OTHER INFORMATION: CDR sequence

<400> SEQUENCE: 199

Gly Phe Ser Phe Ser Ser Phe Gly Met His
1               5                   10

<210> SEQ ID NO 200
<211> LENGTH: 6
<212> TYPE: PRT
<213> ORGANISM: Artificial Sequence
<220> FEATURE:
<223> OTHER INFORMATION: CDR sequence

<400> SEQUENCE: 200

Ser Ser Gly Ser Ser Ala
1               5

<210> SEQ ID NO 201
<211> LENGTH: 5
<212> TYPE: PRT
<213> ORGANISM: Artificial Sequence
<220> FEATURE:
<223> OTHER INFORMATION: CDR sequence

<400> SEQUENCE: 201

Asp Trp Val Asp Tyr
1               5

<210> SEQ ID NO 202
<211> LENGTH: 11
<212> TYPE: PRT
<213> ORGANISM: Artificial Sequence
<220> FEATURE:
<223> OTHER INFORMATION: CDR sequence

<400> SEQUENCE: 202

Arg Ala Ser Glu Asn Ile Tyr Ser Asn Leu Val
1               5                   10

<210> SEQ ID NO 203
<211> LENGTH: 7
<212> TYPE: PRT
<213> ORGANISM: Artificial Sequence
<220> FEATURE:
<223> OTHER INFORMATION: CDR sequence

<400> SEQUENCE: 203

Thr Ala Thr Lys Leu Thr Asn
1               5

<210> SEQ ID NO 204
<211> LENGTH: 9
<212> TYPE: PRT
<213> ORGANISM: Artificial Sequence
<220> FEATURE:
<223> OTHER INFORMATION: CDR sequence

<400> SEQUENCE: 204

Gln His Phe Trp Asp Thr Pro Tyr Thr
1               5
```

```
<210> SEQ ID NO 205
<211> LENGTH: 10
<212> TYPE: PRT
<213> ORGANISM: Artificial Sequence
<220> FEATURE:
<223> OTHER INFORMATION: CDR sequence

<400> SEQUENCE: 205

Gly Tyr Thr Phe Thr Ser Tyr Trp Ile Asn
1               5                   10

<210> SEQ ID NO 206
<211> LENGTH: 6
<212> TYPE: PRT
<213> ORGANISM: Artificial Sequence
<220> FEATURE:
<223> OTHER INFORMATION: CDR sequence

<400> SEQUENCE: 206

Phe Pro Ser Asp Ser Tyr
1               5

<210> SEQ ID NO 207
<211> LENGTH: 14
<212> TYPE: PRT
<213> ORGANISM: Artificial Sequence
<220> FEATURE:
<223> OTHER INFORMATION: CDR sequence

<400> SEQUENCE: 207

Phe Gly Ser Ser Gly Tyr Pro Asp Tyr Tyr Thr Met Glu Tyr
1               5                   10

<210> SEQ ID NO 208
<211> LENGTH: 11
<212> TYPE: PRT
<213> ORGANISM: Artificial Sequence
<220> FEATURE:
<223> OTHER INFORMATION: CDR sequence

<400> SEQUENCE: 208

Arg Ala Ser Gly Asn Ile Asp Asn Tyr Leu Ala
1               5                   10

<210> SEQ ID NO 209
<211> LENGTH: 7
<212> TYPE: PRT
<213> ORGANISM: Artificial Sequence
<220> FEATURE:
<223> OTHER INFORMATION: CDR sequence

<400> SEQUENCE: 209

Asn Ala Lys Thr Leu Ala Glu
1               5

<210> SEQ ID NO 210
<211> LENGTH: 9
<212> TYPE: PRT
<213> ORGANISM: Artificial Sequence
<220> FEATURE:
<223> OTHER INFORMATION: CDR sequence

<400> SEQUENCE: 210

Gln Gln Tyr Trp Thr Ile Pro Tyr Thr
1               5
```

```
<210> SEQ ID NO 211
<211> LENGTH: 10
<212> TYPE: PRT
<213> ORGANISM: Artificial Sequence
<220> FEATURE:
<223> OTHER INFORMATION: CDR sequence

<400> SEQUENCE: 211

Gly Tyr Ala Phe Asn Asn Ser Trp Met Asn
1               5                   10

<210> SEQ ID NO 212
<211> LENGTH: 6
<212> TYPE: PRT
<213> ORGANISM: Artificial Sequence
<220> FEATURE:
<223> OTHER INFORMATION: CDR sequence

<400> SEQUENCE: 212

Tyr Pro Gly Asp Gly Asp
1               5

<210> SEQ ID NO 213
<211> LENGTH: 12
<212> TYPE: PRT
<213> ORGANISM: Artificial Sequence
<220> FEATURE:
<223> OTHER INFORMATION: CDR sequence

<400> SEQUENCE: 213

Leu Asp Gly Asn Tyr Tyr Tyr Trp Tyr Phe Asp Val
1               5                   10

<210> SEQ ID NO 214
<211> LENGTH: 16
<212> TYPE: PRT
<213> ORGANISM: Artificial Sequence
<220> FEATURE:
<223> OTHER INFORMATION: CDR sequence

<400> SEQUENCE: 214

Lys Ser Ser Gln Ser Leu Leu Asp Ser Asp Gly Lys Thr Tyr Leu Asn
1               5                   10                  15

<210> SEQ ID NO 215
<211> LENGTH: 7
<212> TYPE: PRT
<213> ORGANISM: Artificial Sequence
<220> FEATURE:
<223> OTHER INFORMATION: CDR sequence

<400> SEQUENCE: 215

Leu Val Ser Lys Leu Asp Ser
1               5

<210> SEQ ID NO 216
<211> LENGTH: 9
<212> TYPE: PRT
<213> ORGANISM: Artificial Sequence
<220> FEATURE:
<223> OTHER INFORMATION: CDR sequence

<400> SEQUENCE: 216

Trp Gln Gly Thr His Phe Pro Gln Thr
1               5

<210> SEQ ID NO 217
```

<211> LENGTH: 255
<212> TYPE: PRT
<213> ORGANISM: Human
<220> FEATURE:
<221> NAME/KEY: misc_feature
<223> OTHER INFORMATION: Human 41-BB

<400> SEQUENCE: 217

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 218
<211> LENGTH: 256
<212> TYPE: PRT
<213> ORGANISM: Mouse
<220> FEATURE:
<221> NAME/KEY: misc_feature
<223> OTHER INFORMATION: Mouse 41-BB

<400> SEQUENCE: 218

```
Met Gly Asn Asn Cys Tyr Asn Val Val Val Ile Val Leu Leu Leu Val
1               5                   10                  15

Gly Cys Glu Lys Val Gly Ala Val Gln Asn Ser Cys Asp Asn Cys Gln
            20                  25                  30

Pro Gly Thr Phe Cys Arg Lys Tyr Asn Pro Val Cys Lys Ser Cys Pro
        35                  40                  45

Pro Ser Thr Phe Ser Ser Ile Gly Gly Gln Pro Asn Cys Asn Ile Cys
    50                  55                  60
```

-continued

```
Arg Val Cys Ala Gly Tyr Phe Arg Phe Lys Lys Phe Cys Ser Ser Thr
 65                  70                  75                  80

His Asn Ala Glu Cys Glu Cys Ile Glu Gly Phe His Cys Leu Gly Pro
                 85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
        115                 120                 125

Gly Thr Gly Val Cys Arg Pro Trp Thr Asn Cys Ser Leu Asp Gly Arg
130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu Ala
            180                 185                 190

Leu Thr Ser Ala Leu Leu Leu Ala Leu Ile Phe Ile Thr Leu Leu Phe
        195                 200                 205

Ser Val Leu Lys Trp Ile Arg Lys Lys Phe Pro His Ile Phe Lys Gln
210                 215                 220

Pro Phe Lys Lys Thr Thr Gly Ala Ala Gln Glu Glu Asp Ala Cys Ser
225                 230                 235                 240

Cys Arg Cys Pro Gln Glu Glu Glu Gly Gly Gly Gly Tyr Glu Leu
                245                 250                 255

<210> SEQ ID NO 219
<211> LENGTH: 254
<212> TYPE: PRT
<213> ORGANISM: Monkey
<220> FEATURE:
<221> NAME/KEY: misc_feature
<223> OTHER INFORMATION: Monkey 41-BB

<400> SEQUENCE: 219

Met Gly Asn Ser Cys Tyr Asn Ile Val Ala Thr Leu Leu Leu Val Leu
  1               5                  10                  15

Asn Phe Glu Arg Thr Arg Ser Leu Gln Asp Leu Cys Ser Asn Cys Pro
             20                  25                  30

Ala Gly Thr Phe Cys Asp Asn Asn Arg Ser Gln Ile Cys Ser Pro Cys
         35                  40                  45

Pro Pro Asn Ser Phe Ser Ser Ala Gly Gly Gln Arg Thr Cys Asp Ile
     50                  55                  60

Cys Arg Gln Cys Lys Gly Val Phe Lys Thr Arg Lys Glu Cys Ser Ser
 65                  70                  75                  80

Thr Ser Asn Ala Glu Cys Asp Cys Ile Ser Gly Tyr His Cys Leu Gly
                 85                  90                  95

Ala Glu Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
        130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Ala Thr Pro Pro Ala
```

```
                    165                 170                 175
Pro Ala Arg Glu Pro Gly His Ser Pro Gln Ile Ile Phe Phe Leu Ala
                180                 185                 190

Leu Thr Ser Thr Val Val Leu Phe Leu Leu Phe Phe Leu Val Leu Arg
            195                 200                 205

Phe Ser Val Val Lys Arg Ser Arg Lys Lys Leu Leu Tyr Ile Phe Lys
        210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Glu Gly Gly Cys Glu Leu
                245                 250

<210> SEQ ID NO 220
<211> LENGTH: 257
<212> TYPE: PRT
<213> ORGANISM: Artificial Sequence
<220> FEATURE:
<223> OTHER INFORMATION: Chimeric 4-1BB

<400> SEQUENCE: 220

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Leu Gln Val Leu Thr Leu Phe Leu
            180                 185                 190

Ala Leu Thr Ser Ala Leu Leu Leu Ala Leu Ile Phe Ile Thr Leu Leu
        195                 200                 205

Phe Ser Val Leu Lys Trp Ile Arg Lys Lys Phe Pro His Ile Phe Lys
    210                 215                 220

Gln Pro Phe Lys Lys Thr Thr Gly Ala Ala Gln Glu Glu Asp Ala Cys
225                 230                 235                 240

Ser Cys Arg Cys Pro Gln Glu Glu Glu Gly Gly Gly Gly Tyr Glu
                245                 250                 255

Leu

<210> SEQ ID NO 221
```

```
<211> LENGTH: 119
<212> TYPE: PRT
<213> ORGANISM: Artificial Sequence
<220> FEATURE:
<223> OTHER INFORMATION: heavy chain variable domain (VH)

<400> SEQUENCE: 221

Gln Val Gln Met Val Gln Ser Gly Ala Glu Val Lys Lys Pro Gly Ala
1               5                   10                  15

Ser Val Lys Leu Ser Cys Lys Ala Ser Gly Phe Thr Phe Ser Ser Ser
            20                  25                  30

Tyr Ile Asn Trp Leu Arg Gln Ala Pro Gly Gln Arg Leu Glu Trp Met
        35                  40                  45

Gly Trp Ile Phe Ala Gly Thr Gly Thr Tyr Tyr Asn Gln Lys Phe
    50                  55                  60

Thr Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg His Ser Pro Arg Ala Thr Leu Phe Asp Phe Trp Gly Gln Gly
            100                 105                 110

Thr Thr Leu Thr Val Ser Ser
        115

<210> SEQ ID NO 222
<211> LENGTH: 119
<212> TYPE: PRT
<213> ORGANISM: Artificial Sequence
<220> FEATURE:
<223> OTHER INFORMATION: heavy chain variable domain (VH)

<400> SEQUENCE: 222

Gln Val Gln Met Val Gln Ser Gly Ala Glu Val Lys Lys Pro Gly Ala
1               5                   10                  15

Ser Val Lys Leu Ser Cys Lys Ala Ser Gly Phe Thr Phe Ser Ser Ser
            20                  25                  30

Tyr Ile Asn Trp Leu Arg Gln Ala Pro Gly Gln Ser Leu Glu Trp Ile
        35                  40                  45

Gly Trp Ile Phe Ala Gly Thr Gly Thr Tyr Tyr Asn Gln Lys Phe
    50                  55                  60

Thr Gly Arg Val Gln Ile Thr Arg Asp Thr Ser Ala Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg His Ser Pro Arg Ala Thr Leu Phe Asp Phe Trp Gly Gln Gly
            100                 105                 110

Thr Thr Leu Thr Val Ser Ser
        115

<210> SEQ ID NO 223
<211> LENGTH: 119
<212> TYPE: PRT
<213> ORGANISM: Artificial Sequence
<220> FEATURE:
<223> OTHER INFORMATION: heavy chain variable domain (VH)

<400> SEQUENCE: 223

Gln Val Gln Met Val Gln Ser Gly Ala Glu Val Lys Lys Pro Gly Ala
1               5                   10                  15
```

Ser Val Lys Leu Ser Cys Lys Ala Ser Gly Phe Thr Phe Ser Ser Ser
            20                  25                  30

Tyr Ile Asn Trp Leu Arg Gln Ala Pro Gly Gln Ser Leu Glu Trp Ile
            35                  40                  45

Gly Trp Ile Phe Ala Gly Thr Gly Gly Thr Tyr Tyr Asn Gln Lys Phe
 50                      55                  60

Thr Gly Arg Ala Gln Ile Thr Arg Asp Thr Ser Ala Ser Thr Ala Tyr
 65                      70                  75                  80

Met Glu Leu Ser Ser Leu Arg Ser Glu Asp Thr Ala Ile Tyr Tyr Cys
                85                  90                  95

Ala Arg His Ser Pro Arg Ala Thr Leu Phe Asp Phe Trp Gly Gln Gly
                100                 105                 110

Thr Thr Leu Thr Val Ser Ser
            115

<210> SEQ ID NO 224
<211> LENGTH: 119
<212> TYPE: PRT
<213> ORGANISM: Artificial Sequence
<220> FEATURE:
<223> OTHER INFORMATION: heavy chain variable domain (VH)

<400> SEQUENCE: 224

Gln Gly Gln Met Val Gln Ser Gly Ala Glu Val Lys Lys Pro Gly Ala
1               5                   10                  15

Ser Val Lys Leu Ser Cys Lys Thr Ser Gly Phe Thr Phe Ser Ser Ser
            20                  25                  30

Tyr Ile Asn Trp Leu Arg Gln Ala Pro Gly Gln Ser Leu Glu Trp Ile
            35                  40                  45

Ala Trp Ile Phe Ala Gly Thr Gly Gly Thr Tyr Tyr Asn Gln Lys Phe
 50                      55                  60

Thr Gly Arg Ala Gln Leu Thr Val Asp Thr Ser Ala Ser Thr Ala Tyr
 65                      70                  75                  80

Met Glu Leu Ser Ser Leu Arg Ser Glu Asp Thr Ala Ile Tyr Tyr Cys
                85                  90                  95

Ala Arg His Ser Pro Arg Ala Thr Leu Phe Asp Phe Trp Gly Gln Gly
                100                 105                 110

Thr Thr Leu Thr Val Ser Ser
            115

<210> SEQ ID NO 225
<211> LENGTH: 106
<212> TYPE: PRT
<213> ORGANISM: Artificial Sequence
<220> FEATURE:
<223> OTHER INFORMATION: light chain variable domain (VL)

<400> SEQUENCE: 225

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Asn His Met
            20                  25                  30

His Trp Tyr Gln Gln Lys Pro Gly Gln Ala Pro Arg Ala Leu Ile Tyr
            35                  40                  45

Ala Thr Ser Asn Leu Ala Ser Gly Ile Pro Ala Arg Phe Ser Gly Ser
 50                      55                  60

Gly Ser Gly Thr Ser Phe Thr Leu Thr Ile Ser Ser Leu Glu Pro Glu
 65                      70                  75                  80

-continued

Asp Phe Ala Val Tyr Tyr Cys Gln Gln Trp Ser Ser Asn Pro Tyr Thr
                85                  90                  95

Phe Gly Gly Gly Thr Lys Leu Glu Ile Lys
            100                 105

<210> SEQ ID NO 226
<211> LENGTH: 106
<212> TYPE: PRT
<213> ORGANISM: Artificial Sequence
<220> FEATURE:
<223> OTHER INFORMATION: light chain variable domain (VL)

<400> SEQUENCE: 226

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Asn His Met
            20                  25                  30

His Trp Tyr Gln Gln Lys Pro Gly Gln Ala Pro Arg Ala Leu Ile Tyr
            35                  40                  45

Ala Thr Ser Asn Leu Ala Ser Gly Ile Pro Ala Arg Phe Ser Gly Ser
        50                  55                  60

Gly Ser Gly Thr Ser Phe Thr Leu Thr Ile Ser Ser Leu Glu Pro Glu
65                  70                  75                  80

Asp Phe Ala Thr Tyr Tyr Cys Gln Gln Trp Ser Ser Asn Pro Tyr Thr
                85                  90                  95

Phe Gly Gly Gly Thr Lys Leu Glu Ile Lys
            100                 105

<210> SEQ ID NO 227
<211> LENGTH: 106
<212> TYPE: PRT
<213> ORGANISM: Artificial Sequence
<220> FEATURE:
<223> OTHER INFORMATION: light chain variable domain (VL)

<400> SEQUENCE: 227

Glu Ile Val Leu Thr Gln Ser Pro Ala Thr Leu Ser Leu Ser Pro Gly
1               5                   10                  15

Glu Arg Ala Thr Met Ser Cys Arg Ala Ser Ser Val Asn His Met
            20                  25                  30

His Trp Tyr Gln Gln Lys Pro Gly Phe Ser Pro Arg Ala Trp Ile Tyr
            35                  40                  45

Ala Thr Ser Asn Leu Ala Ser Gly Ile Pro Ala Arg Phe Ser Gly Ser
        50                  55                  60

Gly Ser Gly Thr Ser Phe Thr Leu Thr Ile Ser Ser Leu Glu Pro Glu
65                  70                  75                  80

Asp Phe Ala Thr Tyr Tyr Cys Gln Gln Trp Ser Ser Asn Pro Tyr Thr
                85                  90                  95

Phe Gly Gly Gly Thr Lys Leu Glu Ile Lys
            100                 105

<210> SEQ ID NO 228
<211> LENGTH: 106
<212> TYPE: PRT
<213> ORGANISM: Artificial Sequence
<220> FEATURE:
<223> OTHER INFORMATION: light chain variable domain (VL)

<400> SEQUENCE: 228

```
Glu Ile Val Leu Thr Gln Ser Pro Ala Thr Leu Ser Ala Ser Pro Gly
1               5                   10                  15

Glu Arg Val Thr Met Ser Cys Arg Ala Ser Ser Val Asn His Met
            20                  25                  30

His Trp Tyr Gln Gln Arg Pro Gly Phe Ser Pro Arg Ala Trp Ile Tyr
        35                  40                  45

Ala Thr Ser Asn Leu Ala Ser Gly Ile Pro Ala Arg Phe Ser Gly Ser
    50                  55                  60

Gly Ser Gly Thr Ser Tyr Ser Leu Thr Ile Ser Ser Leu Glu Pro Glu
65                  70                  75                  80

Asp Phe Ala Thr Tyr Tyr Cys Gln Gln Trp Ser Ser Asn Pro Tyr Thr
                85                  90                  95

Phe Gly Gly Gly Thr Lys Leu Glu Ile Lys
            100                 105
```

<210> SEQ ID NO 229
<211> LENGTH: 121
<212> TYPE: PRT
<213> ORGANISM: Artificial Sequence
<220> FEATURE:
<223> OTHER INFORMATION: VH

<400> SEQUENCE: 229

```
Gln Val Gln Leu Val Gln Ser Gly Ala Glu Val Lys Lys Pro Gly Ser
1               5                   10                  15

Ser Val Lys Leu Ser Cys Lys Ala Ser Gly Tyr Thr Phe Ser Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Ser Asp Ser Tyr Thr Asn Tyr Asn Gln Lys Phe
    50                  55                  60

Lys Asp Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Trp Glu Phe Tyr Tyr Asp Ser Val Phe Asp Tyr Trp Gly
            100                 105                 110

Gln Gly Thr Leu Val Thr Val Ser Ser
        115                 120
```

<210> SEQ ID NO 230
<211> LENGTH: 121
<212> TYPE: PRT
<213> ORGANISM: Artificial Sequence
<220> FEATURE:
<223> OTHER INFORMATION: VH

<400> SEQUENCE: 230

```
Gln Val Gln Leu Val Gln Ser Gly Ala Glu Val Lys Lys Pro Gly Ser
1               5                   10                  15

Ser Val Lys Leu Ser Cys Lys Ala Ser Gly Tyr Thr Phe Ser Ser Tyr
            20                  25                  30

Trp Ile Asn Trp Val Arg Gln Ala Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Arg Ala Thr Leu Thr Val Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
            85                  90                  95

Thr Arg Thr Trp Glu Phe Tyr Tyr Asp Ser Val Phe Asp Tyr Trp Gly
            100                 105                 110

Gln Gly Thr Leu Val Thr Val Ser Ser
        115                 120

<210> SEQ ID NO 231
<211> LENGTH: 121
<212> TYPE: PRT
<213> ORGANISM: Artificial Sequence
<220> FEATURE:
<223> OTHER INFORMATION: VH

<400> SEQUENCE: 231

Gln Val Gln Leu Val Gln Ser Gly Ala Glu Val Lys Lys Pro Gly Ser
1               5                   10                  15

Ser Val Lys Leu Ser Cys Lys Ala Ser Gly Tyr Thr Phe Ser Ser Tyr
            20                  25                  30

Trp Ile Asn Trp Val Lys Gln Ala Pro Gly Gln Gly Leu Glu Trp Ile
            35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Thr Arg Thr Trp Glu Phe Tyr Tyr Asp Ser Val Phe Asp Tyr Trp Gly
            100                 105                 110

Gln Gly Thr Thr Leu Thr Val Ser Ser
        115                 120

<210> SEQ ID NO 232
<211> LENGTH: 107
<212> TYPE: PRT
<213> ORGANISM: Artificial Sequence
<220> FEATURE:
<223> OTHER INFORMATION: VL

<400> SEQUENCE: 232

Asp Ile Gln Met Thr Gln Ser Pro Ser Ser Leu Ser Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
            35                  40                  45

Tyr Arg Ala Asn Arg Leu Val Asp Gly Val Pro Ser Arg Phe Ser Gly
    50                  55                  60

Ser Gly Ser Gly Gln Asp Phe Thr Leu Thr Ile Ser Ser Leu Gln Pro
65                  70                  75                  80

Glu Asp Ile Ala Thr Tyr Tyr Cys Leu Gln Tyr Asp Glu Leu Pro Pro
            85                  90                  95

Thr Phe Gly Gly Gly Thr Lys Val Glu Ile Lys
            100                 105

<210> SEQ ID NO 233
<211> LENGTH: 107
<212> TYPE: PRT
```

<213> ORGANISM: Artificial Sequence
<220> FEATURE:
<223> OTHER INFORMATION: VL

<400> SEQUENCE: 233

Asp Ile Gln Met Thr Gln Ser Pro Ser Ser Leu Ser Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Phe Thr Leu Thr Ile Ser Ser Leu Gln Pro
65                  70                  75                  80

Glu Asp Ile Ala Thr Tyr Tyr Cys Leu Gln Tyr Asp Glu Leu Pro Pro
                85                  90                  95

Thr Phe Gly Gly Gly Thr Lys Val Glu Ile Lys
            100                 105

<210> SEQ ID NO 234
<211> LENGTH: 107
<212> TYPE: PRT
<213> ORGANISM: Artificial Sequence
<220> FEATURE:
<223> OTHER INFORMATION: VL

<400> SEQUENCE: 234

Asp Ile Gln Met Thr Gln Ser Pro Ser Ser Leu Ser Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Phe Thr Leu Thr Ile Ser Ser Leu Gln Pro
65                  70                  75                  80

Glu Asp Ile Ala Thr Tyr Tyr Cys Leu Gln Tyr Asp Glu Leu Pro Pro
                85                  90                  95

Thr Phe Gly Gly Gly Thr Lys Val Glu Ile Lys
            100                 105

<210> SEQ ID NO 235
<211> LENGTH: 107
<212> TYPE: PRT
<213> ORGANISM: Artificial Sequence
<220> FEATURE:
<223> OTHER INFORMATION: VL

<400> SEQUENCE: 235

Asp Ile Gln Met Thr Gln Ser Pro Ser Ser Leu Ser Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Tyr Thr Leu Thr Ile Ser Ser Leu Gln Pro
65                  70                  75                  80

Glu Asp Ile Ala Thr Tyr Tyr Cys Leu Gln Tyr Asp Glu Leu Pro Pro
                85                  90                  95

Thr Phe Gly Gly Gly Thr Lys Leu Glu Ile Lys
            100                 105

<210> SEQ ID NO 236
<211> LENGTH: 111
<212> TYPE: PRT
<213> ORGANISM: Artificial Sequence
<220> FEATURE:
<223> OTHER INFORMATION: VH

<400> SEQUENCE: 236

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
                20                  25                  30

Asp Ile Ser Trp Val Arg Gln Pro Pro Gly Lys Gly Leu Glu Trp Ile
            35                  40                  45

Gly Val Ile Trp Thr Gly Gly Gly Thr Asn Tyr Asn Ser Ser Phe Met
        50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Glu
                85                  90                  95

Arg Val Asp Tyr Trp Gly Gln Gly Thr Thr Val Thr Val Ser Ser
            100                 105                 110

<210> SEQ ID NO 237
<211> LENGTH: 111
<212> TYPE: PRT
<213> ORGANISM: Artificial Sequence
<220> FEATURE:
<223> OTHER INFORMATION: VH

<400> SEQUENCE: 237

Gln Val Gln Leu Lys Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
                20                  25                  30

Asp Ile Ser Trp Val Arg Gln Pro Pro Gly Lys Gly Leu Glu Trp Leu
            35                  40                  45

Gly Val Ile Trp Thr Gly Gly Gly Thr Asn Tyr Asn Ser Ser Phe Met
        50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Ile Tyr Tyr Cys Glu
                85                  90                  95

Arg Val Asp Tyr Trp Gly Gln Gly Thr Thr Val Thr Val Ser Ser
            100                 105                 110

<210> SEQ ID NO 238
<211> LENGTH: 111
<212> TYPE: PRT
<213> ORGANISM: Artificial Sequence
<220> FEATURE:
<223> OTHER INFORMATION: VH

<400> SEQUENCE: 238

Gln Val Gln Leu Lys Glu Ser Gly Pro Gly Leu Val Lys Pro Ser Glu
1               5                   10                  15

Thr Leu Ser Ile Thr Cys Thr Val Ser Gly Phe Ser Leu Thr Thr Tyr
            20                  25                  30

Asp Ile Ser Trp Val Arg Gln Pro Pro Gly Lys Gly Leu Glu Trp Leu
        35                  40                  45

Gly Val Ile Trp Thr Gly Gly Gly Thr Asn Tyr Asn Ser Ser Phe Met
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Ile Tyr Tyr Cys Glu
                85                  90                  95

Arg Val Asp Tyr Trp Gly Gln Gly Thr Thr Leu Thr Val Ser Ser
            100                 105                 110

<210> SEQ ID NO 239
<211> LENGTH: 112
<212> TYPE: PRT
<213> ORGANISM: Artificial Sequence
<220> FEATURE:
<223> OTHER INFORMATION: VL

<400> SEQUENCE: 239

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Ala Phe Thr Phe Lys Ile
65                  70                  75                  80

Ser Arg Val Glu Ala Glu Asp Val Gly Val Tyr Tyr Cys Ser Gln Asn
                85                  90                  95

Thr His Val Pro Trp Thr Phe Gly Gly Gly Thr Lys Val Glu Ile Lys
            100                 105                 110

<210> SEQ ID NO 240
<211> LENGTH: 112
<212> TYPE: PRT
<213> ORGANISM: Artificial Sequence
<220> FEATURE:
<223> OTHER INFORMATION: VL

<400> SEQUENCE: 240

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Ala Phe Thr Phe Lys Ile
65                  70                  75                  80

Ser Arg Val Glu Ala Glu Asp Val Gly Val Tyr Tyr Cys Ser Gln Asn
             85                  90                  95

Thr His Val Pro Trp Thr Phe Gly Gly Gly Thr Lys Val Glu Ile Lys
            100                 105                 110

<210> SEQ ID NO 241
<211> LENGTH: 112
<212> TYPE: PRT
<213> ORGANISM: Artificial Sequence
<220> FEATURE:
<223> OTHER INFORMATION: VL

<400> SEQUENCE: 241

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Ala Phe Thr Phe Lys Ile
65                  70                  75                  80

Ser Arg Val Glu Ala Glu Asp Val Gly Val Tyr Tyr Cys Ser Gln Asn
             85                  90                  95

Thr His Val Pro Trp Thr Phe Gly Gly Gly Thr Lys Leu Glu Ile Lys
            100                 105                 110

<210> SEQ ID NO 242
<211> LENGTH: 112
<212> TYPE: PRT
<213> ORGANISM: Artificial Sequence
<220> FEATURE:
<223> OTHER INFORMATION: VL

<400> SEQUENCE: 242

Asp Val Val Met Thr Gln Ser Pro Leu Ser Leu Pro Val Thr Leu Gly
1               5                   10                  15

Asp Pro Ala Ser Ile Ser Cys Arg Ser Ser Gln Ser Leu Val His Ser
            20                  25                  30

Asn Gly Asn Thr Tyr Leu His Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Ala Phe Thr Phe Lys Ile
65                  70                  75                  80

Ser Arg Val Glu Ala Glu Asp Val Gly Val Tyr Tyr Cys Ser Gln Asn
             85                  90                  95

Thr His Val Pro Trp Thr Phe Gly Gly Gly Thr Lys Leu Glu Ile Lys
            100                 105                 110

<210> SEQ ID NO 243
<211> LENGTH: 119
<212> TYPE: PRT
<213> ORGANISM: Artificial Sequence
<220> FEATURE:
<223> OTHER INFORMATION: VH

<400> SEQUENCE: 243

Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser Ser Ser
            20                  25                  30

Tyr Ile Asn Trp Leu Lys Gln Lys Pro Gly Gln Ser Leu Glu Trp Ile
        35                  40                  45

Ala Trp Ile Phe Ala Gly Thr Gly Gly Thr Tyr Tyr Asn Gln Lys Phe
50                  55                  60

Thr Gly Lys Ala Gln Leu Thr Val Asp Thr Ser Gly Thr Ala Tyr
65                  70                  75                  80

Met Gln Phe Ser Ser Leu Thr Thr Glu Asp Ser Ala Ile Tyr Tyr Cys
                85                  90                  95

Ala Arg His Ser Pro Arg Ala Thr Leu Phe Asp Phe Trp Gly Gln Gly
                100                 105                 110

Thr Thr Leu Thr Val Ser Ser
            115

<210> SEQ ID NO 244
<211> LENGTH: 106
<212> TYPE: PRT
<213> ORGANISM: Artificial Sequence
<220> FEATURE:
<223> OTHER INFORMATION: VL

<400> SEQUENCE: 244

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Asn His Met
            20                  25                  30

His Trp Tyr Gln Gln Arg Thr Gly Phe Ser Pro Lys Ala Trp Ile Tyr
        35                  40                  45

Ala Thr Ser Asn Leu Ala Ser Gly Val Pro Ala Arg Phe Ser Gly Ser
50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Tyr Thr
                85                  90                  95

Phe Gly Gly Gly Thr Lys Leu Glu Ile Lys
                100                 105

<210> SEQ ID NO 245
<211> LENGTH: 121
<212> TYPE: PRT
<213> ORGANISM: Artificial Sequence
<220> FEATURE:
<223> OTHER INFORMATION: VH

<400> SEQUENCE: 245

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Ser Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
50                  55                  60

Lys Asp Lys Ala Thr Leu Thr Val Asp Lys Ser Ser Ser Thr Ala Tyr
65                  70                  75                  80

```
Met Gln Leu Ser Ser Pro Thr Ser Asp Asp Ser Ala Val Tyr Tyr Cys
                85                  90                  95

Thr Arg Thr Trp Glu Phe Tyr Tyr Asp Ser Val Phe Asp Tyr Trp Gly
            100                 105                 110

Gln Gly Thr Thr Leu Thr Val Ser Ser
        115                 120

<210> SEQ ID NO 246
<211> LENGTH: 107
<212> TYPE: PRT
<213> ORGANISM: Artificial Sequence
<220> FEATURE:
<223> OTHER INFORMATION: VL

<400> SEQUENCE: 246

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Leu Pro Pro
                85                  90                  95

Thr Phe Gly Gly Gly Thr Lys Leu Glu Ile Lys
            100                 105

<210> SEQ ID NO 247
<211> LENGTH: 111
<212> TYPE: PRT
<213> ORGANISM: Artificial Sequence
<220> FEATURE:
<223> OTHER INFORMATION: VH

<400> SEQUENCE: 247

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Tyr
            20                  25                  30

Asp Ile Ser Trp Val Arg Gln Pro Pro Gly Lys Gly Leu Glu Trp Leu
        35                  40                  45

Gly Val Ile Trp Thr Gly Gly Gly Thr Asn Tyr Asn Ser Ser Phe Met
    50                  55                  60

Ser Arg Leu Ser Ile Ser Lys Asp Asn Ser Lys Asn Gln Val Phe Leu
65                  70                  75                  80

Lys Met Asn Ser Leu Gln Val Asp Thr Ala Ile Tyr Tyr Cys Glu
                85                  90                  95

Arg Val Asp Tyr Trp Gly Gln Gly Thr Thr Leu Thr Val Ser Ser
            100                 105                 110

<210> SEQ ID NO 248
<211> LENGTH: 112
<212> TYPE: PRT
<213> ORGANISM: Artificial Sequence
<220> FEATURE:
<223> OTHER INFORMATION: VL
```

-continued

<400> SEQUENCE: 248

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Ala Phe Thr Phe Lys Ile
65                  70                  75                  80

Ser Arg Val Glu Ala Glu Asp Leu Gly Val Tyr Phe Cys Ser Gln Asn
                85                  90                  95

Thr His Val Pro Trp Thr Phe Gly Gly Gly Thr Lys Leu Glu Ile Lys
            100                 105                 110

<210> SEQ ID NO 249
<211> LENGTH: 121
<212> TYPE: PRT
<213> ORGANISM: Artificial Sequence
<220> FEATURE:
<223> OTHER INFORMATION: VH

<400> SEQUENCE: 249

Gln Val Gln Leu Gln Gln Ser Gly Pro Glu Leu Val Lys Pro Gly Ala
1               5                   10                  15

Ser Val Lys Ile Ser Cys Lys Thr Ser Gly Tyr Ala Phe Ser Thr Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Asp Tyr Asn Gly Arg Phe
    50                  55                  60

Lys Gly Lys Ala Thr Leu Thr Ala Asp Lys Ser Ser Ser Thr Ala Tyr
65                  70                  75                  80

Leu Gln Leu Ser Ser Leu Thr Ser Val Asp Ser Ala Val Tyr Phe Cys
                85                  90                  95

Ala Arg Leu Asp Gly Tyr Tyr Glu Val Phe Tyr Phe Asp Tyr Trp Gly
            100                 105                 110

Gln Gly Thr Thr Leu Thr Val Ser Ser
        115                 120

<210> SEQ ID NO 250
<211> LENGTH: 112
<212> TYPE: PRT
<213> ORGANISM: Artificial Sequence
<220> FEATURE:
<223> OTHER INFORMATION: VL

<400> SEQUENCE: 250

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

```
Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Thr His Phe Pro Trp Thr Phe Gly Gly Gly Thr Lys Leu Glu Ile Lys
            100                 105                 110
```

<210> SEQ ID NO 251
<211> LENGTH: 114
<212> TYPE: PRT
<213> ORGANISM: Artificial Sequence
<220> FEATURE:
<223> OTHER INFORMATION: VH

<400> SEQUENCE: 251

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Thr Tyr
            20                  25                  30

Val Met Tyr Trp Val Lys Gln Arg Pro Gly Gln Gly Leu Glu Trp Ile
        35                  40                  45

Gly Tyr Ile Asn Pro Tyr Asn Asp Asp Ile Arg Tyr Asn Glu Lys Phe
50                  55                  60

Lys Gly Lys Ala Thr Leu Thr Ser Asp Arg Ser Ser Thr Ala Tyr
65                  70                  75                  80

Met Glu Leu Ser Ser Leu Thr Ser Glu Asp Ser Ala Val Tyr Leu Cys
                85                  90                  95

Ala Arg Gln Gly Gly Asp Tyr Trp Gly Gln Gly Thr Ile Leu Thr Val
            100                 105                 110

Ser Ser
```

<210> SEQ ID NO 252
<211> LENGTH: 107
<212> TYPE: PRT
<213> ORGANISM: Artificial Sequence
<220> FEATURE:
<223> OTHER INFORMATION: VL

<400> SEQUENCE: 252

```
Asp Val Gln Ile Thr Gln Ser Pro Ser Tyr Leu Ala Ala Ser Pro Gly
1               5                   10                  15

Glu Thr Ile Thr Val Asn Cys Arg Ala Ser Lys Asn Ile Asn Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr His Cys Gln Gln Tyr Asn Glu Tyr Pro Leu
                85                  90                  95

Thr Phe Gly Ala Gly Thr Lys Leu Glu Met Lys
            100                 105
```

<210> SEQ ID NO 253
<211> LENGTH: 118
<212> TYPE: PRT
<213> ORGANISM: Artificial Sequence

<220> FEATURE:
<223> OTHER INFORMATION: VH

<400> SEQUENCE: 253

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Thr Tyr
            20                  25                  30

Gly Val His Trp Val Arg Gln Pro Pro Gly Lys Gly Leu Glu Trp Leu
        35                  40                  45

Gly Val Ile Trp Ser Asp Gly Asn Thr Asp Tyr Asn Asp Ala Phe Ile
    50                  55                  60

Ser Arg Leu Ser Ile Thr Lys Asp Asn Ser Thr Ser Gln Val Phe Phe
65                  70                  75                  80

Lys Met Asn Gly Leu Gln Ala Asp Asp Thr Ala Ile Tyr Tyr Cys Ala
                85                  90                  95

Arg Asn Ser Ile Thr Ser Val Ser Phe Asp Cys Trp Gly Gln Gly Thr
            100                 105                 110

Thr Leu Thr Val Ser Ser
        115
```

<210> SEQ ID NO 254
<211> LENGTH: 107
<212> TYPE: PRT
<213> ORGANISM: Artificial Sequence
<220> FEATURE:
<223> OTHER INFORMATION: VL

<400> SEQUENCE: 254

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Thr
            20                  25                  30

Val Ala Trp Tyr Gln Gln Arg Pro Gly Gln Ser Pro Lys Ala Leu Ile
        35                  40                  45

Cys Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ser Gly Thr Lys Leu Glu Ile Lys
            100                 105
```

<210> SEQ ID NO 255
<211> LENGTH: 117
<212> TYPE: PRT
<213> ORGANISM: Artificial Sequence
<220> FEATURE:
<223> OTHER INFORMATION: VH

<400> SEQUENCE: 255

```
Gln Val Gln Leu Gln Gln Pro Gly Ser Ala Leu Val Arg Pro Gly Ala
1               5                   10                  15

Ser Val Lys Leu Ser Cys Lys Ala Ser Gly Tyr Thr Phe Ser Asn Tyr
            20                  25                  30

Trp Ile His Trp Val Lys Gln Arg His Gly Gln Gly Leu Glu Trp Ile
        35                  40                  45
```

```
Gly Asn Ile Tyr Pro Ala Ser Asp Tyr Thr Asn Tyr Asp Glu Lys Phe
 50                  55                  60

Lys Asn Lys Gly Thr Leu Thr Val Asp Thr Ser Ser Thr Ala Tyr
 65                  70                  75                  80

Met His Leu Ser Ser Leu Thr Ser Glu Asp Ser Ala Val Tyr Tyr Cys
                 85                  90                  95

Ser Arg Gly Tyr Phe Gly Ser Leu Asp Tyr Trp Gly Gln Gly Thr Ser
                100                 105                 110

Val Thr Val Ser Ala
            115

<210> SEQ ID NO 256
<211> LENGTH: 107
<212> TYPE: PRT
<213> ORGANISM: Artificial Sequence
<220> FEATURE:
<223> OTHER INFORMATION: VL

<400> SEQUENCE: 256

Asp Ile Leu Leu Thr Gln Ser Pro Ala Ile Leu Ser Val Asn Pro Gly
 1               5                  10                  15

Glu Arg Val Ser Phe Ser Cys Arg Ala Ser Gln Pro Ile Gly Thr Gly
                20                  25                  30

Ile His Trp Tyr Gln Gln Arg Thr Asn Gly Ser Pro Arg Leu Leu Ile
            35                  40                  45

Lys Ser Ala Ser Glu Ser Ile Ser Gly Ile Pro Ser Arg Phe Ser Gly
 50                  55                  60

Ser Gly Ser Gly Thr Asp Phe Thr Leu Thr Ile Asn Asn Val Glu Ser
 65                  70                  75                  80

Asp Asp Val Gly Asp Tyr Tyr Cys Gln Gln Ser Tyr Ser Trp Pro Thr
                 85                  90                  95

Thr Phe Gly Gly Gly Thr Lys Leu Lys Ile Asn
                100                 105

<210> SEQ ID NO 257
<211> LENGTH: 117
<212> TYPE: PRT
<213> ORGANISM: Artificial Sequence
<220> FEATURE:
<223> OTHER INFORMATION: VH

<400> SEQUENCE: 257

Glu Val Gln Leu Gln Gln Ser Gly Thr Val Leu Ala Arg Pro Gly Ala
 1               5                  10                  15

Ser Val Lys Met Ser Cys Lys Ala Ser Gly Tyr Ser Phe Thr Ser Asn
                20                  25                  30

Trp Met His Trp Val Lys Gln Arg Pro Gly Gln Gly Leu Glu Trp Ile
            35                  40                  45

Gly Val Ile Tyr Pro Gly Asn Ser Asp Thr Ser Tyr Asn Gln Lys Phe
 50                  55                  60

Lys Gly Lys Ala Lys Leu Thr Ala Val Thr Ser Ala Ser Thr Ala Tyr
 65                  70                  75                  80

Met Glu Leu Ser Ser Leu Thr Asn Glu Asp Ser Ala Val Tyr Tyr Cys
                 85                  90                  95

Thr Arg Gly Ile Thr Thr Ala Pro Glu Tyr Trp Gly Gln Gly Thr Thr
                100                 105                 110

Leu Thr Val Ser Ser
            115
```

```
<210> SEQ ID NO 258
<211> LENGTH: 107
<212> TYPE: PRT
<213> ORGANISM: Artificial Sequence
<220> FEATURE:
<223> OTHER INFORMATION: VL

<400> SEQUENCE: 258

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Ile Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Pro
65                  70                  75                  80

Glu Asp Leu Ala Asp Tyr His Cys Gly His Thr Tyr Asn Tyr Pro Phe
                85                  90                  95

Thr Phe Gly Ser Gly Thr Lys Leu Glu Ile Lys
            100                 105

<210> SEQ ID NO 259
<211> LENGTH: 118
<212> TYPE: PRT
<213> ORGANISM: Artificial Sequence
<220> FEATURE:
<223> OTHER INFORMATION: VH

<400> SEQUENCE: 259

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile His Pro Asp Ser Ser Ala Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Ser Tyr Tyr Gly Arg Val Phe Asp Tyr Trp Gly Gln Gly Thr
            100                 105                 110

Thr Leu Thr Val Ser Ser
        115

<210> SEQ ID NO 260
<211> LENGTH: 107
<212> TYPE: PRT
<213> ORGANISM: Artificial Sequence
<220> FEATURE:
<223> OTHER INFORMATION: VL

<400> SEQUENCE: 260

Asp Ile Val Met Thr Gln Ser Pro Ala Thr Leu Ser Val Thr Pro Gly
1               5                   10                  15
```

-continued

```
Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Pro Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Met Tyr Tyr Cys Gln Asp Gly His Ser Phe Pro Pro
                85                  90                  95

Thr Phe Gly Ala Gly Thr Lys Leu Glu Leu Lys
            100                 105
```

<210> SEQ ID NO 261
<211> LENGTH: 117
<212> TYPE: PRT
<213> ORGANISM: Artificial Sequence
<220> FEATURE:
<223> OTHER INFORMATION: VH

<400> SEQUENCE: 261

```
Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Val Ile Tyr Pro Gly Asn Ser Asp Thr Ser Tyr Asn Gln Lys Phe
50                  55                  60

Lys Gly Lys Ala Lys Leu Thr Ala Val Thr Ser Ala Ser Thr Ala Tyr
65                  70                  75                  80

Met Asp Leu Ser Ser Leu Thr Asn Glu Asp Ser Ala Val Tyr Tyr Cys
                85                  90                  95

Thr Arg Gly Ile Thr Thr Ala Pro Asp Tyr Trp Gly Gln Gly Thr Thr
            100                 105                 110

Leu Thr Val Ser Ser
        115
```

<210> SEQ ID NO 262
<211> LENGTH: 107
<212> TYPE: PRT
<213> ORGANISM: Artificial Sequence
<220> FEATURE:
<223> OTHER INFORMATION: VL

<400> SEQUENCE: 262

```
Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Ile His
            20                  25                  30

Val Ser Trp Tyr Gln Gln Lys Pro Glu Gln Ser Pro Lys Leu Leu Ile
        35                  40                  45

Tyr Gly Ala Ser Ser Gly Tyr Asn Gly Val Pro Asp Arg Phe Thr Gly
50                  55                  60

Ser Gly Ser Ala Thr Asp Phe Thr Leu Thr Ile Ser Ser Val Gln Pro
65                  70                  75                  80

Glu Asp Leu Ala Asp Tyr His Cys Gly Gln Thr Tyr Ser Tyr Pro Phe
                85                  90                  95
```

Thr Phe Gly Ser Gly Thr Lys Leu Glu Ile Lys
            100                 105

<210> SEQ ID NO 263
<211> LENGTH: 119
<212> TYPE: PRT
<213> ORGANISM: Artificial Sequence
<220> FEATURE:
<223> OTHER INFORMATION: VH

<400> SEQUENCE: 263

Gln Ile Gln Leu Val Gln Ser Gly Pro Glu Leu Lys Lys Pro Gly Glu
1               5                   10                  15

Thr Val Lys Ile Ser Cys Lys Ala Ser Lys Phe Thr Phe Thr Asn Tyr
            20                  25                  30

Gly Met Asn Trp Val Lys Gln Ala Pro Gly Lys Ala Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Asp Phe Ser Leu Glu Thr Ser Ala Thr Thr Ala Tyr
65                  70                  75                  80

Leu Gln Ile Asn Asn Leu Lys Asn Glu Asp Thr Ala Thr Tyr Phe Cys
                85                  90                  95

Ala Arg Arg Glu Tyr Tyr Pro Trp Val Phe Val Tyr Trp Gly Gln Gly
            100                 105                 110

Thr Leu Val Thr Val Ser Ala
        115

<210> SEQ ID NO 264
<211> LENGTH: 106
<212> TYPE: PRT
<213> ORGANISM: Artificial Sequence
<220> FEATURE:
<223> OTHER INFORMATION: VL

<400> SEQUENCE: 264

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Gly Gly Thr Lys Leu Glu Ile Lys
            100                 105

<210> SEQ ID NO 265
<211> LENGTH: 119
<212> TYPE: PRT
<213> ORGANISM: Artificial Sequence
<220> FEATURE:
<223> OTHER INFORMATION: VH

<400> SEQUENCE: 265

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ile Phe Thr Ser Tyr
            20                  25                  30

Trp Ile Asn Trp Val Lys Gln Arg Pro Gly Gln Gly Leu Glu Trp Ile
            35                  40                  45

Gly Asn Ile Tyr Pro Ser Asp Ser Tyr Thr Asn Tyr Asn Gln Lys Phe
        50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
            85                  90                  95

Thr Arg Phe His Tyr Gly Ser Ser Pro Phe Asp Asn Trp Gly Gln Gly
            100                 105                 110

Thr Thr Leu Thr Val Ser Ser
            115

<210> SEQ ID NO 266
<211> LENGTH: 107
<212> TYPE: PRT
<213> ORGANISM: Artificial Sequence
<220> FEATURE:
<223> OTHER INFORMATION: VL

<400> SEQUENCE: 266

Asp Ile Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser His Tyr
            20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly His Thr Leu Pro Arg
            85                  90                  95

Thr Phe Gly Gly Gly Thr Lys Leu Glu Ile Lys
            100                 105

<210> SEQ ID NO 267
<211> LENGTH: 118
<212> TYPE: PRT
<213> ORGANISM: Artificial Sequence
<220> FEATURE:
<223> OTHER INFORMATION: VH

<400> SEQUENCE: 267

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Phe Lys Trp Met
            35                  40                  45

Gly Trp Ile Asn Thr Tyr Thr Gly Glu Pro Thr Tyr Ala Asp Asp Phe
        50                  55                  60

Lys Gly Arg Phe Ala Phe Ser Leu Glu Ile Ser Ala Ser Thr Ala Tyr
65                  70                  75                  80

Leu Gln Ile Asn Asn Leu Lys Asn Glu Asp Thr Ala Thr Tyr Phe Cys
            85                  90                  95

Ala Arg Arg Asp Tyr Leu Gly Ala Met Asp Tyr Trp Gly Gln Gly Thr
        100                 105                 110

Ser Val Thr Val Ser Ser
        115

<210> SEQ ID NO 268
<211> LENGTH: 108
<212> TYPE: PRT
<213> ORGANISM: Artificial Sequence
<220> FEATURE:
<223> OTHER INFORMATION: VL

<400> SEQUENCE: 268

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Ala Tyr Leu
                85                  90                  95

Tyr Thr Phe Gly Gly Gly Thr Lys Leu Glu Ile Lys
            100                 105

<210> SEQ ID NO 269
<211> LENGTH: 122
<212> TYPE: PRT
<213> ORGANISM: Artificial Sequence
<220> FEATURE:
<223> OTHER INFORMATION: VH

<400> SEQUENCE: 269

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Ile Asn Trp Val Arg Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Ser Leu Thr Val Asp Lys Ser Ser Asn Thr Ala Tyr
65                  70                  75                  80

Met Gln Leu Ser Ser Pro Thr Ser Glu Asp Ser Ala Val Tyr Tyr Cys
                85                  90                  95

Ala Arg Glu Ala Gly Asp Gly Thr His Tyr Tyr Ala Ile Asp Tyr Trp
            100                 105                 110

Gly Gln Gly Thr Ser Val Thr Val Ser Ser
        115                 120

<210> SEQ ID NO 270
<211> LENGTH: 107
<212> TYPE: PRT

<213> ORGANISM: Artificial Sequence
<220> FEATURE:
<223> OTHER INFORMATION: VL

<400> SEQUENCE: 270

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Pro Gly Val Pro Asp Arg Phe Thr Gly
    50                  55                  60

Ser Gly Ser Ala Thr Asp Phe Thr Leu Thr Ile Ser Ser Leu Gln Ala
65                  70                  75                  80

Glu Asp Leu Ala Asp Tyr His Cys Gly Gln Gly Tyr Ser Tyr Leu Arg
                85                  90                  95

Thr Phe Gly Gly Gly Thr Asn Leu Glu Ile Lys
            100                 105

<210> SEQ ID NO 271
<211> LENGTH: 117
<212> TYPE: PRT
<213> ORGANISM: Artificial Sequence
<220> FEATURE:
<223> OTHER INFORMATION: VH

<400> SEQUENCE: 271

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Met His Trp Val Lys Arg Arg Pro Glu Gln Gly Leu Glu Trp Ile
        35                  40                  45

Gly Trp Ile Asp Pro Glu Asn Gly Asn Thr Ile Tyr Asp Pro Lys Phe
    50                  55                  60

Gln Asp Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Glu Gly Leu Pro Trp Tyr Phe Asp Tyr Trp Gly Gln Gly Thr Thr
            100                 105                 110

Leu Thr Val Ser Ser
        115

<210> SEQ ID NO 272
<211> LENGTH: 106
<212> TYPE: PRT
<213> ORGANISM: Artificial Sequence
<220> FEATURE:
<223> OTHER INFORMATION: VL

<400> SEQUENCE: 272

Gln Ile Ile Leu Thr Gln Ser Pro Ala Leu Met Ser Ala Ser Pro Gly
1               5                   10                  15

Glu Lys Val Thr Met Thr Cys Ser Ala Ser Ser Ser Val Ser Asp Met
            20                  25                  30

Asn Trp Tyr Gln Gln Lys Pro Arg Ser Ser Pro Thr Pro Trp Ile Tyr
        35                  40                  45

```
Leu Thr Ser Asn Leu Ser Ser Gly Val Pro Asp Arg Phe Ser Gly Ser
             50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Gly Asn Pro Leu Thr
                 85                  90                  95

Phe Gly Ala Gly Thr Arg Leu Glu Leu Lys
            100                 105

<210> SEQ ID NO 273
<211> LENGTH: 114
<212> TYPE: PRT
<213> ORGANISM: Artificial Sequence
<220> FEATURE:
<223> OTHER INFORMATION: VH

<400> SEQUENCE: 273

Asp Val Gln Leu Val Glu Ser Gly Gly Gly Leu Val Gln Pro Gly Gly
 1               5                  10                  15

Ser Arg Lys Leu Ser Cys Ala Ala Ser Gly Phe Ser Phe Ser Ser Phe
             20                  25                  30

Gly Met His Trp Met Arg Gln Ala Pro Glu Lys Gly Leu Glu Trp Val
         35                  40                  45

Ala Tyr Ile Ser Ser Gly Ser Ser Ala Ile Tyr Tyr Ala Asp Thr Val
     50                  55                  60

Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Arg Asp Trp Val Asp Tyr Trp Gly Gln Gly Thr Thr Leu Thr Val
            100                 105                 110

Ser Ser

<210> SEQ ID NO 274
<211> LENGTH: 107
<212> TYPE: PRT
<213> ORGANISM: Artificial Sequence
<220> FEATURE:
<223> OTHER INFORMATION: VL

<400> SEQUENCE: 274

Asp Ile Gln Met Thr Gln Ser Pro Ala Ser Leu Ser Val Ser Val Gly
 1               5                  10                  15

Glu Thr Val Thr Ile Thr Cys Arg Ala Ser Glu Asn Ile Tyr Ser Asn
             20                  25                  30

Leu Val Trp Tyr Gln Gln Lys Gln Gly Lys Ser Pro Gln Leu Leu Val
         35                  40                  45

Tyr Thr Ala Thr Lys Leu Thr Asn Gly Val Pro Ser Arg Phe Ser Gly
     50                  55                  60

Ser Gly Ser Gly Thr Gln Tyr Ser Leu Lys Ile Asn Ser Leu Gln Ser
 65                  70                  75                  80

Glu Asp Phe Gly Thr Tyr Tyr Cys Gln His Phe Trp Asp Thr Pro Tyr
                 85                  90                  95

Thr Phe Gly Gly Gly Thr Lys Leu Glu Met Lys
            100                 105

<210> SEQ ID NO 275
```

<211> LENGTH: 123
<212> TYPE: PRT
<213> ORGANISM: Artificial Sequence
<220> FEATURE:
<223> OTHER INFORMATION: VH

<400> SEQUENCE: 275

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Phe Pro Ser Asp Ser Tyr Thr Asn Tyr Asn Gln Lys Phe
    50                  55                  60

Lys Asp Arg Ala Lys Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Phe Gly Ser Ser Gly Tyr Pro Asp Tyr Tyr Thr Met Glu Tyr
            100                 105                 110

Trp Gly Gln Gly Thr Ser Val Thr Val Ser Ser
        115                 120

<210> SEQ ID NO 276
<211> LENGTH: 107
<212> TYPE: PRT
<213> ORGANISM: Artificial Sequence
<220> FEATURE:
<223> OTHER INFORMATION: VL

<400> SEQUENCE: 276

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile Asp Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Glu Tyr Ser Leu Lys Ile Asn Ser Leu Gln Pro
65                  70                  75                  80

Glu Asp Phe Gly Ser Tyr His Cys Gln Gln Tyr Trp Thr Ile Pro Tyr
                85                  90                  95

Thr Phe Gly Gly Gly Thr Lys Leu Glu Ile Lys
            100                 105

<210> SEQ ID NO 277
<211> LENGTH: 121
<212> TYPE: PRT
<213> ORGANISM: Artificial Sequence
<220> FEATURE:
<223> OTHER INFORMATION: VH

<400> SEQUENCE: 277

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Asn Asn Ser
            20                  25                  30

```
Trp Met Asn Trp Val Lys Gln Arg Pro Gly Gln Gly Leu Glu Trp Ile
            35                  40                  45

Gly Arg Ile Tyr Pro Gly Asp Gly Asp Thr Asp Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Leu Asp Gly Asn Tyr Tyr Tyr Trp Tyr Phe Asp Val Trp Gly
            100                 105                 110

Ala Gly Thr Thr Val Thr Val Ser Ser
        115                 120
```

```
<210> SEQ ID NO 278
<211> LENGTH: 112
<212> TYPE: PRT
<213> ORGANISM: Artificial Sequence
<220> FEATURE:
<223> OTHER INFORMATION: VL

<400> SEQUENCE: 278
```

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110
```

```
<210> SEQ ID NO 279
<211> LENGTH: 5
<212> TYPE: PRT
<213> ORGANISM: Artificial Sequence
<220> FEATURE:
<223> OTHER INFORMATION: CDR sequence

<400> SEQUENCE: 279
```

```
Gly Tyr Tyr Trp Ser
1               5
```

```
<210> SEQ ID NO 280
<211> LENGTH: 16
<212> TYPE: PRT
<213> ORGANISM: Artificial Sequence
<220> FEATURE:
<223> OTHER INFORMATION: CDR sequence

<400> SEQUENCE: 280
```

```
Glu Ile Asn His Gly Gly Tyr Val Thr Tyr Asn Pro Ser Leu Glu Ser
1               5                   10                  15
```

```
<210> SEQ ID NO 281
<211> LENGTH: 13
<212> TYPE: PRT
```

-continued

<213> ORGANISM: Artificial Sequence
<220> FEATURE:
<223> OTHER INFORMATION: CDR sequence

<400> SEQUENCE: 281

Asp Tyr Gly Pro Gly Asn Tyr Asp Trp Tyr Phe Asp Leu
1               5                   10

<210> SEQ ID NO 282
<211> LENGTH: 11
<212> TYPE: PRT
<213> ORGANISM: Artificial Sequence
<220> FEATURE:
<223> OTHER INFORMATION: CDR sequence

<400> SEQUENCE: 282

Arg Ala Ser Gln Ser Val Ser Ser Tyr Leu Ala
1               5                   10

<210> SEQ ID NO 283
<211> LENGTH: 7
<212> TYPE: PRT
<213> ORGANISM: Artificial Sequence
<220> FEATURE:
<223> OTHER INFORMATION: CDR sequence

<400> SEQUENCE: 283

Asp Ala Ser Asn Arg Ala Thr
1               5

<210> SEQ ID NO 284
<211> LENGTH: 11
<212> TYPE: PRT
<213> ORGANISM: Artificial Sequence
<220> FEATURE:
<223> OTHER INFORMATION: CDR sequence

<400> SEQUENCE: 284

Gln Gln Arg Ser Asn Trp Pro Pro Ala Leu Thr
1               5                   10

<210> SEQ ID NO 285
<211> LENGTH: 5
<212> TYPE: PRT
<213> ORGANISM: Artificial Sequence
<220> FEATURE:
<223> OTHER INFORMATION: CDR sequence

<400> SEQUENCE: 285

Asp Tyr Trp Met Ser
1               5

<210> SEQ ID NO 286
<211> LENGTH: 17
<212> TYPE: PRT
<213> ORGANISM: Artificial Sequence
<220> FEATURE:
<223> OTHER INFORMATION: CDR sequence

<400> SEQUENCE: 286

Asp Ile Lys Asn Asp Gly Ser Tyr Thr Asn Tyr Ala Pro Ser Leu Thr
1               5                   10                  15

Asn

<210> SEQ ID NO 287
<211> LENGTH: 5

```
<212> TYPE: PRT
<213> ORGANISM: Artificial Sequence
<220> FEATURE:
<223> OTHER INFORMATION: CDR sequence

<400> SEQUENCE: 287

Glu Leu Thr Gly Thr
1               5

<210> SEQ ID NO 288
<211> LENGTH: 17
<212> TYPE: PRT
<213> ORGANISM: Artificial Sequence
<220> FEATURE:
<223> OTHER INFORMATION: CDR sequence

<400> SEQUENCE: 288

Lys Ser Ser Gln Ser Leu Leu Ser Ser Gly Asn Gln Lys Asn Tyr Leu
1               5                   10                  15

Ala

<210> SEQ ID NO 289
<211> LENGTH: 7
<212> TYPE: PRT
<213> ORGANISM: Artificial Sequence
<220> FEATURE:
<223> OTHER INFORMATION: CDR sequence

<400> SEQUENCE: 289

Tyr Ala Ser Thr Arg Gln Ser
1               5

<210> SEQ ID NO 290
<211> LENGTH: 9
<212> TYPE: PRT
<213> ORGANISM: Artificial Sequence
<220> FEATURE:
<223> OTHER INFORMATION: CDR sequence

<400> SEQUENCE: 290

Leu Gln Tyr Asp Arg Tyr Pro Phe Thr
1               5

<210> SEQ ID NO 291
<211> LENGTH: 6
<212> TYPE: PRT
<213> ORGANISM: Artificial Sequence
<220> FEATURE:
<223> OTHER INFORMATION: CDR sequence

<400> SEQUENCE: 291

Ser Thr Tyr Trp Ile Ser
1               5

<210> SEQ ID NO 292
<211> LENGTH: 17
<212> TYPE: PRT
<213> ORGANISM: Artificial Sequence
<220> FEATURE:
<223> OTHER INFORMATION: CDR sequence

<400> SEQUENCE: 292

Lys Ile Tyr Pro Gly Asp Ser Tyr Thr Asn Tyr Ser Pro Ser Phe Gln
1               5                   10                  15

Gly
```

<210> SEQ ID NO 293
<211> LENGTH: 8
<212> TYPE: PRT
<213> ORGANISM: Artificial Sequence
<220> FEATURE:
<223> OTHER INFORMATION: CDR sequence

<400> SEQUENCE: 293

Arg Gly Tyr Gly Ile Phe Asp Tyr
1               5

<210> SEQ ID NO 294
<211> LENGTH: 11
<212> TYPE: PRT
<213> ORGANISM: Artificial Sequence
<220> FEATURE:
<223> OTHER INFORMATION: CDR sequence

<400> SEQUENCE: 294

Ser Gly Asp Asn Ile Gly Asp Gln Tyr Ala His
1               5                   10

<210> SEQ ID NO 295
<211> LENGTH: 7
<212> TYPE: PRT
<213> ORGANISM: Artificial Sequence
<220> FEATURE:
<223> OTHER INFORMATION: CDR sequence

<400> SEQUENCE: 295

Gln Asp Lys Asn Arg Pro Ser
1               5

<210> SEQ ID NO 296
<211> LENGTH: 11
<212> TYPE: PRT
<213> ORGANISM: Artificial Sequence
<220> FEATURE:
<223> OTHER INFORMATION: CDR sequence

<400> SEQUENCE: 296

Ala Thr Tyr Thr Gly Phe Gly Ser Leu Ala Val
1               5                   10

<210> SEQ ID NO 297
<211> LENGTH: 5
<212> TYPE: PRT
<213> ORGANISM: Artificial Sequence
<220> FEATURE:
<223> OTHER INFORMATION: CDR sequence

<400> SEQUENCE: 297

Asp Tyr Tyr Met Asn
1               5

<210> SEQ ID NO 298
<211> LENGTH: 19
<212> TYPE: PRT
<213> ORGANISM: Artificial Sequence
<220> FEATURE:
<223> OTHER INFORMATION: CDR sequence

<400> SEQUENCE: 298

Tyr Ile Ser Ser Ser Ala Ser Gly Ser Thr Ile Tyr Tyr Ala Asp Ser
1               5                   10                  15

Val Lys Gly

<210> SEQ ID NO 299
<211> LENGTH: 13
<212> TYPE: PRT
<213> ORGANISM: Artificial Sequence
<220> FEATURE:
<223> OTHER INFORMATION: CDR sequence

<400> SEQUENCE: 299

Val Val Pro Ala Gly Ser Gly Trp Arg Trp Phe Asp Pro
1               5                   10

<210> SEQ ID NO 300
<211> LENGTH: 14
<212> TYPE: PRT
<213> ORGANISM: Artificial Sequence
<220> FEATURE:
<223> OTHER INFORMATION: CDR sequence

<400> SEQUENCE: 300

Thr Gly Ile Ser Ser Asp Val Gly Ala Tyr Asp Tyr Val Ser
1               5                   10

<210> SEQ ID NO 301
<211> LENGTH: 7
<212> TYPE: PRT
<213> ORGANISM: Artificial Sequence
<220> FEATURE:
<223> OTHER INFORMATION: CDR sequence

<400> SEQUENCE: 301

Glu Val Ser Lys Arg Pro Ser
1               5

<210> SEQ ID NO 302
<211> LENGTH: 11
<212> TYPE: PRT
<213> ORGANISM: Artificial Sequence
<220> FEATURE:
<223> OTHER INFORMATION: CDR sequence

<400> SEQUENCE: 302

Ser Ser His Ala Gly Ser Asn Asn Phe Tyr Val
1               5                   10

<210> SEQ ID NO 303
<211> LENGTH: 7
<212> TYPE: PRT
<213> ORGANISM: Artificial Sequence
<220> FEATURE:
<223> OTHER INFORMATION: CDR sequence

<400> SEQUENCE: 303

Ser Asn Ser Ala Ala Trp Asn
1               5

<210> SEQ ID NO 304
<211> LENGTH: 18
<212> TYPE: PRT
<213> ORGANISM: Artificial Sequence
<220> FEATURE:
<223> OTHER INFORMATION: CDR sequence

<400> SEQUENCE: 304

Arg Thr Tyr Tyr Arg Ser Lys Trp Tyr Asn Asp Tyr Ala Pro Ser Val
1               5                   10                  15

Glu Ser

<210> SEQ ID NO 305
<211> LENGTH: 11
<212> TYPE: PRT
<213> ORGANISM: Artificial Sequence
<220> FEATURE:
<223> OTHER INFORMATION: CDR sequence

<400> SEQUENCE: 305

Asp Pro Pro Tyr Val Leu Ser Thr Phe Asp Ile
1               5                   10

<210> SEQ ID NO 306
<211> LENGTH: 13
<212> TYPE: PRT
<213> ORGANISM: Artificial Sequence
<220> FEATURE:
<223> OTHER INFORMATION: CDR sequence

<400> SEQUENCE: 306

Thr Arg Ser Ser Gly Asn Ile Ala Ser Phe Tyr Val Gln
1               5                   10

<210> SEQ ID NO 307
<211> LENGTH: 7
<212> TYPE: PRT
<213> ORGANISM: Artificial Sequence
<220> FEATURE:
<223> OTHER INFORMATION: CDR sequence

<400> SEQUENCE: 307

Glu Asp Asp Gln Arg Pro Ser
1               5

<210> SEQ ID NO 308
<211> LENGTH: 9
<212> TYPE: PRT
<213> ORGANISM: Artificial Sequence
<220> FEATURE:
<223> OTHER INFORMATION: CDR sequence

<400> SEQUENCE: 308

Gln Ser Tyr Asp Thr Asn Asn Val Ile
1               5

<210> SEQ ID NO 309
<211> LENGTH: 7
<212> TYPE: PRT
<213> ORGANISM: Artificial Sequence
<220> FEATURE:
<223> OTHER INFORMATION: CDR sequence

<400> SEQUENCE: 309

Ser Asn Ser Ala Ala Trp Asn
1               5

<210> SEQ ID NO 310
<211> LENGTH: 18
<212> TYPE: PRT
<213> ORGANISM: Artificial Sequence
<220> FEATURE:
<223> OTHER INFORMATION: CDR sequence

<400> SEQUENCE: 310

Arg Thr Tyr Tyr Arg Ser Arg Trp Tyr Ser Asp Tyr Ala Ser Ser Val
1               5                   10                  15

Glu Ser

<210> SEQ ID NO 311
<211> LENGTH: 11
<212> TYPE: PRT
<213> ORGANISM: Artificial Sequence
<220> FEATURE:
<223> OTHER INFORMATION: CDR sequence

<400> SEQUENCE: 311

Asp Pro Pro Tyr Val Leu Ser Thr Phe Asp Ile
1               5                   10

<210> SEQ ID NO 312
<211> LENGTH: 13
<212> TYPE: PRT
<213> ORGANISM: Artificial Sequence
<220> FEATURE:
<223> OTHER INFORMATION: CDR sequence

<400> SEQUENCE: 312

Thr Arg Ser Ser Gly Asn Ile Ala Ser Phe Tyr Val Gln
1               5                   10

<210> SEQ ID NO 313
<211> LENGTH: 7
<212> TYPE: PRT
<213> ORGANISM: Artificial Sequence
<220> FEATURE:
<223> OTHER INFORMATION: CDR sequence

<400> SEQUENCE: 313

Glu Asp Asp Gln Arg Pro Ser
1               5

<210> SEQ ID NO 314
<211> LENGTH: 9
<212> TYPE: PRT
<213> ORGANISM: Artificial Sequence
<220> FEATURE:
<223> OTHER INFORMATION: CDR sequence

<400> SEQUENCE: 314

Gln Ser Tyr Asp Thr Asn Asn Val Ile
1               5

<210> SEQ ID NO 315
<211> LENGTH: 7
<212> TYPE: PRT
<213> ORGANISM: Artificial Sequence
<220> FEATURE:
<223> OTHER INFORMATION: CDR sequence

<400> SEQUENCE: 315

Ser Asp Ser Ala Ala Trp Asn
1               5

<210> SEQ ID NO 316
<211> LENGTH: 18
<212> TYPE: PRT
<213> ORGANISM: Artificial Sequence
<220> FEATURE:
<223> OTHER INFORMATION: CDR sequence

<400> SEQUENCE: 316

Arg Thr Tyr Tyr Arg Ser Lys Trp Tyr Asn Asp Tyr Ala Pro Ser Val

```
1               5                   10                  15

Glu Ser

<210> SEQ ID NO 317
<211> LENGTH: 11
<212> TYPE: PRT
<213> ORGANISM: Artificial Sequence
<220> FEATURE:
<223> OTHER INFORMATION: CDR sequence

<400> SEQUENCE: 317

Asp Pro Pro Tyr Val Leu Ser Thr Phe Asp Ile
1               5                   10

<210> SEQ ID NO 318
<211> LENGTH: 13
<212> TYPE: PRT
<213> ORGANISM: Artificial Sequence
<220> FEATURE:
<223> OTHER INFORMATION: CDR sequence

<400> SEQUENCE: 318

Thr Arg Ser Ser Gly Asn Ile Ala Ser Phe Tyr Val Gln
1               5                   10

<210> SEQ ID NO 319
<211> LENGTH: 7
<212> TYPE: PRT
<213> ORGANISM: Artificial Sequence
<220> FEATURE:
<223> OTHER INFORMATION: CDR sequence

<400> SEQUENCE: 319

Glu Asp Asp Gln Arg Pro Ser
1               5

<210> SEQ ID NO 320
<211> LENGTH: 9
<212> TYPE: PRT
<213> ORGANISM: Artificial Sequence
<220> FEATURE:
<223> OTHER INFORMATION: CDR sequence

<400> SEQUENCE: 320

Gln Ser Tyr Asp Thr Asn Asn Val Ile
1               5

<210> SEQ ID NO 321
<211> LENGTH: 7
<212> TYPE: PRT
<213> ORGANISM: Artificial Sequence
<220> FEATURE:
<223> OTHER INFORMATION: CDR sequence

<400> SEQUENCE: 321

Ser Asn Ser Ala Ala Trp Asn
1               5

<210> SEQ ID NO 322
<211> LENGTH: 18
<212> TYPE: PRT
<213> ORGANISM: Artificial Sequence
<220> FEATURE:
<223> OTHER INFORMATION: CDR sequence

<400> SEQUENCE: 322
```

Arg Thr Tyr Tyr Arg Ser Lys Trp Tyr Asn Asp Tyr Ala Pro Ser Val
1               5                   10                  15

Glu Ser

<210> SEQ ID NO 323
<211> LENGTH: 11
<212> TYPE: PRT
<213> ORGANISM: Artificial Sequence
<220> FEATURE:
<223> OTHER INFORMATION: CDR sequence

<400> SEQUENCE: 323

Asp Pro Pro Tyr Val Leu Ser Thr Phe Asp Ile
1               5                   10

<210> SEQ ID NO 324
<211> LENGTH: 13
<212> TYPE: PRT
<213> ORGANISM: Artificial Sequence
<220> FEATURE:
<223> OTHER INFORMATION: CDR sequence

<400> SEQUENCE: 324

Thr Arg Ser Ser Gly Asn Ile Ala Ser Phe Tyr Val Gln
1               5                   10

<210> SEQ ID NO 325
<211> LENGTH: 7
<212> TYPE: PRT
<213> ORGANISM: Artificial Sequence
<220> FEATURE:
<223> OTHER INFORMATION: CDR sequence

<400> SEQUENCE: 325

Asp Asp Asp Gln Arg Pro Ser
1               5

<210> SEQ ID NO 326
<211> LENGTH: 9
<212> TYPE: PRT
<213> ORGANISM: Artificial Sequence
<220> FEATURE:
<223> OTHER INFORMATION: CDR sequence

<400> SEQUENCE: 326

Gln Ser Tyr Asp Thr Asn Asn Val Ile
1               5

<210> SEQ ID NO 327
<211> LENGTH: 7
<212> TYPE: PRT
<213> ORGANISM: Artificial Sequence
<220> FEATURE:
<223> OTHER INFORMATION: CDR sequence

<400> SEQUENCE: 327

Ser Asn Ser Ala Ala Trp Asn
1               5

<210> SEQ ID NO 328
<211> LENGTH: 18
<212> TYPE: PRT
<213> ORGANISM: Artificial Sequence
<220> FEATURE:
<223> OTHER INFORMATION: CDR sequence

<400> SEQUENCE: 328

Arg Thr Tyr Tyr Arg Ser Lys Trp Tyr Asn Asp Tyr Ala Pro Ser Val
1               5                   10                  15

Glu Ser

<210> SEQ ID NO 329
<211> LENGTH: 11
<212> TYPE: PRT
<213> ORGANISM: Artificial Sequence
<220> FEATURE:
<223> OTHER INFORMATION: CDR sequence

<400> SEQUENCE: 329

Asp Pro Pro Tyr Val Leu Ser Thr Phe Asp Ile
1               5                   10

<210> SEQ ID NO 330
<211> LENGTH: 13
<212> TYPE: PRT
<213> ORGANISM: Artificial Sequence
<220> FEATURE:
<223> OTHER INFORMATION: CDR sequence

<400> SEQUENCE: 330

Thr Arg Ser Ser Gly Asn Ile Ala Ser Phe Tyr Val Gln
1               5                   10

<210> SEQ ID NO 331
<211> LENGTH: 7
<212> TYPE: PRT
<213> ORGANISM: Artificial Sequence
<220> FEATURE:
<223> OTHER INFORMATION: CDR sequence

<400> SEQUENCE: 331

Glu Asp Asp Gln Arg Pro Ser
1               5

<210> SEQ ID NO 332
<211> LENGTH: 9
<212> TYPE: PRT
<213> ORGANISM: Artificial Sequence
<220> FEATURE:
<223> OTHER INFORMATION: CDR sequence

<400> SEQUENCE: 332

Gln Ser Tyr Asp Thr Asn Lys Val Ile
1               5

<210> SEQ ID NO 333
<211> LENGTH: 7
<212> TYPE: PRT
<213> ORGANISM: Artificial Sequence
<220> FEATURE:
<223> OTHER INFORMATION: CDR sequence

<400> SEQUENCE: 333

Ser Asn Ser Ala Ala Trp Asn
1               5

<210> SEQ ID NO 334
<211> LENGTH: 18
<212> TYPE: PRT
<213> ORGANISM: Artificial Sequence
<220> FEATURE:
<223> OTHER INFORMATION: CDR sequence

<400> SEQUENCE: 334

Arg Thr Tyr Tyr Arg Ser Lys Trp Tyr Asn Asp Tyr Ala Pro Ser Val
1               5                   10                  15

Glu Ser

<210> SEQ ID NO 335
<211> LENGTH: 11
<212> TYPE: PRT
<213> ORGANISM: Artificial Sequence
<220> FEATURE:
<223> OTHER INFORMATION: CDR sequence

<400> SEQUENCE: 335

Asp Pro Pro Tyr Val Leu Ser Thr Phe Asp Ile
1               5                   10

<210> SEQ ID NO 336
<211> LENGTH: 13
<212> TYPE: PRT
<213> ORGANISM: Artificial Sequence
<220> FEATURE:
<223> OTHER INFORMATION: CDR sequence

<400> SEQUENCE: 336

Thr Arg Ser Ser Gly Asn Ile Ala Ser Phe Tyr Val Gln
1               5                   10

<210> SEQ ID NO 337
<211> LENGTH: 7
<212> TYPE: PRT
<213> ORGANISM: Artificial Sequence
<220> FEATURE:
<223> OTHER INFORMATION: CDR sequence

<400> SEQUENCE: 337

Glu Asp Asp Gln Arg Pro Ser
1               5

<210> SEQ ID NO 338
<211> LENGTH: 9
<212> TYPE: PRT
<213> ORGANISM: Artificial Sequence
<220> FEATURE:
<223> OTHER INFORMATION: CDR sequence

<400> SEQUENCE: 338

Gln Ser Tyr Asp Ile Asn Lys Val Ile
1               5

<210> SEQ ID NO 339
<211> LENGTH: 7
<212> TYPE: PRT
<213> ORGANISM: Artificial Sequence
<220> FEATURE:
<223> OTHER INFORMATION: CDR sequence

<400> SEQUENCE: 339

Ser Asn Ser Ala Ala Trp Asn
1               5

<210> SEQ ID NO 340
<211> LENGTH: 18
<212> TYPE: PRT
<213> ORGANISM: Artificial Sequence
<220> FEATURE:
<223> OTHER INFORMATION: CDR sequence

<400> SEQUENCE: 340

Arg Thr Tyr Tyr Arg Ser Lys Trp Tyr Asn Asp Tyr Ala Pro Ser Val
1               5                   10                  15

Glu Ser

<210> SEQ ID NO 341
<211> LENGTH: 11
<212> TYPE: PRT
<213> ORGANISM: Artificial Sequence
<220> FEATURE:
<223> OTHER INFORMATION: CDR sequence

<400> SEQUENCE: 341

Asp Pro Pro Tyr Val Leu Ser Thr Phe Asp Ile
1               5                   10

<210> SEQ ID NO 342
<211> LENGTH: 13
<212> TYPE: PRT
<213> ORGANISM: Artificial Sequence
<220> FEATURE:
<223> OTHER INFORMATION: CDR sequence

<400> SEQUENCE: 342

Thr Arg Ser Ser Gly Asn Ile Ala Ser Phe Tyr Val Gln
1               5                   10

<210> SEQ ID NO 343
<211> LENGTH: 7
<212> TYPE: PRT
<213> ORGANISM: Artificial Sequence
<220> FEATURE:
<223> OTHER INFORMATION: CDR sequence

<400> SEQUENCE: 343

Asp Asp Asp Gln Arg Pro Ser
1               5

<210> SEQ ID NO 344
<211> LENGTH: 9
<212> TYPE: PRT
<213> ORGANISM: Artificial Sequence
<220> FEATURE:
<223> OTHER INFORMATION: CDR sequence

<400> SEQUENCE: 344

Gln Ser Tyr Asp Ile Asn Lys Val Ile
1               5

<210> SEQ ID NO 345
<211> LENGTH: 8
<212> TYPE: PRT
<213> ORGANISM: Artificial Sequence
<220> FEATURE:
<223> OTHER INFORMATION: CDR sequence

<400> SEQUENCE: 345

Gly Tyr Met Pro Asp Gly Tyr Tyr
1               5

<210> SEQ ID NO 346
<211> LENGTH: 8
<212> TYPE: PRT
<213> ORGANISM: Artificial Sequence
<220> FEATURE:

<223> OTHER INFORMATION: CDR sequence

<400> SEQUENCE: 346

Ile Asn Pro Arg Thr Gly Gly Thr
1               5

<210> SEQ ID NO 347
<211> LENGTH: 13
<212> TYPE: PRT
<213> ORGANISM: Artificial Sequence
<220> FEATURE:
<223> OTHER INFORMATION: CDR sequence

<400> SEQUENCE: 347

Ala Arg Glu Gly Ala Ala Phe Arg Leu Glu Leu Asp Ala
1               5                   10

<210> SEQ ID NO 348
<211> LENGTH: 6
<212> TYPE: PRT
<213> ORGANISM: Artificial Sequence
<220> FEATURE:
<223> OTHER INFORMATION: CDR sequence

<400> SEQUENCE: 348

Asn Ile Gly Ser Lys Ser
1               5

<210> SEQ ID NO 349
<211> LENGTH: 3
<212> TYPE: PRT
<213> ORGANISM: Artificial Sequence
<220> FEATURE:
<223> OTHER INFORMATION: CDR sequence

<400> SEQUENCE: 349

Tyr Asp Ser
1

<210> SEQ ID NO 350
<211> LENGTH: 9
<212> TYPE: PRT
<213> ORGANISM: Artificial Sequence
<220> FEATURE:
<223> OTHER INFORMATION: CDR sequence

<400> SEQUENCE: 350

Gln Val Trp Asp Ser Ser Ser Val Val
1               5

<210> SEQ ID NO 351
<211> LENGTH: 8
<212> TYPE: PRT
<213> ORGANISM: Artificial Sequence
<220> FEATURE:
<223> OTHER INFORMATION: CDR sequence

<400> SEQUENCE: 351

Gly Tyr Ser Phe Thr Gly Tyr Tyr
1               5

<210> SEQ ID NO 352
<211> LENGTH: 8
<212> TYPE: PRT
<213> ORGANISM: Artificial Sequence
<220> FEATURE:
<223> OTHER INFORMATION: CDR sequence

<400> SEQUENCE: 352

Val Asn Pro Lys Ser Gly Gly Thr
1               5

<210> SEQ ID NO 353
<211> LENGTH: 13
<212> TYPE: PRT
<213> ORGANISM: Artificial Sequence
<220> FEATURE:
<223> OTHER INFORMATION: CDR sequence

<400> SEQUENCE: 353

Ala Arg Glu Gly Trp Ala Arg Arg Ile Asp Leu Asp Glu
1               5                   10

<210> SEQ ID NO 354
<211> LENGTH: 6
<212> TYPE: PRT
<213> ORGANISM: Artificial Sequence
<220> FEATURE:
<223> OTHER INFORMATION: CDR sequence

<400> SEQUENCE: 354

Asn Ile Gly Ser Lys Ser
1               5

<210> SEQ ID NO 355
<211> LENGTH: 3
<212> TYPE: PRT
<213> ORGANISM: Artificial Sequence
<220> FEATURE:
<223> OTHER INFORMATION: CDR sequence

<400> SEQUENCE: 355

Tyr Asp Ser
1

<210> SEQ ID NO 356
<211> LENGTH: 9
<212> TYPE: PRT
<213> ORGANISM: Artificial Sequence
<220> FEATURE:
<223> OTHER INFORMATION: CDR sequence

<400> SEQUENCE: 356

Gln Val Trp Asp Ser Ser Ser Val Val
1               5

<210> SEQ ID NO 357
<211> LENGTH: 8
<212> TYPE: PRT
<213> ORGANISM: Artificial Sequence
<220> FEATURE:
<223> OTHER INFORMATION: CDR sequence

<400> SEQUENCE: 357

Gly Tyr Ser Phe Ser Gly Tyr Tyr
1               5

<210> SEQ ID NO 358
<211> LENGTH: 8
<212> TYPE: PRT
<213> ORGANISM: Artificial Sequence
<220> FEATURE:
<223> OTHER INFORMATION: CDR sequence

<400> SEQUENCE: 358

Val Asn Pro Met Ser Gly Gly Thr
1               5

<210> SEQ ID NO 359
<211> LENGTH: 13
<212> TYPE: PRT
<213> ORGANISM: Artificial Sequence
<220> FEATURE:
<223> OTHER INFORMATION: CDR sequence

<400> SEQUENCE: 359

Ala Arg Glu Gly Met Ala Met Arg Leu Glu Leu Asp Lys
1               5                   10

<210> SEQ ID NO 360
<211> LENGTH: 6
<212> TYPE: PRT
<213> ORGANISM: Artificial Sequence
<220> FEATURE:
<223> OTHER INFORMATION: CDR sequence

<400> SEQUENCE: 360

Asn Ile Gly Ser Lys Ser
1               5

<210> SEQ ID NO 361
<211> LENGTH: 3
<212> TYPE: PRT
<213> ORGANISM: Artificial Sequence
<220> FEATURE:
<223> OTHER INFORMATION: CDR sequence

<400> SEQUENCE: 361

Tyr Asp Ser
1

<210> SEQ ID NO 362
<211> LENGTH: 9
<212> TYPE: PRT
<213> ORGANISM: Artificial Sequence
<220> FEATURE:
<223> OTHER INFORMATION: CDR sequence

<400> SEQUENCE: 362

Gln Val Trp Asp Ser Ser Ser Val Val
1               5

<210> SEQ ID NO 363
<211> LENGTH: 8
<212> TYPE: PRT
<213> ORGANISM: Artificial Sequence
<220> FEATURE:
<223> OTHER INFORMATION: CDR sequence

<400> SEQUENCE: 363

Gly Tyr Asn Phe Gly Gly Tyr Tyr
1               5

<210> SEQ ID NO 364
<211> LENGTH: 8
<212> TYPE: PRT
<213> ORGANISM: Artificial Sequence
<220> FEATURE:
<223> OTHER INFORMATION: CDR sequence

<400> SEQUENCE: 364

Val Asn Pro His Ser Gly Gly Thr
1               5

<210> SEQ ID NO 365
<211> LENGTH: 13
<212> TYPE: PRT
<213> ORGANISM: Artificial Sequence
<220> FEATURE:
<223> OTHER INFORMATION: CDR sequence

<400> SEQUENCE: 365

Ala Arg Glu Gly Glu Ala Trp Gly Leu Asp Leu Asp Leu
1               5                   10

<210> SEQ ID NO 366
<211> LENGTH: 6
<212> TYPE: PRT
<213> ORGANISM: Artificial Sequence
<220> FEATURE:
<223> OTHER INFORMATION: CDR sequence

<400> SEQUENCE: 366

Asn Ile Gly Ser Lys Ser
1               5

<210> SEQ ID NO 367
<211> LENGTH: 3
<212> TYPE: PRT
<213> ORGANISM: Artificial Sequence
<220> FEATURE:
<223> OTHER INFORMATION: CDR sequence

<400> SEQUENCE: 367

Tyr Asp Ser
1

<210> SEQ ID NO 368
<211> LENGTH: 9
<212> TYPE: PRT
<213> ORGANISM: Artificial Sequence
<220> FEATURE:
<223> OTHER INFORMATION: CDR sequence

<400> SEQUENCE: 368

Gln Val Trp Asp Ser Ser Ser Val Val
1               5

<210> SEQ ID NO 369
<211> LENGTH: 8
<212> TYPE: PRT
<213> ORGANISM: Artificial Sequence
<220> FEATURE:
<223> OTHER INFORMATION: CDR sequence

<400> SEQUENCE: 369

Gly Tyr Asn Trp Thr Gly Tyr Tyr
1               5

<210> SEQ ID NO 370
<211> LENGTH: 8
<212> TYPE: PRT
<213> ORGANISM: Artificial Sequence
<220> FEATURE:
<223> OTHER INFORMATION: CDR sequence

<400> SEQUENCE: 370

Ile Asn Pro Met Ala Gly Gly Thr
1               5

<210> SEQ ID NO 371
<211> LENGTH: 13
<212> TYPE: PRT
<213> ORGANISM: Artificial Sequence
<220> FEATURE:
<223> OTHER INFORMATION: CDR sequence

<400> SEQUENCE: 371

Ala Arg Glu Gly Trp Ala Arg Gly Val Glu Leu Asp Met
1               5                   10

<210> SEQ ID NO 372
<211> LENGTH: 6
<212> TYPE: PRT
<213> ORGANISM: Artificial Sequence
<220> FEATURE:
<223> OTHER INFORMATION: CDR sequence

<400> SEQUENCE: 372

Asn Ile Gly Ser Lys Ser
1               5

<210> SEQ ID NO 373
<211> LENGTH: 3
<212> TYPE: PRT
<213> ORGANISM: Artificial Sequence
<220> FEATURE:
<223> OTHER INFORMATION: CDR sequence

<400> SEQUENCE: 373

Tyr Asp Ser
1

<210> SEQ ID NO 374
<211> LENGTH: 9
<212> TYPE: PRT
<213> ORGANISM: Artificial Sequence
<220> FEATURE:
<223> OTHER INFORMATION: CDR sequence

<400> SEQUENCE: 374

Gln Val Trp Asp Ser Ser Ser Val Val
1               5

<210> SEQ ID NO 375
<211> LENGTH: 8
<212> TYPE: PRT
<213> ORGANISM: Artificial Sequence
<220> FEATURE:
<223> OTHER INFORMATION: CDR sequence

<400> SEQUENCE: 375

Gly Tyr Gln Met Arg Gly Tyr Tyr
1               5

<210> SEQ ID NO 376
<211> LENGTH: 8
<212> TYPE: PRT
<213> ORGANISM: Artificial Sequence
<220> FEATURE:
<223> OTHER INFORMATION: CDR sequence

<400> SEQUENCE: 376

Ile Asn Pro Asn Ser Gly Gly Thr

```
1               5
```

<210> SEQ ID NO 377
<211> LENGTH: 13
<212> TYPE: PRT
<213> ORGANISM: Artificial Sequence
<220> FEATURE:
<223> OTHER INFORMATION: CDR sequence

<400> SEQUENCE: 377

```
Ala Arg Glu Gly Glu Ala Val Gly Leu Asp Leu Asp Tyr
1               5                   10
```

<210> SEQ ID NO 378
<211> LENGTH: 6
<212> TYPE: PRT
<213> ORGANISM: Artificial Sequence
<220> FEATURE:
<223> OTHER INFORMATION: CDR sequence

<400> SEQUENCE: 378

```
Asn Ile Gly Ser Lys Ser
1               5
```

<210> SEQ ID NO 379
<211> LENGTH: 3
<212> TYPE: PRT
<213> ORGANISM: Artificial Sequence
<220> FEATURE:
<223> OTHER INFORMATION: CDR sequence

<400> SEQUENCE: 379

```
Tyr Asp Ser
1
```

<210> SEQ ID NO 380
<211> LENGTH: 9
<212> TYPE: PRT
<213> ORGANISM: Artificial Sequence
<220> FEATURE:
<223> OTHER INFORMATION: CDR sequence

<400> SEQUENCE: 380

```
Gln Val Trp Asp Ser Ser Ser Val Val
1               5
```

<210> SEQ ID NO 381
<211> LENGTH: 8
<212> TYPE: PRT
<213> ORGANISM: Artificial Sequence
<220> FEATURE:
<223> OTHER INFORMATION: CDR sequence

<400> SEQUENCE: 381

```
Gly Tyr Asn Phe Gly Gly Tyr Tyr
1               5
```

<210> SEQ ID NO 382
<211> LENGTH: 8
<212> TYPE: PRT
<213> ORGANISM: Artificial Sequence
<220> FEATURE:
<223> OTHER INFORMATION: CDR sequence

<400> SEQUENCE: 382

```
Val Asn Pro Lys Ser Gly Gly Thr
1               5
```

```
<210> SEQ ID NO 383
<211> LENGTH: 13
<212> TYPE: PRT
<213> ORGANISM: Artificial Sequence
<220> FEATURE:
<223> OTHER INFORMATION: CDR sequence

<400> SEQUENCE: 383

Ala Arg Glu Gly Glu Ala Val Gly Leu Asp Leu Asp Tyr
1               5                   10

<210> SEQ ID NO 384
<211> LENGTH: 6
<212> TYPE: PRT
<213> ORGANISM: Artificial Sequence
<220> FEATURE:
<223> OTHER INFORMATION: CDR sequence

<400> SEQUENCE: 384

Asn Ile Gly Ser Lys Ser
1               5

<210> SEQ ID NO 385
<211> LENGTH: 3
<212> TYPE: PRT
<213> ORGANISM: Artificial Sequence
<220> FEATURE:
<223> OTHER INFORMATION: CDR sequence

<400> SEQUENCE: 385

Tyr Asp Ser
1

<210> SEQ ID NO 386
<211> LENGTH: 9
<212> TYPE: PRT
<213> ORGANISM: Artificial Sequence
<220> FEATURE:
<223> OTHER INFORMATION: CDR sequence

<400> SEQUENCE: 386

Gln Val Trp Asp Ser Ser Ser Val Val
1               5

<210> SEQ ID NO 387
<211> LENGTH: 8
<212> TYPE: PRT
<213> ORGANISM: Artificial Sequence
<220> FEATURE:
<223> OTHER INFORMATION: CDR sequence

<400> SEQUENCE: 387

Gly Tyr Thr Phe Thr Gly Tyr Tyr
1               5

<210> SEQ ID NO 388
<211> LENGTH: 8
<212> TYPE: PRT
<213> ORGANISM: Artificial Sequence
<220> FEATURE:
<223> OTHER INFORMATION: CDR sequence

<400> SEQUENCE: 388

Ile Asn Pro Asn Ser Gly Gly Thr
1               5
```

<210> SEQ ID NO 389
<211> LENGTH: 13
<212> TYPE: PRT
<213> ORGANISM: Artificial Sequence
<220> FEATURE:
<223> OTHER INFORMATION: CDR sequence

<400> SEQUENCE: 389

Ala Arg Glu Gly Glu Ala Val Gly Leu Asp Leu Asp Tyr
1               5                   10

<210> SEQ ID NO 390
<211> LENGTH: 6
<212> TYPE: PRT
<213> ORGANISM: Artificial Sequence
<220> FEATURE:
<223> OTHER INFORMATION: CDR sequence

<400> SEQUENCE: 390

Asn Ile Gly Ser Lys Ser
1               5

<210> SEQ ID NO 391
<211> LENGTH: 3
<212> TYPE: PRT
<213> ORGANISM: Artificial Sequence
<220> FEATURE:
<223> OTHER INFORMATION: CDR sequence

<400> SEQUENCE: 391

Tyr Asp Ser
1

<210> SEQ ID NO 392
<211> LENGTH: 9
<212> TYPE: PRT
<213> ORGANISM: Artificial Sequence
<220> FEATURE:
<223> OTHER INFORMATION: CDR sequence

<400> SEQUENCE: 392

Gln Val Trp Asp Ser Ser Ser Val Val
1               5

<210> SEQ ID NO 393
<211> LENGTH: 8
<212> TYPE: PRT
<213> ORGANISM: Artificial Sequence
<220> FEATURE:
<223> OTHER INFORMATION: CDR sequence

<400> SEQUENCE: 393

Gly Tyr Thr Phe Thr Gly Tyr Tyr
1               5

<210> SEQ ID NO 394
<211> LENGTH: 8
<212> TYPE: PRT
<213> ORGANISM: Artificial Sequence
<220> FEATURE:
<223> OTHER INFORMATION: CDR sequence

<400> SEQUENCE: 394

Ile Asn Pro Asn Ser Gly Gly Thr
1               5

```
<210> SEQ ID NO 395
<211> LENGTH: 13
<212> TYPE: PRT
<213> ORGANISM: Artificial Sequence
<220> FEATURE:
<223> OTHER INFORMATION: CDR sequence

<400> SEQUENCE: 395

Ala Arg Glu Gly Glu Ala Val Gly Leu Asp Leu Asp Tyr
1               5                   10

<210> SEQ ID NO 396
<211> LENGTH: 6
<212> TYPE: PRT
<213> ORGANISM: Artificial Sequence
<220> FEATURE:
<223> OTHER INFORMATION: CDR sequence

<400> SEQUENCE: 396

Asn Ile Gly Ser Lys Ser
1               5

<210> SEQ ID NO 397
<211> LENGTH: 3
<212> TYPE: PRT
<213> ORGANISM: Artificial Sequence
<220> FEATURE:
<223> OTHER INFORMATION: CDR sequence

<400> SEQUENCE: 397

Tyr Asp Ser
1

<210> SEQ ID NO 398
<211> LENGTH: 9
<212> TYPE: PRT
<213> ORGANISM: Artificial Sequence
<220> FEATURE:
<223> OTHER INFORMATION: CDR sequence

<400> SEQUENCE: 398

Gln Val Trp Asp Ser Ser Ser Val Val
1               5

<210> SEQ ID NO 399
<211> LENGTH: 10
<212> TYPE: PRT
<213> ORGANISM: Artificial Sequence
<220> FEATURE:
<223> OTHER INFORMATION: CDR sequence

<400> SEQUENCE: 399

Gly Tyr Thr Phe Thr Ser Tyr Tyr Ile Tyr
1               5                   10

<210> SEQ ID NO 400
<211> LENGTH: 17
<212> TYPE: PRT
<213> ORGANISM: Artificial Sequence
<220> FEATURE:
<223> OTHER INFORMATION: CDR sequence

<400> SEQUENCE: 400

Asn Ile Trp Pro Gly Asn Gly Gly Thr Phe Tyr Gly Glu Lys Phe Met
1               5                   10                  15

Gly
```

<210> SEQ ID NO 401
<211> LENGTH: 12
<212> TYPE: PRT
<213> ORGANISM: Artificial Sequence
<220> FEATURE:
<223> OTHER INFORMATION: CDR sequence

<400> SEQUENCE: 401

Arg Pro Asp Tyr Ser Gly Asp Asp Tyr Phe Asp Tyr
1               5                   10

<210> SEQ ID NO 402
<211> LENGTH: 13
<212> TYPE: PRT
<213> ORGANISM: Artificial Sequence
<220> FEATURE:
<223> OTHER INFORMATION: CDR sequence

<400> SEQUENCE: 402

Lys Leu Asn Ser Gly Asn Ile Gly Ser Tyr Tyr Val His
1               5                   10

<210> SEQ ID NO 403
<211> LENGTH: 7
<212> TYPE: PRT
<213> ORGANISM: Artificial Sequence
<220> FEATURE:
<223> OTHER INFORMATION: CDR sequence

<400> SEQUENCE: 403

Arg Asp Asp Lys Arg Pro Asp
1               5

<210> SEQ ID NO 404
<211> LENGTH: 10
<212> TYPE: PRT
<213> ORGANISM: Artificial Sequence
<220> FEATURE:
<223> OTHER INFORMATION: CDR sequence

<400> SEQUENCE: 404

His Ser Tyr Asp Ser Thr Ile Thr Pro Val
1               5                   10

<210> SEQ ID NO 405
<211> LENGTH: 10
<212> TYPE: PRT
<213> ORGANISM: Artificial Sequence
<220> FEATURE:
<223> OTHER INFORMATION: CDR sequence

<400> SEQUENCE: 405

Asp Tyr Thr Phe Asn Asp Tyr Trp Val Ser
1               5                   10

<210> SEQ ID NO 406
<211> LENGTH: 17
<212> TYPE: PRT
<213> ORGANISM: Artificial Sequence
<220> FEATURE:
<223> OTHER INFORMATION: CDR sequence

<400> SEQUENCE: 406

Glu Ile Tyr Pro Asn Ser Gly Ala Thr Asn Phe Asn Gly Lys Phe Arg
1               5                   10                  15

Gly

```
<210> SEQ ID NO 407
<211> LENGTH: 9
<212> TYPE: PRT
<213> ORGANISM: Artificial Sequence
<220> FEATURE:
<223> OTHER INFORMATION: CDR sequence

<400> SEQUENCE: 407

Glu Tyr Thr Arg Asp Trp Phe Ala Tyr
1               5

<210> SEQ ID NO 408
<211> LENGTH: 16
<212> TYPE: PRT
<213> ORGANISM: Artificial Sequence
<220> FEATURE:
<223> OTHER INFORMATION: CDR sequence

<400> SEQUENCE: 408

Arg Ser Ser Gln Ser Leu Leu Asp Ser Asp Gly Asn Thr Tyr Leu Tyr
1               5                   10                  15

<210> SEQ ID NO 409
<211> LENGTH: 7
<212> TYPE: PRT
<213> ORGANISM: Artificial Sequence
<220> FEATURE:
<223> OTHER INFORMATION: CDR sequence

<400> SEQUENCE: 409

Leu Val Ser Asn Leu Gly Ser
1               5

<210> SEQ ID NO 410
<211> LENGTH: 9
<212> TYPE: PRT
<213> ORGANISM: Artificial Sequence
<220> FEATURE:
<223> OTHER INFORMATION: CDR sequence

<400> SEQUENCE: 410

Met Gln Pro Thr His Ala Pro Tyr Thr
1               5

<210> SEQ ID NO 411
<211> LENGTH: 10
<212> TYPE: PRT
<213> ORGANISM: Artificial Sequence
<220> FEATURE:
<223> OTHER INFORMATION: CDR sequence

<400> SEQUENCE: 411

Asp Tyr Thr Phe Asn Asp Tyr Trp Val Ser
1               5                   10

<210> SEQ ID NO 412
<211> LENGTH: 17
<212> TYPE: PRT
<213> ORGANISM: Artificial Sequence
<220> FEATURE:
<223> OTHER INFORMATION: CDR sequence

<400> SEQUENCE: 412

Glu Ile Tyr Pro Asn Ser Gly Ala Thr Asn Phe Asn Gly Lys Phe Arg
1               5                   10                  15
```

Gly

<210> SEQ ID NO 413
<211> LENGTH: 9
<212> TYPE: PRT
<213> ORGANISM: Artificial Sequence
<220> FEATURE:
<223> OTHER INFORMATION: CDR sequence

<400> SEQUENCE: 413

Glu Tyr Thr Arg Asp Trp Phe Ala Tyr
1               5

<210> SEQ ID NO 414
<211> LENGTH: 16
<212> TYPE: PRT
<213> ORGANISM: Artificial Sequence
<220> FEATURE:
<223> OTHER INFORMATION: CDR sequence

<400> SEQUENCE: 414

Arg Ser Ser Gln Ser Leu Leu Asp Ser Asp Gly Asn Thr Tyr Leu Tyr
1               5                   10                  15

<210> SEQ ID NO 415
<211> LENGTH: 7
<212> TYPE: PRT
<213> ORGANISM: Artificial Sequence
<220> FEATURE:
<223> OTHER INFORMATION: CDR sequence

<400> SEQUENCE: 415

Leu Val Ser Asn Leu Gly Ser
1               5

<210> SEQ ID NO 416
<211> LENGTH: 8
<212> TYPE: PRT
<213> ORGANISM: Artificial Sequence
<220> FEATURE:
<223> OTHER INFORMATION: CDR sequence

<400> SEQUENCE: 416

Gln Pro Thr His Ala Pro Tyr Thr
1               5

<210> SEQ ID NO 417
<211> LENGTH: 8
<212> TYPE: PRT
<213> ORGANISM: Artificial Sequence
<220> FEATURE:
<223> OTHER INFORMATION: CDR sequence

<400> SEQUENCE: 417

Gly Phe Thr Phe Gly Tyr Ser Tyr
1               5

<210> SEQ ID NO 418
<211> LENGTH: 8
<212> TYPE: PRT
<213> ORGANISM: Artificial Sequence
<220> FEATURE:
<223> OTHER INFORMATION: CDR sequence

<400> SEQUENCE: 418

Ile Gly Ser Gly Ser Ser Tyr Thr
1               5

```
<210> SEQ ID NO 419
<211> LENGTH: 11
<212> TYPE: PRT
<213> ORGANISM: Artificial Sequence
<220> FEATURE:
<223> OTHER INFORMATION: CDR sequence

<400> SEQUENCE: 419

Ala Arg Val Tyr Ser Ser Pro Gly Ile Asp Tyr
1               5                   10

<210> SEQ ID NO 420
<211> LENGTH: 6
<212> TYPE: PRT
<213> ORGANISM: Artificial Sequence
<220> FEATURE:
<223> OTHER INFORMATION: CDR sequence

<400> SEQUENCE: 420

Gln Ser Ile Ser Ser Tyr
1               5

<210> SEQ ID NO 421
<211> LENGTH: 3
<212> TYPE: PRT
<213> ORGANISM: Artificial Sequence
<220> FEATURE:
<223> OTHER INFORMATION: CDR sequence

<400> SEQUENCE: 421

Ala Ala Ser
1

<210> SEQ ID NO 422
<211> LENGTH: 10
<212> TYPE: PRT
<213> ORGANISM: Artificial Sequence
<220> FEATURE:
<223> OTHER INFORMATION: CDR sequence

<400> SEQUENCE: 422

Gln Gln Tyr Tyr Thr Trp Val Pro Phe Thr
1               5                   10

<210> SEQ ID NO 423
<211> LENGTH: 8
<212> TYPE: PRT
<213> ORGANISM: Artificial Sequence
<220> FEATURE:
<223> OTHER INFORMATION: CDR sequence

<400> SEQUENCE: 423

Gly Phe Asn Phe Gly Tyr Ser Tyr
1               5

<210> SEQ ID NO 424
<211> LENGTH: 8
<212> TYPE: PRT
<213> ORGANISM: Artificial Sequence
<220> FEATURE:
<223> OTHER INFORMATION: CDR sequence

<400> SEQUENCE: 424

Ile Gly Ser Thr Ser Ser His Thr
1               5
```

```
<210> SEQ ID NO 425
<211> LENGTH: 11
<212> TYPE: PRT
<213> ORGANISM: Artificial Sequence
<220> FEATURE:
<223> OTHER INFORMATION: CDR sequence

<400> SEQUENCE: 425

Ala Arg Val Tyr Ser Ser Pro Gly Ile Asp Tyr
1               5                   10

<210> SEQ ID NO 426
<211> LENGTH: 6
<212> TYPE: PRT
<213> ORGANISM: Artificial Sequence
<220> FEATURE:
<223> OTHER INFORMATION: CDR sequence

<400> SEQUENCE: 426

Gln Ser Ile Gly Ser Thr
1               5

<210> SEQ ID NO 427
<211> LENGTH: 3
<212> TYPE: PRT
<213> ORGANISM: Artificial Sequence
<220> FEATURE:
<223> OTHER INFORMATION: CDR sequence

<400> SEQUENCE: 427

Gly Ala Ser
1

<210> SEQ ID NO 428
<211> LENGTH: 10
<212> TYPE: PRT
<213> ORGANISM: Artificial Sequence
<220> FEATURE:
<223> OTHER INFORMATION: CDR sequence

<400> SEQUENCE: 428

Gln Gln Tyr Tyr Thr Trp Val Pro Phe Thr
1               5                   10

<210> SEQ ID NO 429
<211> LENGTH: 5
<212> TYPE: PRT
<213> ORGANISM: Artificial Sequence
<220> FEATURE:
<223> OTHER INFORMATION: CDR sequence

<400> SEQUENCE: 429

Asp Tyr Ala Met His
1               5

<210> SEQ ID NO 430
<211> LENGTH: 17
<212> TYPE: PRT
<213> ORGANISM: Artificial Sequence
<220> FEATURE:
<223> OTHER INFORMATION: CDR sequence

<400> SEQUENCE: 430

Gly Ile Ser Thr Tyr Asn Gly Asp Ala Ser Tyr Asn Gln Lys Phe Lys
1               5                   10                  15

Gly
```

```
<210> SEQ ID NO 431
<211> LENGTH: 9
<212> TYPE: PRT
<213> ORGANISM: Artificial Sequence
<220> FEATURE:
<223> OTHER INFORMATION: CDR sequence

<400> SEQUENCE: 431

Ser Asn Tyr Gly Tyr Ala Met Asp Tyr
1               5

<210> SEQ ID NO 432
<211> LENGTH: 17
<212> TYPE: PRT
<213> ORGANISM: Artificial Sequence
<220> FEATURE:
<223> OTHER INFORMATION: CDR sequence

<400> SEQUENCE: 432

Lys Ser Ser Gln Ser Leu Leu Tyr Ser Ser Asn Gln Lys Asn Tyr Leu
1               5                   10                  15

Ala

<210> SEQ ID NO 433
<211> LENGTH: 7
<212> TYPE: PRT
<213> ORGANISM: Artificial Sequence
<220> FEATURE:
<223> OTHER INFORMATION: CDR sequence

<400> SEQUENCE: 433

Trp Ala Ser Thr Arg Glu Ser
1               5

<210> SEQ ID NO 434
<211> LENGTH: 9
<212> TYPE: PRT
<213> ORGANISM: Artificial Sequence
<220> FEATURE:
<223> OTHER INFORMATION: CDR sequence

<400> SEQUENCE: 434

Gln Gln Tyr Leu Ser Tyr Pro Trp Thr
1               5

<210> SEQ ID NO 435
<211> LENGTH: 5
<212> TYPE: PRT
<213> ORGANISM: Artificial Sequence
<220> FEATURE:
<223> OTHER INFORMATION: CDR sequence

<400> SEQUENCE: 435

Thr Tyr Ala Met His
1               5

<210> SEQ ID NO 436
<211> LENGTH: 17
<212> TYPE: PRT
<213> ORGANISM: Artificial Sequence
<220> FEATURE:
<223> OTHER INFORMATION: CDR sequence

<400> SEQUENCE: 436

Tyr Ile Asn Pro Thr Thr Val Tyr Thr Ile Tyr Asn Gln Lys Phe Lys
```

```
1               5                  10                  15

Asp

<210> SEQ ID NO 437
<211> LENGTH: 9
<212> TYPE: PRT
<213> ORGANISM: Artificial Sequence
<220> FEATURE:
<223> OTHER INFORMATION: CDR sequence

<400> SEQUENCE: 437

Leu Gly Gly His Trp Tyr Phe Asp Val
1               5

<210> SEQ ID NO 438
<211> LENGTH: 15
<212> TYPE: PRT
<213> ORGANISM: Artificial Sequence
<220> FEATURE:
<223> OTHER INFORMATION: CDR sequence

<400> SEQUENCE: 438

Arg Ala Ser Glu Ser Val Asp Asn Tyr Gly Ile Ser Phe Met Asn
1               5                  10                  15

<210> SEQ ID NO 439
<211> LENGTH: 7
<212> TYPE: PRT
<213> ORGANISM: Artificial Sequence
<220> FEATURE:
<223> OTHER INFORMATION: CDR sequence

<400> SEQUENCE: 439

Ser Ala Ser Asn Gln Gly Ser
1               5

<210> SEQ ID NO 440
<211> LENGTH: 9
<212> TYPE: PRT
<213> ORGANISM: Artificial Sequence
<220> FEATURE:
<223> OTHER INFORMATION: CDR sequence

<400> SEQUENCE: 440

Gln Gln Ser Lys Glu Val Pro Trp Thr
1               5

<210> SEQ ID NO 441
<211> LENGTH: 5
<212> TYPE: PRT
<213> ORGANISM: Artificial Sequence
<220> FEATURE:
<223> OTHER INFORMATION: CDR sequence

<400> SEQUENCE: 441

Gly Tyr Trp Ile Glu
1               5

<210> SEQ ID NO 442
<211> LENGTH: 17
<212> TYPE: PRT
<213> ORGANISM: Artificial Sequence
<220> FEATURE:
<223> OTHER INFORMATION: CDR sequence

<400> SEQUENCE: 442
```

```
Glu Ile Leu Pro Gly Gly Gly Thr Val Tyr Tyr Asn Glu Lys Phe Lys
1               5                   10                  15

Gly

<210> SEQ ID NO 443
<211> LENGTH: 8
<212> TYPE: PRT
<213> ORGANISM: Artificial Sequence
<220> FEATURE:
<223> OTHER INFORMATION: CDR sequence

<400> SEQUENCE: 443

Trp Gly Arg Ser Trp Phe Thr His
1               5

<210> SEQ ID NO 444
<211> LENGTH: 16
<212> TYPE: PRT
<213> ORGANISM: Artificial Sequence
<220> FEATURE:
<223> OTHER INFORMATION: CDR sequence

<400> SEQUENCE: 444

Arg Ser Ser Gln Ser Ile Val His Ser Asn Gly Asn Thr Tyr Leu Glu
1               5                   10                  15

<210> SEQ ID NO 445
<211> LENGTH: 7
<212> TYPE: PRT
<213> ORGANISM: Artificial Sequence
<220> FEATURE:
<223> OTHER INFORMATION: CDR sequence

<400> SEQUENCE: 445

Glu Val Ser Asn Arg Phe Ser
1               5

<210> SEQ ID NO 446
<211> LENGTH: 9
<212> TYPE: PRT
<213> ORGANISM: Artificial Sequence
<220> FEATURE:
<223> OTHER INFORMATION: CDR sequence

<400> SEQUENCE: 446

Phe Gln Gly Ser His Val Pro Arg Thr
1               5

<210> SEQ ID NO 447
<211> LENGTH: 5
<212> TYPE: PRT
<213> ORGANISM: Artificial Sequence
<220> FEATURE:
<223> OTHER INFORMATION: CDR sequence

<400> SEQUENCE: 447

Ser Tyr Trp Met Asp
1               5

<210> SEQ ID NO 448
<211> LENGTH: 17
<212> TYPE: PRT
<213> ORGANISM: Artificial Sequence
<220> FEATURE:
<223> OTHER INFORMATION: CDR sequence

<400> SEQUENCE: 448
```

```
Asn Ile Tyr Pro Asp Ser Gly Gly Thr Asn Tyr Ala Glu Lys Phe Lys
1               5                   10                  15

Ser

<210> SEQ ID NO 449
<211> LENGTH: 12
<212> TYPE: PRT
<213> ORGANISM: Artificial Sequence
<220> FEATURE:
<223> OTHER INFORMATION: CDR sequence

<400> SEQUENCE: 449

Glu Glu Ala Leu Gly Gly Tyr Tyr Glu Leu Thr Tyr
1               5                   10

<210> SEQ ID NO 450
<211> LENGTH: 15
<212> TYPE: PRT
<213> ORGANISM: Artificial Sequence
<220> FEATURE:
<223> OTHER INFORMATION: CDR sequence

<400> SEQUENCE: 450

Arg Ala Ser Gln Ser Val Ser Thr Ser Ser Tyr Ser Tyr Met His
1               5                   10                  15

<210> SEQ ID NO 451
<211> LENGTH: 7
<212> TYPE: PRT
<213> ORGANISM: Artificial Sequence
<220> FEATURE:
<223> OTHER INFORMATION: CDR sequence

<400> SEQUENCE: 451

Tyr Ala Ser Asn Leu Glu Ser
1               5

<210> SEQ ID NO 452
<211> LENGTH: 9
<212> TYPE: PRT
<213> ORGANISM: Artificial Sequence
<220> FEATURE:
<223> OTHER INFORMATION: CDR sequence

<400> SEQUENCE: 452

Gln His Ser Trp Glu Ile Pro Tyr Thr
1               5

<210> SEQ ID NO 453
<211> LENGTH: 5
<212> TYPE: PRT
<213> ORGANISM: Artificial Sequence
<220> FEATURE:
<223> OTHER INFORMATION: CDR sequence

<400> SEQUENCE: 453

Asn Tyr Trp Leu Gly
1               5

<210> SEQ ID NO 454
<211> LENGTH: 17
<212> TYPE: PRT
<213> ORGANISM: Artificial Sequence
<220> FEATURE:
<223> OTHER INFORMATION: CDR sequence
```

-continued

```
<400> SEQUENCE: 454

Asp Ile Tyr Pro Gly Asn Gly Asn Asn Tyr Tyr Ser Glu Lys Phe Lys
1               5                   10                  15

Asp

<210> SEQ ID NO 455
<211> LENGTH: 10
<212> TYPE: PRT
<213> ORGANISM: Artificial Sequence
<220> FEATURE:
<223> OTHER INFORMATION: CDR sequence

<400> SEQUENCE: 455

His Gly Ser Phe Arg Ser Ala Met Asp Tyr
1               5                   10

<210> SEQ ID NO 456
<211> LENGTH: 11
<212> TYPE: PRT
<213> ORGANISM: Artificial Sequence
<220> FEATURE:
<223> OTHER INFORMATION: CDR sequence

<400> SEQUENCE: 456

Arg Ala Ser Glu Asn Ile Tyr Ser Tyr Leu Ala
1               5                   10

<210> SEQ ID NO 457
<211> LENGTH: 7
<212> TYPE: PRT
<213> ORGANISM: Artificial Sequence
<220> FEATURE:
<223> OTHER INFORMATION: CDR sequence

<400> SEQUENCE: 457

Asn Ala Lys Thr Leu Ala Asp
1               5

<210> SEQ ID NO 458
<211> LENGTH: 9
<212> TYPE: PRT
<213> ORGANISM: Artificial Sequence
<220> FEATURE:
<223> OTHER INFORMATION: CDR sequence

<400> SEQUENCE: 458

Gln His His Tyr Gly Thr Pro Pro Thr
1               5

<210> SEQ ID NO 459
<211> LENGTH: 121
<212> TYPE: PRT
<213> ORGANISM: Artificial Sequence
<220> FEATURE:
<223> OTHER INFORMATION: VH

<400> SEQUENCE: 459

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Ser Pro Glu Lys Gly Leu Glu Trp Ile
            35                  40                  45

Gly Glu Ile Asn His Gly Gly Tyr Val Thr Tyr Asn Pro Ser Leu Glu
```

```
                 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                     85                  90                  95

Arg Asp Tyr Gly Pro Gly Asn Tyr Asp Trp Tyr Phe Asp Leu Trp Gly
                100                 105                 110

Arg Gly Thr Leu Val Thr Val Ser Ser
            115                 120

<210> SEQ ID NO 460
<211> LENGTH: 109
<212> TYPE: PRT
<213> ORGANISM: Artificial Sequence
<220> FEATURE:
<223> OTHER INFORMATION: VL

<400> SEQUENCE: 460

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Ala Leu Thr Phe Gly Gly Gly Thr Lys Val Glu Ile Lys
                100                 105

<210> SEQ ID NO 461
<211> LENGTH: 114
<212> TYPE: PRT
<213> ORGANISM: Artificial Sequence
<220> FEATURE:
<223> OTHER INFORMATION: VH

<400> SEQUENCE: 461

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
                 20                  25                  30

Trp Met Ser Trp Val Arg Gln Ala Pro Gly Lys Gly Leu Glu Trp Val
             35                  40                  45

Ala Asp Ile Lys Asn Asp Gly Ser Tyr Thr Asn Tyr Ala Pro Ser Leu
         50                  55                  60

Thr Asn Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Leu Thr Gly Thr Trp Gly Gln Gly Thr Met Val Thr Val
                100                 105                 110

Ser Ser
```

```
<210> SEQ ID NO 462
<211> LENGTH: 113
<212> TYPE: PRT
<213> ORGANISM: Artificial Sequence
<220> FEATURE:
<223> OTHER INFORMATION: VL

<400> SEQUENCE: 462

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Leu Leu Ser Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Tyr Ala Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Leu Gln
                85                  90                  95

Tyr Asp Arg Tyr Pro Phe Thr Phe Gly Gln Gly Thr Lys Leu Glu Ile
            100                 105                 110

Lys

<210> SEQ ID NO 463
<211> LENGTH: 116
<212> TYPE: PRT
<213> ORGANISM: Artificial Sequence
<220> FEATURE:
<223> OTHER INFORMATION: VH

<400> SEQUENCE: 463

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115

<210> SEQ ID NO 464
<211> LENGTH: 108
<212> TYPE: PRT
<213> ORGANISM: Artificial Sequence
<220> FEATURE:
<223> OTHER INFORMATION: VL

<400> SEQUENCE: 464

Ser Tyr Glu Leu Thr Gln Pro Pro Ser Val Ser Val Pro Gly Gln
1               5                   10                  15
```

```
Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
            100                 105
```

<210> SEQ ID NO 465
<211> LENGTH: 124
<212> TYPE: PRT
<213> ORGANISM: Artificial Sequence
<220> FEATURE:
<223> OTHER INFORMATION: VH

<400> SEQUENCE: 465

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asp Tyr
            20                  25                  30

Tyr Met Asn Trp Ile Arg Gln Ala Pro Gly Lys Gly Leu Glu Trp Val
        35                  40                  45

Ser Tyr Ile Ser Ser Ser Ala Ser Gly Ser Thr Ile Tyr Tyr Ala Asp
50                  55                  60

Ser Val Lys Gly Arg Phe Thr Ile Ser Arg Asp Asn Ala Asn Asn Ser
65                  70                  75                  80

Leu Tyr Leu His Met Asp Ser Leu Arg Ala Glu Asp Thr Ala Ile Tyr
                85                  90                  95

Phe Cys Ala Arg Val Val Pro Ala Gly Ser Gly Trp Arg Trp Phe Asp
            100                 105                 110

Pro Trp Gly Gln Gly Thr Leu Val Thr Val Ser Ser
        115                 120
```

<210> SEQ ID NO 466
<211> LENGTH: 111
<212> TYPE: PRT
<213> ORGANISM: Artificial Sequence
<220> FEATURE:
<223> OTHER INFORMATION: VL

<400> SEQUENCE: 466

```
Gln Ser Val Leu Ile Gln Pro Pro Ser Ala Ser Gly Ser Pro Gly Gln
1               5                   10                  15

Ser Val Thr Ile Ser Cys Thr Gly Ile Ser Ser Asp Val Gly Ala Tyr
            20                  25                  30

Asp Tyr Val Ser Trp Tyr Gln Gln His Pro Gly Lys Val Pro Lys Leu
        35                  40                  45

Met Ile Tyr Glu Val Ser Lys Arg Pro Ser Gly Val Pro Asp Arg Phe
50                  55                  60

Ser Gly Ser Lys Ser Gly Asp Thr Ala Ser Leu Thr Val Ser Gly Leu
65                  70                  75                  80

Gln Ala Glu Asp Glu Ala Asp Tyr Tyr Cys Ser Ser His Ala Gly Ser
                85                  90                  95
```

```
Asn Asn Phe Tyr Val Phe Gly Thr Gly Thr Lys Leu Thr Val Leu
                100                 105                 110
```

<210> SEQ ID NO 467
<211> LENGTH: 123
<212> TYPE: PRT
<213> ORGANISM: Artificial Sequence
<220> FEATURE:
<223> OTHER INFORMATION: VH

<400> SEQUENCE: 467

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Pro Ser Val Glu Ser Arg Ile Thr Ile Asn Pro Asp Thr Ser Lys Asn
65                  70                  75                  80

Gln Phe Ser Leu Gln Leu Ser Ser Val Thr Pro Glu Asp Thr Ala Val
                85                  90                  95

Tyr Tyr Cys Ala Arg Asp Pro Tyr Val Leu Ser Thr Phe Asp Ile
                100                 105                 110

Trp Gly Gln Gly Thr Met Val Thr Val Ser Ser
            115                 120
```

<210> SEQ ID NO 468
<211> LENGTH: 110
<212> TYPE: PRT
<213> ORGANISM: Artificial Sequence
<220> FEATURE:
<223> OTHER INFORMATION: VL

<400> SEQUENCE: 468

```
Asn Phe Met Leu Thr Gln Pro Pro Ser Val Ser Glu Ser Pro Gly Lys
1               5                   10                  15

Thr Val Thr Ile Ser Cys Thr Arg Ser Ser Gly Asn Ile Ala Ser Phe
                20                  25                  30

Tyr Val Gln Trp Phe Gln Gln Arg Pro Gly Ser Ser Pro Thr Thr Val
            35                  40                  45

Ile Tyr Glu Asp Asp Gln Arg Pro Ser Gly Val Pro Asp Arg Phe Ser
        50                  55                  60

Gly Ser Ile Asp Arg Ser Ser Asn Ser Ala Ser Leu Thr Ile Ser Gly
65                  70                  75                  80

Leu Thr Thr Asp Asp Glu Ala Asp Tyr Tyr Cys Gln Ser Tyr Asp Thr
                85                  90                  95

Asn Asn Val Ile Phe Gly Gly Gly Thr Lys Leu Thr Val Leu
                100                 105                 110
```

<210> SEQ ID NO 469
<211> LENGTH: 123
<212> TYPE: PRT
<213> ORGANISM: Artificial Sequence
<220> FEATURE:
<223> OTHER INFORMATION: VH

<400> SEQUENCE: 469

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Arg Trp Tyr Ser Asp Tyr Ala
    50                  55                  60

Ser Ser Val Glu Ser Arg Ile Thr Ile Asn Pro Asp Thr Ser Lys Asn
65                  70                  75                  80

Gln Phe Ser Leu Gln Leu Ser Ser Val Thr Pro Glu Asp Thr Ala Val
            85                  90                  95

Tyr Tyr Cys Ala Arg Asp Pro Pro Tyr Val Leu Ser Thr Phe Asp Ile
            100                 105                 110

Trp Gly Gln Gly Thr Met Val Thr Val Ser Ser
            115                 120

<210> SEQ ID NO 470
<211> LENGTH: 110
<212> TYPE: PRT
<213> ORGANISM: Artificial Sequence
<220> FEATURE:
<223> OTHER INFORMATION: VL

<400> SEQUENCE: 470

Asn Phe Met Leu Thr Gln Pro Pro Ser Val Ser Glu Ser Pro Gly Lys
1               5                   10                  15

Thr Val Thr Ile Ser Cys Thr Arg Ser Ser Gly Asn Ile Ala Ser Phe
            20                  25                  30

Tyr Val Gln Trp Phe Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Arg Ser Ser Asn Ser Ala Ser Leu Thr Ile Ser Gly
65                  70                  75                  80

Leu Thr Thr Asp Asp Glu Ala Asp Tyr Tyr Cys Gln Ser Tyr Asp Thr
            85                  90                  95

Asn Asn Val Ile Phe Gly Gly Gly Thr Lys Leu Thr Val Leu
            100                 105                 110

<210> SEQ ID NO 471
<211> LENGTH: 123
<212> TYPE: PRT
<213> ORGANISM: Artificial Sequence
<220> FEATURE:
<223> OTHER INFORMATION: VH

<400> SEQUENCE: 471

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Pro Ser Val Glu Ser Arg Ile Thr Ile Asn Pro Asp Thr Ser Lys Asn
65                  70                  75                  80

```
Gln Phe Ser Leu Gln Leu Ser Ser Val Thr Pro Glu Asp Thr Ala Val
                85                  90                  95

Tyr Tyr Cys Ala Arg Asp Pro Pro Tyr Val Leu Ser Thr Phe Asp Ile
            100                 105                 110

Trp Gly Gln Gly Thr Met Val Thr Val Ser Ser
        115                 120

<210> SEQ ID NO 472
<211> LENGTH: 110
<212> TYPE: PRT
<213> ORGANISM: Artificial Sequence
<220> FEATURE:
<223> OTHER INFORMATION: VL

<400> SEQUENCE: 472

Asn Phe Met Leu Thr Gln Pro Pro Ser Val Ser Glu Ser Pro Gly Lys
1               5                   10                  15

Thr Val Thr Ile Ser Cys Thr Arg Ser Ser Gly Asn Ile Ala Ser Phe
            20                  25                  30

Tyr Val Gln Trp Phe Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Arg Ser Ser Asn Ser Ala Ser Leu Thr Ile Ser Gly
65                  70                  75                  80

Leu Thr Thr Asp Asp Glu Ala Asp Tyr Tyr Cys Gln Ser Tyr Asp Thr
                85                  90                  95

Asn Asn Val Ile Phe Gly Gly Gly Thr Lys Leu Thr Val Leu
            100                 105                 110

<210> SEQ ID NO 473
<211> LENGTH: 123
<212> TYPE: PRT
<213> ORGANISM: Artificial Sequence
<220> FEATURE:
<223> OTHER INFORMATION: VH

<400> SEQUENCE: 473

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Pro Ser Val Glu Ser Arg Ile Thr Ile Asn Pro Asp Thr Ser Lys Asn
65                  70                  75                  80

Gln Phe Ser Leu Gln Leu Ser Ser Val Thr Pro Glu Asp Thr Ala Val
                85                  90                  95

Tyr Tyr Cys Ala Arg Asp Pro Pro Tyr Val Leu Ser Thr Phe Asp Ile
            100                 105                 110

Trp Gly Gln Gly Thr Met Val Thr Val Ser Ser
        115                 120

<210> SEQ ID NO 474
<211> LENGTH: 110
<212> TYPE: PRT
```

<213> ORGANISM: Artificial Sequence
<220> FEATURE:
<223> OTHER INFORMATION: VL

<400> SEQUENCE: 474

Asn Phe Met Leu Thr Gln Pro Pro Ser Val Ser Glu Ser Pro Gly Lys
1               5                   10                  15

Thr Val Thr Ile Ser Cys Thr Arg Ser Ser Gly Asn Ile Ala Ser Phe
            20                  25                  30

Tyr Val Gln Trp Phe Gln Gln Arg Pro Gly Ser Ser Pro Thr Thr Val
        35                  40                  45

Ile Tyr Asp Asp Asp Gln Arg Pro Ser Gly Val Pro Asp Arg Phe Ser
50                  55                  60

Gly Ser Ile Asp Arg Ser Ser Asn Ser Ala Ser Leu Thr Ile Ser Gly
65                  70                  75                  80

Leu Thr Thr Asp Asp Glu Ala Asp Tyr Tyr Cys Gln Ser Tyr Asp Thr
                85                  90                  95

Asn Asn Val Ile Phe Gly Gly Gly Thr Lys Leu Thr Val Leu
            100                 105                 110

<210> SEQ ID NO 475
<211> LENGTH: 123
<212> TYPE: PRT
<213> ORGANISM: Artificial Sequence
<220> FEATURE:
<223> OTHER INFORMATION: VH

<400> SEQUENCE: 475

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
50                  55                  60

Pro Ser Val Glu Ser Arg Ile Thr Ile Asn Pro Asp Thr Ser Lys Asn
65                  70                  75                  80

Gln Phe Ser Leu Gln Leu Ser Ser Val Thr Pro Glu Asp Thr Ala Val
                85                  90                  95

Tyr Tyr Cys Ala Arg Asp Pro Pro Tyr Val Leu Ser Thr Phe Asp Ile
            100                 105                 110

Trp Gly Gln Gly Thr Met Val Thr Val Ser Ser
        115                 120

<210> SEQ ID NO 476
<211> LENGTH: 110
<212> TYPE: PRT
<213> ORGANISM: Artificial Sequence
<220> FEATURE:
<223> OTHER INFORMATION: VL

<400> SEQUENCE: 476

Asn Phe Met Leu Thr Gln Pro Pro Ser Val Ser Glu Ser Pro Gly Lys
1               5                   10                  15

Thr Val Thr Ile Ser Cys Thr Arg Ser Ser Gly Asn Ile Ala Ser Phe
            20                  25                  30

Tyr Val Gln Trp Phe Gln Gln Arg Pro Gly Ser Ser Pro Thr Thr Val
        35                  40                  45

```
Ile Tyr Glu Asp Asp Gln Arg Pro Ser Gly Val Pro Asp Arg Phe Ser
    50                  55                  60

Gly Ser Ile Asp Arg Ser Ser Asn Ser Ala Ser Leu Thr Ile Ser Gly
65                  70                  75                  80

Leu Thr Thr Asp Asp Glu Ala Asp Tyr Tyr Cys Gln Ser Tyr Asp Thr
                85                  90                  95

Asn Lys Val Ile Phe Gly Gly Gly Thr Lys Leu Thr Val Leu
            100                 105                 110
```

<210> SEQ ID NO 477
<211> LENGTH: 123
<212> TYPE: PRT
<213> ORGANISM: Artificial Sequence
<220> FEATURE:
<223> OTHER INFORMATION: VH

<400> SEQUENCE: 477

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Pro Ser Val Glu Ser Arg Ile Thr Ile Asn Pro Asp Thr Ser Lys Asn
65                  70                  75                  80

Gln Phe Ser Leu Gln Leu Ser Ser Val Thr Pro Glu Asp Thr Ala Val
                85                  90                  95

Tyr Tyr Cys Ala Arg Asp Pro Pro Tyr Val Leu Ser Thr Phe Asp Ile
            100                 105                 110

Trp Gly Gln Gly Thr Met Val Thr Val Ser Ser
        115                 120
```

<210> SEQ ID NO 478
<211> LENGTH: 110
<212> TYPE: PRT
<213> ORGANISM: Artificial Sequence
<220> FEATURE:
<223> OTHER INFORMATION: VL

<400> SEQUENCE: 478

```
Asn Phe Met Leu Thr Gln Pro Pro Ser Val Ser Glu Ser Pro Gly Lys
1               5                   10                  15

Thr Val Thr Ile Ser Cys Thr Arg Ser Ser Gly Asn Ile Ala Ser Phe
            20                  25                  30

Tyr Val Gln Trp Phe Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Arg Ser Ser Asn Ser Ala Ser Leu Thr Ile Ser Gly
65                  70                  75                  80

Leu Thr Thr Asp Asp Glu Ala Asp Tyr Tyr Cys Gln Ser Tyr Asp Ile
                85                  90                  95

Asn Lys Val Ile Phe Gly Gly Gly Thr Lys Leu Thr Val Leu
            100                 105                 110
```

```
<210> SEQ ID NO 479
<211> LENGTH: 123
<212> TYPE: PRT
<213> ORGANISM: Artificial Sequence
<220> FEATURE:
<223> OTHER INFORMATION: VH

<400> SEQUENCE: 479

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Pro Ser Val Glu Ser Arg Ile Thr Ile Asn Pro Asp Thr Ser Lys Asn
65                  70                  75                  80

Gln Phe Ser Leu Gln Leu Ser Val Thr Pro Glu Asp Thr Ala Val
                85                  90                  95

Tyr Tyr Cys Ala Arg Asp Pro Pro Tyr Val Leu Ser Thr Phe Asp Ile
            100                 105                 110

Trp Gly Gln Gly Thr Met Val Thr Val Ser Ser
        115                 120

<210> SEQ ID NO 480
<211> LENGTH: 110
<212> TYPE: PRT
<213> ORGANISM: Artificial Sequence
<220> FEATURE:
<223> OTHER INFORMATION: VL

<400> SEQUENCE: 480

Asn Phe Met Leu Thr Gln Pro Pro Ser Val Ser Glu Ser Pro Gly Lys
1               5                   10                  15

Thr Val Thr Ile Ser Cys Thr Arg Ser Ser Gly Asn Ile Ala Ser Phe
            20                  25                  30

Tyr Val Gln Trp Phe Gln Gln Arg Pro Gly Ser Ser Pro Thr Thr Val
        35                  40                  45

Ile Tyr Asp Asp Asp Gln Arg Pro Ser Gly Val Pro Asp Arg Phe Ser
    50                  55                  60

Gly Ser Ile Asp Arg Ser Ser Asn Ser Ala Ser Leu Thr Ile Ser Gly
65                  70                  75                  80

Leu Thr Thr Asp Asp Glu Ala Asp Tyr Tyr Cys Gln Ser Tyr Asp Ile
                85                  90                  95

Asn Lys Val Ile Phe Gly Gly Gly Thr Lys Leu Thr Val Leu
            100                 105                 110

<210> SEQ ID NO 481
<211> LENGTH: 120
<212> TYPE: PRT
<213> ORGANISM: Artificial Sequence
<220> FEATURE:
<223> OTHER INFORMATION: VH

<400> SEQUENCE: 481

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Met Pro Asp Gly Tyr
            20                  25                  30
```

Tyr Met His Trp Val Arg Gln Ala Pro Gly Gln Gly Leu Glu Trp Met
            35                  40                  45

Gly Trp Ile Asn Pro Arg Thr Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ala Ala Phe Arg Leu Glu Leu Asp Ala Trp Gly Gln
                100                 105                 110

Gly Thr Leu Val Thr Val Ser Ser
            115                 120

<210> SEQ ID NO 482
<211> LENGTH: 106
<212> TYPE: PRT
<213> ORGANISM: Artificial Sequence
<220> FEATURE:
<223> OTHER INFORMATION: VL

<400> SEQUENCE: 482

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Val Val
                85                  90                  95

Phe Gly Gly Gly Thr Gln Leu Thr Val Leu
                100                 105

<210> SEQ ID NO 483
<211> LENGTH: 120
<212> TYPE: PRT
<213> ORGANISM: Artificial Sequence
<220> FEATURE:
<223> OTHER INFORMATION: VH

<400> SEQUENCE: 483

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Met
            35                  40                  45

Gly Trp Val Asn Pro Lys Ser Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Trp Ala Arg Arg Ile Asp Leu Asp Glu Trp Gly Gln

```
            100             105             110
Gly Thr Leu Val Thr Val Ser Ser
        115             120
```

<210> SEQ ID NO 484
<211> LENGTH: 106
<212> TYPE: PRT
<213> ORGANISM: Artificial Sequence
<220> FEATURE:
<223> OTHER INFORMATION: VL

<400> SEQUENCE: 484

```
Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Val Val
                85                  90                  95

Phe Gly Gly Gly Thr Gln Leu Thr Val Leu
            100                 105
```

<210> SEQ ID NO 485
<211> LENGTH: 117
<212> TYPE: PRT
<213> ORGANISM: Artificial Sequence
<220> FEATURE:
<223> OTHER INFORMATION: VH

<400> SEQUENCE: 485

```
Gln Met Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Gly Tyr
            20                  25                  30

Tyr Met His Trp Val Arg Gln Ala Pro Gly Gln Gly Leu Glu Trp Met
        35                  40                  45

Gly Trp Val Asn Pro Met Ser Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Met Ala Met Arg Leu Glu Leu Asp Lys Trp Gly Gln
            100                 105                 110

Gly Thr Leu Val Thr
        115
```

<210> SEQ ID NO 486
<211> LENGTH: 106
<212> TYPE: PRT
<213> ORGANISM: Artificial Sequence
<220> FEATURE:
<223> OTHER INFORMATION: VL

<400> SEQUENCE: 486

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Val Val
                85                  90                  95

Phe Gly Gly Gly Thr Gln Leu Thr Val Leu
            100                 105

<210> SEQ ID NO 487
<211> LENGTH: 120
<212> TYPE: PRT
<213> ORGANISM: Artificial Sequence
<220> FEATURE:
<223> OTHER INFORMATION: VH

<400> SEQUENCE: 487

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Gly Gly Tyr
            20                  25                  30

Tyr Met His Trp Val Arg Gln Ala Pro Gly Gln Gly Leu Glu Trp Met
        35                  40                  45

Gly Trp Val Asn Pro His Ser Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Ala Trp Gly Leu Asp Leu Asp Leu Trp Gly Gln
            100                 105                 110

Gly Thr Leu Val Thr Val Ser Ser
        115                 120

<210> SEQ ID NO 488
<211> LENGTH: 106
<212> TYPE: PRT
<213> ORGANISM: Artificial Sequence
<220> FEATURE:
<223> OTHER INFORMATION: VL

<400> SEQUENCE: 488

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly

```
                65                  70                  75                  80
Asp Glu Ala Asp Tyr Tyr Cys Gln Val Trp Asp Ser Ser Val Val
                    85                  90                  95

Phe Gly Gly Gly Thr Gln Leu Thr Val Leu
                100                 105

<210> SEQ ID NO 489
<211> LENGTH: 120
<212> TYPE: PRT
<213> ORGANISM: Artificial Sequence
<220> FEATURE:
<223> OTHER INFORMATION: VH

<400> SEQUENCE: 489

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Asn Trp Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Met Ala Gly Gly Thr Asn Tyr Ala Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Trp Ala Arg Val Glu Leu Asp Met Trp Gly Gln
                100                 105                 110

Gly Thr Leu Val Thr Val Ser Ser
        115                 120

<210> SEQ ID NO 490
<211> LENGTH: 106
<212> TYPE: PRT
<213> ORGANISM: Artificial Sequence
<220> FEATURE:
<223> OTHER INFORMATION: VL

<400> SEQUENCE: 490

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Val Val
                85                  90                  95

Phe Gly Gly Gly Thr Gln Leu Thr Val Leu
                100                 105

<210> SEQ ID NO 491
<211> LENGTH: 120
<212> TYPE: PRT
<213> ORGANISM: Artificial Sequence
<220> FEATURE:
```

<223> OTHER INFORMATION: VH

<400> SEQUENCE: 491

Gln Met Gln Leu Val Gln Ser Gly Ala Glu Val Lys Lys Pro Gly Ala
1               5                   10                  15
Ser Val Lys Val Ser Cys Lys Ala Ser Gly Tyr Asn Phe Gly Gly Tyr
            20                  25                  30
Tyr Met His Trp Val Arg Gln Ala Pro Gly Gln Gly Leu Glu Trp Met
        35                  40                  45
Gly Trp Val Asn Pro Lys Ser Gly Gly Thr Asn Tyr Ala Gln Lys Phe
    50                  55                  60
Gln Gly Arg Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Gly Glu Ala Val Gly Leu Asp Leu Asp Tyr Trp Gly Gln
            100                 105                 110
Gly Thr Leu Val Thr Val Ser Ser
        115                 120

<210> SEQ ID NO 492
<211> LENGTH: 106
<212> TYPE: PRT
<213> ORGANISM: Artificial Sequence
<220> FEATURE:
<223> OTHER INFORMATION: VL

<400> SEQUENCE: 492

Ser Tyr Glu Leu Thr Gln Pro Pro Ser Val Ser Val Ala Pro Gly Lys
1               5                   10                  15
Thr Ala Arg Ile Thr Cys Gly Gly Asn Asn Ile Gly Ser Lys Ser Val
            20                  25                  30
His Trp Tyr Gln Gln Lys Pro Gly Gln Ala Pro Val Leu Val Ile Tyr
        35                  40                  45
Tyr Asp Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Ser Ser Val Val
                85                  90                  95
Phe Gly Gly Gly Thr Gln Leu Thr Val Leu
            100                 105

<210> SEQ ID NO 493
<211> LENGTH: 120
<212> TYPE: PRT
<213> ORGANISM: Artificial Sequence
<220> FEATURE:
<223> OTHER INFORMATION: VH

<400> SEQUENCE: 493

Gln Met Gln Leu Val Gln Ser Gly Ala Glu Val Lys Lys Pro Gly Ala
1               5                   10                  15
Ser Val Lys Val Ser Cys Lys Ala Ser Gly Tyr Ser Leu Glu Gly Tyr
            20                  25                  30
Tyr Met His Trp Val Arg Gln Ala Pro Gly Gln Gly Leu Glu Trp Met
        35                  40                  45
Gly Trp Ile Asn Pro Asn Ser Gly Gly Thr Asn Tyr Ala Gln Lys Phe

```
                 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Glu Ala Val Gly Leu Asp Leu Asp Tyr Trp Gly Gln
                100                 105                 110

Gly Thr Leu Val Thr Val Ser Ser
            115                 120

<210> SEQ ID NO 494
<211> LENGTH: 106
<212> TYPE: PRT
<213> ORGANISM: Artificial Sequence
<220> FEATURE:
<223> OTHER INFORMATION: VL

<400> SEQUENCE: 494

Ser Tyr Glu Leu Thr Gln Pro Pro Ser Val Ser Val Ala Pro Gly Lys
  1               5                  10                  15

Thr Ala Arg Ile Thr Cys Gly Gly Asn Asn Ile Gly Ser Lys Ser Val
             20                  25                  30

His Trp Tyr Gln Gln Lys Pro Gly Gln Ala Pro Val Leu Val Ile Tyr
         35                  40                  45

Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Val Val
                 85                  90                  95

Phe Gly Gly Gly Thr Gln Leu Thr Val Leu
                100                 105

<210> SEQ ID NO 495
<211> LENGTH: 120
<212> TYPE: PRT
<213> ORGANISM: Artificial Sequence
<220> FEATURE:
<223> OTHER INFORMATION: VH

<400> SEQUENCE: 495

Gln Met Gln Leu Val Gln Ser Gly Ala Glu Val Lys Lys Pro Gly Ala
  1               5                  10                  15

Ser Val Lys Val Ser Cys Lys Ala Ser Gly Tyr Ser Leu Glu Gly Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Glu Ala Val Gly Leu Asp Leu Asp Tyr Trp Gly Gln
                100                 105                 110

Gly Thr Leu Val Thr Val Ser Ser
            115                 120
```

<210> SEQ ID NO 496
<211> LENGTH: 106
<212> TYPE: PRT
<213> ORGANISM: Artificial Sequence
<220> FEATURE:
<223> OTHER INFORMATION: VL

<400> SEQUENCE: 496

```
Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Val Val
                85                  90                  95

Phe Gly Gly Gly Thr Gln Leu Thr Val Leu
            100                 105
```

<210> SEQ ID NO 497
<211> LENGTH: 120
<212> TYPE: PRT
<213> ORGANISM: Artificial Sequence
<220> FEATURE:
<223> OTHER INFORMATION: VH

<400> SEQUENCE: 497

```
Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Ala Val Gly Leu Asp Leu Asp Tyr Trp Gly Gln
            100                 105                 110

Gly Thr Leu Val Thr Val Ser Ser
        115                 120
```

<210> SEQ ID NO 498
<211> LENGTH: 106
<212> TYPE: PRT
<213> ORGANISM: Artificial Sequence
<220> FEATURE:
<223> OTHER INFORMATION: VL

<400> SEQUENCE: 498

```
Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
```

```
            20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Val Val
                    85                  90                  95

Phe Gly Gly Gly Thr Gln Leu Thr Val Leu
            100                 105

<210> SEQ ID NO 499
<211> LENGTH: 121
<212> TYPE: PRT
<213> ORGANISM: Artificial Sequence
<220> FEATURE:
<223> OTHER INFORMATION: VH

<400> SEQUENCE: 499

Glu Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Ser Tyr
            20                  25                  30

Tyr Ile Tyr Trp Val Arg Gln Ala Pro Gly Gln Gly Leu Glu Trp Ile
            35                  40                  45

Gly Asn Ile Trp Pro Gly Asn Gly Gly Thr Phe Tyr Gly Glu Lys Phe
 50                  55                  60

Met Gly Arg Ala Thr Phe Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                    85                  90                  95

Ala Arg Arg Pro Asp Tyr Ser Gly Asp Asp Tyr Phe Asp Tyr Trp Gly
            100                 105                 110

Gln Gly Thr Leu Val Thr Val Ser Ser
            115                 120

<210> SEQ ID NO 500
<211> LENGTH: 111
<212> TYPE: PRT
<213> ORGANISM: Artificial Sequence
<220> FEATURE:
<223> OTHER INFORMATION: VL

<400> SEQUENCE: 500

Ser Val Glu Leu Thr Gln Pro Pro Ser Val Ser Val Ser Pro Gly Gln
 1               5                  10                  15

Thr Ala Arg Ile Thr Cys Lys Leu Asn Ser Gly Asn Ile Gly Ser Tyr
            20                  25                  30

Tyr Val His Trp Tyr Gln Gln Lys Pro Gly Gln Ala Pro Val Thr Met
            35                  40                  45

Ile Tyr Arg Asp Asp Lys Arg Pro Asp Gly Ile Pro Glu Arg Phe Ser
 50                  55                  60

Gly Ser Ser Asp Ser Ser Asn Ser Ala Phe Leu Thr Ile Ser Gly
 65                  70                  75                  80

Val Gln Ala Glu Asp Glu Ala Asp Tyr Tyr Cys His Ser Tyr Asp Ser
                    85                  90                  95
```

Thr Ile Thr Pro Val Phe Gly Gly Gly Thr Lys Leu Thr Val Leu
            100                 105                 110

<210> SEQ ID NO 501
<211> LENGTH: 118
<212> TYPE: PRT
<213> ORGANISM: Artificial Sequence
<220> FEATURE:
<223> OTHER INFORMATION: VH

<400> SEQUENCE: 501

Glu Val Gln Leu Val Gln Ser Gly Ala Glu Val Lys Lys Pro Gly Ser
1               5                   10                  15

Ser Val Lys Val Ser Cys Lys Ala Ser Asp Tyr Thr Phe Asn Asp Tyr
            20                  25                  30

Trp Val Ser Trp Val Arg Gln Ala Pro Gly Gln Gly Leu Glu Trp Ile
        35                  40                  45

Gly Glu Ile Tyr Pro Asn Ser Gly Ala Thr Asn Phe Asn Gly Lys Phe
    50                  55                  60

Arg Gly Arg Ala Thr Leu Thr Val Asp Asn Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Tyr Thr Arg Asp Trp Phe Ala Tyr Trp Gly Gln Gly Thr
            100                 105                 110

Leu Val Thr Val Ser Ser
        115

<210> SEQ ID NO 502
<211> LENGTH: 112
<212> TYPE: PRT
<213> ORGANISM: Artificial Sequence
<220> FEATURE:
<223> OTHER INFORMATION: VL

<400> SEQUENCE: 502

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Asn Thr Tyr Leu Tyr Trp Phe Gln Arg Pro Gly Gln Ser
        35                  40                  45

Pro Arg Arg Leu Ile Tyr Leu Val Ser Asn Leu Gly Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Pro
                85                  90                  95

Thr His Ala Pro Tyr Thr Phe Gly Gln Gly Thr Lys Leu Glu Ile Lys
            100                 105                 110

<210> SEQ ID NO 503
<211> LENGTH: 118
<212> TYPE: PRT
<213> ORGANISM: Artificial Sequence
<220> FEATURE:
<223> OTHER INFORMATION: VH

<400> SEQUENCE: 503

Glu Val Gln Leu Val Gln Ser Gly Ala Glu Val Lys Lys Pro Gly Ser

```
                1               5                   10                  15
Ser Val Lys Val Ser Cys Lys Ala Ser Asp Tyr Thr Phe Asn Asp Tyr
                20                  25                  30

Trp Val Ser Trp Val Arg Gln Ala Pro Gly Gln Gly Leu Glu Trp Ile
            35                  40                  45

Gly Glu Ile Tyr Pro Asn Ser Gly Ala Thr Asn Phe Asn Gly Lys Phe
        50                  55                  60

Arg Gly Arg Ala Thr Leu Thr Val Asp Asn Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Tyr Thr Arg Asp Trp Phe Ala Tyr Trp Gly Gln Gly Thr
                100                 105                 110

Leu Val Thr Val Ser Ser
            115
```

<210> SEQ ID NO 504
<211> LENGTH: 112
<212> TYPE: PRT
<213> ORGANISM: Artificial Sequence
<220> FEATURE:
<223> OTHER INFORMATION: VL

<400> SEQUENCE: 504

```
Asp Val Gln Leu Thr Gln Ser Pro Ser Ser Leu Ser Ala Ser Val Gly
1               5                   10                  15

Asp Arg Val Thr Ile Thr Cys Arg Ser Ser Gln Ser Leu Leu Asp Ser
                20                  25                  30

Asp Gly Asn Thr Tyr Leu Tyr Trp Phe Gln Gln Lys Pro Gly Lys Ala
            35                  40                  45

Pro Lys Arg Leu Ile Tyr Leu Val Ser Asn Leu Gly Ser Gly Val Pro
        50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Met Gln Pro
                85                  90                  95

Thr His Ala Pro Tyr Thr Phe Gly Gln Gly Thr Lys Val Glu Ile Lys
                100                 105                 110
```

<210> SEQ ID NO 505
<211> LENGTH: 117
<212> TYPE: PRT
<213> ORGANISM: Artificial Sequence
<220> FEATURE:
<223> OTHER INFORMATION: VH

<400> SEQUENCE: 505

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Tyr Ser
                20                  25                  30

Tyr Met Ser Trp Val Arg Gln Ala Pro Gly Lys Gly Leu Glu Val Ser
            35                  40                  45

Ser Ile Gly Ser Gly Ser Ser Tyr Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80
```

Gln Met Asn Ser Leu Arg Ala Glu Asp Thr Ala Val Tyr Tyr Cys Ala
                85                  90                  95

Arg Val Tyr Ser Ser Pro Gly Ile Asp Tyr Trp Gly Gln Gly Thr Leu
            100                 105                 110

Val Thr Val Ser Ser
        115

<210> SEQ ID NO 506
<211> LENGTH: 107
<212> TYPE: PRT
<213> ORGANISM: Artificial Sequence
<220> FEATURE:
<223> OTHER INFORMATION: VL

<400> SEQUENCE: 506

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Trp Val Pro
                85                  90                  95

Phe Thr Phe Gly Gln Gly Thr Lys Leu Glu Ile
            100                 105

<210> SEQ ID NO 507
<211> LENGTH: 120
<212> TYPE: PRT
<213> ORGANISM: Artificial Sequence
<220> FEATURE:
<223> OTHER INFORMATION: VH

<400> SEQUENCE: 507

Val His Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Asn Phe Gly
            20                  25                  30

Tyr Ser Tyr Met Ser Trp Val Arg Gln Ala Pro Gly Lys Gly Leu Glu
        35                  40                  45

Trp Val Ser Ser Ile Gly Ser Thr Ser His Thr Tyr Tyr Ala Asp
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Val Tyr Ser Ser Pro Gly Ile Asp Tyr Trp Gly Gln
            100                 105                 110

Gly Thr Leu Val Thr Val Ser Ser
        115                 120

<210> SEQ ID NO 508
<211> LENGTH: 107
<212> TYPE: PRT
<213> ORGANISM: Artificial Sequence

<220> FEATURE:
<223> OTHER INFORMATION: VL

<400> SEQUENCE: 508

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Thr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Trp Val Pro
                85                  90                  95

Phe Phe Gly Gln Gly Thr Lys Leu Glu Ile Lys
            100                 105

<210> SEQ ID NO 509
<211> LENGTH: 118
<212> TYPE: PRT
<213> ORGANISM: Artificial Sequence
<220> FEATURE:
<223> OTHER INFORMATION: VH

<400> SEQUENCE: 509

Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Val Lys Ser Leu Glu Trp Ile
        35                  40                  45

Gly Gly Ile Ser Thr Tyr Asn Gly Asp Ala Ser Tyr Asn Gln Lys Phe
50                  55                  60

Lys Gly Lys Ala Thr Met Thr Val Asp Lys Ser Ser Arg Thr Ala Tyr
65                  70                  75                  80

Met Glu Leu Val Arg Leu Thr Ser Glu Asp Ser Ala Ile Tyr Tyr Cys
                85                  90                  95

Ala Pro Ser Asn Tyr Gly Tyr Ala Met Asp Tyr Trp Gly Gln Gly Thr
            100                 105                 110

Ser Val Thr Val Ser Ser
        115

<210> SEQ ID NO 510
<211> LENGTH: 113
<212> TYPE: PRT
<213> ORGANISM: Artificial Sequence
<220> FEATURE:
<223> OTHER INFORMATION: VL

<400> SEQUENCE: 510

Asp Ile Val Met Ser Gln Ser Pro Ser Ser Leu Ala Val Ser Val Gly
1               5                   10                  15

Glu Lys Val Ser Val Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
            85                  90                  95

Tyr Leu Ser Tyr Pro Trp Thr Phe Gly Gly Gly Thr Lys Leu Glu Ile
                100                 105                 110

Asn

<210> SEQ ID NO 511
<211> LENGTH: 118
<212> TYPE: PRT
<213> ORGANISM: Artificial Sequence
<220> FEATURE:
<223> OTHER INFORMATION: VH

<400> SEQUENCE: 511

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Ile Phe Thr Thr Tyr
            20                  25                  30

Ala Met His Trp Val Lys Gln Arg Pro Gly Gln Gly Leu Glu Trp Ile
        35                  40                  45

Gly Tyr Ile Asn Pro Thr Thr Val Tyr Thr Ile Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Leu Gly Gly His Trp Tyr Phe Asp Val Trp Gly Ala Gly Thr
                100                 105                 110

Thr Val Thr Val Ser Ser
        115

<210> SEQ ID NO 512
<211> LENGTH: 111
<212> TYPE: PRT
<213> ORGANISM: Artificial Sequence
<220> FEATURE:
<223> OTHER INFORMATION: VL

<400> SEQUENCE: 512

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ser Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
            85                  90                  95

Glu Val Pro Trp Thr Phe Gly Gly Gly Thr Lys Leu Glu Ile Lys
                100                 105                 110

```
<210> SEQ ID NO 513
<211> LENGTH: 117
<212> TYPE: PRT
<213> ORGANISM: Artificial Sequence
<220> FEATURE:
<223> OTHER INFORMATION: VH

<400> SEQUENCE: 513

Gln Val Gln Leu Gln Gln Ser Gly Thr Glu Leu Met Lys Pro Gly Ala
1               5                   10                  15

Ser Val Lys Leu Ser Cys Lys Ala Ser Gly Tyr Ile Phe Thr Gly Tyr
                20                  25                  30

Trp Ile Glu Trp Val Lys Gln Arg Pro Gly His Gly Leu Glu Trp Ile
            35                  40                  45

Gly Glu Ile Leu Pro Gly Gly Gly Thr Val Tyr Tyr Asn Glu Lys Phe
        50                  55                  60

Lys Gly Lys Ala Thr Phe Thr Ala Glu Thr Ser Ser Asn Thr Ala Tyr
65                  70                  75                  80

Val Gln Leu Ser Ser Leu Thr Glu Asp Ser Ala Val Tyr Tyr Cys
                85                  90                  95

Ala Arg Trp Gly Arg Ser Trp Phe Thr His Trp Gly Gln Gly Thr Leu
            100                 105                 110

Val Thr Val Ser Ala
            115

<210> SEQ ID NO 514
<211> LENGTH: 112
<212> TYPE: PRT
<213> ORGANISM: Artificial Sequence
<220> FEATURE:
<223> OTHER INFORMATION: VL

<400> SEQUENCE: 514

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Glu Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Arg Thr Phe Gly Gly Gly Thr Lys Leu Glu Ile Lys
            100                 105                 110

<210> SEQ ID NO 515
<211> LENGTH: 121
<212> TYPE: PRT
<213> ORGANISM: Artificial Sequence
<220> FEATURE:
<223> OTHER INFORMATION: VH

<400> SEQUENCE: 515

Gln Val Gln Leu Gln Gln Pro Gly Glu Ser Glu Leu Val Arg Pro Gly
1               5                   10                  15

Ser Val Lys Leu Ser Cys Lys Ala Ser Gly Tyr Thr Phe Thr Ser Tyr
```

```
                    20                  25                  30

Trp Met Asp Trp Val Lys Gln Arg His Gly Gln Gly Leu Glu Trp Ile
            35                  40                  45

Gly Asn Ile Tyr Pro Asp Ser Gly Gly Thr Asn Tyr Ala Glu Lys Phe
        50                  55                  60

Lys Ser Lys Ala Thr Leu Thr Val Asp Thr Ser Ser Thr Ala Tyr
65                  70                  75                  80

Met His Leu Ser Ser Leu Thr Ser Glu Asp Ser Ala Val Tyr Tyr Cys
                85                  90                  95

Thr Arg Glu Glu Ala Leu Gly Gly Tyr Tyr Glu Leu Thr Tyr Trp Gly
            100                 105                 110

Gln Gly Thr Leu Val Thr Val Ser Ala
        115                 120

<210> SEQ ID NO 516
<211> LENGTH: 111
<212> TYPE: PRT
<213> ORGANISM: Artificial Sequence
<220> FEATURE:
<223> OTHER INFORMATION: VL

<400> SEQUENCE: 516

Asp Ile Val Leu Thr Gln Ser Pro Ala Ser Leu Pro Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Glu
            100                 105                 110

<210> SEQ ID NO 517
<211> LENGTH: 119
<212> TYPE: PRT
<213> ORGANISM: Artificial Sequence
<220> FEATURE:
<223> OTHER INFORMATION: VH

<400> SEQUENCE: 517

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Ala Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Asn Gly Asn Asn Tyr Tyr Ser Glu Lys Phe
    50                  55                  60

Lys Asp Lys Ala Thr Leu Thr Ala Asp Lys Ser Ser Ser Thr Val Tyr
65                  70                  75                  80

Ile Arg Leu Ser Ser Leu Thr Ser Glu Asp Ser Ala Val Tyr Phe Cys
                85                  90                  95
```

-continued

```
Ala Arg His Gly Ser Phe Arg Ser Ala Met Asp Tyr Trp Gly Gln Gly
                100                 105                 110

Thr Ser Val Thr Val Ser Ser
        115

<210> SEQ ID NO 518
<211> LENGTH: 107
<212> TYPE: PRT
<213> ORGANISM: Artificial Sequence
<220> FEATURE:
<223> OTHER INFORMATION: VL

<400> SEQUENCE: 518

Asp Ile Gln Met Thr Gln Ser Pro Ala Ser Pro Ser Ala Ser Val Gly
1               5                   10                  15

Glu Thr Val Thr Ile Thr Cys Arg Ala Ser Glu Asn Ile Tyr Ser Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Ala Asp Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Pro
                85                  90                  95

Thr Phe Gly Gly Gly Thr Lys Leu Glu Ile Lys
                100                 105
```